United States Patent
Reddy et al.

(10) Patent No.: US 10,383,831 B2
(45) Date of Patent: Aug. 20, 2019

(54) 2,4,6-TRIALKOXYSTRYL ARYL SULFONES, SULFONAMIDES AND CARBOXAMIDES, AND METHODS OF PREPARATION AND USE

(71) Applicant: Temple University—Of The Commonwealth System Of Higher Education, Philadelphia, PA (US)

(72) Inventors: M. V. Ramana Reddy, Upper Darby, PA (US); E. Premkumar Reddy, White Plains, NY (US)

(73) Assignee: Temple University—Of The Commonwealth System Of Higher Education, Philadelphia, PA (US)

(*) Notice: Subject to any disclaimer, the term of this patent is extended or adjusted under 35 U.S.C. 154(b) by 0 days.

(21) Appl. No.: 15/750,427

(22) PCT Filed: Aug. 2, 2016

(86) PCT No.: PCT/US2016/045125
§ 371 (c)(1),
(2) Date: Feb. 5, 2018

(87) PCT Pub. No.: WO2017/023912
PCT Pub. Date: Feb. 9, 2017

(65) Prior Publication Data
US 2018/0243239 A1 Aug. 30, 2018

Related U.S. Application Data
(60) Provisional application No. 62/200,266, filed on Aug. 3, 2015.

(51) Int. Cl.
| | | |
|---|---|---|
| *A61K 31/136* | (2006.01) | |
| *C07C 311/27* | (2006.01) | |
| *C07D 213/74* | (2006.01) | |
| *C07D 317/58* | (2006.01) | |
| *C07C 317/28* | (2006.01) | |
| *C07C 235/38* | (2006.01) | |
| *C07D 295/185* | (2006.01) | |
| *C07D 213/64* | (2006.01) | |
| *C07D 213/65* | (2006.01) | |
| *A61P 35/00* | (2006.01) | |
| *A61K 31/167* | (2006.01) | |
| *A61K 31/4412* | (2006.01) | |

(52) U.S. Cl.
CPC .......... *A61K 31/136* (2013.01); *A61K 31/167* (2013.01); *A61K 31/4412* (2013.01); *A61P 35/00* (2018.01); *C07C 235/38* (2013.01); *C07C 311/27* (2013.01); *C07C 317/28* (2013.01); *C07D 213/64* (2013.01); *C07D 213/65* (2013.01); *C07D 213/74* (2013.01); *C07D 295/185* (2013.01); *C07D 317/58* (2013.01)

(58) Field of Classification Search
None
See application file for complete search history.

(56) References Cited

U.S. PATENT DOCUMENTS

| | | | |
|---|---|---|---|
| 4,443,477 | A | 4/1984 | Witte et al. |
| 5,059,595 | A | 10/1991 | Le Grazie |
| 5,070,099 | A | 12/1991 | Hall et al. |
| 5,073,543 | A | 12/1991 | Marshall et al. |
| 5,120,548 | A | 6/1992 | McClelland et al. |
| 5,545,750 | A | 8/1996 | Kempf et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,201,154 | B1 | 3/2001 | Reddy et al. |
| 6,359,013 | B1 | 3/2002 | Reddy et al. |
| 6,414,034 | B1 | 7/2002 | Reddy et al. |
| 6,486,210 | B2 | 11/2002 | Reddy et al. |
| 6,541,475 | B2 | 4/2003 | Reddy et al. |
| 6,548,553 | B2 | 4/2003 | Reddy et al. |
| 6,576,675 | B1 | 6/2003 | Reddy et al. |
| 6,599,932 | B1 | 7/2003 | Reddy et al. |
| 6,642,410 | B2 | 11/2003 | Reddy et al. |
| 6,646,009 | B2 | 11/2003 | Reddy et al. |
| 6,656,968 | B1 | 12/2003 | Reddy et al. |
| 6,656,973 | B2 | 12/2003 | Cosenza et al. |
| 6,667,346 | B2 | 12/2003 | Reddy et al. |
| 6,762,207 | B1 | 7/2004 | Reddy et al. |
| 6,767,926 | B1 | 7/2004 | Cosenza et al. |
| 6,787,667 | B2 | 9/2004 | Reddy et al. |
| 6,833,480 | B2 | 12/2004 | Reddy et al. |
| 7,053,123 | B2 | 5/2006 | Reddy et al. |

(Continued)

FOREIGN PATENT DOCUMENTS

| | | |
|---|---|---|
| JP | H09-003037 A | 1/1997 |
| WO | WO-0178712 A1 | 10/2001 |

(Continued)

OTHER PUBLICATIONS

Divakar, et al., "Abstract LB-108: Targeting the Ras-Binding domain of RAS effector proteins by a small molecule inhibitor, Rigosertib", Cancer Res, 74(19 Suppl):Abstract LB-108 (2014).

(Continued)

*Primary Examiner* — Nyeemah A Grazier
(74) *Attorney, Agent, or Firm* — Drinker Biddle & Reath LLP

(57) ABSTRACT

Compounds according to Formula I are provided:

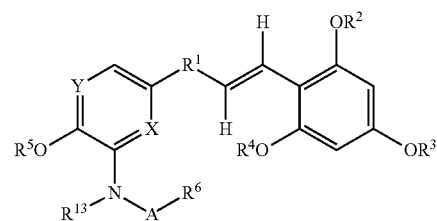

and salts thereof, wherein $R^1$, $R^2$, $R^3$, $R^4$, $R^5$, $R^6$, $R^{13}$, A, X and Y are as defined herein. Methods for preparing compounds of Formula I are also provided, as well as methods of treating cellular proliferative disorders, such as cancer, using compounds of Formula I.

93 Claims, No Drawings

(56) References Cited

U.S. PATENT DOCUMENTS

| | | | |
|---|---|---|---|
| 7,161,031 B2* | 1/2007 | Reddy | C07C 311/27 |
| | | | 530/402 |
| 7,482,488 B2 | 1/2009 | Reddy et al. | |
| 7,595,347 B2 | 9/2009 | Cosenza et al. | |
| 7,598,232 B2 | 10/2009 | Reddy et al. | |
| 7,744,889 B2* | 6/2010 | Reddy | C07C 317/10 |
| | | | 424/155.1 |
| 7,932,242 B2 | 4/2011 | Reddy et al. | |
| 8,058,313 B2 | 11/2011 | Reddy et al. | |
| 8,106,033 B2 | 1/2012 | Reddy et al. | |
| 8,143,428 B2 | 3/2012 | Reddy et al. | |
| 8,143,453 B2 | 3/2012 | Reddy et al. | |
| 8,324,190 B2 | 12/2012 | Reddy et al. | |
| 8,664,272 B2 | 3/2014 | Reddy et al. | |
| 2009/0124828 A1* | 5/2009 | Reddy | C07C 315/02 |
| | | | 562/429 |
| 2009/0191193 A1* | 7/2009 | Reddy | C07C 311/12 |
| | | | 424/133.1 |
| 2009/0306207 A1 | 12/2009 | Reddy et al. | |
| 2010/0152096 A1 | 6/2010 | Bell et al. | |
| 2011/0054037 A1 | 3/2011 | Safavy | |

FOREIGN PATENT DOCUMENTS

| | | |
|---|---|---|
| WO | WO-03072062 A2 | 9/2003 |
| WO | WO-03072063 A2 | 9/2003 |
| WO | WO-04037751 A2 | 5/2004 |
| WO | WO-2008/027049 A1 | 3/2008 |
| WO | WO-2009/009041 A2 | 1/2009 |
| WO | WO-2010/003127 A2 | 1/2010 |
| WO | WO-2010/130970 A1 | 11/2010 |
| WO | WO-2011/161446 A1 | 12/2011 |
| WO | WO-2014/047110 A2 | 3/2014 |

OTHER PUBLICATIONS

Gysin et al., "Therapeutic Strategies for Targeting Ras Proteins", Genes Cancer, 2(3): 359-372 (2011).

Lu et al., "Discovery of (E)-3-((Styrylsulfonyl)methyl)pyridine and (E)-2((Styrylsulfonyl)methyl)pyridine Derivatives as Anticancer Agents: Synthesis, Structure-Activity Relationships, and Biological Activities", J Med Chem, 57(6):2275-2291 (2014).

National Center for Biotechnology Information. PubChem Compound Database; CID=10435976, https://pubchem.ncbi.nlm.nih.gov/compound/10435976 (accessed Oct. 12, 2006).

Prior et al., "A Comprehensive Survey of Ras Mutations in Cancer", Cancer Res, 72(10):2457-2467 (2012).

Reddy et al., "Discovery of a Clinical Stage Multi-Kinase Inhibitor Sodium (E)-2-{2-Methoxy-5-[(20,40,60-trimethoxystyrylsulfonyl)methyl]phenylamino}-acetate (ON 01910. Na): Synthesis, Structure-Activity Relationship, and Biological Activity", J. Med. Chem, 54:6254-6276 (2011).

Reddy et al, "Rigosertib Blocks RAS Signaling by Acting as a Small Molecule RAS Mimetic That Binds to the RAS-Binding Domains of RAS Effector Proteins", Blood, 124(21), 5616 (2014). Retrieved from http://www.bloodjournal.org/content/124/21/5616.

International Search Report dated Dec. 9, 2016 for International Patent Application No. PCT/US16/45125, filed Aug. 2, 2016.

International Preliminary Report on Patentability dated Feb. 6, 2018 for International Patent Application No. PCT/US16/45125, filed Aug. 2, 2016.

Mitin et al., "Palladium-Catalyzed Arylation of Sulfones", Russian Journal of Organic Chemistry, vol. 40, No. 6, pp. 802-812 (2004).

Higuchi et al., "Flash Pyrolysis of Selenides. Syntheses of Bibenzyls, Olefins, and Related Compounds", Bull. Chem. Soc. Jpn., vol. 55, No. 1, pp. 182-187 (1982).

Dodson et al., "Reactions of Sulphones with Grignard Reagents", Chem. Commun. (London), pp. 352-353 (1965).

Padama et al., "Synthesis of a new class of 2-oxazolines and 2-thiazolines", Indian J. Chem., vol. 47B, pp. 1713-1725 (Nov. 2008).

Padmavathi et al., "Michael adducts of vinyl sulfones; source for thiadiazoles, oxadiazoles and triazoles", J. Heterocyclic Chem., vol. 45(6), pp. 1633-1639 (2008).

Biellmann et al., "Allylic and Benzylic Carbanions Substituted by Heteroatoms", Organic Reactions, pp. 1-300 (1982).

Padmavathi et al., "Michael Adducts—Synthons for a New Class of 1,4-dispirocyclohexane Derivatives", Indian J. of Chem., vol. 45B, pp. 808-812 (Mar. 2006).

Padmavathi et al., "Synthesis and Bioassay of Amino-pyrazolone, Amino-isoxazolone and Amino-pyrimidinone Derivatives", Chem. Pharm. Bull., vol. 55(12), pp. 1704-1709 (2007).

Tishchenko et al., "Synthesis of propoxy- and butoxyphenacyl arcylthio ethers by thiolysis of alkoxyl-substituted acyloxiranes", Caplus, Accession No. 1978:22294, CAN 88:22294, Abstract (1977).

Reddy et al., "Stereospecific synthesis of some new Z- and E-cyclopropyl benzyl sulfones and E,Z- and E,Ebis(cyclopropyl)sulfones by PTC method", Caplus, Accession No. 1995:259329, CAN 122:132682, Abstract (1994).

Evans et al., "The Epoxy-Ramberg-Backlund Reaction:A New Route to Allylic Alcohols", Tetrahedron .Letters, vol. 38, No. 17, pp. 3055-3058 (1997).

Bin et al., "Potassium Hydroxide-Mediated Novel Rearrangement of 2-Alkyl-sulfonyl-2-arylsulfonyl-1-phenylethanones to 1-Aryl-2-(arylsulfonylmethanesulfonyl)ethanones", Organic Letters vol. 6, No. 23, pp. 4297-4300 (2004).

Padmavathi et al., Michael Addition of Active Methylene Compounds to a,β-unsaturated Sulfones, Indian J. Chem., vol. 44B, pp. 2569-2574 (Dec. 2005).

Evans et al., "The Epoxy-Ramberg-Bäcklund Reaction (ERBR): A Sulfone-Based Method for the Synthesis of Allylic Alcohols", Eur. J. Org. Chem., pp. 1740-1754 (2006).

Castang et al., "N-Sulfonyl homoserine lactones as antagonists of bacterial quorum sensing", Bioorganic & Medicinal Chemistry Letters, 14, pp. 5145-5149 (2004).

Sohmiya et al., "Solid-State Organic Reactions Proceeding by Pulverization: Oxidation and Halogenation with Iodosobenzene and Inorganic Solid Supports", Tetrahedron, vol. 54, pp. 13737-13750 (1998).

Lv et al., "Screening candidate anticancer drugs for brain tumor chemotherapy: Pharmacokinetic-driven approach for a series of (E)-N-(substituted aryl)-3-(substituted phenyl) propenamide analogues", (Invest New Drugs: DOI 10.1007/s10637-012-9806-x) Springer Science+Business Media, LLC (Published online Mar. 1, 2012).

Treu et al., "12H-[2]-benzothiepino[6,5a,5-bc]benzofuran: synthesis of a sulfur-analog of galanthamine", Heterocycles, vol. 55, Issue 9, pp. 1727-1735 (2001).

Reddy et al., "Synthesis and Cyclopropanation of (E)- and (Z)-Stryl Benxyl Sulfones", Sulfur Letters, vol. 13, No. 2, pp. 83-87 (1991).

Flanagan et al., "Chemical and computational methods for the characterization of covalent reactive groups for the prospective design of irreversible inhibitors", J Med Chem., 57(23):10072-10079 (2014). Epub Nov. 26, 2014.

\* cited by examiner

2,4,6-TRIALKOXYSTRYL ARYL SULFONES, SULFONAMIDES AND CARBOXAMIDES, AND METHODS OF PREPARATION AND USE

CROSS-REFERENCE TO RELATED APPLICATION

The application is a National Stage Application under 35 U.S.C. § 371 of International Application No. PCT/US2016/045125, filed Aug. 2, 2016, which claims the benefit of the filing date of U.S. Provisional Patent Application No. 62/200,266, filed Aug. 3, 2015, the entire disclosure of which is incorporated herein by reference.

FIELD OF THE INVENTION

The invention relates to compounds, methods for their preparation, and compositions including them. The invention further provides methods for the treatment of cellular proliferative disorders, including, but not limited to, cancer.

BACKGROUND OF THE INVENTION

Cellular proliferative disorders such as cancer are among the most common causes of death in developed countries. Many cellular proliferative disorders have no available cures or few, if any, treatment options to slow the progression of the disease. For cellular proliferative diseases for which treatments exist, undesirable side effects and limited efficacy often call into question the utility of a given treatment. This is particularly true when the available treatment option(s) may not appreciably prolong life, but have a definitive adverse effect on the quality of time remaining. Thus, identifying new effective drugs for cellular proliferative disorders, and in particular cancer, is a continuing focus of medical research.

Oncogenic activation of the gene RAS via point mutations occurs in more than 30% of all human cancers. RAS-driven human cancers remain the most difficult to treat. Constitutive activation of downstream effector pathways by oncogenic RAS results in the uncontrolled growth, proliferation, and survival of cancer cells. See Gysin et al., *Genes Cancer.* 2011 March; 2(3): 359-372 for a review of therapeutic strategies for targeting RAS proteins. Aberrant RAS activity as a result of oncogenic mutations causes de novo cell transformation and promotes tumor growth and progression.

RAS interacts with a large number of effector proteins by a highly conserved mechanism that involves the switch region of RAS and the RAS-binding domains (RBDs) of its effector proteins, such as the effector protein RAF. Upon activation by RAS, RAF phosphorylates and activates the serine/threonine kinase MEK, which in turn phosphorylates and activates the serine/threonine kinase ERK. This series of signaling events results in the activation of transcriptional regulators that promote a wide variety of cellular events, including cell cycle progression and cell proliferation. Tight regulation of the RAS activation status is critical for cell physiology. Mutations that convert RAS into an oncoprotein are found in up to 25% of human tumors. Prior et al., *Cancer Res* 2012, 72(10):2457-2467.

Because RAS' interactions with its effector proteins plays an essential role in oncogenic RAS function, inhibiting those interactions constitutes an attractive therapeutic approach for treatment of cancer.

Rigosertib, a benzylstyryl sulfone, been shown to binds to the RBDs of various RAS effector proteins. See, Divakar, et al., *Cancer Res* 2014; 74(19 Suppl): Abstract nr LB-108; Reddy et al., *Blood*, December 2014; 124 (21) 5616. The compound inhibits RAS binding to RAF and other RAS effector proteins such as the PI3K family of proteins as well as RalGDS, thereby blocking the effector protein's interaction with RAS. A consequence of inhibiting RAS binding to RAF appears to be a block in growth factor-induced activation of RAF kinase activity in vivo, and the resulting inability of RAF proteins to form dimers and activate MEK and ERK. A block in the activation of MEK/ERK pathways results.

SUMMARY OF THE INVENTION

It has been found that certain compounds and compositions are useful for the treatment of cancer and other cellular proliferative disorders In one aspect, a compound according to Formula I, or a pharmaceutically acceptable salt thereof, is provided:

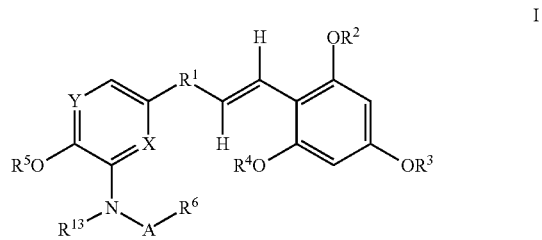

I wherein:
X and Y are independently selected from CH and N, provided that both X and Y may not be N;
A is —(CH$_2$)$_m$—;
m is 0, 1 or 2;
R$^1$ is —CH(R)SO$_2$—, —NHSO$_2$— or —NHC(=O)—;
R is H or —(C$_1$-C$_6$)alkyl;
each of R$^2$, R$^3$, R$^4$ and R$^5$ is independently selected from —(C$_1$-C$_6$)alkyl;
R$^6$ is:
 —CH=CH—C(=O)—R$^7$;
 —CH=C[C(=O)O—(C$_1$-C$_6$)alkyl]$_2$;
 —C(=O)—CH=CH—R$^8$;
 —(C$_2$-C$_6$) unsaturated hydrocarbyl;
 —C(=O)—(C$_2$-C$_6$) unsaturated hydrocarbyl; or
 —SO$_2$—CH=CH—R$^9$;
R$^7$ is selected from —OR$^{10}$; —(C$_1$-C$_4$)alkyl; —NR$^{11}$R$^{12}$; aryl; substituted aryl with one or more substituents selected from halo, —(C$_1$-C$_4$)alkoxy, —(C$_1$-C$_4$)alkyl and methylenedioxy; heteroaryl and substituted heteroaryl, said heteroaryl and substituted heteroaryl containing up to ten ring atoms selected from carbon and nitrogen, wherein the ring contains up to three nitrogen atoms, and said substituted heteroaryl has one or more substituents on said ring atoms selected from halo, —(C$_1$-C$_4$)alkoxy, —(C$_1$-C$_4$)alkyl and methylenedioxy;
R$^8$ is selected from —H, —CN, —NO$_2$, —C(=O)OH, —C(=O)O(C$_1$-C$_6$)alkyl, —(C$_1$-C$_4$)alkyl, aryl, substituted aryl, heteroaryl and substituted heteroaryl; wherein said substituted aryl and said substituted heteroaryl are substituted with one or more substituents independently selected from the group consisting of halogen, —CN, —NR$^{14}$$_2$, —(CH$_2$)$_n$NR$^{14}$$_2$, —O(CH$_2$)$_n$NR$^{14}$$_2$, —NR$^{14}$C(=O)(C$_1$-C$_6$)alkyl, —NR$^{14}$C(=O)O(C$_1$-C$_6$)alkyl, —NR$^{14}$C(=O)NR$^{14}$$_2$, —NR$^{14}$C(=NR$^{14}$)NR$^{14}$$_2$, —NH(CH$_2$)$_n$C(=O)OR$^{14}$, —OH, —NO$_2$, —(C$_1$-C$_6$)alkyl, —(CH$_2$)$_n$O(C$_1$-C$_6$)alkyl, —(C$_1$-C$_6$)alkoxy, —(C$_2$-C$_6$)alkenyl, —(C$_2$-C$_6$)alkynyl, —(C$_1$-C$_6$)perfluoroalkyl, —(C$_1$-C$_6$)perfluoroalkoxy, —C(=O)R$^{14}$, —C(=O)OR$^{14}$, —C(=O)NR$^{14}$$_2$, —OC(=O)R$^{14}$, —OC(=O)NR$^{14}$$_2$, —OC(=O)O(C$_1$-C$_6$)alkyl, —SO$_2$NH$_2$ and —SO$_2$(C$_1$-C$_6$)alkyl;

n is 1, 2, 3, 4, or 5;

R$^9$ is —H or —(C$_1$-C$_6$)alkyl;

R$^{10}$ is —H or —(C$_1$-C$_6$)alkyl;

R$^{11}$ and R$^{12}$
  are independently selected from —H, —(C$_1$-C$_4$)alkyl and —(C$_2$-C$_4$)acyl, or R$^{11}$ and R$^{12}$, with the nitrogen atom to which they are attached, form a 5-, 6- or 7-membered heterocyclic ring containing said nitrogen atom and optionally another heteroatom, wherein when said optional hetroatom is a nitrogen atom, said nitrogen atom is optionally substituted with —(C$_1$-C$_4$)alkyl;

R$^{13}$ is —H or (C$_2$-C$_6$) unsaturated hydrocarbyl; and each R$^{14}$ is independently selected from the group consisting of —H and —(C$_1$-C$_6$)alkyl; or two occurrences of R$^{14}$ bound to the same nitrogen form a (C$_2$-C$_6$)heterocycle, together with the nitrogen atom to which they are bound.

In another aspect, provided are processes for preparing compounds according to Formula I, wherein the compounds have the Formula IV, VI, VIII, X or XII.

In one embodiment, the process is for preparing a compound of Formula IV, or pharmaceutically acceptable salt thereof,

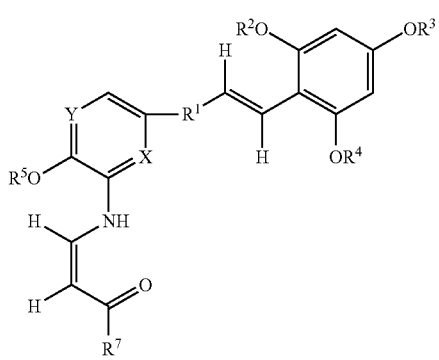

IV comprising reacting a compound of Formula II:

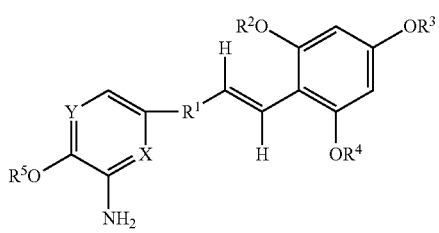

II with a compound of Formula III:

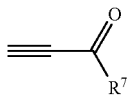

III wherein X, Y, R$^1$, R$^2$, R$^3$, R$^4$, R$^5$ and R$^7$ are as defined for Formula I, and isolating from the reaction mixture the compound having the Formula IV, and optionally converting the compound to a pharmaceutically acceptable salt thereof.

In one embodiment, the process is for preparing a compound of Formula VI, or pharmaceutically acceptable salt thereof,

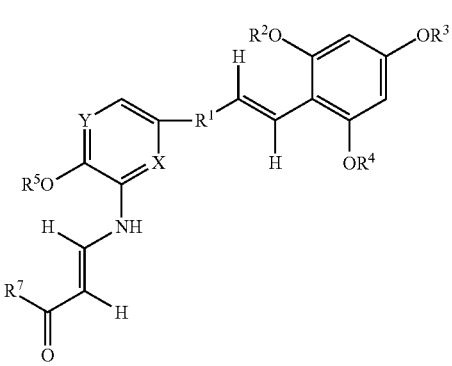

VI comprising reacting a compound of Formula II:

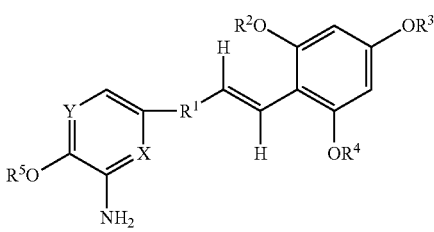

II with a compound of Formula V:

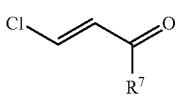

V wherein X, Y, R$^1$, R$^2$, R$^3$, R$^4$, R$^5$ and R$^7$ are as defined for Formula I, and isolating from the reaction mixture the compound having the Formula VI, and optionally converting the compound to a pharmaceutically acceptable salt thereof.

In one embodiment, the process is for preparing a compound of Formula VIII, or pharmaceutically acceptable salt thereof,

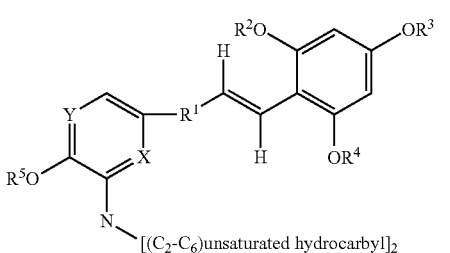

VIII comprising reacting a compound of Formula II:

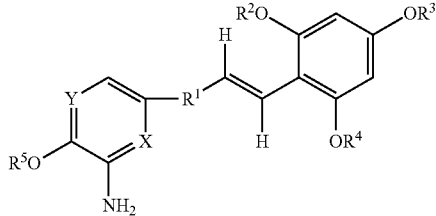

with a $(C_2-C_6)$ unsaturated hydrocarbyl halide, wherein X, Y, $R^1$, $R^2$, $R^3$, $R^4$ and $R^5$ are as defined for Formula I, and isolating from the reaction mixture the compound having the Formula VIII, and optionally converting the compound to a pharmaceutically acceptable salt thereof.

In one embodiment, the process is for preparing a compound of Formula X, or pharmaceutically acceptable salt thereof,

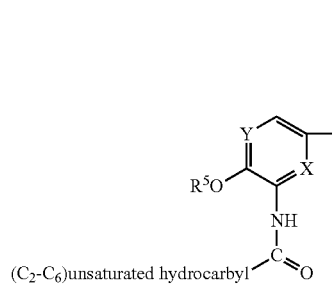

comprising reacting a compound of Formula II:

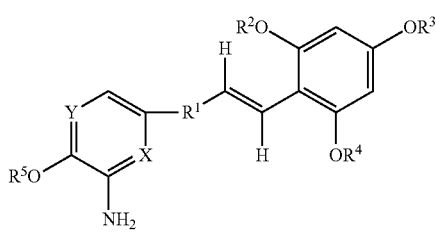

with a compound of Formula IX:

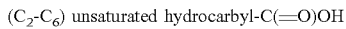

wherein X, Y, $R^1$, $R^2$, $R^3$, $R^4$ and $R^5$ are as defined for Formula I, and isolating from the reaction mixture the compound having the Formula X, and optionally converting the compound to a pharmaceutically acceptable salt thereof.

In one embodiment, the process is for preparing a compound of Formula XII, or pharmaceutically acceptable salt thereof,

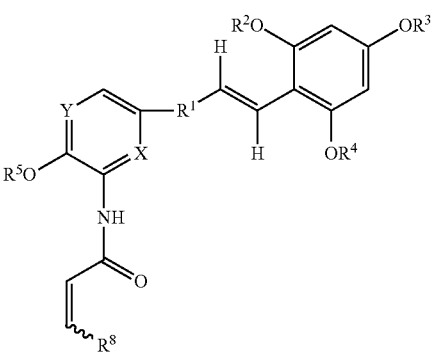

comprising reacting a compound of Formula II:

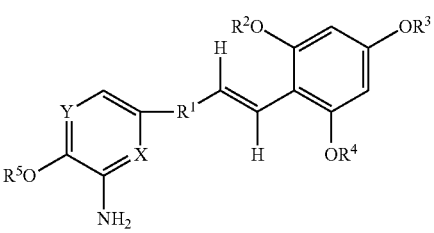

with a compound of Formula XI:

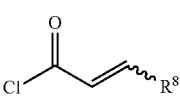

wherein X, Y, $R^1$, $R^2$, $R^3$, $R^4$, $R^5$ and $R^8$ are as defined for Formula I, and isolating from the reaction mixture the compound having the Formula XII, and optionally converting the compound to a pharmaceutically acceptable salt thereof.

In another aspect, provided are pharmaceutical compositions comprising a pharmaceutically acceptable carrier, and a compound according to Formula I, or a pharmaceutically acceptable salt thereof.

According to another embodiment of the invention, a method of treating an individual suffering from a cellular proliferative disorder, particularly cancer, is provided, comprising administering to said individual an effective amount of at least one compound according to Formula I, or a pharmaceutically acceptable salt thereof, either alone, or in combination with a pharmaceutically acceptable carrier.

Also provided is a method of inducing apoptosis of cancer cells, preferably tumor cells, in an individual afflicted with cancer is provided, comprising administering to said individual an effective amount of at least one compound according to Formula I, or a pharmaceutically acceptable salt thereof, either alone, or in combination with a pharmaceutically acceptable carrier.

Also provided is a method for inhibiting RAS activity in an individual in need of such treatment, comprising administering to the individual an effective amount of at least one compound of Formula I, or a pharmaceutically acceptable salt thereof.

Also provided is a compound of Formula I, or pharmaceutically acceptable salt thereof, for use in medicine.

Also provided is a compound of Formula I, or pharmaceutically acceptable salt thereof, for treatment of a cellular proliferative disorder.

Also provided is a compound of Formula I, or pharmaceutically acceptable salt thereof, for inhibiting RAS activity.

Also provided is a compound of Formula I, or pharmaceutically acceptable salt thereof, for preparation of a medicament for treatment of a cellular proliferative disorder.

Also provided is a compound of Formula I, or pharmaceutically acceptable salt thereof, for preparation of a medicament for inhibiting RAS activity.

Also provided is a medicament for treatment of a cellular proliferative disorder, containing a compound of Formula I, or a pharmaceutically acceptable salt thereof.

Also provided is a medicament for inhibiting RAS activity, comprising a compound of Formula I, or pharmaceutically acceptable salt thereof.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION OF THE INVENTION

The compounds and compositions of the invention are believed to selectively inhibit proliferation of cancer cells, and kill various tumor cell types without killing (or with reduced killing of) normal cells. Cancer cells are killed at concentrations where normal cells may be temporarily growth-arrested but not killed.

The compounds of the invention are believed to inhibit the proliferation of tumor cells, and for some compounds, induce cell death. Cell death results from the induction of apoptosis. The compounds are believed effective against a broad range of cancer types, including but not limited to the following: lung cancer, pancreatic cancer, colorectal cancer, stomach cancer, kidney cancer, bladder cancer, prostate cancer, testicular cancer, liver cancer, head and neck cancer, brain cancer, uterine cancer, cervical cancer, ovarian cancer, vaginal cancer, breast cancer, skin cancer, leukemia or lymphoma.

The compounds are also believed useful in the treatment of non-cancer cellular proliferative disorders, including but not limited to the following: hemangiomatosis in newborn, secondary progressive multiple sclerosis, atherosclerosis, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy, noncancerous lymphocellular proliferative disorders, and cancer.

It is believed that the compounds of the invention bind RBDs on RAS effector proteins such as RAF, thereby blocking RAS signaling through those effector proteins. Without wishing to be bound by any theory, it is believed that the compounds of the present invention, by virtue of presence of an unsaturated carbon-carbon bond in the moiety $R^6$ in Formula I, undergo irreversible (covalent) binding to RBDs on RAS effector proteins, such as RAF, thereby providing sustained blockade of oncogenic RAS signaling. It is believed that the compounds of the invention, by virtue of their ability to covalently bind RBDs, possess advantages over reversible, noncovalent binding counterparts, such as increased biochemical efficiency, longer duration of action, improved therapeutic index, and possible avoidance of drug resistance. In particular as demonstrated in Example 176, (Z)-ethyl 3-((2-methoxy-5-(((E)-2,4,6-trimethoxystyrylsulfonyl)methyl)phenyl)amino)acrylate, a compound of Formula I, is 10-100 fold more cytotoxic across a wide range of tumor cell lines than Rigosertib, a compound of similar structure lacking unsaturation in a moiety corresponding to $R^6$ in Formula I.

I. Definitions

1. General

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds. The individual is, in one embodiment, a human being.

The expression "effective amount", when used to describe therapy to an individual suffering from a cancer or other cellular proliferative disorder, refers to the amount of a compound according to Formula I, or pharmaceutically acceptable salt thereof, that inhibits the abnormal growth or proliferation, or alternatively induces apoptosis of cancer cells, preferably tumor cells, resulting in a therapeutically useful and selective cytotoxic effect on proliferative cells.

The term "cellular proliferative disorder" means a disorder wherein unwanted cell proliferation of one or more subsets of cells in a multicellular organism occurs. In some such disorders, cells are made by the organism at an atypically accelerated rate.

2. Chemical

In the following paragraphs some of the definitions include examples. The examples are intended to be illustrative, and not limiting.

The term "alkyl", by itself or as part of another substituent means, unless otherwise stated, a straight or branched chain hydrocarbyl having the number of carbon atoms designated (i.e. $C_1$-$C_6$ means one to six carbons). Examples include: methyl, ethyl, propyl, isopropyl, butyl, isobutyl, tert-butyl, pentyl, neopentyl, and hexyl. Most preferred is ($C_1$-$C_3$) alkyl, particularly methyl and ethyl.

The term "alkenyl" employed alone or in combination with other terms, means, unless otherwise stated, a straight chain or branched chain hydrocarbyl having the stated number of carbon atoms, and containing one or more double bonds. Examples include ethenyl (vinyl), propenyl (allyl), crotyl, isopentenyl, butadienyl, 1,3-pentadienyl, and 1,4- pentadienyl. A functional group representing an alkenyl is exemplified by —CH$_2$—CH=CH$_2$—.

The term "alkynyl" employed alone or in combination with other terms, means, unless otherwise stated, a straight chain or branched chain hydrocarbyl having the stated number of carbon atoms, and containing on or more triple bonds.

The term "alkoxy" employed alone or in combination with other terms means, unless otherwise stated, an alkyl group, as defined above, connected to the rest of the molecule via an oxygen atom, such as, for example, methoxy, ethoxy, 1-propoxy, 2-propoxy (isopropoxy) and the higher homologs and isomers. The alkyl portion of the alkoxy group can have a designated number of carbon atoms as defined for alkyl groups above. Preferred are (C$_1$-C$_3$)alkoxy, particularly methoxy and ethoxy.

The term "carbocyclic ring" refers to an cycloalkane ring formed by combining substituents attached to different carbon atoms.

The terms "halo" or "halogen" by themselves or as part of another substituent mean, unless otherwise stated, a fluorine, chlorine, bromine, or iodine atom. Preferably, a halogen includes fluorine, chlorine, or bromine, more preferably, fluorine or chlorine.

The term "hydrocarbyl", by itself or as part of another substituent means, unless otherwise stated, a straight or branched chain, cyclic or acyclic, hydrocarbon having the number of carbon atoms designated (i.e. C$_1$-C$_6$ means one to six carbons). Examples include: methyl, ethyl, propyl, isopropyl, butyl, isobutyl, tert-butyl, pentyl, neopentyl, and hexyl.

Most preferred is (C$_1$-C$_3$) alkyl, particularly methyl and ethyl. The term "unsaturated hydrocarbyl" means a hydrocarbyl that contains at least one double or triple bond. In preferred embodiments, the unsaturated hydrocarbyl will contain one or two double bonds or one or two triple bonds, typically one double bond or one triple bond.

The term "perfluoroalkyl" means an alkyl group wherein all hydrogen atoms are replaced by fluorine atoms. Preferred is —(C$_1$-C$_6$)perfluoroalkyl; more preferred is —(C$_1$-C$_3$) perfluoroalkyl; most preferred is —CF$_3$.

The term "perfluoroalkoxy" means an alkoxy group wherein all hydrogen atoms are replaced by fluorine atoms. Preferred is —(C$_1$-C$_6$)perfluoroalkoxy; more preferred is —(C$_1$-C$_3$)perfluoroalkoxy; most preferred is —OCF$_3$.

The term "aromatic" refers to a carbocycle or heterocycle having one or more polyunsaturated rings having aromatic character (i.e. having (4n+2) delocalized π (pi) electrons where n is an integer).

The term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

"Substituted aryl" means an aryl, as defined above, substituted by one, two, three, four, or five substituents.

The term "unsubstituted aryl" refers to an aryl, as defined above, which has no substituents.

The term "heterocycle" or "heterocyclyl" or "heterocyclic" by itself or as part of another substituent means, unless otherwise stated, an unsubstituted or substituted, mono- or multi-cyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocycle typically contains from five to ten ring atoms. The heterocyclic system may be attached to another atom, unless otherwise stated, at any heteroatom or carbon atom of the heterocyclic system which affords a structural isomer.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

The term "heteroaryl" or "heteroaromatic" refers to a heterocycle having aromatic character. A polycyclic heteroaryl may include one or more rings which are partially saturated. Examples of heteroaryl groups include: pyridyl, pyrazinyl, pyrimidinyl, particularly 2- and 4-pyrimidinyl, pyridazinyl, indolyl (2-, 3-, 4-, 5-, 6- and 7-), thienyl, furyl, and pyrrolyl, preferably 2-, 3- and 4-pyridyl.

Examples of polycyclic heteroaryls include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarinyl, dihydrocoumarinyl, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl and quinolizidinyl.

The aforementioned listing of heteroaryl moieties is intended to be representative and not limiting.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

II. Compounds of the Invention

In one aspect, the invention is directed to a compound of Formula I, or a pharmaceutically acceptable salt thereof:

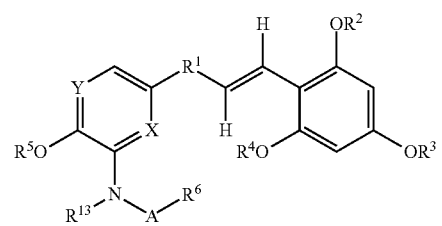

I wherein:
X and Y are independently selected from CH and N, provided that both X and Y may not be N;
A is —(CH$_2$)$_m$;
m is 0, 1 or 2;
R$^1$ is —CH(R)SO$_2$—, —NHSO$_2$— or —NHC(=O)—;
R is H or —(C$_1$-C$_6$)alkyl;

each of $R^2$, $R^3$, $R^4$ and $R^5$ is independently selected from —$(C_1$-$C_6)$alkyl;

$R^6$ is:
—CH=CH—C(=O)—$R^7$,
CH=C[C(=O)O—$(C_1$-$C_6)$alkyl]$_2$,
—C(=O)—CH=CH—$R^8$,
—$(C_2$-$C_6)$ unsaturated hydrocarbyl;
—C(=O)—$(C_2$-$C_6)$ unsaturated hydrocarbyl; or
—SO$_2$—CH=CH—$R^9$;

$R^7$ is selected from —O$R^{10}$; —$(C_1$-$C_4)$alkyl; —N$R^{11}R^{12}$; aryl; substituted aryl with one or more substituents selected from halo, —$(C_1$-$C_4)$alkoxy, —$(C_1$-$C_4)$alkyl and methylenedioxy; heteroaryl and substituted heteroaryl, said heteroaryl and substituted heteroaryl containing up to ten ring atoms selected from carbon and nitrogen, wherein the ring contains up to three nitrogen atoms, and said substituted heteroaryl has one or more substituents on said ring atoms selected from halo, —$(C_1$-$C_4)$alkoxy, —$(C_1$-$C_4)$alkyl and methylenedioxy;

$R^8$ is selected from —H, —CN, —NO$_2$, —C(=O)OH, —C(=O)O$(C_1$-$C_6)$alkyl, —$(C_1$-$C_4)$alkyl, aryl, substituted aryl, heteroaryl and substituted heteroaryl; wherein said substituted aryl and said substituted heteroaryl are substituted with one or more substituents independently selected from the group consisting of halogen, —CN, —N$R^{14}_2$, —(CH$_2$)$_n$N$R^{14}_2$, —O(CH$_2$)$_n$N$R^{14}$2, —N$R^{14}$C(=O)$(C_1$-$C_6)$alkyl, —N$R^{14}$C(=O)O$(C_1$-$C_6)$alkyl, —N$R^{14}$C(=O)N$R^{14}_2$, —N$R^{14}$C(=N$R^{14}$)N$R^{14}_2$, —NH(CH$_2$)$_n$C(=O)O$R^{14}$, —OH, —NO$_2$, —$(C_1$-$C_6)$alkyl, —(CH$_2$)$_n$O$(C_1$-$C_6)$alkyl, —$(C_1$-$C_6)$alkoxy, —$(C_2$-$C_6)$alkenyl, —$(C_2$-$C_6)$alkynyl, —$(C_1$-$C_6)$perfluoroalkyl, —$(C_1$-$C_6)$perfluoroalkoxy, —C(=O)$R^{14}$, —C(=O)O$R^{14}$, —C(=O)N$R^{14}_2$, —OC(=O)$R^{14}$, —OC(=O)N$R^{14}_2$, —OC(=O)O$(C_1$-$C_6)$alkyl, —SO$_2$NH$_2$ and —SO$_2(C_1$-$C_6)$alkyl;

n is independently at each occurrence 1, 2, 3, 4, or 5;
$R^9$ is —H or —$(C_1$-$C_6)$alkyl;
$R^{10}$ is —H or —$(C_1$-$C_6)$alkyl;
$R^{11}$ and $R^{12}$
are independently selected from —H, —$(C_1$-$C_4)$alkyl and —$(C_2$-$C_4)$acyl, or
$R^{11}$ and $R^{12}$, with the nitrogen atom to which they are attached, form a 5-, 6- or 7-membered heterocyclic ring containing said nitrogen atom and optionally another heteroatom, wherein when said optional hetroatom is a nitrogen atom, said nitrogen atom is optionally substituted with —$(C_1$-$C_4)$alkyl;
$R^{13}$ is —H or $(C_2$-$C_6)$ unsaturated hydrocarbyl group; and
each $R^{14}$ is independently selected from the group consisting of —H and —$(C_1$-$C_6)$alkyl; or two occurrences of $R^{14}$ bound to the same nitrogen form a $(C_2$-$C_6)$heterocycle, together with the nitrogen atom to which they are bound;
or
a pharmaceutically acceptable salt thereof.

In certain embodiments, m is zero, i.e., A is absent, and $R^{13}$ is —H.

In certain embodiments when $R^6$ is —$(C_2$-$C_6)$ unsaturated hydrocarbyl, it is —$(C_2$-$C_4)$alkenyl or —$(C_2$-$C_4)$alkynyl. In certain embodiments, the —$(C_2$-$C_6)$ unsaturated hydrocarbyl is —CH$_2$—CH=CH$_2$, —CH$_2$—C≡CH or —CH$_2$—C≡C—CH$_3$.

In certain embodiments, $R^6$ is —$(C_2$-$C_6)$ unsaturated hydrocarbyl and $R^{13}$ is also —$(C_2$-$C_6)$ unsaturated hydrocarbyl.

In certain embodiments, R is hydrogen, methyl, ethyl or propyl; preferably hydrogen, methyl or ethyl; more preferably hydrogen or methyl; most preferably hydrogen.

In certain embodiments, $R^1$, $R^2$, $R^3$, $R^4$ and $R^5$ are independently methyl, ethyl or propyl, most preferably methyl or ethyl, most preferably methyl.

In certain embodiments, when $R^6$ is —C(=O)—$(C_2$-$C_6)$ unsaturated hydrocarbyl, it is —C(=O)—$(C_2$-$C_4)$alkynyl, particularly —C(=O)—C≡CH or —C(=O)—C≡C—CH$_3$, or is —C(=O)—$(C_2$-$C_4)$alkenyl, particularly —C(=O)—CH=CH$_2$.

In certain embodiments, when $R^6$ is —$(C_2$-$C_6)$ unsaturated hydrocarbyl, it is preferably —$(C_2$-$C_4)$alkynyl, particularly —CH=CH$_2$, —CH$_2$C≡CH, or —$(C_2$-$C_4)$alkenyl, particularly —CH$_2$CH=CH$_2$.

When $R^7$ is —$(C_1$-$C_4)$alkyl, it is preferably methyl, ethyl or propyl, most preferably methyl or ethyl, most preferably methyl.

When $R^7$ is unsubstituted aryl or substituted aryl, it preferably contains 6 or 10 ring carbon atoms, with the substituents selected as in the manner defined above. Preferred such aryl/substituted aryl include, phenyl; naphthyl; phenyl mono-substituted with halogen, particularly 4-halophenyl; phenyl mono-substituted with $(C_1$-$C_4)$alkoxyphenyl, particularly 4-$(C_1$-$C_4)$alkoxy; phenyl mono-substituted with $(C_1$-$C_4)$alkyl, particularly 4-$(C_1$-$C_4)$alkyl; phenyl di-substituted with alkoxy, particularly 3,4-dialkoxy; and phenyl tri-substituted with alkoxy, particularly, 3,4,5- and 2,4,6-trialkoxy. The aforementioned alkyl and alkoxy groups preferably comprise one, two or three carbon atoms, preferably one or two carbon atoms, most preferably one carbon atom.

When $R^8$ is —$(C_1$-$C_4)$alkyl or —C(=O)O$(C_1$-$C_6)$alkyl, the alkyl group contained therein is preferably methyl, ethyl or propyl, most preferably methyl or ethyl, most preferably methyl.

When $R^8$ is heteroaryl or substituted heteroaryl, the heteroaryl may be, for example, pyridyl, particularly 2-, 3- and 4-pyridyl; pyrazinyl; pyrimidinyl, particularly 2- and 4-pyrimidinyl; pyridazinyl; thienyl; furyl; pyrrolyl; indolyl (2-, 3-, 4-, 5-, 6- and 7-); indolinyl; quinolyl; tetrahydroquinolyl; isoquinolyl, particularly 1- and 5-isoquinolyl; 1,2,3,4-tetrahydroisoquinolyl; cinnolinyl; quinoxalinyl, particularly 2- and 5-quinoxalinyl; quinazolinyl; phthalazinyl; 1,8-naphthyridinyl; 1,4-benzodioxanyl; coumarinyl; dihydrocoumarinyl; benzofuryl, particularly 3-, 4-; 1,5-naphthyridinyl; 5-, 6- and 7-benzofuryl; 2,3-dihydrobenzofuryl; 1,2-benzisoxazolyl; benzothienyl, particularly 3-, 4-, 5-, 6- and 7-benzothienyl; benzoxazolyl; benzthiazolyl, particularly 2-benzothiazolyl and 5-benzothiazolyl; purinyl; benzimidazolyl, particularly 2-benzimidazolyl; benztriazolyl; thioxanthinyl; carbazolyl; carbolinyl; acridinyl; pyrrolizidinyl; and quinolizidinyl.

When $R^8$ is substituted aryl or substituted heteroaryl, preferred substitutents include halogen, —CN, —NH$_2$, —NO$_2$, —$(C_1$-$C_6)$alkyl, —$(C_1$-$C_6)$alkoxy, —C(=O)NH$_2$, —COOH, —SO$_2$NH$_2$ and —SO$_2(C_1$-$C_6)$alkyl.

When $R^9$ is —$(C_1$-$C_6)$alkyl, it is preferably methyl, ethyl or propyl, most preferably methyl or ethyl, most preferably methyl.

When $R^{10}$ is —$(C_1$-$C_6)$alkyl, it is preferably methyl, ethyl or propyl, most preferably methyl or ethyl, most preferably methyl.

When $R^{11}$ or $R^{12}$ is —$(C_1$-$C_4)$alkyl, it is preferably methyl, ethyl or propyl, most preferably methyl or ethyl, most preferably methyl. When $R^{11}$ or $R^{12}$ is —$(C_2$-$C_4)$acyl, it is preferably acetyl or propionyl.

When $R^{11}$ and $R^{12}$, with the nitrogen atom to which they are attached, form a 5- to 7-membered heterocyclyl ring containing said nitrogen atom and optionally another heteroatom, the other heteroatom may be nitrogen, oxygen or sulfur. When the other heteroatom is nitrogen, it may be optionally substituted with —$(C_1$-$C_4)$alkyl. The 5- to 7-membered heterocyclyl ring containing said nitrogen atom and optionally another heteroatom is preferably a 6-membered ring. Examples of such 6-membered rings include piperazinyl and 4-methyl piperazinyl. Other examples of heterocyclic ring systems formed by $R^{11}$ and $R^{12}$, with the nitrogen atom to which they are attached, include pyrrolidine (5 ring atoms), piperidine (6 ring atoms) and azepine (7 ring atoms).

When $R^{14}$ is —$(C_1$-$C_6)$alkyl, it is preferably methyl, ethyl or propyl, most preferably methyl or ethyl, most preferably methyl.

A. Compounds of Formula I Wherein X and Y are CH

In one aspect, compounds of Formula I are provided wherein X and Y are CH.

1. Compound of Formula I Wherein X and Y are CH and $R^1$ is —CH(R)$SO_2$—

In certain embodiments, compound of Formula I are provided wherein X and Y are CH, and $R^1$ is —CH(R)$SO_2$—.

In certain embodiments, $R^1$ is —CH(R)$SO_2$— and $R^6$ is —CH=CH—C(=O)—$R^7$. In certain embodiments thereof, m is zero and $R^{13}$ is —H. In certain embodiments thereof, $R^7$ is —$OR^{10}$ or —$(C_1$-$C_4)$alkyl. In particular embodiments, $R^7$ is hydroxyl, methyl, methoxy, ethyl or ethoxy. Such compounds include, for example, (E)-3-((2-methoxy-5-(((E)-2,4,6-trimethoxystyrylsulfonyl)methyl)-phenyl)amino)acrylic acid;
(Z)-ethyl 3-((2-methoxy-5-(((E)-2,4,6-trimethoxystyrylsulfonyl)methyl)phenyl)amino) acrylate;
(Z)-4-((2-methoxy-5-(((E)-2,4,6-trimethoxystyrylsulfonyl)methyl)phenyl)amino)but-3-en-2-one;
(Z)-methyl 3-((2-methoxy-5-(((E)-2,4,6-trimethoxystyrylsulfonyl)methyl)phenyl)amino) acrylate;
(E)-methyl 3-((2-methoxy-5-(((E)-2,4,6-trimethoxystyrylsulfonyl)methyl)phenyl)amino) acrylate;
(E)-ethyl 3-((2-methoxy-5-(((E)-2,4,6-trimethoxystyrylsulfonyl)methyl)phenyl)amino) acrylate;
(Z)-ethyl 3-((2-methoxy-5-(((E)-2,4,6-trimethoxystyrylsulfonyl)methyl)phenyl)amino) acrylate;
(E)-ethyl 4-((2-methoxy-5-(((E)-2,4,6-trimethoxystyrylsulfonyl)methyl)phenyl)-amino)but-2-enoate;

In certain embodiments, $R^1$ is —CH(R)$SO_2$—, $R^6$ is —CH=CH—C(=O)—$R^7$, and $R^7$ is —$NR^{11}R^{12}$. In certain embodiments thereof, —$NR^{11}R^{12}$ is piperazinyl or 4-methylpiperazinyl. Such compounds include, for example, (Z)-3-((2-methoxy-5-(((E)-2,4,6-trimethoxystyrylsulfonyl)methyl) phenyl) amino)-1-(4-methylpiperazin-1-µl)prop-2-en-1-one, (Z)-3-((2-methoxy-5-(((E)-2,4,6-trimethoxystyrylsulfonyl)methyl)phenyl)amino)-1-(piperazin-1-yl)prop-2-en-1-one, or pharmaceutically acceptable salt thereof.

In certain embodiments, $R^1$ is —CH(R)$SO_2$—, $R^6$ is —CH=CH—C(=O)—$R^7$, and $R^7$ is aryl having up to ten carbon atoms, or substituted aryl having up to ten ring carbons with one or more substituents selected from halo, —$(C_1$-$C_4)$alkoxy, —$(C_1$-$C_4)$alkyl and methylenedioxy, or pharmaceutically acceptable salt thereof. One such compound is (Z)-1-(benzo[d][1,3]dioxol-5-yl)-3-((2-methoxy-5-(((E)-2,4,6-trimethoxystyrylsulfonyl)methyl)phenyl)amino)prop-2-en-1-one, or pharmaceutically acceptable salt thereof. In certain embodiments, $R^7$ is phenyl, naphthyl, 4-halophenyl, 4-$(C_1$-$C_4)$alkoxy, 4-$(C_1$-$C_4)$alkyl, dialkoxyphenyl or trialkoxyphenyl. Such compounds include, for example, (Z)-1-(4-methoxyphenyl)-3-((2-methoxy-5-(((E)-2,4,6-trimethoxystyrylsulfonyl)methyl)phenyl)-amino)prop-2-en-1-one;
(E)-1-(4-methoxyphenyl)-3-((2-methoxy-5-(((E)-2,4,6-trimethoxystyrylsulfonyl)methyl)phenyl)amino)prop-2-en-1-one;
(Z)-1-(3,4,5-trimethoxyphenyl)-3-((2-methoxy-5-(((E)-2,4,6-trimethoxystyrylsulfonyl)methyl)phenyl)amino)prop-2-en-1-one;
(E)-1-(3,4,5-trimethoxyphenyl)-3-((2-methoxy-5-(((E)-2,4,6-trimethoxystyrylsulfonyl)methyl)phenyl)amino)prop-2-en-1-one;
(Z)-1-(2,4,6-trimethoxyphenyl)-3-((2-methoxy-5-(((E)-2,4,6-trimethoxystyrylsulfonyl)methyl)phenyl)amino)prop-2-en-1-one;
(E)-1-(2,4,6-trimethoxyphenyl)-3-((2-methoxy-5-(((E)-2,4,6-trimethoxystyrylsulfonyl)methyl)phenyl)amino)prop-2-en-1-one
(Z)-1-(2-chloro-3,4,5-trimethoxyphenyl)-3-((2-methoxy-5-(((E)-2,4,6-trimethoxystyrylsulfonyl)methyl)phenyl)amino)prop-2-en-1-one;
(E)-1-(2-chloro-3,4,5-trimethoxyphenyl)-3-((2-methoxy-5-(((E)-2,4,6-trimethoxystyrylsulfonyl)methyl)phenyl)amino)prop-2-en-1-one;
(Z)-1-(2-bromo-3,4,5-trimethoxyphenyl)-3-((2-methoxy-5-(((E)-2,4,6-trimethoxystyrylsulfonyl)methyl)phenyl)amino)prop-2-en-1-one;
(E)-1-(2-bromo-3,4,5-trimethoxyphenyl)-3-((2-methoxy-5-(((E)-2,4,6-trimethoxystyrylsulfonyl)methyl)phenyl)amino)prop-2-en-1-one;
(Z)-3-((2-methoxy-5-(((E)-2,4,6-trimethoxystyrylsulfonyl)methyl)phenyl)amino)-1-phenylprop-2-en-1-one;
(E)-3-((2-methoxy-5-(((E)-2,4,6-trimethoxystyrylsulfonyl)methyl)phenyl)amino)-1-phenylprop-2-en-1-one;
(Z)-1-(4-fluorophenyl)-3-((2-methoxy-5-(((E)-2,4,6-trimethoxystyrylsulfonyl)methyl)phenyl)amino)prop-2-en-1-one; (E)-1-(4-fluorophenyl)-3-((2-methoxy-5-(((E)-2,4,6-trimethoxystyrylsulfonyl)methyl)phenyl)amino)prop-2-en-1-one;
(Z)-1-(4-chlorophenyl)-3-((2-methoxy-5-(((E)-2,4,6-trimethoxystyrylsulfonyl)methyl)phenyl)amino)prop-2-en-1-one;
(E)-1-(4-chlorophenyl)-3-((2-methoxy-5-(((E)-2,4,6-trimethoxystyrylsulfonyl)methyl)phenyl)amino)prop-2-en-1-one
(Z)-1-(4-bromophenyl)-3-((2-methoxy-5-(((E)-2,4,6-trimethoxystyrylsulfonyl)methyl)phenyl)amino) prop-2-en-1-one;
(E)-1-(4-bromophenyl)-3-((2-methoxy-5-(((E)-2,4,6-trimethoxystyrylsulfonyl)methyl)phenyl)amino)prop-2-en-1-one;
(Z)-1-(4-methylphenyl)-3-((2-methoxy-5-(((E)-2,4,6-trimethoxystyrylsulfonyl)methyl)phenyl)amino)prop-2-en-1-one; E)-1-(4-methylphenyl)-3-((2-methoxy-5-(((E)-2,4,6-trimethoxystyrylsulfonyl)methyl)phenyl)amino) prop-2-en-1-one;
(Z)-1-(3,4-dimethoxylphenyl)-3-((2-methoxy-5-(((E)-2,4,6-trimethoxystyrylsulfonyl)methyl)phenyl)amino)prop-2-en-1-one;
(E)-1-(3,4-dimethoxyphenyl)-3-((2-methoxy-5-(((E)-2,4,6-trimethoxystyrylsulfonyl)methyl)phenyl)amino)prop-2-en-1-one;
(Z)-1-(naphthalen-3-yl)-3-((2-methoxy-5-(((E)-2,4,6-trimethoxystyrylsulfonyl)methyl)phenyl)amino)prop-2-en-1-one;
or pharmaceutically acceptable salt thereof.

In certain embodiments, $R^1$ is —CH(R)SO$_2$— and $R^6$ is —CH=C[C(=O)O—(C$_1$-C$_6$)alkyl]$_2$. In certain embodiments thereof, m is zero and $R^{13}$ is —H. Such compounds include, for example, (E)-diethyl-2-(((2-methoxy-5-(((2,4,6-trimethoxystyryl)sulfonyl)methyl)phenyl)amino)methylene)malonate, or pharmaceutically acceptable salt thereof.

In certain embodiments, $R^1$ is —CH(R)SO$_2$— and $R^6$ is —C(=O)—CH=CH—R$^8$. In certain embodiments thereof, m is zero and $R^{13}$ is —H. In certain embodiments thereof, $R^8$ is —H, —C(=O)OH, or —C(=O)O(C$_1$-C$_6$)alkyl. Such compounds include, for example, (E)-N-(2-methoxy-5-(((2,4,6-trimethoxystyryl) sulfonyl)methyl)phenyl)acrylamide; (Z)-4-((2-methoxy-5-(((E)-2,4,6-trimethoxystyrylsulfonyl) methyl) phenyl)amino)-4-oxobut-2-enoic acid; (E)-4-((2-methoxy-5-(((E)-2,4,6-trimethoxystyrylsulfonyl)methyl) phenyl) amino)-4-oxobut-2-enoic acid; (Z)-methyl 4-((2-methoxy-5-(((E)-2,4,6-trimethoxystyrylsulfonyl) methyl) phenyl)amino)-4-oxobut-2-enoate; or pharmaceutically acceptable salt thereof. In certain embodiments, $R^8$ is aryl or substituted aryl. Where $R^8$ is aryl or substituted aryl, it is preferably phenyl or substituted phenyl. Such compounds include, for example, (Z)—N-(2-methoxy-5-(((E)-2,4,6-trimethoxystyrylsulfonyl)methyl)phenyl)-3-phenylacrylamide and halogen substituted derivatives thereof, such as (Z)-3-(4-fluorophenyl)-N-(2-methoxy-5-(((E)-2,4,6-trimethoxystyrylsulfonyl)methyl)phenyl)acrylamide.

In certain embodiments, $R^1$ is —CH(R)SO$_2$— and $R^6$ is —(C$_2$-C$_6$) unsaturated hydrocarbyl or —C(=O)—(C$_2$-C$_6$) unsaturated hydrocarbyl. In certain embodiments, when $R^6$ is —(C$_2$-C$_6$) unsaturated hydrocarbyl, $R^{13}$ is also —(C$_2$-C$_6$) unsaturated hydrocarbyl. In other embodiments, when $R^6$ is —(C$_2$-C$_6$) unsaturated hydrocarbyl or —C(=O)—(C$_2$-C$_6$) unsaturated hydrocarbyl, m is zero and $R^{13}$ is —H. Such compounds include, for example, (E)-2-methoxy-N,N-di(prop-2-yn-1-yl)-5-(((2,4,6-trimethoxystyryl)sulfonyl)methyl)aniline, (E)-N-(2-methoxy-5-(((2,4,6-trimethoxystyryl)sulfonyl)methyl)phenyl)propiolamide, (E)-2-methoxy-N-(prop-2-yn-1-yl)-5-(((2,4,6-trimethoxystyryl)sulfonyl)methyl)aniline or pharmaceutically acceptable salt thereof.

In certain embodiments, $R^1$ is —CH(R)SO$_2$— and $R^6$ is —SO$_2$—CH=CH—R$^9$. In certain embodiments, m is zero and $R^{13}$ is —H. Such compounds include, for example, (E)-N-(2-methoxy-5-(((2,4,6-trimethoxystyryl) sulfonyl)methyl)phenyl)ethenesulfonamide, or pharmaceutically acceptable salt thereof.

2. Compound of Formula I Wherein X and Y are CH and $R^1$ is —NHSO$_2$—

In certain embodiments, compounds of Formula I are provided wherein X and Y are CH, and $R^1$ is —NHSO$_2$—.

In certain embodiments, $R^1$ is —NHSO$_2$— and $R^6$ is —CH=CH—C(=O)—R$^7$. In certain embodiments thereof, m is zero and $R^{13}$ is —H. In certain embodiments thereof, $R^7$ is —OR$^{10}$ or —(C$_1$-C$_4$)alkyl. In particular embodiments, $R^7$ is hydroxyl, methyl, methoxy, ethyl or ethoxy. Such compounds include, for example:

(E)-3-((2-methoxy-5-((E)-2-(2,4,6-trimethoxyphenyl)vinylsulfonamido)phenyl)amino) acrylic acid;
(Z)-ethyl 3-((2-methoxy-5-((E)-2-(2,4,6-trimethoxyphenyl) vinylsulfonamido)phenyl)amino) acrylate;
(E)-N-(4-methoxy-3-(((Z)-3-oxobut-1-en-1-yl)amino)phenyl)-2-(2,4,6-trimethoxyphenyl)ethenesulfonamide;
(Z)-methyl 3-((2-methoxy-5-((E)-2-(2,4,6-trimethoxyphenyl) vinylsulfonamido)phenyl)amino) acrylate;
(E)-methyl 3-((2-methoxy-5-((E)-2-(2,4,6-trimethoxyphenyl) vinylsulfonamido)phenyl)amino) acrylate;
(E)-ethyl 3-((2-methoxy-5-((E)-2-(2,4,6-trimethoxyphenyl) vinylsulfonamido)phenyl)amino) acrylate;
(E)-ethyl 4-((2-methoxy-5-((E)-2-(2,4,6-trimethoxyphenyl) vinylsulfonamido)phenyl)amino)but-2-enoate;
or pharmaceutically acceptable salt thereof.

In certain embodiments, $R^1$ is —NHSO$_2$—, $R^6$ is —CH=CH—C(=O)—R$^7$, and $R^7$ is —NR$^{11}$R$^{12}$. In certain embodiments thereof, —NR$^{11}$R$^{12}$ is piperazinyl or 4-methylpiperazinyl. Such compounds include, for example, (E)-N-(4-methoxy-3-(((Z)-3-(4-methylpiperazin-1-yl)-3-oxoprop-1-en-1yl)amino)phenyl)-2-(2,4,6-trimethoxyphenyl)ethenesulfonamide, (E)-N-(4-methoxy-3-(((Z)-3-(piperazin-1-yl)-3-oxoprop-1-en-1yl)amino)phenyl)-2-(2,4,6-trimethoxyphenyl)ethenesulfonamide.

In certain embodiments, $R^1$ is —NHSO$_2$—, $R^6$ is —CH=CH—C(=O)—R$^7$, and $R^7$ is aryl having up to ten carbon atoms, or substituted aryl having up to ten ring carbons with one or more substituents selected from halo, —(C$_1$-C$_4$)alkoxy, —(C$_1$-C$_4$)alkyl and methylenedioxy, or pharmaceutically acceptable salt thereof. One such compound is (E)-N-(3-(((Z)-3-(benzo[d][1,3]dioxol-5-yl)-3-oxoprop-1-en-1-yl)amino)-4-methoxy phenyl)-2-(2,4,6-trimethoxyphenyl)ethenesulfonamide, or pharmaceutically acceptable salt thereof. In certain embodiments, $R^7$ is phenyl, naphthyl, 4-halophenyl, 4-(C$_1$-C$_4$)alkoxy, 4-(C$_1$-C$_4$)alkyl, dialkoxyphenyl or trialkoxyphenyl. Such compounds include, for example, (E)-N-(4-methoxy-3-(((Z)-3-oxo-3-phenylprop-1-en-1yl) amino)phenyl)-2-(2,4,6-trimethoxyphenyl)ethenesulfonamide;
(E)-N-(4-methoxy-3-(((E)-3-oxo-3-phenylprop-1-en-1-yl) amino)phenyl)-2-(2,4,6-trimethoxyphenyl)ethenesulfonamide;
(E)-N-(3-(((Z)-3-(4-methoxyphenyl)-3-oxoprop-1-en-1-yl) amino)-4-methoxyphenyl)-2-(2,4,6-trimethoxyphenyl) ethenesulfonamide;
(E)-N-(3-(((E)-3-(4-methoxyphenyl)-3-oxoprop-1-en-1-yl) amino)-4-methoxyphenyl)-2-(2,4,6-trimethoxyphenyl) ethane sulfonamide;
(E)-N-(3-(((Z)-3-(4-fluorophenyl)-3-oxoprop-1-en-1-yl) amino)-4-methoxy phenyl)-2-(2,4,6-trimethoxyphenyl) ethenesulfonamide;
(E)-N-(3-(((E)-3-(4-fluorophenyl)-3-oxoprop-1-en-1-yl) amino)-4-methoxyphenyl)-2-(2,4,6-trimethoxyphenyl) ethenesulfonamide;
(E)-N-(3-(((Z)-3-(4-chlorophenyl)-3-oxoprop-1-en-1-yl) amino)-4-methoxy phenyl)-2-(2,4,6-trimethoxyphenyl) ethenesulfonamide;
(E)-N-(3-(((E)-3-(4-chlorophenyl)-3-oxoprop-1-en-1-yl) amino)-4-methoxyphenyl)-2-(2,4,6-trimethoxyphenyl) ethenesulfonamide;
(E)-N-(3-(((Z)-3-(4-bromophenyl)-3-oxoprop-1-en-1-yl) amino)-4-methoxy phenyl)-2-(2,4,6-trimethoxyphenyl) ethenesulfonamide;
(E)-N-(3-(((E)-3-(4-bromophenyl)-3-oxoprop-1-en-1-yl) amino)-4-methoxyphenyl)-2-(2,4,6-trimethoxyphenyl) ethenesulfonamide;
(E)-N-(3-(((Z)-3-(4-methylphenyl)-3-oxoprop-1-en-1-yl) amino)-4-methoxy phenyl)-2-(2,4,6-trimethoxyphenyl) ethenesulfonamide;
(E)-N-(3-(((E)-3-(4-methylphenyl)-3-oxoprop-1-en-1-yl) amino)-4-methoxyphenyl)-2-(2,4,6-trimethoxyphenyl) ethenesulfonamide;
(E)-N-(3-(((Z)-3-(3,4-dimethoxyphenyl)-3-oxoprop-1-en-1-yl)amino)-4-methoxy phenyl)-2-(2,4,6-trimethoxyphenyl)ethenesulfonamide;

(E)-N-(3-(((E)-3-(3,4-dimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(3,4,5-trimethoxyphenyl)-3-oxoprop-1-en-1-yl)amino)-4-methoxy phenyl)-2-(2,4,6-trimethoxyphenyl)ethenesulfonamide;
(E)-N-(3-(((E)-3-(3,4,5-trimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(2,4,6-trimethoxyphenyl)-3-oxoprop-1-en-1-yl)amino)-4-methoxy phenyl)-2-(2,4,6-trimethoxyphenyl)ethenesulfonamide;
(E)-N-(3-(((E)-3-(2,4,6-trimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(2-chloro-3,4,5-trimethoxyphenyl)-3-oxoprop-1-en-1-yl)amino)-4-methoxy phenyl)-2-(2,4,6-trimethoxyphenyl)ethenesulfonamide;
(E)-N-(3-(((E)-3-(2-chloro-3,4,5-trimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(2-bromo-3,4,5-trimethoxyphenyl)-3-oxoprop-1-en-1-yl)amino)-4-methoxy phenyl)-2-(2,4,6-trimethoxyphenyl)ethenesulfonamide;
(E)-N-(3-(((E)-3-(2-bromo-3,4,5-trimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(naphthalen-3-yl)-3-oxoprop-1-en-1-yl)amino)-4-methoxy phenyl)-2-(2,4,6-trimethoxyphenyl)ethenesulfonamide;
or pharmaceutically acceptable salt thereof.

In certain embodiments, $R^1$ is —CH(R)SO$_2$— and $R^6$ is —CH=C[C(=O)O—(C$_1$-C$_6$)alkyl]$_2$.

In certain embodiments thereof, m is zero and $R^{13}$ is —H. Such compounds include, for example, (E)-diethyl 2-(((2-methoxy-5-(2-(2,4,6-trimethoxyphenyl)vinylsulfonamido)phenyl)amino)methylene)malonate, or pharmaceutically acceptable salt thereof.

In certain embodiments, $R^1$ is —NHSO$_2$— and $R^6$ is —C(=O)—CH=CH—$R^8$. In certain embodiments thereof, m is zero and $R^{13}$ is —H. In certain embodiments thereof, $R^8$ is —H, —C(=O)OH, or —C(=O)O(C$_1$-C$_6$)alkyl. Such compounds include, for example, (E)-N-(2-methoxy-5-(2-(2,4,6-trimethoxyphenyl)vinylsulfonamido)phenyl)acrylamide; (Z)-4-((2-methoxy-5-((E)-2-(2,4,6-trimethoxyphenyl)vinylsulfonamido)phenyl)amino)-4-oxobut-2-enoic acid; (E)-4-((2-methoxy-5-((E)-2-(2,4,6-trimethoxyphenyl)vinylsulfonamido)phenyl)amino)-4-oxobut-2-enoic acid; (Z)-methyl 4-((2-methoxy-5-((E)-2-(2,4,6-trimethoxyphenyl)vinylsulfonamido)phenyl)amino)-4-oxobut-2-enoate; or pharmaceutically acceptable salt thereof. In certain embodiments, $R^8$ is aryl or substituted aryl. Where $R^8$ is aryl or substituted aryl, it is preferably phenyl or substituted phenyl. Such compounds include, for example, (Z)—N-(2-methoxy-5-((E)-2-(2,4,6-trimethoxyphenyl)vinylsulfonamido)phenyl)-3-phenylacrylamide and halogen substituted derivatives thereof, such as (Z)-3-(4-fluorophenyl)-N-(2-methoxy-5-((E)-2-(2,4,6-trimethoxyphenyl)vinylsulfonamido)phenyl)acrylamide.

In certain embodiments, $R^1$ is —NHSO$_2$— and $R^6$ is —(C$_2$-C$_6$) unsaturated hydrocarbyl or —C(=O)—(C$_2$-C$_6$) unsaturated hydrocarbyl. In certain embodiments, when $R^6$ is —(C$_2$-C$_6$) unsaturated hydrocarbyl, $R^{13}$ is also —(C$_2$-C$_6$) unsaturated hydrocarbyl. In other embodiments, when $R^6$ is —(C$_2$-C$_6$) unsaturated hydrocarbyl or —C(=O)—(C$_2$-C$_6$) unsaturated hydrocarbyl, m is zero and $R^{13}$ is —H.

Such compounds include, for example, (E)-N-(3-(di(prop-2-yn-1-yl)amino)-4-methoxyphenyl)-2-(2,4,6-trimethoxyphenyl)ethenesulfonamide, (E)-N-(2-methoxy-5-(2-(2,4,6-trimethoxyphenyl)vinylsulfonamido)phenyl)propiolamide, (E)-N-(4-methoxy-3-(prop-2-yn-1-ylamino)phenyl)-2-(2,4,6-trimethoxyphenyl)ethenesulfonamide, or pharmaceutically acceptable salt thereof.

In certain embodiments, $R^1$ is —NHSO$_2$— and $R^6$ is —SO$_2$—CH=CH—$R^9$. In certain embodiments thereof, m is zero and $R^{13}$ is —H. Such compounds include, for example, (E)-N-(4-methoxy-3-(vinylsulfonamido)phenyl)-2-(2,4,6-trimethoxyphenyl)ethenesulfonamide, or pharmaceutically acceptable salt thereof.

3. Compound of Formula I Wherein X and Y are CH and $R^1$ is —NH(C=O)—

In certain embodiments, compounds of Formula I are provided wherein X and Y are CH, and $R^1$ is —NH(C=O)—.

In certain embodiments, $R^1$ is —NH(C=O)— and $R^6$ is —CH=CH—C(=O)—$R^7$. In certain embodiments thereof, m is zero and $R^{13}$ is —H. In certain embodiments thereof, $R^7$ is —OR$^{10}$ or —(C$_1$-C$_4$)alkyl. In particular embodiments, $R^7$ is hydroxyl, methyl, methoxy, ethyl or ethoxy. Such compounds include, for example,
(E)-3-((2-methoxy-5-((E)-3-(2,4,6-trimethoxyphenyl)acrylamido)phenyl)amino)acrylic acid;
(E)-N-(4-methoxy-3-(((Z)-3-oxobut-1-en-1-yl)amino)phenyl)-3-(2,4,6-trimethoxyphenyl)acrylamide, or pharmaceutically acceptable salt thereof.
(Z)-methyl 3-((2-methoxy-5-((E)-3-(2,4,6-trimethoxyphenyl) acrylamido)phenyl)amino)acrylate;
((Z)-ethyl 3-((2-methoxy-5-((E)-3-(2,4,6-trimethoxyphenyl) acrylamido)phenyl)amino)acrylate;
(E)-methyl 3-((2-methoxy-5-((E)-2-(2,4,6-trimethoxyphenyl)acrylamido)phenyl)amino)acrylate;
(E)-ethyl 3-((2-methoxy-5-((E)-2-(2,4,6-trimethoxyphenyl)acrylamido)phenyl)amino)acrylate;
(E)-ethyl 4-((2-methoxy-5-((E)-3-(2,4,6-trimethoxyphenyl)acrylamido)phenyl)amino)but-2-enoate;
or pharmaceutically acceptable salt thereof.

In certain embodiments, $R^1$ is —NH(C=O)—, $R^6$ is —CH=CH—C(=O)—$R^7$, and $R^7$ is —NR$^{11}$R$^{12}$. In certain embodiments thereof, —NR$^{11}$R$^{12}$ is piperazinyl or 4-methylpiperazinyl. Such compounds include, for example, (E)-N-(4-methoxy-3-(((Z)-3-(4-methylpiperazin-1-yl)-3-oxoprop-1-en-1yl)amino)phenyl)-2-(2,4,6-trimethoxyphenyl)ethenecarboxamide, (E)-N-(4-methoxy-3-(((Z)-3-(piperazin-1-yl)-3-oxoprop-1-en-1yl)amino)phenyl)-2-(2,4,6-trimethoxyphenyl)ethenecarboxamide, or pharmaceutically acceptable salt thereof.

In certain embodiments, $R^1$ is —NH(C=O)—, $R^6$ is —CH=CH—C(=O)—$R^7$, and $R^7$ is aryl having up to ten carbon atoms, or substituted aryl having up to ten ring carbons with one or more substituents selected from halo, —(C$_1$-C$_4$)alkoxy, —(C$_1$-C$_4$)alkyl and methylenedioxy, or pharmaceutically acceptable salt thereof. One such compound is (E)-N-(3-(((Z)-3-(benzo[d][1,3]dioxol-5-yl)-3-oxoprop-1-en-1-yl)amino)-4-methoxy phenyl)-2-(2,4,6-trimethoxyphenyl)ethenecarboxamide, or pharmaceutically acceptable salt thereof. In certain embodiments, $R^7$ is phenyl, naphthyl, 4-halophenyl, 4-(C$_1$-C$_4$)alkoxy, 4-(C$_1$-C$_4$)alkyl, dialkoxyphenyl or trialkoxyphenyl. Such compounds include, for example,
(E)-N-(4-methoxy-3-(((Z)-3-oxo-3-phenylprop-1-en-yl)amino)phenyl)-2-(2,4,6-trimethoxyphenyl)ethenecarboxamide;

(E)-N-(4-methoxy-3-(((E)-3-oxo-3-phenylprop-1-en-1-yl)amino)phenyl)-2-(2,4,6-trimethoxyphenyl)ethenecarboxamide;
(E)-N-(3-(((Z)-3-(4-methoxyphenyl)-3-oxoprop-1-en-1-yl)amino)-4-methoxyphenyl)-2-(2,4,6-trimethoxyphenyl)ethenecarboxmnide;
(E)-N-(3-(((E)-3-(4-methoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(4-fluorophenyl)-3-oxoprop-1-en-1-yl)amino)-4-methoxyphenyl)-2-(2,4,6-trimethoxyphenyl)ethenecarboxamide;
(E)-N-(3-(((E)-3-(4-fluorophenyl)-3-oxoprop-1-en-1-yl)amino)-4-methoxyphenyl)-2-(2,4,6-trimethoxyphenyl)ethenecarboxamide;
(E)-N-(3-(((Z)-3-(4-chlorophenyl)-3-oxoprop-1-en-1-yl)amino)-4-methoxyphenyl)-2-(2,4,6-trimethoxyphenyl)ethenecarboxamide;
(E)-N-(3-(((E)-3-(4-chlorophenyl)-3-oxoprop-1-en-1-yl)amino)-4-methoxyphenyl)-2-(2,4,6-trimethoxyphenyl)ethenecarboxamide;
(E)-N-(3-(((Z)-3-(4-bromophenyl)-3-oxoprop-1-en-1-yl)amino)-4-methoxyphenyl)-2-(2,4,6-trimethoxyphenyl)ethenecarboxamide;
(E)-N-(3-(((E)-3-(4-bromophenyl)-3-oxoprop-1-en-1-yl)amino)-4-methoxyphenyl)-2-(2,4,6-trimethoxyphenyl)ethenecarboxamide;
(E)-N-(3-(((Z)-3-(4-methylphenyl)-3-oxoprop-1-en-1-yl)amino)-4-methoxyphenyl)-2-(2,4,6-trimethoxyphenyl)ethenecarboxamide;
(E)-N-(3-(((E)-3-(4-methylphenyl)-3-oxoprop-1-en-1-yl)amino)-4-methoxyphenyl)-2-(2,4,6-trimethoxyphenyl)ethenecarboxamide;
(E)-N-(3-(((Z)-3-(3,4-dimethoxyphenyl)-3-oxoprop-1-en-1-yl)amino)-4-methoxy phenyl)-2-(2,4,6-trimethoxyphenyl)ethenecarboxamide;
(E)-N-(3-(((E)-3-(3,4-dimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((E)-3-(3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(2,4,6-trimethoxyphenyl)-3-oxoprop-1-en-1-yl)amino)-4-methoxyphenyl)-2-(2,4,6-trimethoxyphenyl)ethenecarboxamide;
(E)-N-(3-(((E)-3-(2,4,6-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(2-chloro-3,4,5-trimethoxyphenyl)-3-oxoprop-1-en-1-yl)amino)-4-methoxy phenyl)-2-(2,4,6-trimethoxyphenyl)ethenecarboxamide;
(E)-N-(3-(((E)-3-(2-chloro-3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(2-bromo-3,4,5-trimethoxyphenyl)-3-oxoprop-1-en-1-yl)amino)-4-methoxy phenyl)-2-(2,4,6-trimethoxyphenyl)ethenecarboxamide;
(E)-N-(3-(((E)-3-(2-bromo-3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(naphthalen-3-yl)-3-oxoprop-1-en-1-yl)amino)-4-methoxyphenyl)-2-(2,4,6-trimethoxyphenyl)ethenecarboxamide;
or a pharmaceutically acceptable salt thereof.

In certain embodiments, $R^1$ is —NH(C=O)— and $R^6$ is —C(=O)—CH=CH—$R^8$. In certain embodiments thereof, m is zero and $R^{13}$ is —H. In certain embodiments thereof, $R^8$ is —H, —C(=O)OH, or —C(=O)O($C_1$-$C_6$)alkyl. Such compounds include, for example, (E)-N-(3-acrylamido-4-methoxyphenyl)-3-(2,4,6-trimethoxyphenyl)acrylamide; (Z)-4-((2-methoxy-5-((E)-3-(2,4,6-trimethoxyphenyl)acrylamido)phenyl)amino)-4-oxobut-2-enoic acid; (E)-4-((2-methoxy-5-((E)-3-(2,4,6-trimethoxyphenyl) acrylamido) phenyl)amino)-4-oxobut-2-enoic acid; (Z)-methyl 4-((2-methoxy-5-((E)-3-(2,4,6-trimethoxyphenyl)acrylamido) phenyl)amino)-4-oxobut-2-enoate; or pharmaceutically acceptable salt thereof. In certain embodiments, $R^8$ is aryl or substituted aryl. Where $R^8$ is aryl or substituted aryl, it is preferably phenyl or substituted phenyl. Such compounds include, for example, (E)-N-(4-methoxy-3-((Z)-3-phenylacrylamido)phenyl)-3-(2,4,6-trimethoxyphenyl)acrylamide and halogen substituted derivatives thereof, such as (Z)-3-(4-fluorophenyl)-N-(2-methoxy-5-((E)-3-(2,4,6-trimethoxyphenyl) acrylamido)phenyl)acrylamide.

In certain embodiments, $R^1$ is —NH(C=O)— and $R^6$ is —CH=C[C(=O)O—($C_1$-$C_6$)alkyl]$_2$.

In certain embodiments thereof, m is zero and $R^{13}$ is —H. Such compounds include, for example, (E)-diethyl 2-(((2-methoxy-5-(3-(2,4,6-trimethoxyphenyl)acrylamido)phenyl)amino)methylene)malonate, or pharmaceutically acceptable salt thereof.

In certain embodiments, $R^1$ is —NH(C=O)— and $R^6$ is —($C_2$-$C_6$) unsaturated hydrocarbyl or —C(=O)—($C_2$-$C_6$) unsaturated hydrocarbyl. In certain embodiments, when $R^6$ is —($C_2$-$C_6$) unsaturated hydrocarbyl, $R^{13}$ is also —($C_2$-$C_6$) unsaturated hydrocarbyl. In other embodiments, when $R^6$ is —($C_2$-$C_6$) unsaturated hydrocarbyl or —C(=O)—($C_2$-$C_6$) unsaturated hydrocarbyl, m is zero and $R^{13}$ is —H.

Such compounds include, for example, (E)-N-(3-(di(prop-2-yn-1-yl)amino)-4-methoxyphenyl)-3-(2,4,6-trimethoxyphenyl) acrylamide, (E)-N-(4-methoxy-3-propiolamidophenyl)-3-(2,4,6-trimethoxyphenyl)acrylamide, (E)-N-(4-methoxy-3-(prop-2-yn-1-ylamino)phenyl)-3-(2,4,6-trimethoxyphenyl)acrylamide, or pharmaceutically acceptable salt thereof.

In certain embodiments, $R^1$ is —NH(C=O)— and $R^6$ is —$SO_2$—CH=CH—$R^9$. In certain embodiments thereof, m is zero and $R^{13}$ is —H. Such compounds include, for example, (E)-N-(4-methoxy-3-(vinylsulfonamido)phenyl)-3-(2,4,6-trimethoxyphenyl)acrylamide, or pharmaceutically acceptable salt thereof.

B. Compounds of Formula I Wherein One of X or Y is N

In one aspect, compounds of Formula I are provided wherein one of X or Y is N and the other is CH.

1. Compound of Formula I Wherein One of X or Y is N, and $R^1$ is —CH(R)$SO_2$—

In certain embodiments, compounds of Formula I are provided wherein one of X or Y is N, and $R^1$ is —CH(R)$SO_2$—.

In certain embodiments, $R^1$ is —CH(R)$SO_2$— and $R^6$ is —CH=CH—C(=O)—$R^7$. In certain embodiments thereof, m is zero and $R^{13}$ is —H. In certain embodiments, $R^7$ is —$OR^{10}$ or —($C_1$-$C_4$)alkyl. In particular embodiments, $R^7$ is hydroxyl, methyl, methoxy, ethyl or ethoxy. Such compounds include, for example,
(Z)-4-((3-methoxy-6-(((E)-2,4,6-trimethoxystyrylsulfonyl)methyl)pyridin-2-yl)amino)but-3-en-2-one;
(Z)-methyl 3-((3-methoxy-6(((E)-2,4,6-trimethoxystyrylsulfonyl)methyl)pyridine-2-yl)amino)acrylate;
(Z)-ethyl 3-((3-methoxy-6(((E)-2,4,6-trimethoxystyrylsulfonyl)methyl)pyridine-2-yl)amino)acrylate;

(Z)-4-((2-methoxy-5-(((E)-2,4,6-trimethoxystyrylsulfonyl)methyl)pyridin-3-yl)amino)but-3-en-2-one;
(Z)-methyl 3-((2-methoxy-5-(((E)-2,4,6-trimethoxystyrylsulfonyl)methyl)pyridine-3-yl)amino)acrylate;
(Z)-ethyl 3-((2-methoxy-5-(((E)-2,4,6-trimethoxystyrylsulfonyl)methyl)pyridine-3-yl)amino)acrylate;
(E)-3-((3-methoxy-6-(((E)-2,4,6-trimethoxystyrylsulfonyl)methyl)pyridin-2-yl)amino)acrylic acid;
(E)-methyl 3-((3-methoxy-6-(((E)-2,4,6-trimethoxystyrylsulfonyl)methyl)pyridin-2-yl)amino)acrylate;
(E)-methyl 3-((3-methoxy-6-(((E)-2,4,6-trimethoxystyrylsulfonyl)methyl)pyridin-2-yl)amino)acrylate;
(E)-3-((2-methoxy-5-(((E)-2,4,6-trimethoxystyrylsulfonyl)methyl)pyridin-3-yl)amino)acrylic acid;
(E)-methyl 3-((2-methoxy-5-(((E)-2,4,6-trimethoxystyrylsulfonyl)methyl)pyridin-3-yl)amino)acrylate;
(E)-ethyl 3-((2-methoxy-5-(((E)-2,4,6-trimethoxystyrylsulfonyl)methyl)pyridin-3-yl)amino)acrylate;
(E)-ethyl 4-((3-methoxy-6-(((E)-2,4,6-trimethoxystyrylsulfonyl)methyl)pyridin-2-yl)amino)but-2-enoate;
(E)-ethyl 4-((2-methoxy-5-(((E)-2,4,6-trimethoxystyrylsulfonyl)methyl)pyridin-3-yl)amino)but-2-enoate;
or pharmaceutically acceptable salt thereof.

In certain embodiments, $R^1$ is —CH(R)SO$_2$—, $R^6$ is —CH=CH—C(=O)—$R^7$, and $R^7$ is —NR$^{11}$R$^{12}$. In certain embodiments thereof, —NR$^{11}$R$^{12}$ is piperazinyl or 4-methylpiperazinyl. Such compounds include, for example,
(Z)-3-((3-methoxy-6-(((E)-2,4,6-trimethoxystyrylsulfonyl)methyl)pyridine-2-yl)amino)-1-(4-methylpiperazin-1 yl)prop-2-en-1-one;
(Z)-3-((3-methoxy-6-(((E)-2,4,6-trimethoxystyrylsulfonyl)methyl)pyridine-2-yl)amino)-1-(piperazin-1 yl)prop-2-en-1-one;
(Z)-3-((2-methoxy-5-(((E)-2,4,6-trimethoxystyrylsulfonyl)methyl)pyridine-3-yl)amino)-1-(4-methylpiperazin-1 yl)prop-2-en-1-one;
(Z)-3-((2-methoxy-5-(((E)-2,4,6-trimethoxystyrylsulfonyl)methyl)pyridine-3-yl)amino)-1-(piperazin-1 yl)prop-2-en-1-one;
or pharmaceutically acceptable salt thereof.

In certain embodiments, $R^1$ is —CH(R)SO$_2$—, $R^6$ is —CH=CH—C(=O)—$R^7$, and $R^7$ is aryl having up to ten carbon atoms, or substituted aryl having up to ten ring carbons with one or more substituents selected from halo, —(C$_1$-C$_4$)alkoxy, —(C$_1$-C$_4$)alkyl and methylenedioxy, or pharmaceutically acceptable salt thereof. In certain embodiments, $R^7$ is phenyl, naphthyl, 4-halophenyl, 4-(C$_1$-C$_4$)alkoxy, 4-(C$_1$-C$_4$)alkyl, dialkoxyphenyl or trialkoxyphenyl. Such compounds include, for example,
(Z)-3-((3-methoxy-6-(((E)-2,4,6-trimethoxystyrylsulfonyl)methyl)pyridine-2-yl)amino)-1-phenylprop-2-en-1-one;
(Z)-1-(4-methoxyphenyl)-3-((3-methoxy-6-(((E)-2,4,6-trimethoxystyrylsulfonyl)methyl)pyridine-2-yl)amino)prop-2-en-1-one;
(Z)-1-(4-fluoroyphenyl)-3-((3-methoxy-6-(((E)-2,4,6-trimethoxystyrylsulfonyl)methyl)pyridine-2-yl)amino)prop-2-en-1-one;
(Z)-1-(4-chlorophenyl)-3-((3-methoxy-6-(((E)-2,4,6-trimethoxystyrylsulfonyl)methyl)pyridine-2-yl)amino)prop-2-en-1-one;
(Z)-1-(4-bromophenyl)-3-((3-methoxy-6-(((E)-2,4,6-trimethoxystyrylsulfonyl)methyl)pyridine-2-yl)amino)prop-2-en-1-one;
(Z)-1-(4-methylphenyl)-3-((3-methoxy-6-(((E)-2,4,6-trimethoxystyrylsulfonyl)methyl)pyridine-2-yl)amino)prop-2-en-1-one;
(Z)-1-(3,4-dimethoxyphenyl)-3-((3-methoxy-6-(((E)-2,4,6-trimethoxystyrylsulfonyl)methyl)pyridine-2-yl)amino)prop-2-en-1-one;
(Z)-1-(3,4,5-trimethoxyphenyl)-3-((3-methoxy-6-(((E)-2,4,6-trimethoxystyrylsulfonyl)methyl)pyridine-2-yl)amino)prop-2-en-1-one;
(Z)-1-(2,4,6-trimethoxyphenyl)-3-((3-methoxy-6-(((E)-2,4,6-trimethoxystyrylsulfonyl)methyl)pyridine-2-yl)amino)prop-2-en-1-one;
(Z)-1-(2-chloro-3,4,5-trimethoxyphenyl)-3-((3-methoxy-6(((E)-2,4,6-trimethoxystyrylsulfonyl)methyl)pyridine-2-yl)amino)prop-2-en-1-one;
(Z)-1-(2-bromo-3,4,5-trimethoxyphenyl)-3-((3-methoxy-6(((E)-2,4,6-trimethoxystyrylsulfonyl) methyl)pyridine-2-yl)amino)prop-2-en-1-one;
(Z)-1-(naphthalen-3-yl)-3-((3-methoxy-6-(((E)-2,4,6-trimethoxystyrylsulfonyl)methyl)pyridine-2-yl)amino)prop-2-en-1-one;
(Z)-1-(benzo[d][1,3]dioxol-5-yl))-3-((3-methoxy-6(((E)-2,4,6-trimethoxystyrylsulfonyl)methyl)pyridine-2-yl)amino)prop-2-en-1-one;
(Z)-3-((2-methoxy-5-(((E)-2,4,6-trimethoxystyrylsulfonyl)methyl)pyridine-3-yl)amino)-1-phenylprop-2-en-1-one;
(Z)-1-(4-methoxyphenyl)-3-((2-methoxy-5-(((E)-2,4,6-trimethoxystyrylsulfonyl)methyl)pyridine-3-yl)amino)prop-2-en-1-one;
(Z)-1-(4-fluoroyphenyl)-3-((2-methoxy-5-(((E)-2,4,6-trimethoxystyrylsulfonyl)methyl)pyridine-3-yl)amino)prop-2-en-1-one;
(Z)-1-(4-chlorophenyl)-3-((2-methoxy-5-(((E)-2,4,6-trimethoxystyrylsulfonyl)methyl)pyridine-3-yl)amino)prop-2-en-1-one;
(Z)-1-(4-bromophenyl)-3-((2-methoxy-5-(((E)-2,4,6-trimethoxystyrylsulfonyl)methyl)pyridine-3-yl)amino)prop-2-en-1-one;
(Z)-1-(4-methylphenyl)-3-((2-methoxy-5-(((E)-2,4,6-trimethoxystyrylsulfonyl)methyl)pyridine-3-yl)amino)prop-2-en-1-one;
(Z)-1-(3,4-dimethoxyphenyl)-3-((2-methoxy-5-(((E)-2,4,6-trimethoxystyrylsulfonyl)methyl)pyridine-3-yl)amino)prop-2-en-1-one;
(Z)-1-(3,4,5-timethoxyphenyl)-3-((2-methoxy-5-(((E)-2,4,6-trimethoxystyrylsulfonyl) methyl)pyridine-3-yl)amino)prop-2-en-1-one;
(Z)-1-(2,4,6-timethoxyphenyl)-3-((2-methoxy-5-(((E)-2,4,6-trimethoxystyrylsulfonyl)methyl)pyridine-3-yl)amino)prop-2-en-1-one;
(Z)-1-(2-chloro-3,4,5-timethoxyphenyl)-3-((2-methoxy-5-(((E)-2,4,6-trimethoxystyryl sulfonyl)methyl)pyridine-3-yl)amino)prop-2-en-1-one;
(Z)-1-(2-bromo-3,4,5-timethoxyphenyl)-3-((2-methoxy-5-(((E)-2,4,6-trimethoxystyrylsulfonyl)methyl)pyridine-3-yl)amino)prop-2-en-1-one;
(Z)-1-(naphthalen-3-yl)-3-((2-methoxy-5-(((E)-2,4,6-trimethoxystyrylsulfonyl)methyl)pyridine-3-yl)amino)prop-2-en-1-one;
(Z)-1-(benzo[d][1,3]dioxol-5-yl))-3-((2-methoxy-5-(((E)-2,4,6-trimethoxystyrylsulfonyl) methyl)pyridine-3-yl)amino)prop-2-en-1-one;
(E)-3-((3-methoxy-6-(((E)-2,4,6-trimethoxystyrylsulfonyl)methyl)pyridine-2-yl)amino)-1-phenylprop-2-en-1-one;
(E)-1-(4-methoxyphenyl)-3-((3-methoxy-6-(((E)-2,4,6-trimethoxystyrylsulfonyl)methyl)pyridin-2-yl)amino)prop-2-en-1-one;
(E)-1-(4-fluorophenyl)-3-((3-methoxy-6-(((E)-2,4,6-trimethoxystyrylsulfonyl)methyl)pyridin-2-yl)amino)prop-2-en-1-one;

(E)-1-(4-chlorophenyl)-3-((3-methoxy-6-(((E)-2,4,6-trimethoxystyrylsulfonyl)methyl)pyridin-2-yl)amino)prop-2-en-1-one;
(E)-1-(4-bromophenyl)-3-((3-methoxy-6-(((E)-2,4,6-trimethoxystyrylsulfonyl)methyl)pyridin-2-yl)amino)prop-2-en-1-one;
(E)-1-(4-methylphenyl)-3-((3-methoxy-6-(((E)-2,4,6-trimethoxystyrylsulfonyl)methyl)pyridin-2-yl)amino)prop-2-en-1-one;
(E)-1-(3,4-dimethoxyphenyl)-3-((3-methoxy-6-(((E)-2,4,6-trimethoxystyrylsulfonyl)methyl)pyridin-2-yl)amino)prop-2-en-1-one;
(E)-1-(3,4,5-timethoxyphenyl)-3-((3-methoxy-6-(((E)-2,4,6-trimethoxystyrylsulfonyl)methyl)pyridin-2-yl)amino)prop-2-en-1-one;
(E)-1-(2,4,6-trimethoxyphenyl)-3-((3-methoxy-6-(((E)-2,4,6-trimethoxystyrylsulfonyl)methyl)pyridin-2-yl)amino)prop-2-en-1-one;
(E)-1-(2-chloro-3,4,5-trimethoxyphenyl)-3-((3-methoxy-6-(((E)-2,4,6-trimethoxystyrylsulfonyl)methyl)pyridin-2-yl)amino)prop-2-en-1-one;
(E)-1-(2-bromo-3,4,5-trimethoxyphenyl)-3-((3-methoxy-6-(((E)-2,4,6-trimethoxystyrylsulfonyl)methyl)pyridin-2-yl)amino)prop-2-en-1-one;
(E)-3-((2-methoxy-5-(((E)-2,4,6-trimethoxystyrylsulfonyl)methyl)pyridin-3-yl)amino)-1-phenylprop-2-en-1-one;
(E)-1-(4-methoxyphenyl)-3-((2-methoxy-5-(((E)-2,4,6-trimethoxystyrylsulfonyl)methyl)pyridin-3-yl)amino)prop-2-en-1-one;
(E)-1-(4-fluorophenyl)-3-((2-methoxy-5-(((E)-2,4,6-trimethoxystyrylsulfonyl)methyl)pyridin-3-yl)amino)prop-2-en-1-one;
(E)-1-(4-chlorophenyl)-3-((2-methoxy-5-(((E)-2,4,6-trimethoxystyrylsulfonyl)methyl)pyridin-3-yl)amino)prop-2-en-1-one;
(E)-1-(4-bromophenyl)-3-((2-methoxy-5-(((E)-2,4,6-trimethoxystyrylsulfonyl)methyl)pyridin-3-yl)amino)prop-2-en-1-one;
(E)-1-(4-methylphenyl)-3-((2-methoxy-5-(((E)-2,4,6-trimethoxystyrylsulfonyl)methyl)pyridin-3-yl)amino)prop-2-en-1-one;
(E)-1-(3,4-dimethoxyphenyl)-3-((2-methoxy-5-(((E)-2,4,6-trimethoxystyrylsulfonyl)methyl)pyridin-3-yl)amino)prop-2-en-1-one;
(E)-1-(3,4,5-trimethoxyphenyl)-3-((2-methoxy-5-(((E)-2,4,6-trimethoxystyrylsulfonyl)methyl)pyridin-3-yl)amino)prop-2-en-1-one;
(E)-1-(2,4,6-trimethoxyphenyl)-3-((2-methoxy-5-(((E)-2,4,6-trimethoxystyrylsulfonyl)methyl)pyridin-3-yl)amino)prop-2-en-1-one;
(E)-1-(2-chloro-3,4,5-trimethoxyphenyl)-3-((2-methoxy-5-(((E)-2,4,6-trimethoxystyrylsulfonyl)methyl)pyridin-3-yl)amino)prop-2-en-1-one;
(E)-1-(2-bromo-3,4,5-trimethoxyphenyl)-3-((2-methoxy-5-(((E)-2,4,6-trimethoxystyrylsulfonyl)methyl)pyridin-3-yl)amino)prop-2-en-1-one;
or pharmaceutically acceptable salt thereof.

In certain embodiments, $R^1$ is —CH(R)SO$_2$— and $R^6$ is —CH=C[C(=O)O—(C$_1$-C$_6$)alkyl]$_2$.

In certain embodiments thereof, m is zero and $R^{13}$ is —H. Such compounds include, for example, (E)-diethyl 2-(((3-methoxy-6-(((2,4,6-trimethoxystyryl)sulfonyl)methyl)pyridin-2-yl)amino)methylene)malonate, (E)-diethyl 2-(((2-methoxy-5-(((2,4,6-trimethoxystyryl)sulfonyl)methyl)pyridin-3-yl)amino)methylene)malonate, or pharmaceutically acceptable salt thereof.

In certain embodiments, $R^1$ is —CH(R)SO$_2$— and $R^6$ is —C(=O)—CH=CH—$R^8$. In certain embodiments thereof, m is zero and $R^{13}$ is —H. In certain embodiments thereof, $R^8$ is —H, —C(=O)OH, or —C(=O)O(C$_1$-C$_6$)alkyl. Such compounds include, for example, (E)-N-(3-methoxy-6-(((2,4,6-trimethoxystyryl)sulfonyl)methyl)pyridin-2-yl)acrylamide; (E)-N-(2-methoxy-5-(((2,4,6-trimethoxystyryl)sulfonyl)methyl)pyridin-3-yl)acrylamide; (Z)-4-((3-methoxy-6-(((E)-2,4,6-trimethoxystyrylsulfonyl)methyl)pyridin-2-yl)amino)-4-oxobut-2-enoic acid; (Z)-4-((2-methoxy-5-(((E)-2,4,6-trimethoxystyrylsulfonyl)methyl)pyridin-3-yl)amino)-4-oxobut-2-enoic acid; (E)-4-((3-methoxy-6-(((E)-2,4,6-trimethoxystyrylsulfonyl)methyl)pyridin-2-yl)amino)-4-oxobut-2-enoic acid; (E)-4-((2-methoxy-5-(((E)-2,4,6-trimethoxystyrylsulfonyl)methyl)pyridin-3-yl)amino)-4-oxobut-2-enoic acid; (Z)-methyl 4-((3-methoxy-6-(((E)-2,4,6-trimethoxystyrylsulfonyl)methyl)pyridin-2-yl)amino)-4-oxobut-2-enoate; (Z)-methyl 4-((2-methoxy-5-(((E)-2,4,6-trimethoxystyrylsulfonyl)methyl)pyridin-3-yl)amino)-4-oxobut-2-enoate; or pharmaceutically acceptable salt thereof. In certain embodiments, $R^8$ is aryl or substituted aryl. Where $R^8$ is aryl or substituted aryl, it is preferably phenyl or substituted phenyl. Such compounds include, for example, (Z)—N-(3-methoxy-6-(((E)-2,4,6-trimethoxystyrylsulfonyl)methyl)pyridin-2-yl)-3-phenylacrylamide and (Z)—N-(2-methoxy-5-(((E)-2,4,6-trimethoxystyrylsulfonyl)methyl)pyridin-3-yl)-3-phenylacrylamide, and halogen substituted derivatives thereof, such as (Z)-3-(4-fluorophenyl)-N-(3-methoxy-6-(((E)-2,4,6-trimethoxystyrylsulfonyl)methyl)pyridin-2-yl)acrylamide and (Z)-3-(4-fluorophenyl)-N-(2-methoxy-5-(((E)-2,4,6-trimethoxystyrylsulfonyl)methyl)pyridin-3-yl)acrylamide.

In certain embodiments, $R^1$ is —CH$_2$SO$_2$— and $R^6$ is —(C$_2$-C$_6$) unsaturated hydrocarbyl or —C(=O)—(C$_2$-C$_6$) unsaturated hydrocarbyl. In certain embodiments, when $R^6$ is —(C$_2$-C$_6$) unsaturated hydrocarbyl, $R^{13}$ is also —(C$_2$-C$_6$) unsaturated hydrocarbyl. In other embodiments, when $R^6$ is —(C$_2$-C$_6$) unsaturated hydrocarbyl or —C(=O)—(C$_2$-C$_6$) unsaturated hydrocarbyl, m is zero and $R^{13}$ is —H.

Such compounds include, for example,
(E)-3-methoxy-N,N-di(prop-2-yn-1-yl)-6-(((2,4,6-trimethoxystyryl) sulfonyl)methyl)pyridin-2-amine;
(E)-2-methoxy-N,N-di(prop-2-yn-1-yl)-5-(((2,4,6-trimethoxystyryl) sulfonyl)methyl)pyridin-3-amine;
(E)-3-methoxy-N-(prop-2-yn-1-yl)-6-(((2,4,6-trimethoxystyryl) sulfonyl)methyl)pyridin-2-amine;
(E)-2-methoxy-N-(prop-2-yn-1-yl)-5-(((2,4,6-trimethoxystyryl) sulfonyl)methyl)pyridin-3-amine;
(E)-N-(3-methoxy-6-(((2,4,6-trimethoxystyryl) sulfonyl)methyl)pyridin-2-yl)propiolamide;
(E)-N-(2-methoxy-5-(((2,4,6-trimethoxystyryl) sulfonyl)methyl)pyridin-3-yl)propiolamide;
or pharmaceutically acceptable salt thereof.

In certain embodiments, $R^1$ is —CH(R)SO$_2$— and $R^6$ is —SO$_2$—CH=CH—$R^9$. In certain embodiments thereof, m is zero and $R^{13}$ is —H. Such compounds include, for example, (E)-N-(3-methoxy-6-(((2,4,6-trimethoxystyryl) sulfonyl)methyl)pyridin-2-yl)ethenesulfonamide, (E)-N-(2-methoxy-5-(((2,4,6-trimethoxystyryl) sulfonyl)methyl)pyridin-3-yl)ethenesulfonamide, or pharmaceutically acceptable salt thereof.

III. Methods for Preparing Compounds of the Invention and Intermediates Useful in the Synthesis of Compounds of the Invention There are provided processes for preparing compounds according to Formula I, intermediates that are useful in the preparation of such compounds, and processes for preparing such intermediates. In the formulas and schemes that follow, unless otherwise indicated, X, Y, R, and $R_1$, through $R_{13}$, are as defined above for Formula I.

Certain compounds of Formula I wherein $R^6$ is the group —CH=CH—C(=O)—$R^7$ and the geometric configuration of the double bond in $R^6$ is (Z), i.e. compounds of Formula IV, are prepared according to Scheme 1:

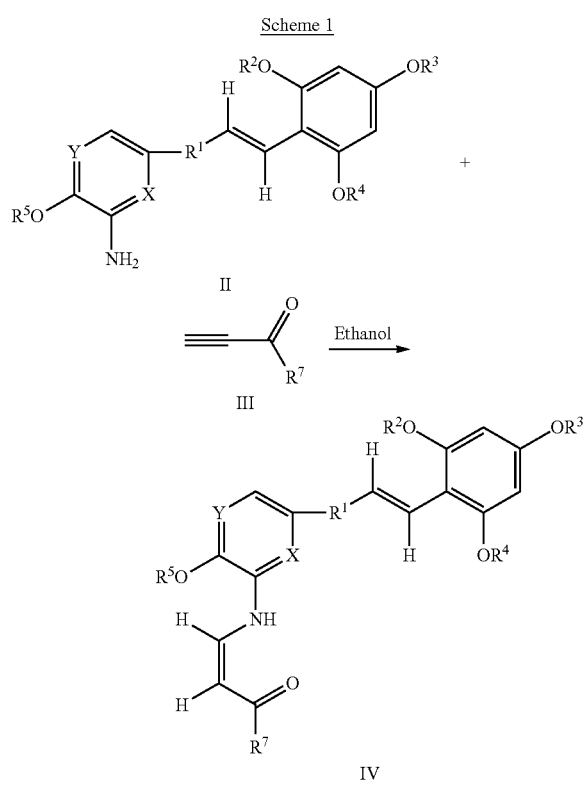

Briefly, the ethynylketone of Formula III (7.5 mmol) is dissolved in absolute ethanol and the amine of Formula II (5 mmol) is added. The reaction is stirred for 4 h at room temperature to reflux temperature. After the completion of reaction (checked by TLC), the reaction mixture is diluted with water and filtered to provide the product. The crude product of Formula IV is purified by flash chromatography to obtain pure compound.

Certain compounds of Formula I wherein $R^6$ is the group —CH=CH—C(=O)—$R^7$ and the configuration of the double bond in the group is (E), i.e. compounds of Formula VI, are prepared according to Scheme 2:

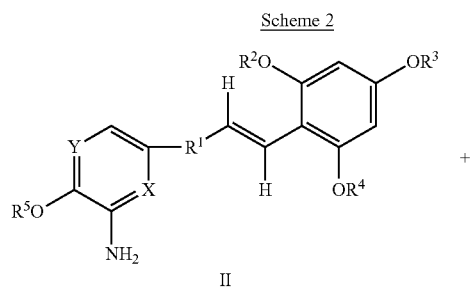

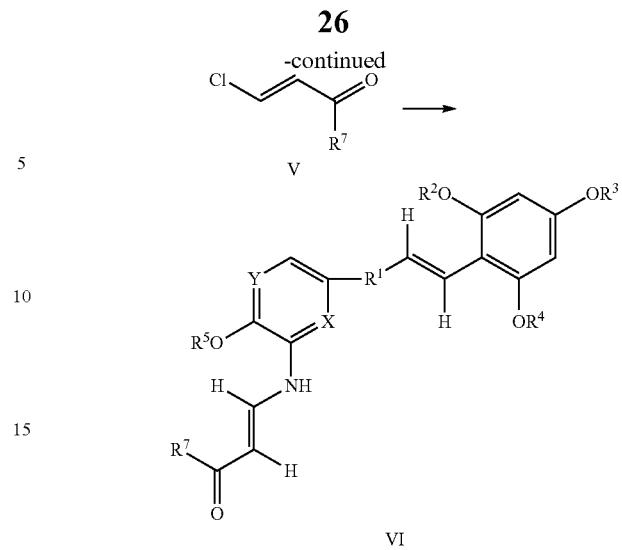

Briefly, a mixture of the amine of Formula II (1 eq), the (E)-3-chloro-1-substituted prop-2-en-1-one of Formula V (1.2 eq), anhydrous $K_2CO_3$ (1.5 eq), and dimethylformamide (DMF) is stirred at 100° C. for 15 h. When it is cooled to room temperature, the inorganic material is removed by filtration and washed with ethyl acetate. The resulting solution is treated with ethyl acetate and water. The organic layer is separated, washed with brine, dried over $Na_2SO_4$, and concentrated. The crude product of Formula VI is purified by flash chromatography.

Compounds of Formula I wherein $R^6$ and $R^{13}$ are —($C_2$-$C_6$) unsaturated hydrocarbyl, i.e., compounds of Formula VIII, are prepared according to Scheme 3:

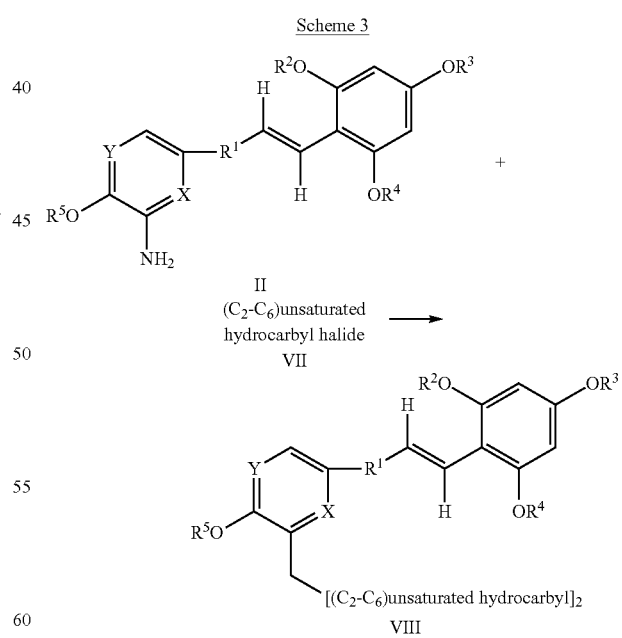

Briefly, A mixture of the amine shown in the scheme (1 eq), and the appropriate ($C_2$-$C_6$) unsaturated hydrocarbyl halide of Formula VII (2 eq), anhydrous $K_2CO_3$ (7 eq), and DMF is stirred at room temperature for 5 h. The reaction mixture is poured over crushed ice with stirring and the separated solid is filtered, washed with water and dried. The crude product of Formula VIII is purified by flash chromatography.

Certain compounds of Formula I wherein $R^6$ is the group —C(=O)—($C_2$-$C_6$) unsaturated hydrocarbyl, i.e., compounds of Formula X, are prepared according to Scheme 4:

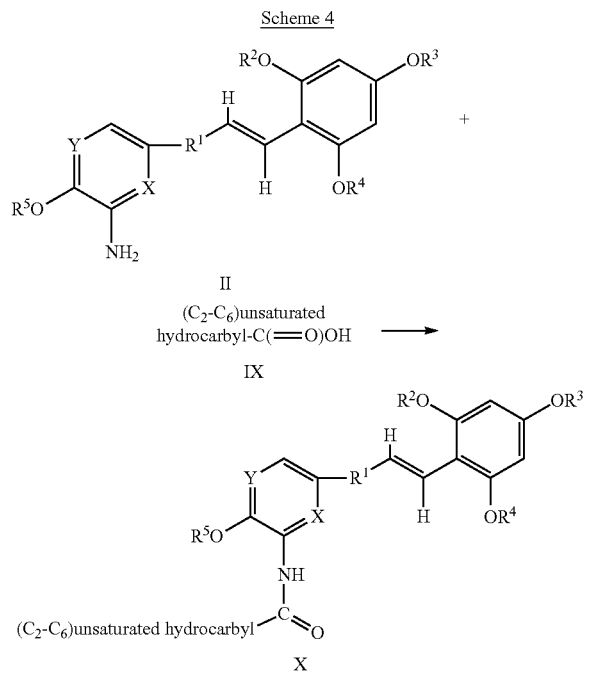

Briefly, the appropriate acid of Formula IX (e.g., propiolic acid) (1.5 eq) is combined with EDC (1.5 eq), DMAP (0.2 eq) in methylene chloride and stirred at RT for 1 hr. The amine of Formula II is added in a single portion and the reaction is stirred at RT for 12 hrs.

The mixture is diluted with ethyl acetate, washed with saturated sodium bicarbonate solution, dried over sodium sulfate and concentrated under reduced pressure. The crude material is purified by flash chromatography to obtain pure compound of Formula X.

Certain compounds of Formula I wherein $R^6$ is the group —C(=O)—CH=CH—$R^8$, i.e., compounds of Formula XII, are prepared according to Scheme 5, where the wavy bond from $R^8$ to the carbon atom to which it is connected indicates either (E) or (Z) geometry of the double bond to that carbon atom:

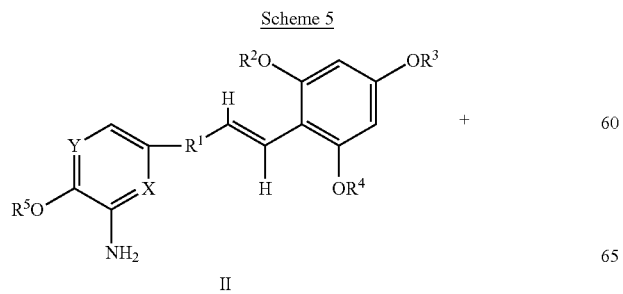

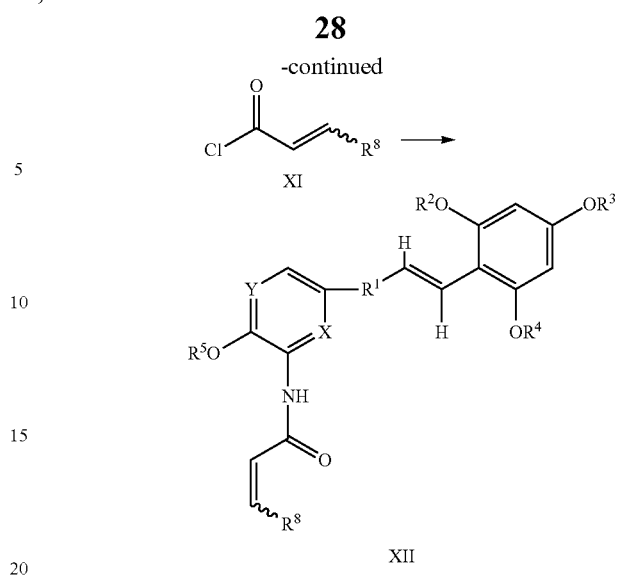

Briefly, the substituted acryloyl chloride of Formula XI (1.2 eq) is dissolved in dichloromethane followed by addition of the amine of Formula II (1 eq), at 0° C. Triethylamine (1 eq.) is then added to the reaction mixture and the solution is stirred overnight and allowed to come to ambient temperature. After completion of the reaction, the organic phase which is then washed with water, saturated sodium bicarbonate, and brine solution. The organic phase is then dried over anhydrous sodium sulfate, filtered, concentrated, and purified by flash chromatography to obtain pure compound of Formula XII.

Certain compounds of Formula I wherein $R^6$ is the group —$SO_2$—CH=CH—$R^9$ are prepared according to Scheme 5a:

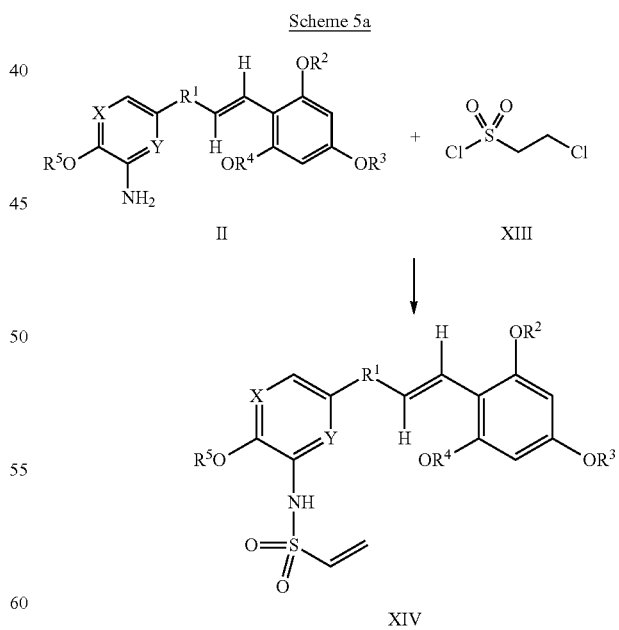

To a stirring solution of 2-chloroethane-1-sulfonyl chloride (1 g, 6.134 mmol), compound XIII in DCM (10 mL) at −15° C., is added dropwise a premixed suspension of amino compound II, $R^1$=—CH(R)$SO_2$—; X=Y=—CH— (2.65 g, 6.74 mmol) and $NEt_3$ (1.24 g, 12.27 mmol) in DCM (2.5 mL). The reaction mixture is left to stir for a further 30 minutes after addition, and then left to warm to RT. The reaction is diluted with more DCM (5-10 mL) and washed with 2M HCl (3×10 mL), H₂O (1×10 mL), dried (anhydrous MgSO₄), and filtered. The filtrate collected is concentrated in vacuo to give the crude product, which is purified by flash chromatography to furnish the desired product (2.67 g, 90%) as off-white crystals.

Similarly, treatment of amine compound II, wherein (i) $R^1$ is —NH—SO₂— and X=Y=—CH—; (ii) $R^1$ is —NH—CO— and X=Y=—CH—; (iii) $R^1$ is —CH(R)SO₂—, X=N and Y=—CH—; (iv) $R^1$ is —CH(R)SO₂—, X=—CH— and Y=N, with XIII gives the corresponding XIV analogs.

For the preparation of compounds of Formula I where $R^1$ is —CH(R)SO₂— and X and Y are —CH₂— (exemplified by R=H in —CH(R)SO₂—), the intermediate (E)-2-alkoxy-5-(((2,4,6-trialkoxystyryl)sulfonyl)methyl)aniline may be prepared from (E)-2,4,6-trialkoxystyryl-3'-nitro-4'-alkoxy-benzylsulfone according to Scheme 6, utilizing Method A, B or C (see below) in the scheme second step:

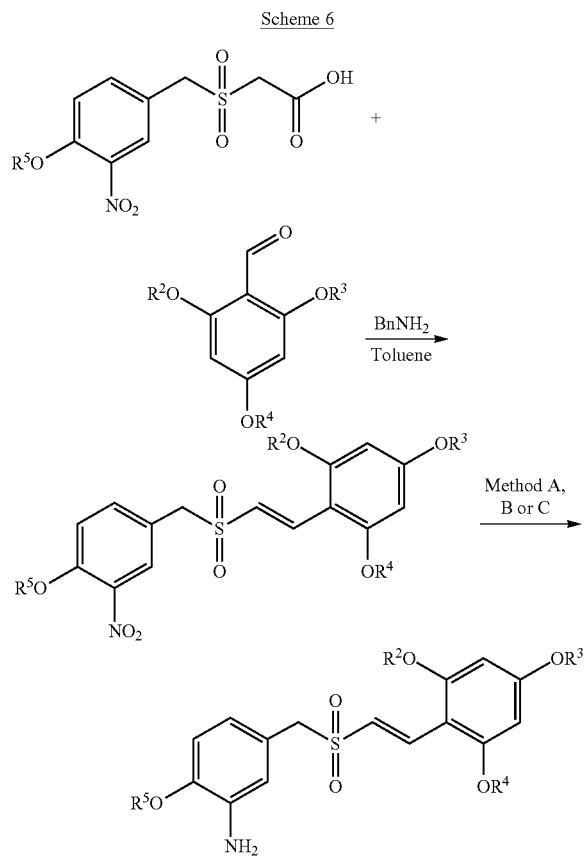

Scheme 6

Synthesis of (E)-2,4,6-Trialkoxystyryl-3'-nitro-4'-alkoxy-benzylsulfone

A mixture of 4-alkoxy-3-nitrobenzylsulfonylacetic acid (10 mmol) and 2,4,6-trialkoxybenzaldehyde (10 mmol) in 25 ml toluene is heated to about 60° C. under a nitrogen atmosphere and 58 mg of benzylamine is added slowly, followed by a rinse with 5 ml of toluene. The reaction content is refluxed for about 4 h at 65-70° C. The temperature of the reaction mass is raised to reflux temperature and maintained for additional 4 hours. After completion of the reaction (TLC monitoring), the contents are cooled to room temperature, the precipitated product is filtered and dried. Yield: 3 g (73.5%). An analytically pure sample is obtained by recrystallization from 2-propanol.

Synthesis of (E)-2-Alkoxy-5-(((2,4,6-trialkoxystyryl)sulfonyl)methyl)aniline

Method A (Pt/H₂)

A hydrogenation apparatus is charged with 3 g of (E)-2,4,6-trialkoxystyryl-3'-nitro-4'-alkoxy-benzylsulfone, and 50 mL of acetonitrile. The reaction mass is stirred under nitrogen atmosphere for 30 min at 30±5° C. 300 mg of 3% Pt/C-catalyst is suspended under a nitrogen atmosphere in 1 ml of water and is transferred to the hydrogenation apparatus and washed with another 0.5 ml water for complete transfer. The hydrogenation apparatus is purged with nitrogen, then is purged with hydrogen. Hydrogen pressure is applied to the reaction and the temperature of reaction mass is raised to 65° C. to 70° C. When hydrogen absorption is stopped, the contents are cooled and the hydrogen pressure is gently released. The reactor is purged with nitrogen atmosphere and the cooled reaction mass is filtered. After washing the reaction with a small amount of acetonitrile, the solvent is distilled under vacuum. The collected precipitate is washed with chilled aqueous acetonitrile and dried. The yield is 2.14 g (76.8%).

Method B (Fe/HCl):

To a solution of 1 g (2.33 mmol) of (E)-2,4,6-trialkoxystyryl-3'-nitro-4'-alkoxy-benzylsulfone in 70 ml of methanol/acetic acid (2:1) is added 650 mg (11.66 mmol) of iron powder and the reaction contents are heated at reflux for 3 h. The reaction mixture is concentrated and the residue is taken in 40 ml of methylene chloride and 20 ml of 1M sodium hydroxide. The aqueous solution is extracted twice with 20 ml of methylene chloride. The organic phase and the extracts are combined and concentrated to obtain 825 mg (95%) of (E)-2-alkoxy-5-(((2,4,6-trialkoxystyryl)sulfonyl)methyl)aniline.

Method C (Sodium Hydrosulfite):

(E)-2,4,6-Trialkoxystyryl-4-alkoxy-3-nitrobenzylsulfone (2.5 mmol) is dissolved in acetone:water (40:20 mL) and heated to 50° C. After 30 min sodium hydrosulfite (50.0 mmol) is added slowly and the temperature is maintained at 50° C. for further 30 min. After completion of reaction (TLC monitoring, chloroform on silica gel plate), the contents are cooled to room temperature, water is added, and the product is isolated by extraction with ethyl acetate. The organic phase is washed with water (3×100 mL), brine (50 mL), dried over anhydrous sodium sulfate, filtered, and concentrated under vacuum to obtain the desired crude product. The crude product is then purified by flash chromatography.

For the preparation of compounds of Formula I where $R^1$ is —CH(R)SO₂— and one of X or Y is N (exemplified by R=H in —CH(R)SO₂—), the intermediates (E)-3-alkoxy-6-(((2,4,6-trialkoxystyryl)sulfonyl)methyl)pyridin-2-amine (X=N; Y=CH) and (E)-2-alkoxy-5-(((2,4,6-trialkoxystyryl)sulfonyl)methyl)pyridin-3-amine (Y=N; X=CH), are prepared from the intermediates (E)-3-methoxy-2-nitro-6-(((2,4,6-trimethoxystyryl) sulfonyl)-methyl)pyridine and (E)-2-methoxy-3-nitro-5-(((2,4,6-trimethoxystyryl)sulfonyl)methyl)pyridine, respectively, in a manner analogous to the preceding Scheme 6.

For the preparation of compounds of Formula I where $R^1$ is —NHSO₂— the intermediate (E)-N-(3-amino-4-alkoxyphenyl)-2-(2,4,6-trialkoxyphenyl)ethenesulfon amide may be prepared. For the preparation of compounds of Formula I where $R^1$ is —NHC(=O)— the intermediate (E)-N-(3-amino-4-methoxyphenyl)-2-(2,4,6-trimethoxyphenyl)ethenecarboxamide may be prepared. These intermediates, (E)-N-(3-amino-4-alkoxyphenyl)-2-(2,4,6-trialkoxyphenyl) ethenesulfon amide (D=SO$_2$) and (E)-N-(3-amino-4-methoxyphenyl)-2-(2,4,6-trimethoxyphenyl) ethenecarboxamide (D=C(=O)) may be prepared according to Scheme 7:

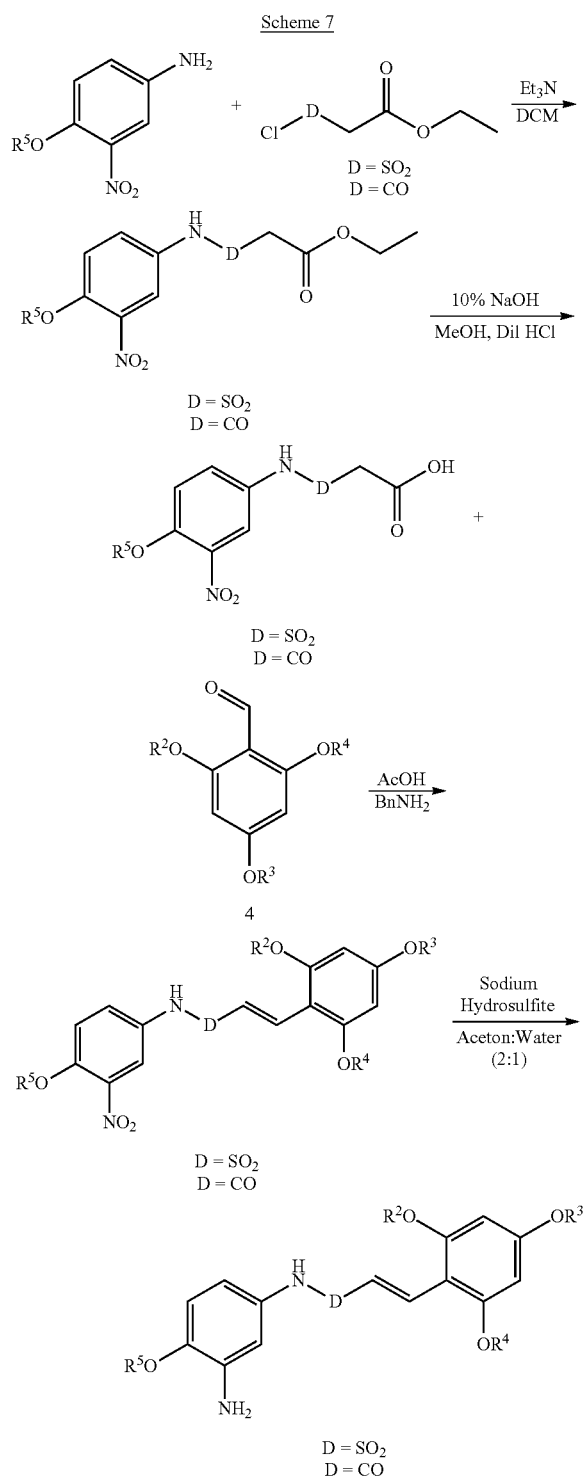

IV. Treatment of Cellular Proliferative Disorders Using Compounds of the Invention According to another embodiment of the invention, a method of treating an individual suffering from a cellular proliferative disorder, particularly cancer, is provided, comprising administering to said individual an effective amount of at least one compound according to Formula I, or a pharmaceutically acceptable salt thereof, either alone, or in combination with a pharmaceutically acceptable carrier.

According to another embodiment of the invention, a method of inducing apoptosis of cancer cells, preferably tumor cells, in an individual afflicted with cancer is provided, comprising administering to said individual an effective amount of at least one compound according to Formula I, or a pharmaceutically acceptable salt thereof, either alone, or in combination with a pharmaceutically acceptable carrier.

The compounds according to the invention may be administered to individuals (mammals, including animals and humans) afflicted with a cellular proliferative disorder such as cancer, malignant and benign tumors, blood vessel proliferative disorders, and fibrotic disorders. In a particular embodiment of the invention, the individual treated is a human.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, small cell, Large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma; colorectal cancer;

genitourinary tract cancers, including, for example, cancers of the kidney, e.g., adenocarcinoma, Wilm's tumor (nephroblastoma); cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

head and neck cancers;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

breast cancer;

hematologic cancers, including, for example, lymphoma (including but not limited to B- and T-cell lymphomas, and mantle cell lymphomas) and leukemia, e.g., acute myeloid leukemia, chronic myeloid leukemia (also known as chronic myelogenous leukemia), acute lymphoblastic leukemia, chronic lymphocytic leukemia, myeloproliferative disorders, multiple myeloma, myelodysplastic syndrome, Hodgkin's lymphoma, non-Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

In particular, the compounds are believed effective against lung cancer, pancreatic, cancer, colorectal cancer, stomach cancer, kidney cancer, bladder cancer, prostate cancer, testicular cancer, head and neck cancers, liver cancer, brain cancer, uterine cancer, cervical cancer, ovarian cancer, vaginal cancer, breast cancer, skin cancer, leukemia or lymphoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate. Non-cancer cellular proliferative disorders believed treatable by compounds according to the invention include, for example: hemangiomatosis in newborn, secondary progressive multiple sclerosis, atherosclerosis, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X-linked lymphocellular proliferative disorder (Duncan disease), post-transplantation lymphocellular proliferative disorder (PTLD), macular degeneration, and retinopathies, such as diabetic retinopathies and proliferative vitreoretinopathy (PVR).

Other non-cancer cellular proliferative disorders believed treatable by compounds according to the invention include the presence of pre-cancerous lymphoproliferative cells associated with an elevated risk of progression to a cancerous disorder. Many non-cancerous lymphocellular proliferative disorders are associated with latent viral infections such as Epstein-Barr virus (EBV) and Hepatitis C. These disorders often begin as a benign pathology and progress into lymphoid neoplasia as a function of time.

V. Salts of Compounds According to the Invention

The compounds of the present invention may take the form of salts when appropriately substituted with groups or atoms capable of forming salts. Such groups and atoms are well known to those of ordinary skill in the art of organic chemistry. The term "salts" embraces addition salts of free acids or free bases which are compounds of the invention. The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, pivalic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, tromethamine, meglumine (N-methylglucamine) and procaine. Examples of pharmaceutically unacceptable base addition salts include lithium salts and cyanate salts.

All of these salts may be prepared by conventional means from the corresponding compound according to Formula I by reacting, for example, the appropriate acid or base with the compound according to Formula I. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

VI. Pharmaceutical Compositions

A pharmaceutical composition comprises a pharmaceutically acceptable carrier and a compound, or a pharmaceutically acceptable salt thereof, according to any of Formula I.

The compounds of the invention may be administered in the form of a pharmaceutical composition, in combination with a pharmaceutically acceptable carrier. The active ingredient or agent in such formulations (i.e. a compound of Formula I) may comprise from 0.1 to 99.99 weight percent of the formulation. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the cellular proliferative disorder, the aggressiveness of the cellular proliferative disorder, and the route of administration of the compound.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive.

U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade).

Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VII. Routes of Administration of Compounds and Compositions of the Invention The compounds of Formula I, including pharmaceutically acceptable salts thereof, may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present inventions may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

VIII. Examples

The following non-limiting examples are provided to illustrate the invention. The synthetic procedures described as "general methods" describe what it is believed will be typically effective to perform the synthesis indicated. However, the person skilled in the art will appreciate that it may be necessary to vary the procedures for any given embodiment of the invention. For example, reaction monitoring, such as by using thin layer chromatography, or HPLC may be used to determine the optimum reaction time. Products may be purified by conventional techniques that will vary, for example, according to the amount of side products produced and the physical properties of the compounds. On a laboratory scale, recrystallization from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al., *Experimental Organic Chemistry: Standard and Microscale*, by L. M. Harwood et al. ($2^{nd}$ Ed., Blackwell Scientific Publications, 1998), and Advanced Practical Organic Chemistry, by J. Leonard, et al. ($2^{nd}$ Edition, CRC Press 1994).

Preparation of Intermediates

1. Synthesis of (E)-2-methoxy-5-(((2,4,6-trimethoxystyryl)sulfonyl)methyl)aniline (36)

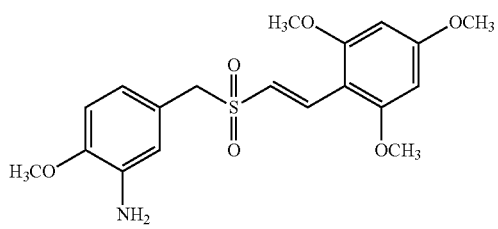 [SMILES: COc1cc(OC)c(/C=C/S(=O)(=O)Cc2ccc(OC)c(N)c2)c(OC)c1]

Step 1:

A mixture of 4-methoxy-3-nitrobenzylsulfonylacetic acid (10 mmol) and 2,4,6-trimethoxybenzaldehyde (10 mmol) in 25 ml toluene was heated to about 60° C. under a nitrogen atmosphere and 58 mg of benzylamine was added slowly, followed by a rinse with 5 ml of toluene. The reaction content was refluxed for about 4 h at 65-70° C. The temperature of the reaction mass was raised to reflux temperature and maintained for additional 4 hours. After completion of the reaction (TLC monitoring), the contents were cooled to room temperature, and the precipitated product was filtered and dried. Yield: 3 g (73.5%). An analytically pure sample was obtained by recrystallization from 2-propanol, mp 184-186° C. $^1$H NMR (CDCl$_3$, 300 MHz): δ 3.84 (s, 6H, 2×OCH$_3$), 3.86 (s, 3H, OCH$_3$), 3.98 (s, 3H, OCH$_3$), 4.23 (s, 2H, CH$_2$), 6.09 (s, 2H, Ar—H), 7.03 (d, J=15.6 Hz, 1H, =CH), 7.10 (d, J=8.7 Hz, 1H, Ar—H), 7.63 (dd, J=8.7, 2.4 Hz, 1H, Ar—H), 7.80 (d, J=15.6 Hz, 1H, CH=), 7.85 (d, J=2.1 Hz, 1H, Ar—H).

Step 2:

Method A: A hydrogenation apparatus was charged with 3 g of (E)-2,4,6-trialkoxystyryl-3'-nitro-4'-alkoxy-benzylsulfone, and 50 mL of acetonitrile. The reaction mass was stirred under nitrogen atmosphere for 30 min at 30±5° C. 300 mg of 3% Pt/C-catalyst was suspended under a nitrogen atmosphere in 1 ml of water and was transferred to the hydrogenation apparatus and washed with another 0.5 ml water for complete transfer. The hydrogenation apparatus was purged with nitrogen, then was purged with hydrogen. Hydrogen pressure was applied to the reaction and the temperature of reaction mass was raised to 65° C. to 70° C. When hydrogen absorption was stopped, the contents were cooled and the hydrogen pressure was gently released. The reactor was purged with nitrogen atmosphere and the cooled reaction mass was filtered. After washing the reaction with a small amount of acetonitrile, the solvent was distilled under reduced pressure. The collected precipitate was washed with chilled aqueous acetonitrile and dried. The yield was 2.14 g (76.8%), mp 146-148° C. $^1$H NMR (CDCl$_3$, 400 MHz): δ 3.77 (s, 3H, OCH$_3$), 3.84 (s, 6H, 2×OCH$_3$), 3.85 (s, 3H, OCH$_3$), 4.24 (s, 2H, CH$_2$), 4.33 (br s, 2H, NH$_2$), 6.10 (s, 2H, Ar—H), 6.31-6.35 (m, 2H, Ar—H), 6.97 (d, J=8.3 Hz, 1H, Ar—H), 7.12 (d, J=15.6 Hz, 1H, =CH), 7.93 (d, J=15.6 Hz, 1H, CH=). $^{13}$C NMR (CDCl$_3$, 75 MHz): δ 163.7, 161.4, 147.6, 136.4, 135.1, 122.8, 121.1, 121.0, 117.2, 110.2, 103.8, 90.3, 61.7, 55.7, 55.5, 55.4.

Method B: To a solution of 1 g (2.33 mmol) of (E)-2,4,6-trialkoxystyryl-3'-nitro-4'-alkoxy-benzylsulfone in 70 ml of methanol/acetic acid (2:1) is added 650 mg (11.66 mmol) of iron powder and the reaction contents are heated at reflux for 3 h. The reaction mixture is concentrated and the residue is taken in 40 ml of methylene chloride and 20 ml of 1M sodium hydroxide. The aqueous solution is extracted twice with 20 ml of methylene chloride. The organic phase and the extracts are combined and concentrated to obtain 825 mg (95%) of (E)-2-alkoxy-5-(((2,4,6-trialkoxystyryl)sulfonyl)methyl)aniline.

Method C: (E)-2,4,6-Trimethoxystyryl-4-methoxy-3-nitrobenzylsulfone (2.5 mmol) was dissolved in acetone:water (40:20 mL) and heated to 50° C. After 30 min sodium hydrosulfite (50.0 mmol) was added slowly and maintained temperature at 50° C. for further 30 min. After completion of reaction (TLC monitoring, chloroform on silica gel plate), the contents cooled to room temperature, water was added, and the product was isolated by extraction with ethyl acetate. The organic phase was washed with water (3×100 mL), brine (50 mL), dried over anhydrous sodium sulfate, filtered, and concentrated under vacuum to obtain the desired crude product (E)-2-methoxy-5-(((2,4,6-trimethoxystyryl)sulfonyl)methyl)aniline (36). The crude product was purified by flash chromatography.

The synthesis of (36) is also described in U.S. Pat. No. 7,598,232 and in Reddy et al., *J. Med. Chem.* 2011, 54, 6254-6276, the entire disclosures of which are incorporated herein by reference.

2. Synthesis of 1-aryl-2-propyn-1-one Intermediates (23-33)

1-Aryl-2-propyn-1-ones intermediates (unsubstituted and substituted) for preparing certain compounds of Formula I where R$^6$ is the group —CH=CH—C(=O)—R$^7$ and the configuration of the double bond therein is (Z) are prepared according to Scheme 8, via General Procedures A and B.

Scheme 8: Synthesis of 1-aryl-2-propyn-1-ones (23-33)

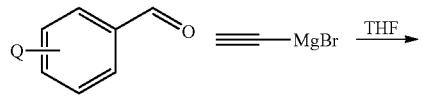

1: Q = 3,4,5-(OCH$_3$)$_3$
2: Q = 2-Cl-3,4,5-(OCH$_3$)$_3$
3: Q = 2-Br-3,4,5-(OCH$_3$)$_3$
4: Q = 2,4,6-(OCH$_3$)$_3$
5: Q = 3,4-(OMe)$_2$
6: Q = 4-OMe
7: Q = 4-F
8: Q = 4-Cl
9: Q = 4-Br
10: Q = 4-Me
11: Q = 2-Naphthaldehyde

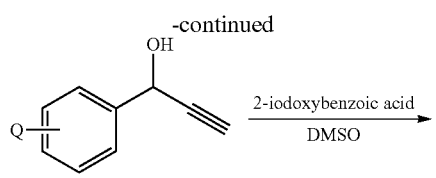

12: Q = 3,4,5-(OCH$_3$)$_3$
13: Q = 2-Cl-3,4,5-(OCH$_3$)$_3$
14: Q = 2-Br-3,4,5-(OCH$_3$)$_3$
15: Q = 2,4,6-(OCH$_3$)$_3$
16: Q = 3,4-(OMe)$_2$
17: Q = 4-OMe
18: Q = 4-F
19: Q = 4-Cl
20: Q = 4-Br
21: Q = 4-Me
22: Q = 2-(naphthalen-3-yl)prop-2-yn-1-ol

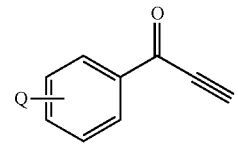

23: Q = 3,4,5-(OCH$_3$)$_3$
24: Q = 2-Cl-3,4,5-(OCH$_3$)$_3$
25: Q = 2-Br-3,4,5-(OCH$_3$)$_3$
26: Q = 2,4,6-(OCH$_3$)$_3$
27: Q = 3,4-(OMe)$_2$
28: Q = 4-OMe
29: Q = 4-F
30: Q = 4-Cl
31: Q = 4-Br
32: Q = 4-Me
33: Q = 2-(naphthalen-3-yl)prop-2-yn-1-one A. General Procedure A for Synthesis of 1-aryl-2-propyn-1-ols (12-22)

A solution of aldehyde 1-11 (5 mmol) in dry tetrahydrofuran (THF) is added to a stirred solution of ethynylmagnesium bromide in THF (0.5 M solution, 7.5 mmol) at 0° C. The solution is stirred at 0° C. temperature for 2 h then warmed to room temperature and stirred for another 6-7 h. Saturated aqueous ammonium chloride solution 5 mL is added, the mixture is evaporated in vacuo and partitioned between ethyl acetate and saturated ammonium chloride solution. The organic layer is washed with brine, dried over anhydrous Na$_2$SO$_4$ and evaporated in vacuo to obtain pure 1-aryl-2-propyn-1-ols (12-22), which are used without further purification for the preparation of 1-aryl-2-propyn-1-ones (23-33) according to General Procedure B.

Preparative Example 1: 1-(3,4,5-Trimethoxyphenyl)prop-2-yn-1-ol (12)

Following the method described in General Procedure A, 3,4,5-trimethoxybenzaldehyde 1 was treated with ethynylmagnesium bromide and 12 was obtained as a brown solid. M.p. 51-52° C.; $^1$H NMR (CDCl3, 400 MHz): δ 2.62 (d, 1H, J=2.1 Hz, ≡—H), 3.83 (s, 3H, OCH$_3$), 3.86 (s, 6H, OCH$_3$), 5.39-5-54 (m, 1H, H—C—OH), 6.77 (s, 2H, Ar—H).

Preparative Example 2: 1-(2-Chloro-3,4,5-trimethoxyphenyl)prop-2-yn-1-ol (13)

a. 2-Chloro-3,4,5-trimethoxybenzaldehyde (2)

3,4,5-Trimethoxybenzaldehyde 1 (1.0 g, 5 mmol) was dissolved in 25 mL of dichloromethane and sulfuryl chloride (0.49 mL, 6.1 mmol) was added and stirred at 10° C. for 2 h. After the reaction was completed (checked by TLC) the solvent was concentrated under vacuum and washed with hexane to obtain a pure 2-chloro-3,4,5-trimethoxybenzaldehyde 2. Semi solid; $^1$H NMR (CDCl$_3$, 300 MHz): δ 3.91 (s, 3H, OCH$_3$), 3.93 (s, 3H, OCH$_3$), 3.99 (s, 3H, OCH$_3$), 7.27 (s, 1H, Ar—H), 10.39 (s, 1H, H—C=O).

b. 1-(2-Chloro-3,4,5-trimethoxyphenyl)prop-2-yn-1-ol (13)

Following the method described in General Procedure A, 2-chloro-3,4,5-trimethoxybenzaldehyde 2 was treated with ethynylmagnesium bromide to obtain 13 as a brown solid. M.p, 65-66° C.; $^1$H NMR (CDCl3, 400 MHz): δ 2.66 (d, 1H, J=2.4 Hz, ≡H), 3.89 (s, 3H, OCH3), 3.90 (s, 6H, OCH$_3$), 5.79-5-80 (m, 1H, H̲—C—OH), 7.14 (s, 1H, Ar—H).

Preparative Example 3: 1-(2-Bromo-3,4,5-trimethoxyphenyl)prop-2-yn-1-ol (14)

a. 2-Bromo-3,4,5-trimethoxybenzaldehyde (3)

To a solution of 3,4,5-trimethoxy benzaldehyde 1 (5.0 g, 25.4 mmol) in 50 mL chloroform (CHCl$_3$), was added N-bromosuccinimide (5.44 g, 30.5 mmol). The solution was heated at reflux temperature for 3 h. After the reaction was found to be complete by TLC analysis, the reaction mixture was brought to room temperature, the solution was washed with water and extracted with diethyl ether (Et$_2$O). The combined extracts were dried over anhydrous Na$_2$SO$_4$ and concentrated. The crude 2-bromo-3,4,5-trimethoxybenzaldehyde was recrystallized from hexanes and Et$_2$O to obtain a pure white solid. M.p 69-70 OC; $^1$H NMR (CDCl$_3$, 300 MHz): δ 3.90 (s, 3H, OCH$_3$), 3.92 (s, 6H, OCH$_3$), 7.30 (s, 1H, Ar—H), 10.15 (s, 1H, H—C=O).

b. 1-(2-Bromo-3,4,5-trimethoxyphenyl)prop-2-yn-1-ol (14)

Following the method described in General Procedure A, 2-bromo-3,4,5-trimethoxybenzaldehyde 3 was treated with ethynylmagnesium bromide to obtain 14 as a brown solid. M.p. 59-60 OC; $^1$H NMR (CDCl3, 400 MHz): δ 2.66 (d, 1H, J=2.1 Hz, ≡H), 3.88 (s, 3H, OCH$_3$), 3.89 (s, 6H, OCH$_3$), 5.79-5-80 (m, 1H, H̲—C—OH), 7.18 (s, 1H, Ar—H).

Preparative Example 4: 1-(2,4,6-Trimethoxyphenyl)prop-2-yn-1-ol (15)

Following the method described in General Procedure A, 2,4,6-trimethoxybenzaldehyde 4 was treated with ethynylmagnesium bromide to obtain 15 as a brown solid. M.p 119-120° C.; $^1$H NMR (CDCl$_3$, 400 MHz): δ 2.42 (d, 1H, J=2.3 Hz, ≡H), 3.80 (s, 3H, OCH$_3$), 3.86 (s, 6H, OCH$_3$), 5.80-5-84 (m, 1H, H̲—C—OH), 6.14 (s, 2H, Ar—H).

Preparative Example 5: 1-(3,4-Dimethoxyphenyl)prop-2-yn-1-ol (16)

Following the method described in General Procedure A, 3,4-dimethoxybenzaldehyde 5 was treated with ethynylmagnesium bromide to obtain 16, which was used directly in the preparation of compound 27 in Preparative Example 16, below.

Preparative Example 6: 1-(4-Methoxyphenyl)prop-2-yn-1-ol (17)

Following the method described in General Procedure A, 4-methoxybenzaldehyde 6 was treated with ethynylmagnesium bromide to obtain 17 as a liquid; $^1$H NMR (CDCl$_3$, 400 MHz): δ 2.65 (d, 1H, J=2.2 Hz, ≡H), 3.79 (s, 3H, OCH$_3$), 5.37-5-40 (m, 1H, H—C—OH), 6.87-6.90 (m, 2H, Ar—H), 7.43-7.47 (m, 2H, Ar—H).

Preparative Example 7: 1-(4-Fluorophenyl)prop-2-yn-1-ol (18)

Following the method described in General Procedure A, 4-fluorobenzaldehyde 7 was treated with ethynylmagnesium bromide to obtain 18, which was used directly in the preparation of compound 29 in Preparative Example 18, below.

Preparative Example 8: 1-(4-Chlorophenyl)prop-2-yn-1-ol (19)

Following the method described in General Procedure A, 4-chlorobenzaldehyde 8 was treated with ethynylmagnesium bromide to obtain 19, was used directly in the preparation of compound 30 in Preparative Example 19, below.

Preparative Example 9: 1-(4-Bromophenyl)prop-2-yn-1-ol (20)

Following the method described in General Procedure A, 4-bromobenzaldehyde 9 was treated with ethynylmagnesium bromide to obtain 20, which was used directly in the preparation of compound 31 in Preparative Example 20, below.

Preparative Example 10: 1-(4-Methylphenyl)prop-2-yn-1-ol (21)

Following the method described in General Procedure A, 4-methylbenzaldehyde 10 was treated with ethynylmagnesium bromide to obtain 21, which was used directly in the preparation of compound 32 in Preparative Example 21, below.

Preparative Example 11: 1-(naphthalen-3-yl))prop-2-yn-1-ol (22)

Following the method described in General Procedure A, 2-naphthaldehyde 11 was treated with ethynylmagnesium bromide to obtain 22, which was used directly in the preparation of compound 33 in Preparative Example 22, below.

B. General Procedure B for the synthesis of 1-aryl-2-propyn-1-ones (23-33).

A solution of 2-iodoxy-benzoic acid (IBX) (12.5 mmol) in dimethyl sulfoxide (DMSO) (90 mL) is stirred for 5 min at room temperature until homogeneous. A solution of secondary alcohol 12-22 (5 mmol) in DMSO (5 mL) is added and the mixture is stirred for 5 h. Water (10 mL) is added and the mixture is stirred at room temperature for 10 min, cooled in ice and partitioned between water and ethyl acetate. The mixture is filtered through celite and the aqueous layer is further extracted with ethyl acetate. The organic extracts are combined, washed with water followed by saturated sodium bicarbonate solutions and brine, dried over anhydrous sodium sulfate and evaporated in vacuo to obtain the pure product. The pure product is then used without further purification in further steps.

Preparative Example 12: 1-(3,4,5-Trimethoxyphenyl)prop-2-yn-1-one (23)

Following the method described in General Procedure B, oxidation of 1-(3,4,5-trimethoxy-phenyl)prop-2-yn-1-ol 12 gave 23 as a pale yellow solid. M.p. 123-124° C.; $^1$H NMR (CDCl$_3$, 400 MHz): δ 3.35 (s, 1H, ≡—H), 3.86 (s, 3H, OCH$_3$), 3.88 (s, 6H, OCH$_3$), 7.36 (s, 2H, Ar—H).

Preparative Example 13: 1-(2-Chloro-3,4,5-trimethoxyphenyl)prop-2-yn-1-one (24)

Following the method described in General Procedure B, oxidation of 1-(2-chloro-3,4,5-trimethoxyphenyl)prop-2-yn-1-ol 13 gave 24 as a brown solid. M.p. 84-85° C.; $^1$H NMR (CDCl$_3$, 400 MHz): δ 3.50 (s, 1H, ≡—H), 3.91 (s, 3H, OCH$_3$), 3.93 (s, 3H, OCH$_3$), 3.99 (s, 3H, OCH$_3$), 7.44 (s, 1H, Ar—H).

Preparative Example 14: 1-(2-Bromo-3,4,5-trimethoxyphenyl)prop-2-yn-1-one (25)

Following the method described in General Procedure B, oxidation of 1-(2-bromo-3,4,5-trimethoxyphenyl)prop-2-yn-1-ol 14 gave 25 as a brown solid. M.p. 80-81° C.; $^1$H NMR (CDCl3, 400 MHz): δ 3.50 (s, 1H, ≡—H), 3.90 (s, 3H, OCH$_3$), 3.93 (s, 3H, OCH$_3$), 3.98 (s, 3H, OCH$_3$), 7.47 (s, 1H, Ar—H).

Preparative Example 15: 1-(2,4,6-Trimethoxyphenyl)prop-2-yn-1-one (26)

Following the method described in General Procedure B, oxidation of 1-(2,4,6-trimethoxy-phenyl)prop-2-yn-1-ol 15 gave 26 as a pale yellow solid. M.p. 83-84° C.; $^1$H NMR (CDCl$_3$, 400 MHz): δ 3.14 (s, 1H, ≡—H), 3.76 (s, 6H, OCH$_3$), 3.77 (s, 3H, OCH$_3$), 6.03 (s, 2H, Ar—H).

Preparative Example 16: 1-(3,4-Dimethoxyphenyl)prop-2-yn-1-one (27)

Following the method described in General Procedure B, oxidation of 1-(3,4-dimethoxyphenyl)prop-2-yn-1-ol 16 gave 27 as a solid. M.p. 81-82 OC; $^1$H NMR (CDCl$_3$, 400 MHz): δ 3.40 (s, 1H, ≡—H), 3.97 (s, 3H, OCH$_3$), 4.00 (s, OCH$_3$), 6.96 (d, 1H, Ar—H), 7.63 (d, 1H, Ar—H), 7.89-7.92 (m, 1H, Ar—H).

Preparative Example 17: 1-(4-Methoxyphenyl)prop-2-yn-1-one (28)

Following the method described in General Procedure B, oxidation of 1-(4-methoxyphenyl)prop-2-yn-1-ol 17 gave 28 as a solid. M.p. 81-82 OC; $^1$H NMR (CDCl$_3$, 400 MHz): δ 3.36 (s, 1H, ≡—H), 3.88 (s, 3H, OCH$_3$), 6.94-6.96 (m, 2H, Ar—H), 8.11-8.13 (m, 2H, Ar—H).

Preparative Example 18: 1-(4-Fluorophenyl)prop-2-yn-1-one (29)

Following the method described in General Procedure B, oxidation of 1-(4-fluorophenyl)prop-2-yn-1-ol 18 gave 29 as a pale yellow solid. $^1$H NMR (CDCl$_3$, 300 MHz): δ 3.48 (s, 1H, ≡—H), 7.16-7.22 (m, 2H, Ar—H), 8.15-8.23 (m, 2H, Ar—H).

Preparative Example 19: 1-(4-Chlorophenyl)prop-2-yn-1-one (30)

Following the method described in General Procedure B, oxidation of 1-(4-chlorophenyl)prop-2-yn-1-ol 19 gave 30 as a solid. $^1$H NMR (CDCl$_3$, 400 MHz): δ 3.48 (s, 1H, ≡—H), 7.50 (d, 2H, Ar—H), 8.13 (d, 2H, Ar—H).

Preparative Example 20: 1-(4-Bromophenyl)prop-2-yn-1-one (31)

Following the method described in General Procedure B, oxidation of 1-(4-bromophenyl)prop-2-yn-1-ol 20 gave 31 as a solid.

Preparative Example 21: 1-(4-Methylphenyl)prop-2-yn-1-one (32)

Following the method described in General Procedure B, oxidation of 1-(4-methylphenyl)prop-2-yn-1-ol 21 gave 32 as a solid.

Preparative Example 22: 1-(Naphthalene-3-yl)prop-2-yn-1-one (33)

Following the method described in General Procedure B, oxidation of 1-(naphthalene-3-yl)prop-2-yn-1-ol 22 gave 33 as a solid.

3. Synthesis of (E)-3-chloro-1-arylprop-2-en-1-one intermediates

The substituted (E)-3-chloro-1-arylprop-2-en-1-one intermediates 138-148 (ClCH=CH(C=O)R$^7$; R$^7$=substituted phenyl), for preparation of certain compounds according to Formula I wherein R$^6$ is the group —CH=CH—C(=O)—R$^7$ and the configuration of the double bond in the group is (E), are prepared according to Scheme 8a, via General Procedure C.

Scheme 8a:

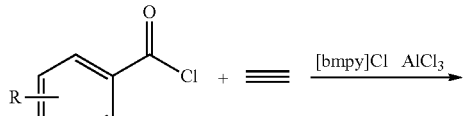

138: R = H
139: R = Cl
142: R = CH$_3$
143: R = OCH$_3$
146: R = 2-Cl-3,4,5-(OCH$_3$)$_3$
148: R = 2,4,6-(OCH$_3$)$_3$

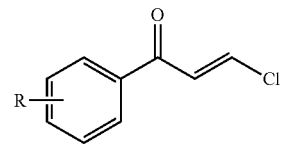

140: R = F
141: R = Br
144: R = 3,4-(OCH$_3$)$_2$
145: R = 3,4,5-(OCH$_3$)$_3$
147: R = 2-Br-3,4,5-(OCH$_3$)$_3$

General Procedure for the Synthesis of (E)-3-chloro-1-arylprop-2-en-1-one Intermediates 138-148

A suspension of [bimpy]Cl—AlCl$_3$ (1.25 eq) in 1,2-dichloroethane is cooled to 0° C. An aroyl chloride (1 eq) is added drop wise. The mixture is stirred at 0° C. for 15 min and then heated to 50° C. and acetylene is passed through the mixture for 2 h. The mixture is then poured into ice (50 mL) and extracted with CH$_2$Cl$_2$ (3×50 mL). The organic layer is dried over anhydrous Na$_2$SO$_4$, filtered and concentrated under vacuum. The resulting black oil is purified by flash column chromatography and used directly to prepare compounds of Examples 1-90 wherein R$^7$ is aryl or substituted aryl.

The following (E)-3-chloro-1-arylprop-2-en-1-ones are prepared:

138

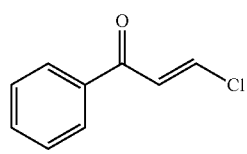

(E)-3-chloro-1-phenylprop-2-en-1-one

139

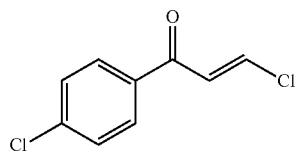

(E)-3-chloro-1-(4-chlorophenyl)prop-2-en-1-one

140

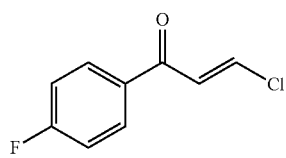

(E)-3-chloro-1-(4-fluorophenyl)prop-2-en-1-one

141

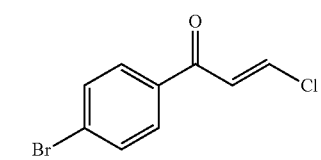

(E)-1-(4-bromophenyl)-3-chloroprop-2-en-1-one

142

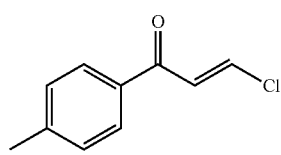

(E)-3-chloro-1-p-tolylprop-2-en-1-one

143

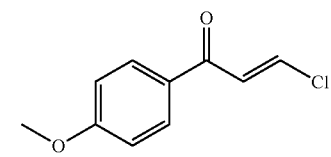

(E)-3-chloro-1-(4-methoxyphenyl)prop-2-en-1-one

144

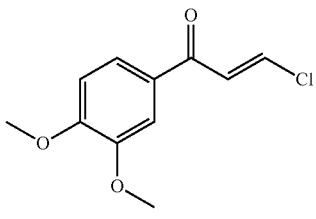

(E)-3-chloro-1-(3,4-dimethoxyphenyl)prop-2-en-1-one

145

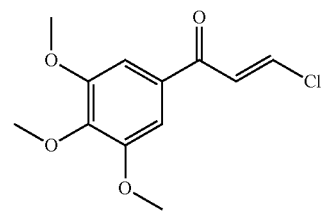

(E)-3-chloro-1-(3,4,5-trimethoxyphenyl)prop-2-en-1-one

146

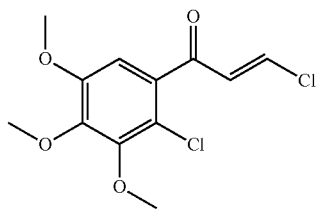

(E)-3-chloro-1-(2-chloro-3,4,5-trimethoxyphenyl)prop-2-en-1-one

147

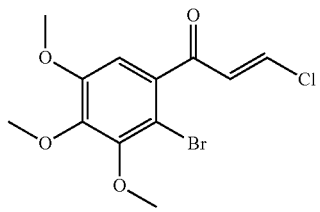

(E)-1-(2-bromo-3,4,5-trimethoxyphenyl)-3-chloroprop-2-en-1-one

148

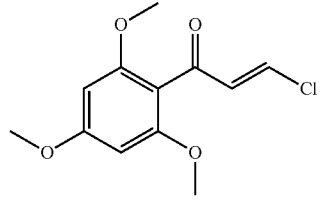

(E)-3-chloro-1-(2,4,6-trimethoxyphenyl)prop-2-en-1-one

4. Synthesis of (E)-N-(3-amino-4-alkoxyphenyl)-2-(2,4,6-trialkoxyphenyl)ethenesulfonamide (44)

Synthesis of (E)-N-(3-amino-4-methoxyphenyl)-2-(2,4,6-trimethoxyphenyl)ethenecarboxamide (45)

(E)-N-(3-amino-4-alkoxyphenyl)-2-(2,4,6-trialkoxyphenyl)ethenesulfonamide 44 and (E)-N-(3-amino-4-methoxyphenyl)-2-(2,4,6-trimethoxyphenyl)ethenecarboxamide 45, useful as intermediates for making certain compounds according to Formula I where R¹ is —NHSO₂— or —NHC(=O)—, respectively, may be prepared according to Scheme 9 as follows:

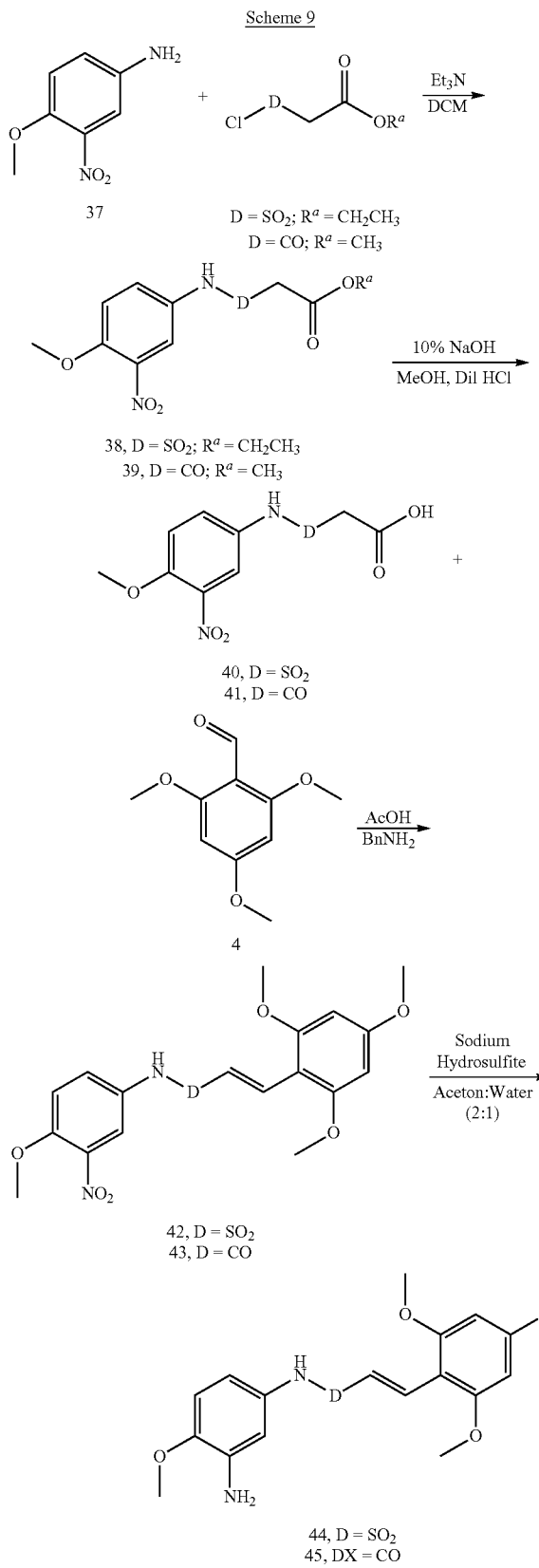

Scheme 9

Preparative Example 23: Ethyl 2-(N-(4-Methoxy-3-nitrophenyl)sulfamoyl)acetate (38)

To a solution of 3-nitro-4-methoxyaniline, 37 (107 mmol) in dichloromethane (150 mL) at 10° C., was added triethylamine (161 mmol) drop wise and stirred for 15 min at the same temperature. To this, ethyl 2-(chlorosulfonyl)acetate (22.0 g, 118 mmol) dissolved in dichloromethane (25 mL) was added slowly at the same temperature. Once the addition was over, the reaction mixture was allowed to warm to room temperature and stirred for 3 h. After completion of the reaction, water was added, and the reaction mixture was stirred for 15 min. The organic layer was separated, dried over anhydrous sodium sulfate and evaporated under reduced pressure to obtain crude 38. The crude 38 was purified on a silica gel column purification (1:1, ethyl acetate:hexane), resulting in pure 38 as a white crystalline sold, mp 115-119° C. ¹H NMR (CDCl₃, 300 MHz): δ 1.36 (t, J=7.2 Hz, 3H, CH₃), 3.94 (s, 2H, CH₂), 3.99 (s, 3H, OCH₃), 4.32 (q, J=7.2 Hz, 2H, OCH₂), 7.07 (br s, 1H, NH), 7.13 (d, J=9.0 Hz, 1H, Ar—H), 7.62 (dd, J=2.7, 9.0 Hz, 1H, Ar—H), 7.86 (d, J=2.7 Hz, 1H, Ar—H).

Preparative Example 24: Methyl 2-(N-(4-Methoxy-3-nitrophenyl)carbamoyl)acetate (39)

To a solution of 3-nitro-4-methoxyaniline, 37 (107 mmol) in dichloromethane (150 mL) at 10° C., was added triethylamine (161 mmol) drop wise and stirred for 15 min at the same temperature. To this, methyl 2-(chlorocarbonyl)acetate (22.0 g, 118 mmol) dissolved in dichloromethane (25 mL) was added slowly at the same temperature. Once the addition was complete, the reaction mixture was allowed to warm to room temperature and stirred for 3 h. After completion of the reaction, water was added, and stirring was continued for an additional 15 min. The organic layer was separated, dried over anhydrous sodium sulfate and evaporated under reduced pressure to obtain crude 39. The crude 39 was purified on a silica gel column purification (1:1, ethyl acetate:hexane), resulting in pure 39. M.p. 125-127° C. ¹H NMR (CDCl₃, 300 MHz): δ 3.52 (s, 2H, CH₂), 3.83 (s, 3H, OCH₃), 3.96 (s, 3H, OCH₃), 7.07 (d, J=9.3 Hz, 1H, Ar—H), 7.79 (dd, J=2.7, 9.3 Hz, 1H, Ar—H), 8.09 (d, J=2.7 Hz, 1H, Ar—H), 9.39 (br s, 1H, NH). HRMS found [M+H]⁺ (m/z): 269.0729. Calcd for C₁₁H₁₂N₂O₆ m/z: 268.0695.

Preparative Example 25: 2-(N-(4-methoxy-3-nitrophenyl)sulfamoyl)acetic acid (40)

A cooled solution of sodium hydroxide (122 mmol) in water (122 mL) was added to ethyl 2-(N-(4-methoxy-3-nitrophenyl)sulfamoyl)acetate 38 (18.1 mmol) slowly with continued stirring for 3 h at room temperature. After completion of the reaction, the reaction mixture was cooled to 0° C. Concentrated hydrochloric acid was added slowly at 0° C. until the pH of the reaction mixture was between 3.0-4.0, followed by stirring for an additional 30 min. The solid formed was filtered, washed with cold water and dried under vacuum. The dried product was used without further purification. Light yellow sold, mp 154-156° C. ¹H NMR (DMSO-d₆, 300 MHz): δ 3.91 (s, 3H, OCH₃), 4.14 (s, 2H, CH₂), 7.39 (d, J=9.0 Hz, 1H, Ar—H), 7.50 (dd, J=2.7, 9.0 Hz, 1H, Ar—H), 7.73 (d, J=2.7 Hz, 1H, Ar—H), 10.22 (br s, 1H, NH), 12.71 (br s, 1H, COOH).

Preparative Example 26: 2-(N-(4-methoxy-3-nitrophenyl)carbamoyl)acetic acid (41)

A cooled solution of sodium hydroxide (122 mmol) in water (122 mL) was added to methyl 2-(N-(4-methoxy-3- nitrophenyl)carbamoyl) acetate 39 (18.1 mmol) slowly with continued stirring for 3 h at room temperature. After completion of the reaction, the reaction mixture was cooled to 0° C. Concentrated hydrochloric acid was added slowly at 0° C. until the pH of the reaction mixture was between 3.0-4.0, followed by stirring for an additional 30 min. The solid formed was filtered, washed with cold water and dried under vacuum. The dried product was used without further purification. M.p. 160-162° C. $^1$H NMR (DMSO-d$_6$, 300 MHz): δ 3.36 (s, 2H, CH$_2$), 3.89 (s, 3H, OCH$_3$), 7.35 (d, J=9.3 Hz, 1H, Ar—H), 7.73 (dd, J=2.7, 9.3 Hz, 1H, Ar—H), 8.25 (d, J=2.7 Hz, 1H, Ar—H), 10.47 (br s, 1H, NH). HRMS found [M–H]$^+$ (m/z): 253.0572. Calcd for C$_{10}$H$_{10}$N$_2$O$_6$ m/z: 254.0539.

Preparative Example 27: (E)-N-(3-nitro-4-methoxyphenyl)-2-(2,4,6-trimethoxyphenyl)ethenesulfonamide (42)

The title compound was prepared by following the procedure described for the synthesis of compound 35, by substituting 2-(N-(4-methoxy-3-nitrophenyl) sulfamoyl) acetic acid 40 for 4-methoxy-3-nitrobenzylsulfonylacetic acid 34, and reacting with 2,4,6-trimethoxybenzaldehyde in toluene having a catalytic amount of benzyl amine. M.p. 113-115° C. $^1$H NMR (DMSO-d$_6$, 300 MHz): δ 3.83 (s, 9H, 3×OCH$_3$), 3.86 (s, 3H, OCH$_3$), 6.28 (s, 2H, Ar—H), 6.95 (d, J=15.3 Hz, 1H, =CH), 7.34 (d, J=9.0 Hz, 1H, Ar—H), 7.42 (dd, J=2.7, 9.0 Hz, 1H, Ar—H), 7.61 (d, J=15.6 Hz, 1H, CH=), 7.65 (d, J=2.7 Hz, 1H, Ar—H), 9.94 (br s, 1H, NH).

Preparative Example 28: (E)-N-(3-nitro-4-methoxyphenyl)-2-(2,4,6-trimethoxyphenyl)ethanecarboxamide (43)

The title compound was prepared by following the procedure described for the synthesis of compound 35, by substituting 2-(N-(4-methoxy-3-nitrophenyl) carbamoyl) acetic acid 41 for 4-methoxy-3-nitrobenzylsulfonylacetic acid 34 and reacting with 2,4,6-trimethoxybenzaldehyde in toluene having a catalytic amount of benzyl amine. M.p. 174-177° C. $^1$H NMR (DMSO-d$_6$, 300 MHz): δ 3.85 (s, 3H, OCH$_3$), 3.89 (s, 6H, 2×OCH$_3$), 3.90 (s, 3H, OCH$_3$), 6.31 (s, 2H, Ar—H), 6.97 (d, J=15.6 Hz, 1H, =C), 7.36 (d, J=9.3 Hz, 1H, Ar—H), 7.86 (dd, J=2.4, 9.3 Hz, 1H, Ar—H), 7.90 (d, J=15.6 Hz, 1H, CH=), 8.40 (d, J=2.4 Hz, 1H, Ar—H), 10.32 (br s, 1H, NH). HRMS found [M+H]$^+$ (m/z): 389.1304. Calcd for C$_{19}$H$_{20}$N$_2$O$_7$ m/z: 388.1271.

Preparative Example 29: (E)-N-(3-amino-4-methoxyphenyl)-2-(2,4,6-trimethoxyphenyl)ethenesulfonamide (44)

The title compound was prepared by following the procedure described in Method C for the synthesis of compound 36, substituting (E)-N-(4-methoxy-3-nitrophenyl)-2-(2,4,6-trimethoxyphenyl)ethanesulfonamide 42 for 2,4,6-trialkoxystyryl-4-alkoxy-3-nitrobenzylsulfone 35. M.p. 113-115° C. $^1$H NMR (CDCl$_3$, 300 MHz): δ 3.82 (s, 3H, OCH$_3$), 3.84 (s, 6H, 2×OCH$_3$), 3.85 (s, 3H, OCH$_3$), 6.07 (br s, 1H, NH), 6.09 (s, 2H, Ar—H), 6.53 (dd, J=2.4, 8.4 Hz, 1H, Ar—H), 6.67-6.69 (m, 2H, Ar—H), 7.12 (d, J=15.6 Hz, 1H, =CH), 7.85 (d, J=15.6 Hz, 1H, CH=). $^{13}$C NMR (CDCl$_3$, 75 MHz): δ 163.3, 161.2, 145.1, 136.8, 133.1, 130.2, 123.1, 112.3, 110.6, 109.7, 104.0, 90.4, 55.8, 55.7, 55.4.

The preparation of 44 is also described in WO03072063, the entire disclosure of which is incorporated by reference.

Preparative Example 30: (E)-N-(3-amino-4-methoxyphenyl)-2-(2,4,6-trimethoxyphenyl)ethenecarboxa amide (45)

The title compound was prepared by following the procedure described in Method C for the synthesis of compound 36, substituting (E)-N-(4-methoxy-3-nitrophenyl)-2-(2,4,6-trimethoxyphenyl)ethenecarboxamide 43 for 2,4,6-trialkoxystyryl-4-alkoxy-3-nitrobenzylsulfone 35. M.p. 143-144° C. $^1$H NMR (CDCl$_3$, 300 MHz): δ 3.84 (s, 3H, OCH$_3$), 3.86 (s, 3H, OCH$_3$), 3.88 (s, 6H, 2×OCH$_3$), 6.14 (s, 2H, Ar—H), 6.73 (d, J=8.4 Hz, 1H, Ar—H), 6.82 (br s, 1H, NH), 6.88 (d, J=15.9 Hz, 1H, =C), 7.23-7.28 (m, 2H, Ar—H), 8.12 (d, J=15.6 Hz, 1H, CH=). HRMS found [M+H]$^+$ (m/z): 359.1562. Calcd for C$_{19}$H$_{22}$N$_2$O$_5$ m/z: 358.1529.

The preparation of 45 is also described in WO04037751, the entire disclosure of which is incorporated by reference.

Preparative Example 31: (E)-3-methoxy-6-(((2,4,6-trimethoxystyryl)sulfonyl)methyl)pyridin-2-amine (46)

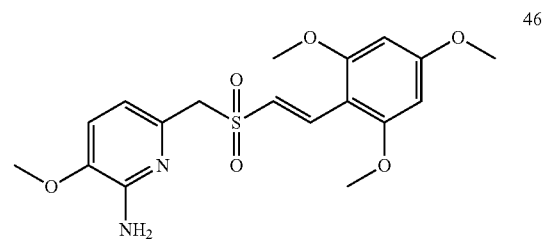

46

(E)-3-methoxy-6-(((2,4,6-trimethoxystyryl)sulfonyl) methyl)pyridin-2-amine 46, useful as an intermediate for making compounds according to Formula I where R$^1$ is —CH(R)SO$_2$— and X and Y are respectively N and CH, is prepared in a manner analogous to Scheme 6, by substituting 2-(((5-methoxy-6-nitropyridin-2-yl)methyl)sulfonyl)acetic acid for 4-alkoxy-3-nitrobenzylsulfonylacetic acid as the staring material and reacting with 2,4,6-trimethoxybenzaldehyde to obtain (E)-3-methoxy-2-nitro-6-(((2,4,6-trimethoxystyryl)sulfonyl)-methyl)pyridine, which is then reduced according to Method B to (E)-3-methoxy-6-(((2,4,6-trimethoxystyryl)sulfonyl)methyl)pyridin-2-amine (46).

Preparative Example 32: (E)-2-methoxy-5-(((2,4,6-trimethoxystyryl) sulfonyl)methyl)pyridin-3-amine (47)

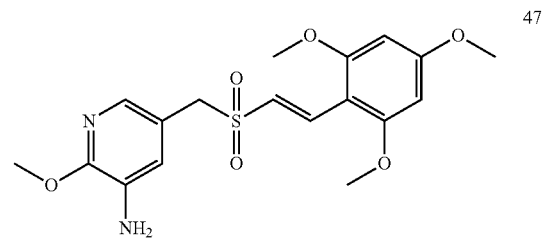

47

(E)-2-methoxy-5-(((2,4,6-trimethoxystyryl) sulfonyl) methyl)pyridin-3-amine 47, useful as an intermediate for making compounds according to Formula I where R$^1$ is —CH(R)SO$_2$— and X and Y are respectively CH and N, is prepared in a manner analogous to Scheme 6, substituting 2-(((6-methoxy-5-nitropyridin-3-yl)methyl)sulfonyl)acetic acid for 4-alkoxy-3-nitrobenzylsulfonylacetic acid as the staring material and reacting with 2,4,6-trimethoxybenzaldehyde to obtain (E)-2-methoxy-3-nitro-5-(((2,4,6-trimethoxystyryl)sulfonyl)methyl)pyridine, which is then reduced according to Method B to (E)-2-methoxy-5-(((2,4,6-trimethoxystyryl) sulfonyl)methyl)pyridin-3-amine (47).

Compounds 46 and 47 may also be prepared according to WO2011/161446 and Lu et al., J Med Chem, 2014; 57(6): 2275-91, the entire disclosures of which are incorporated by reference.

General Procedure 1 for Examples 1-90 (Formula I, $R^6$=—CH=CH—C(=O)—$R^7$; $R^{13}$=—H; m=Zero)

The compounds of Examples 1-90 (Table 1) are prepared according to Scheme 10 and General Procedure 1, starting with intermediates 36, 44, 45, 46, or 47:

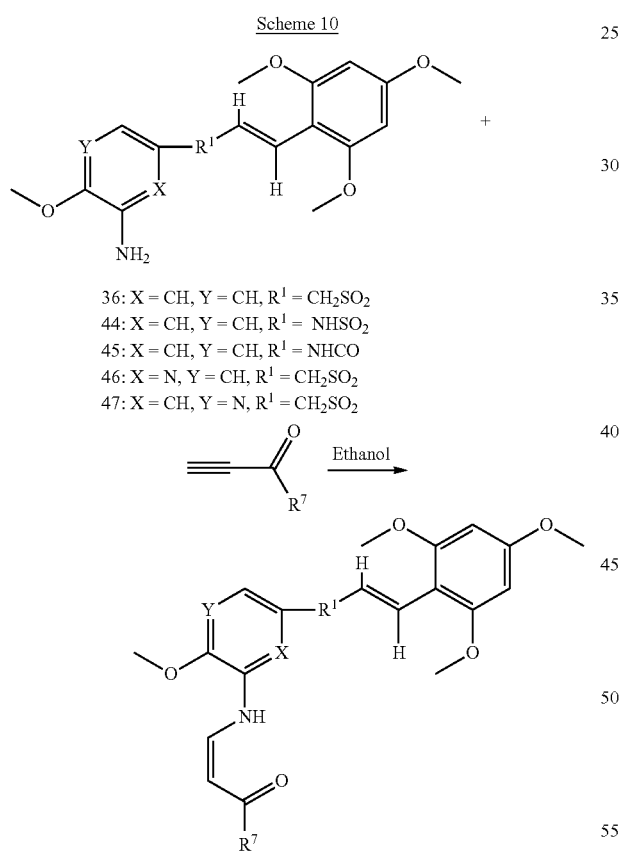

36: X = CH, Y = CH, $R^1$ = $CH_2SO_2$
44: X = CH, Y = CH, $R^1$ = $NHSO_2$
45: X = CH, Y = CH, $R^1$ = NHCO
46: X = N, Y = CH, $R^1$ = $CH_2SO_2$
47: X = CH, Y = N, $R^1$ = $CH_2SO_2$

General Procedure 1:

In Scheme 10, the ethynylketone (7.5 mmol), is dissolved in absolute ethanol and 36, 44, 45, 46 or 47 (5 mmol) is added. The reaction is stirred for 4 h at room temperature and then to reflux temperature. After the completion of reaction (checked by TLC), the reaction mixture is diluted with water and the product filtered. The crude product is purified by flash chromatography to get pure compound of Examples 1-90.

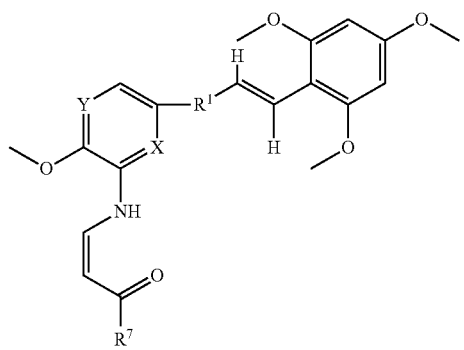

TABLE 1

| Ex. No. | X | Y | $R^1$ | $R^7$ |
|---|---|---|---|---|
| 1 | CH | CH | —$CH_2SO_2$— | ethoxy group |
| 2 | CH | CH | —$CH_2SO_2$— | isopropyl group |
| 3 | CH | CH | —$CH_2SO_2$— | methoxy group |
| 4 | CH | CH | —$CH_2SO_2$— | 4-methoxyphenyl |
| 5 | CH | CH | —$CH_2SO_2$— | 3,4,5-trimethoxyphenyl |
| 6 | CH | CH | —$CH_2SO_2$— | 2,4,6-trimethoxyphenyl |
| 7 | CH | CH | —$CH_2SO_2$— | 2-chloro-3,4,5-trimethoxyphenyl |

TABLE 1-continued

| Ex. No. | X | Y | R¹ | R⁷ |
|---|---|---|---|---|
| 8 | CH | CH | —CH₂SO₂— | 2-bromo-3,4,5-trimethoxyphenyl |
| 9 | CH | CH | —CH₂SO₂— | 4-methylpiperazin-1-yl |
| 10 | CH | CH | —CH₂SO₂— | piperazin-1-yl |
| 11 | CH | CH | —CH₂SO₂— | phenyl |
| 12 | CH | CH | —CH₂SO₂— | 4-fluorophenyl |
| 13 | CH | CH | —CH₂SO₂— | 4-chlorophenyl |
| 14 | CH | CH | —CH₂SO₂— | 4-bromophenyl |
| 15 | CH | CH | —CH₂SO₂— | 4-methylphenyl |
| 16 | CH | CH | —CH₂SO₂— | benzo[1,3]dioxol-5-yl |
| 17 | CH | CH | —CH₂SO₂— | 3,4-dimethoxyphenyl |
| 18 | CH | CH | —CH₂SO₂— | naphthalen-2-yl |
| 19 | CH | CH | —NHSO₂— | methyl |
| 20 | CH | CH | —NHSO₂— | ethoxymethyl |
| 21 | CH | CH | —NHSO₂— | methoxymethyl |
| 22 | CH | CH | —NHSO₂— | 4-methylpiperazin-1-yl |
| 23 | CH | CH | —NHSO₂— | piperazin-1-yl |
| 24 | CH | CH | —NHSO₂— | phenyl |
| 25 | CH | CH | —NHSO₂— | 4-methoxyphenyl |
| 26 | CH | CH | —NHSO₂— | 4-fluorophenyl |
| 27 | CH | CH | —NHSO₂— | 4-chlorophenyl |
| 28 | CH | CH | —NHSO₂— | 4-bromophenyl |
| 29 | CH | CH | —NHSO₂— | 4-methylphenyl |

TABLE 1-continued

| Ex. No. | X | Y | R¹ | R⁷ |
|---|---|---|---|---|
| 30 | CH | CH | —NHSO₂— | benzo[1,3]dioxol-5-yl |
| 31 | CH | CH | —NHSO₂— | 3,4-dimethoxyphenyl |
| 32 | CH | CH | —NHSO₂— | 3,4,5-trimethoxyphenyl |
| 33 | CH | CH | —NHSO₂— | 2,4,6-trimethoxyphenyl |
| 34 | CH | CH | —NHSO₂— | 2-chloro-3,4,5-trimethoxyphenyl |
| 35 | CH | CH | —NHSO₂— | 2-bromo-3,4,5-trimethoxyphenyl |
| 36 | CH | CH | —NHSO₂— | naphthalen-2-yl |
| 37 | CH | CH | —NH(C=O)— | isopropyl |
| 38 | CH | CH | —NH(C=O)— | ethoxymethyl |
| 39 | CH | CH | —NH(C=O)— | methoxymethyl |
| 40 | CH | CH | —NH(C=O)— | 4-methylpiperazin-1-yl |
| 41 | CH | CH | —NH(C=O)— | piperazin-1-yl |
| 42 | CH | CH | —NH(C=O)— | phenyl |
| 43 | CH | CH | —NH(C=O)— | 4-methoxyphenyl |
| 44 | CH | CH | —NH(C=O)— | 4-fluorophenyl |
| 45 | CH | CH | —NH(C=O)— | 4-chlorophenyl |
| 46 | CH | CH | —NH(C=O)— | 4-bromophenyl |
| 47 | CH | CH | —NH(C=O)— | 4-methylphenyl |
| 48 | CH | CH | —NH(C=O)— | benzo[1,3]dioxol-5-yl |
| 49 | CH | CH | —NH(C=O)— | 3,4-dimethoxyphenyl |

TABLE 1-continued

| Ex. No. | X | Y | R¹ | R⁷ |
|---|---|---|---|---|
| 50 | CH | CH | —NH(C=O)— | 3,4,5-trimethoxyphenyl |
| 51 | CH | CH | —NH(C=O)— | 2,4,6-trimethoxyphenyl |
| 52 | CH | CH | —NH(C=O)— | 2-chloro-3,4,5-trimethoxyphenyl |
| 53 | CH | CH | —NH(C=O)— | 2-bromo-3,4,5-trimethoxyphenyl |
| 54 | CH | CH | —NH(C=O)— | naphthalen-2-yl |
| 55 | N | CH | —CH₂SO₂— | methyl |
| 56 | N | CH | —CH₂SO₂— | ethoxy |
| 57 | N | CH | —CH₂SO₂— | methoxy |
| 58 | N | CH | —CH₂SO₂— | 4-methylpiperazin-1-yl |
| 59 | N | CH | —CH₂SO₂— | piperazin-1-yl |
| 60 | N | CH | —CH₂SO₂— | phenyl |
| 61 | N | CH | —CH₂SO₂— | 4-methoxyphenyl |
| 62 | N | CH | —CH₂SO₂— | 4-fluorophenyl |
| 63 | N | CH | —CH₂SO₂— | 4-chlorophenyl |
| 64 | N | CH | —CH₂SO₂— | 4-bromophenyl |
| 65 | N | CH | —CH₂SO₂— | 4-methylphenyl |
| 66 | N | CH | —CH₂SO₂— | benzo[1,3]dioxol-5-yl |
| 67 | N | CH | —CH₂SO₂— | 3,4-dimethoxyphenyl |
| 68 | N | CH | —CH₂SO₂— | 3,4,5-trimethoxyphenyl |
| 69 | N | CH | —CH₂SO₂— | 2,4,6-trimethoxyphenyl |

TABLE 1-continued

| Ex. No. | X | Y | R¹ | R⁷ |
|---|---|---|---|---|
| 70 | N | CH | —CH₂SO₂— | 2,3,4-trimethoxy-6-chlorophenyl |
| 71 | N | CH | —CH₂SO₂— | 2,3,4-trimethoxy-6-bromophenyl |
| 72 | N | CH | —CH₂SO₂— | naphthalen-2-yl |
| 73 | CH | N | —CH₂SO₂— | (bond) |
| 74 | CH | N | —CH₂SO₂— | —OEt |
| 75 | CH | N | —CH₂SO₂— | —OMe |
| 76 | CH | N | —CH₂SO₂— | 4-methylpiperazin-1-yl |
| 77 | CH | N | —CH₂SO₂— | piperazin-1-yl |
| 78 | CH | N | —CH₂SO₂— | phenyl |
| 79 | CH | N | —CH₂SO₂— | 4-methoxyphenyl |
| 80 | CH | N | —CH₂SO₂— | 4-fluorophenyl |
| 81 | CH | N | —CH₂SO₂— | 4-chlorophenyl |
| 82 | CH | N | —CH₂SO₂— | 4-bromophenyl |
| 83 | CH | N | —CH₂SO₂— | 4-methylphenyl |
| 84 | CH | N | —CH₂SO₂— | benzo[1,3]dioxol-5-yl |
| 85 | CH | N | —CH₂SO₂— | 3,4-dimethoxyphenyl |
| 86 | CH | N | —CH₂SO₂— | 3,4,5-trimethoxyphenyl |
| 87 | CH | N | —CH₂SO₂— | 2,4,6-trimethoxyphenyl |
| 88 | CH | N | —CH₂SO₂— | 2,3,4-trimethoxy-6-chlorophenyl |

TABLE 1-continued

| Ex. No. | X | Y | R¹ | R⁷ |
|---|---|---|---|---|
| 89 | CH | N | —CH₂SO₂— | 2-bromo-3,4,5-trimethoxyphenyl |
| 90 | CH | N | —CH₂SO₂— | 2-naphthyl |

Example 1

(Z)-ethyl 3-((2-methoxy-5-(((E)-2,4,6-trimethoxystyrylsulfonyl)methyl)phenyl)amino) acrylate

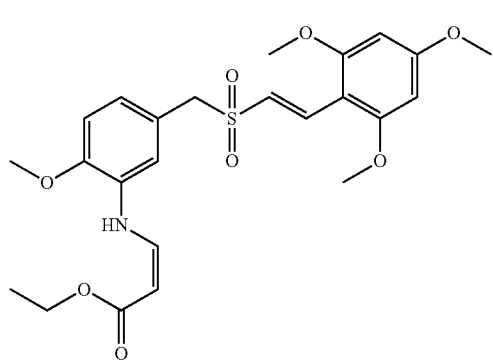

The title compound was obtained from (E)-2-methoxy-5-(((2,4,6-trimethoxystyryl)sulfonyl)methyl)aniline 36 and ethyl propiolate, following General Procedure 1. M.p. 160 OC, $^1$H NMR (CDCl₃, 300 MHz): δ 1.21 (t, 3H), 3.84 (s, 9H), 3.87 (s, 3H), 4.09 (q, 2H), 4.35 (s, 2H), 4.80 (d, 1H), 6.29 (s, 2H), 6.95-6.96 (m, 1H), 7.02-7.10 (m, 2H), 7.28 (d, 1H), 7.42-7.54 (m, 2H), 10.03 (d, 1H).

Comparative Example 1

Sodium (E)-2-(5-((2,4,6-trimethoxystyrylsulfonyl)methyl)-2-methoxyphenylamino) acetate (Rigosertib)

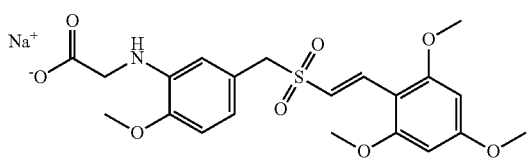

The title compound, described in U.S. Pat. No. 7,598,232, was prepared for comparison of biological activity.

Example 2

(Z)-4-((2-Methoxy-5-(((E)-2,4,6-trimethoxystyrylsulfonyl)methyl) phenyl)amino)but-3-en-2-one

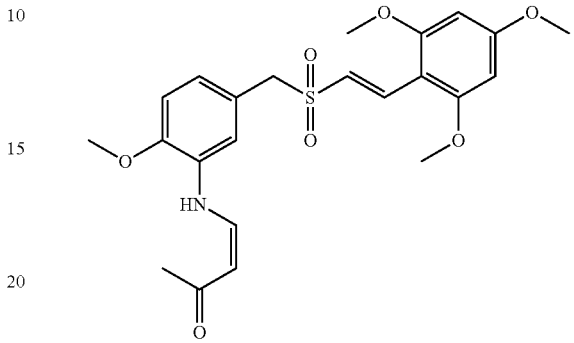

The title compound was obtained from (E)-2-methoxy-5-(((2,4,6-trimethoxystyryl)sulfonyl)methyl)aniline 36 and but-3-yn-2-one, following General Procedure 1. M.p. 120 OC, $^1$H NMR (CDCl₃, 600 MHz): δ 2.06 (s, 3H), 3.83 (s, 6H), 3.84 (s, 3H), 3.87 (s, 3H), 4.35 (s, 2H), 5.35 (d, 1H), 6.29 (s, 2H), 6.97-6.99 (m, 1H), 7.03-7.09 (m, 2H), 7.35 (d, 1H), 7.40 (dd, 1H), 7.51 (d, 1H), 11.55 (d, 1H).

Example 3

(Z)-methyl 3-((2-methoxy-5-(((E)-2,4,6-trimethoxystyrylsulfonyl)methyl)phenyl)amino) acrylate

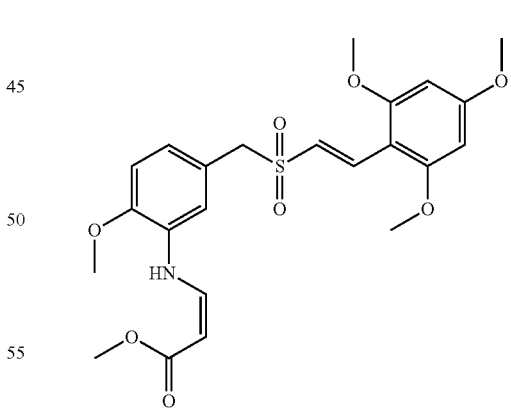

The title compound was obtained from (E)-2-methoxy-5-(((2,4,6-trimethoxystyryl)sulfonyl)methyl)aniline 36 and methyl propiolate, following General Procedure 1. M.p. 150 OC, $^1$H NMR (CDCl₃, 300 MHz): δ 3.75 (s, 3H), 3.83 (s, 6H), 3.87 (s, 3H), 3.94 (s, 3H), 4.20 (s, 2H), 4.84 (d, 1H), 6.10 (s, 2H), 6.86-6.89 (m, 1H), 6.96-7.01 (m, 3H), 7.06-7.22 (m, 1H), 7.83 (d, 1H), 10.15 (d, 1H).

Example 4

(Z)-1-(4-methoxyphenyl)-3-((2-methoxy-5-(((E)-2,4,6-trimethoxystyrylsulfonyl)methyl)phenyl) amino)prop-2-en-1-one

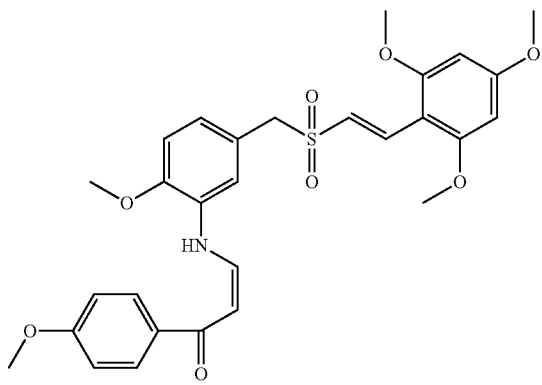

The title compound was obtained from (E)-2-methoxy-5-(((2,4,6-trimethoxystyryl)sulfonyl)methyl)aniline 36 and 1-(4-methoxyphenyl)prop-2-yn-1-one 28, following General Procedure 1. M.p. 211° C., $^1$H NMR (CDCl$_3$, 300 MHz): δ 3.83-3.85 (m, 9H), 3.89 (s, 3H), 3.99 (s, 3H), 4.23 (s, 2H), 5.80 (bs, 1H), 6.10 (s, 2H), 6.89-6.92 (m, 5H), 7.02-7.10 (m, 1H), 7.42-7.46 (m, 1H), 7.78-7.83 (d, 1H), 7.95-7.98 (d, 2H), 12.11 (d, 1H).

Example 5

(Z)-1-(3,4,5-trimethoxyphenyl)-3-((2-methoxy-5-(((E)-2,4,6-trimethoxystyrylsulfonyl)methyl)phenyl) amino) prop-2-en-1-one

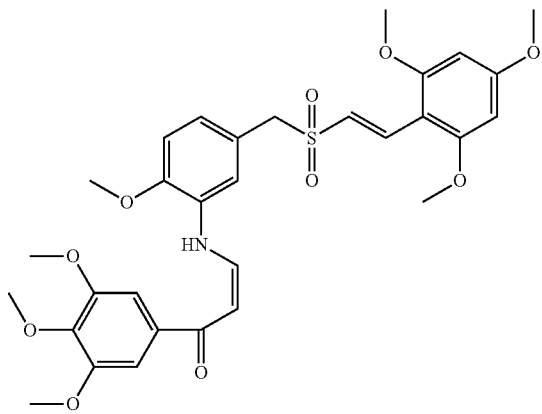

The title compound was obtained from (E)-2-methoxy-5-(((2,4,6-trimethoxystyryl)sulfonyl)methyl)aniline 36 and 1-(3,4,5-trimethoxyphenyl)prop-2-yn-1-one 23, following General Procedure 1. M.p. 202 OC, $^1$H NMR (DMSO-d$_6$, 600 MHz): δ 3.73 (s, 3H), 3.82-3.87 (m, 15H), 3.93 (s, 3H), 4.40 (s, 2H), 6.21 (d, 1H), 6.21 (s, 2H), 7.04-7.08 (m, 3H), 7.26 (s, 2H), 7.46-7.56 (m, 2H), 7.67-7.74 (m, 1H), 12.14 (d, 1H).

Example 6

(Z)-1-(2,4,6-trimethoxyphenyl)-3-((2-methoxy-5-(((E)-2,4,6-trimethoxystyryl sulfonyl)methyl)phenyl) amino) prop-2-en-1-one

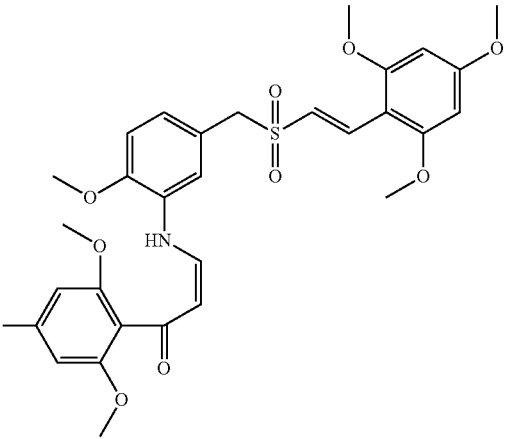

The title compound was obtained from (E)-2-methoxy-5-(((2,4,6-trimethoxystyryl)sulfonyl)methyl)aniline 36 and 1-(2,4,6-trimethoxyphenyl)prop-2-yn-1-one 26, following General Procedure 1. M.p. 200 OC, $^1$H NMR (CDCl$_3$, 300 MHz): δ 3.83-3.91 (m, 18H), 3.93 (s, 3H), 4.21 (s, 2H), 5.50 (d, 1H), 6.10 (s, 2H), 6.15 (s, 2H), 6.86-6.89 (m, 1H), 6.99-7.04 (m, 2H), 7.18 (bs, 1H), 7.25-7.30 (m, 1H), 7.78 (d, 1H), 11.80 (d, 1H).

Example 7

(Z)-1-(2-chloro-3,4,5-trimethoxyphenyl)-3-((2-methoxy-5-(((E)-2,4,6-trimethoxystyrylsulfonyl)methyl)phenyl) amino)prop-2-en-1-one

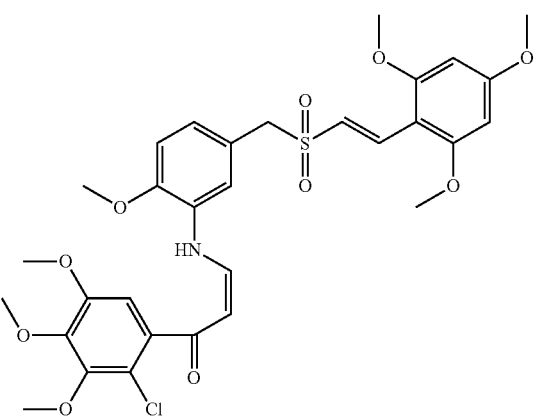

The title compound was obtained from (E)-2-methoxy-5-(((2,4,6-trimethoxystyryl)sulfonyl) methyl)aniline 36 and 1-(2-chloro-3,4,5-trimethoxyphenyl)prop-2-yn-1-one 24, following General Procedure 1. M.p. 165 OC, $^1$H NMR (CDCl$_3$, 300 MHz): δ 3.90-3.98 (m, 21H), 4.23 (s, 2H), 5.77 (d, 1H), 6.10 (s, 2H), 6.95-7.02 (m, 2H), 7.06-7.09 (m, 2H), 7.23 (bs, 1H), 7.41-7.47 (m, 1H), 7.79 (d, 1H), 12.00 (d, 1H).

Example 8

(Z)-1-(2-bromo-3,4,5-trimethoxyphenyl)-3-((2-methoxy-5-(((E)-2,4,6-trimethoxystyrylsulfonyl)methyl)phenyl)amino)prop-2-en-1-one

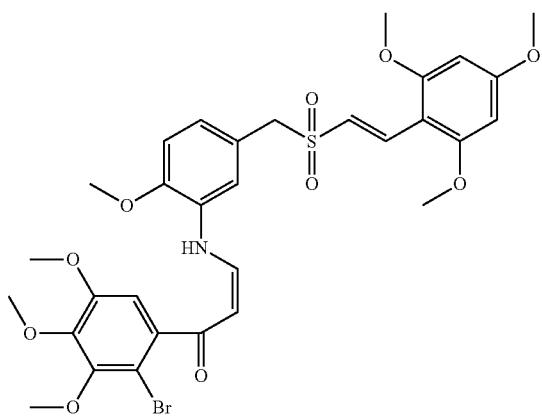

The title compound was obtained from (E)-2-methoxy-5-(((2,4,6-trimethoxystyryl)sulfonyl)methyl)aniline 36 and 1-(2-bromo-3,4,5-trimethoxyphenyl)prop-2-yn-1-one 25, following General Procedure 1. M.p. 121 °C, $^1$H NMR (CDCl$_3$, 300 MHz): δ 3.84-3.98 (m, 21H), 4.23 (s, 2H), 5.70 (d, 1H), 6.10 (s, 2H), 6.89-6.93 (m, 2H), 7.01-7.08 (m, 2H), 7.23 (bs, 1H), 7.43-7.45 (m, 1H), 7.80 (d, 1H), 11.91 (d, 1H).

Examples 9-18

(E)-2-methoxy-5-(((2,4,6-trimethoxystyryl)sulfonyl)methyl)aniline 36 is reacted according to General Procedure 1 with a reactant in Table 2 to provide the corresponding product identified in Table 2.

TABLE 2

| Ex. | Reactant | Product |
|---|---|---|
| 9 | 1-(4-methylpiperazin-1-yl)prop-2-yn-1-one | (Z)-3-((2-methoxy-5-(((E)-2,4,6-trimethoxystyrylsulfonyl)methyl)phenyl)amino)-1-(4-methylpiperazin-1-yl)prop-2-en-1-one |
| 10 | 1-(piperazin-1-yl)prop-2-yn-1-one | (Z)-3-((2-methoxy-5-(((E)-2,4,6-trimethoxystyrylsulfonyl)methyl)phenyl)amino)-1-(piperazin-1-yl)prop-2-en-1-one |

TABLE 2-continued

| Ex. | Reactant | Product |
| --- | --- | --- |
| 11 | 1-phenylprop-2-yn-1-one | (Z)-3-((2-methoxy-5-(((E)-2,4,6-trimethoxystyryl-sulfonyl)methyl)phenyl)amino)-1-phenylprop-2-en-1-one |
| 12 | 1-(4-fluorophenyl)prop-2-yn-1-one | (Z)-1-(4-fluorophenyl)-3-((2-methoxy-5-(((E)-2,4,6-trimethoxystyrylsulfonyl)methyl)phenyl)amino)prop-2-en-1-one |
| 13 | 1-(4-chlorophenyl)prop-2-yn-1-one | (Z)-1-(4-chlorophenyl)-3-((2-methoxy-5-(((E)-2,4,6-trimethoxystyrylsulfonyl)methyl)phenyl)amino)prop-2-en-1-one |

TABLE 2-continued

| Ex. | Reactant | Product |
| --- | --- | --- |
| 14 | 1-(4-bromophenyl)prop-2-yn-1-one | (Z)-1-(4-bromophenyl)-3-((2-methoxy-5-(((E)-2,4,6-trimethoxystyrylsulfonyl)methyl)phenyl)amino)prop-2-en-1-one |
| 15 | 1-(4-methylphenyl)prop-2-yn-1-one | (Z)-1-(4-methylphenyl)-3-((2-methoxy-5-(((E)-2,4,6-trimethoxystyrylsulfonyl)methyl)phenyl)amino)prop-2-en-1-one |
| 16 | 1-(benzo[d][1,3]dioxol-5-yl)prop-2-yn-1-one | (Z)-1-(benzo[d][1,3]dioxol-5-yl)-3-((2-methoxy-5-(((E)-2,4,6-trimethoxystyrylsulfonyl)methyl)phenyl)amino)prop-2-en-1-one |

TABLE 2-continued

| Ex. | Reactant | Product |
|---|---|---|
| 17 | 1-(3,4-dimethoxyphenyl)prop-2-yn-1-one | (Z)-1-(3,4-dimethoxyphenyl)-3-((2-methoxy-5-(((E)-2,4,6-trimethoxystyrylsulfonyl)methyl)phenyl)amino)prop-2-en-1-one |
| 18 | 1-(naphthalen-3-yl)prop-2-yn-1-one | (Z)-1-(naphthalen-3-yl)-3-((2-methoxy-5-(((E)-2,4,6-trimethoxystyrylsulfonyl)methyl)phenyl)amino)prop-2-en-1-one |

Example 19

(Z)-ethyl 3-((2-methoxy-5-((E)-2-(2,4,6-trimethoxyphenyl) vinylsulfonamido)phenyl)amino) acrylate

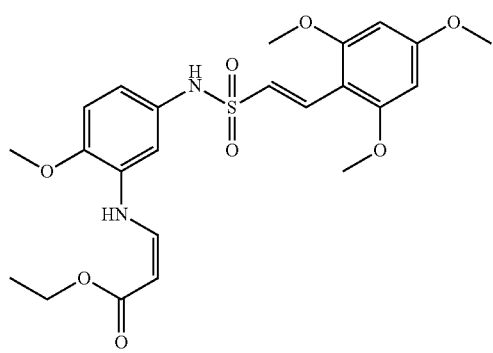

The title compound was obtained from (E)-N-(3-amino-4-methoxyphenyl)-2-(2,4,6-trimethoxyphenyl)ethenesulfonamide 44 and ethyl propiolate, following General Procedure 1. M.p. 140° C., $^1$H NMR (CDCl$_3$, 300 MHz): δ 1.18 (t, 3H), 3.81 (s, 3H), 3.82 (s, 3H), 3.83 (s, 6H), 4.05 (q, 2H), 4.87 (d, 1H), 6.27 (s, 2H), 6.72 (d, 1H), 6.69-7.03 (m, 3H), 7.34-7.39 (dd, 1H), 7.57 (d, 1H), 9.50 (s, 1H), 10.04 (d, 1H).

Examples 20-36

(E)-N-(3-amino-4-methoxyphenyl)-2-(2,4,6-trimethoxyphenyl)ethenesulfonamide 44 is reacted according to General Procedure 1 with a reactant in Table 3 to provide the corresponding products identified in Table 3.

TABLE 3

| Ex. | Reactant | Product |
|---|---|---|
| 20 | but-3-yn-2-one | (E)-N-(4-Methoxy-3-(((Z)-3-oxobut-1-en-1-yl)amino)phenyl-2-(2,4,6-trimethoxyphenyl)ethenesulfonamide |
| 21 | methyl propiolate | (Z)-methyl 3-((2-methoxy-5-((E)-2-(2,4,6-trimethoxyphenyl)vinylsulfonamido)phenyl)amino)acrylate |
| 22 | 1-(4-methylpiperazin-1-yl)prop-2-yn-1-one | (E)-N-(4-methoxy-3-(((Z)-3-(4-methylpiperazin-1-yl)-3-oxoprop-1-en-1yl)amino)phenyl)-2-(2,4,6-trimethoxyphenyl)ethenesulfonamide |
| 23 | 1-(4-methylpiperazin-1-yl)prop-2-yn-1-one | (E)-N-(4-methoxy-3-(((Z)-3-(piperazin-1-yl)-3-oxoprop-1-en-1yl)amino)phenyl)-2-(2,4,6-trimethoxyphenyl)ethenesulfonamide |

TABLE 3-continued

| Ex. | Reactant | Product |
|---|---|---|
| 24 | 1-phenylprop-2-yn-1-one | (E)-N-(4-methoxy-3-(((Z)-3-oxo-3-phenylprop-1-en-1-yl)amino)phenyl)-2-(2,4,6-trimethoxyphenyl)ethenesulfonamide |
| 25 | 1-(4-methoxyphenyl)prop-2-yn-1-one | (E)-N-(3-(((Z)-3-(4-methoxyphenyl)-3-oxoprop-1-en-1-yl)amino)-4-methoxyphenyl)-2-(2,4,6-trimethoxyphenyl)ethenesulfonamide |
| 26 | 1-(4-fluorophenyl)prop-2-yn-1-one | (E)-N-(3-(((Z)-3-(4-fluorophenyl)-3-oxoprop-1-en-1-yl)amino)-4-methoxyphenyl)-2-(2,4,6-trimethoxyphenyl)ethenesulfonamide |
| 27 | 1-(4-chlorophenyl)prop-2-yn-1-one | (E)-N-(3-(((Z)-3-(4-chlorophenyl)-3-oxoprop-1-en-1-yl)amino)-4-methoxyphenyl)-2-(2,4,6-trimethoxyphenyl)ethenesulfonamide |

TABLE 3-continued

| Ex. | Reactant | Product |
|---|---|---|
| 28 | 1-(4-bromo-phenyl)prop-2-yn-1-one | (E)-N-(3-(((Z)-3-(4-bromophenyl)-3-oxoprop-1-en-1-yl)amino)-4-methoxyphenyl)-2-(2,4,6-trimethoxyphenyl)ethenesulfonamide |
| 29 | 1-(4-methyl-phenyl)prop-2-yn-1-one | (E)-N-(3-(((Z)-3-(4-methylphenyl)-3-oxoprop-1-en-1-yl)amino)-4-methoxyphenyl)-2-(2,4,6-trimethoxyphenyl)ethenesulfonamide |
| 30 | 1-(benzo[d][1,3]dioxol-5-yl)prop-2-yn-1-one | (E)-N-(3-(((Z)-3-(benzo[d][1,3]dioxol-5-yl)-3-oxoprop-1-en-1-yl)amino)-4-methoxyphenyl)-2-(2,4,6-trimethoxyphenyl)ethenesulfonamide |
| 31 | 1-(3,4-dimethoxy-phenyl)prop-2-yn-1-one | (E)-N-(3-(((Z)-3-(3,4-dimethoxyphenyl)-3-oxoprop-1-en-1-yl)amino)-4-methoxyphenyl)-2-(2,4,6-trimethoxyphenyl)ethenesulfonamide |

TABLE 3-continued

| Ex. | Reactant | Product |
|---|---|---|
| 32 | 1-(3,4,5-trimethoxy-phenyl)prop-2-yn-1-one | (E)-N-(3-(((Z)-3-(3,4,5-trimethoxyphenyl)-3-oxoprop-1-en-1-yl)amino)-4-methoxyphenyl)-2-(2,4,6-trimethoxyphenyl)ethenesulfonamide |
| 33 | 1-(2,4,6-trimethoxy-phenyl)prop-2-yn-1-one | (E)-N-(3-(((Z)-3-(2,4,6-trimethoxyphenyl)-3-oxoprop-1-en-1-yl)amino)-4-methoxyphenyl)-2-(2,4,6-trimethoxyphenyl)ethenesulfonamide |
| 34 | 1-(2-chloro-3,4,5-trimethoxy-phenyl)prop-2-yn-1-one | (E)-N-(3-(((Z)-3-(2-chloro-3,4,5-trimethoxyphenyl)-3-oxoprop-1-en-1-yl)amino)-4-methoxyphenyl)-2-(2,4,6-trimethoxyphenyl)ethenesulfonamide |

TABLE 3-continued

| Ex. | Reactant | Product |
|---|---|---|
| 35 | 1-(2-bromo-3,4,5-trimethoxyphenyl)prop-2-yn-1-one | (E)-N-(3-(((Z)-3-(2-bromo-3,4,5-trimethoxyphenyl)-3-oxoprop-1-en-1-yl)amino)-4-methoxyphenyl)-2-(2,4,6-trimethoxyphenyl)ethenesulfonamide |
| 36 | 1-(naphthalen-3-yl)prop-2-yn-1-one | (E)-N-(3-(((Z)-3-(naphthalen-3-yl)-3-oxoprop-1-en-1-yl)amino)-4-methoxyphenyl)-2-(2,4,6-trimethoxyphenyl)ethenesulfonamide |

Example 37

(E)-N-(4-Methoxy-3-(((Z)-3-oxobut-1-en-1-yl)amino)phenyl)-3-(2,4,6-trimethoxyphenyl) acrylamide

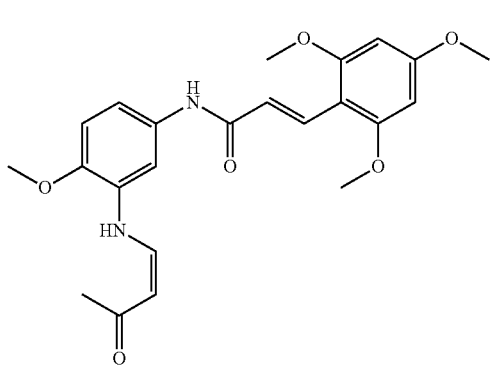

The title compound is obtained from (E)-N-(3-amino-4-methoxyphenyl)-2-(2,4,6-trimethoxyphenyl)ethenecarboxamide 45 and but-3-yn-2-one, following General Procedure 1.

Example 38

(Z)-ethyl 3-((2-methoxy-5-((E)-3-(2,4,6-trimethoxyphenyl)acrylamido)phenyl)amino)acrylate

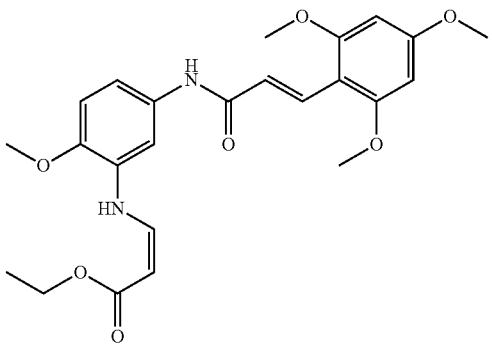

The title compound was obtained from (E)-N-(3-amino-4-methoxyphenyl)-2-(2,4,6-trimethoxyphenyl)ethenecarboxamide 45 and ethyl propiolate, following General Procedure 1. M.p. 118° C., $^1$H NMR (DMSO-$d_6$, 600 MHz): δ 1.22 (t, 3H), 3.83 (s, 3H), 3.85 (s, 3H), 3.87 (s, 6H), 4.11 (q, 2H), 4.87 (d, 1H), 6.29 (s, 2H), 6.95 (d, 1H), 7.00 (d, 1H), 7.15-7.17 (m, 1H), 7.42-7.46 (dd, 1H), 7.75 (d, 1H), 7.85 (d, 1H), 9.90 (s, 1H), 10.06 (d, 1H).

Examples 39-54

(E)-N-(3-amino-4-methoxyphenyl)-2-(2,4,6-trimethoxyphenyl)ethenecarboxamide 45 is reacted according to General Procedure 1 with a reactant in Table 4 to provide the corresponding product identified in Table 4.

TABLE 4

| Ex. | Reactant | Product |
| --- | --- | --- |
| 39 | methyl propiolate | (Z)-methyl 3-((2-methoxy-5-((E)-3-(2,4,6-trimethoxyphenyl)acrylamido)phenyl)amino)acrylate |
| 40 | 1-(4-methylpiperazin-1-yl)prop-2-yn-1-one | (E)-N-(4-methoxy-3-(((Z)-3-(4-methylpiperazin-1-yl)-3-oxoprop-1-en-1yl)amino)phenyl)-2-(2,4,6-trimethoxyphenyl)ethenecarboxamide |
| 41 | 1-(piperazin-1-yl)prop-2-yn-1-one | (E)-N-(4-methoxy-3-(((Z)-3-(piperazin-1-yl)-3-oxoprop-1-en-1yl)amino)phenyl)-2-(2,4,6-trimethoxyphenyl)ethenecarboxamide |

TABLE 4-continued

| Ex. | Reactant | Product |
|---|---|---|
| 42 | 1-phenylprop-2-yn-1-one | (E)-N-(4-methoxy-3-(((Z)-3-oxo-3-phenylprop-1-en-1yl)amino)phenyl)-2-(2,4,6-trimethoxyphenyl)ethenecarboxamide |
| 43 | 1-(4-methoxy-phenyl)prop-2-yn-1-one | (E)-N-(3-(((Z)-3-(4-methoxyphenyl)-3-oxoprop-1-en-1-yl)amino)-4-methoxyphenyl)-2-(2,4,6-trimethoxyphenyl)ethenecarboxamide |
| 44 | 1-(4-fluoro-phenyl)prop-2-yn-1-one | (E)-N-(3-(((Z)-3-(4-fluorophenyl)-3-oxoprop-1-en-1-yl)amino)-4-methoxyphenyl)-2-(2,4,6-trimethoxyphenyl)ethenecarboxamide |
| 45 | 1-(4-chloro-phenyl)prop-2-yl-1-one | (E)-N-(3-(((Z)-3-(4-chlorophenyl)-3-oxoprop-1-en-1-yl)amino)-4-methoxyphenyl)-2-(2,4,6-trimethoxyphenyl)ethenecarboxamide |

TABLE 4-continued

| Ex. | Reactant | Product |
|---|---|---|
| 46 | 1-(4-bromo-phenyl)prop-2-yn-1-one | (E)-N-(3-(((Z)-3-(4-bromophenyl)-3-oxoprop-1-en-1-yl)amino)-4-methoxyphenyl)-2-(2,4,6-trimethoxyphenyl)ethenecarboxamide |
| 47 | 1-(4-methyl-phenyl)prop-2-yn-1-one | (E)-N-(3-(((Z)-3-(4-methylphenyl)-3-oxoprop-1-en-1-yl)amino)-4-methoxyphenyl)-2-(2,4,6-trimethoxyphenyl)ethenecarboxamide |
| 48 | 1-(benzo[d][1,3]dioxol-5-yl)prop-2-yn-1-one | (E)-N-(3-(((Z)-3-(benzo[d][1,3]dioxol-5-yl)-3-oxoprop-1-en-1-yl)amino)-4-methoxyphenyl)-2-(2,4,6-trimethoxyphenyl)ethenecarboxamide |
| 49 | 1-(3,4-dimethoxy-phenyl)prop-2-yn-1-one | (E)-N-(3-(((Z)-3-(3,4-dimethoxyphenyl)-3-oxoprop-1-en-1-yl)amino)-4-methoxyphenyl)-2-(2,4,6-trimethoxyphenyl)ethenecarboxamide |

TABLE 4-continued

| Ex. | Reactant | Product |
|---|---|---|
| 50 | 1-(3,4,5-trimethoxyphenyl)prop-2-yn-1-one | (E)-N-(3-(((Z)-3-(3,4,5-trimethoxyphenyl)-3-oxoprop-1-en-1-yl)amino)-4-methoxyphenyl)-2-(2,4,6-trimethoxyphenyl)ethenecarboxamide |
| 51 | 1-(2,4,6-trimethoxyphenyl)prop-2-yn-1-one | (E)-N-(3-(((Z)-3-(2,4,6-trimethoxyphenyl)-3-oxoprop-1-en-1-yl)amino)-4-methoxyphenyl)-2-(2,4,6-trimethoxyphenyl)ethenecarboxamide |
| 52 | 1-(2-chloro-3,4,5-trimethoxyphenyl)prop-2-yn-1-one | (E)-N-(3-(((Z)-3-(2-chloro-3,4,5-trimethoxyphenyl)-3-oxoprop-1-en-1-yl)amino)-4-methoxyphenyl)-2-(2,4,6-trimethoxyphenyl)ethenesulfonamide |

TABLE 4-continued

| Ex. | Reactant | Product |
|---|---|---|
| 53 | 1-(2-bromo-3,4,5-trimethoxyphenyl)prop-2-yn-1-one | (E)-N-(3-(((Z)-3-(2-bromo-3,4,5-trimethoxyphenyl)-3-oxoprop-1-en-1-yl)amino)-4-methoxyphenyl)-2-(2,4,6-trimethoxyphenyl)ethenesulfonamide |
| 54 | 1-(naphthalen-3-yl)prop-2-yn-1-one | (E)-N-(3-(((Z)-3-(naphthalen-3-yl)-3-oxoprop-1-en-1-yl)amino)-4-methoxyphenyl)-2-(2,4,6-trimethoxyphenyl)ethenecarboxamide |

Examples 55-72

(E)-3-methoxy-6-(((2,4,6-trimethoxystyryl) sulfonyl) methyl)pyridin-2-amine 46 is reacted according to General Procedure 1 with a reactant in Table 5 to provide the corresponding product identified in Table 5.

TABLE 5

| Ex. | Reactant | Product |
|---|---|---|
| 55 | but-3-yn-2-one | (Z)-4-((3-methoxy-6-(((E)-2,4,6-trimethoxystyrylsulfonyl)methyl)pyridine-2-yl)amino)but-3-en-2-one |

TABLE 5-continued

| Ex. | Reactant | Product |
|---|---|---|
| 56 | ethyl propiolate | (Z)-ethyl 3-((3-methoxy-6(((E)-2,4,6-trimethoxystyrylsulfonyl)methyl)pyridine-2-yl)amino)acrylate |
| 57 | methyl propiolate | (Z)-methyl 3-((3-methoxy-6(((E)-2,4,6-trimethoxystyrylsulfonyl)methyl)pyridine-2-yl)amino)acrylate |
| 58 | 1-(4-methyl-piperazin-1-yl)prop-2-yn-1-one | (Z)-3-((3-methoxy-6(((E)-2,4,6-trimethoxystyrylsulfonyl)methyl)pyridine-2-yl)amino)-1-(4-methylpiperazin-1yl)prop-2-en-1-one |
| 59 | 1-(piperazin-1-yl)prop-2-yn-1-one | (Z)-3-((3-methoxy-6(((E)-2,4,6-trimethoxystyrylsulfonyl)methyl)pyridine-2-yl)amino)-1-(piperazin-1yl)prop-2-en-1-one |

TABLE 5-continued

| Ex. | Reactant | Product |
|---|---|---|
| 60 | 1-phenylprop-2-yn-1-one | (Z)-3-((3-methoxy-6(((E)-2,4,6-trimethoxystyrylsulfonyl)methyl)pyridine-2-yl)amino)-1-phenylprop-2-en-1-one |
| 61 | 1-(4-methoxyphenyl)prop-2-yn-1-one | (Z)-1-(4-methoxyphenyl)-3-((3-methoxy-6(((E)-2,4,6-trimethoxystyrylsulfonyl)methyl)pyridine-2-yl)amino)prop-2-en-1-one |
| 62 | 1-(4-fluorophenyl)prop-2-yn-1-one | (Z)-1-(4-fluorophenyl)-3-((3-methoxy-6(((E)-2,4,6-trimethoxystyrylsulfonyl)methyl)pyridine-2-yl)amino)prop-2-en-1-one |
| 63 | 1-(4-chlorophenyl)prop-2-yn-1-one | (Z)-1-(4-chloroyphenyl)-3-((3-methoxy-6(((E)-2,4,6-trimethoxystyrylsulfonyl)methyl)pyridine-2-yl)amino)prop-2-en-1-one |

TABLE 5-continued

| Ex. | Reactant | Product |
|---|---|---|
| 64 | 1-(4-bromophenyl)prop-2-yn-1-one | (Z)-1-(4-bromophenyl)-3-((3-methoxy-6(((E)-2,4,6-trimethoxystyrylsulfonyl)methyl)pyridine-2-yl)amino)prop-2-en-1-one |
| 65 | 1-(4-methylphenyl)prop-2-yn-1-one | (Z)-1-(4-methylphenyl)-3-((3-methoxy-6(((E)-2,4,6-trimethoxystyrylsulfonyl)methyl)pyridine-2-yl)amino)prop-2-en-1-one |
| 66 | 1-(benzo[d][1,3]dioxol-5-yl)prop-2-yn-1-one | (Z)-1-(benzo[d][1,3]dioxol-5-yl)-3-((3-methoxy-6(((E)-2,4,6-trimethoxystyrylsulfonyl)methyl)pyridine-2-yl)amino)prop-2-en-1-one |

TABLE 5-continued

| Ex. | Reactant | Product |
|---|---|---|
| 67 | 1-(3,4-dimethoxyphenyl)prop-2-yn-1-one | (Z)-1-(3,4-dimethoxyphenyl)-3-((3-methoxy-6(((E)-2,4,6-trimethoxystyrylsulfonyl)methyl)pyridine-2-yl)amino)prop-2-en-1-one |
| 68 | 1-(3,4,5-trimethoxyphenyl)prop-2-yn-1-one | (Z)-1-(3,4,5-trimethoxyphenyl)-3-((3-methoxy-6(((E)-2,4,6-trimethoxystyrylsulfonyl)methyl)pyridine-2-yl)amino)prop-2-en-1-one |
| 69 | 1-(2,4,6-trimethoxyphenyl)prop-2-yn-1-one | (Z)-1-(2,4,6-trimethoxyphenyl)-3-((3-methoxy-6(((E)-2,4,6-trimethoxystyrylsulfonyl)methyl)pyridine-2-yl)amino)prop-2-en-1-one |

TABLE 5-continued

| Ex. | Reactant | Product |
|---|---|---|
| 70 | 1-(2-chloro-3,4,5-trimethoxyphenyl)prop-2-yn-1-one | (Z)-1-(2-chloro-3,4,5-trimethoxyphenyl)-3-((3-methoxy-6(((E)-2,4,6-trimethoxystyrylsulfonyl)methyl)pyridine-2-yl)amino)prop-2-en-1-one |
| 71 | 1-(2-bromo3,4,5-trimethoxyphenyl)prop-2-yn-1-one | (Z)-1-(2-bromo-3,4,5-trimethoxyphenyl)-3-((3-methoxy-6(((E)-2,4,6-trimethoxystyrylsulfonyl)methyl)pyridine-2-yl)amino)prop-2-en-1-one |
| 72 | 1-(naphthalen-3-yl)prop-2-yn-1-one | (Z)-1-(naphthalen-3-yl)-3-((3-methoxy-6(((E)-2,4,6-trimethoxystyrylsulfonyl)methyl)pyridine-2-yl)amino)prop-2-en-1-one |

Examples 73-90

(E)-2-methoxy-5-(((2,4,6-trimethoxystyryl) sulfonyl)methyl)pyridin-3-amine 47 is reacted according to General Procedure 1 with a reactant in Table 6 to provide the corresponding product identified in Table 6.

TABLE 6

| Ex. | Reactant | Product |
|---|---|---|
| 73 | but-3-yn-2-one | (Z)-4-((2-methoxy-5-(((E)-2,4,6-trimethoxystyrylsulfonyl)methyl)pyridin-3-yl)amino)but-3-en-2-one |
| 74 | ethyl propiolate | (Z)-ethyl 3-((2-methoxy-5-(((E)-2,4,6-trimethoxystyrylsulfonyl)methyl)pyridine-3-yl)amino)acrylate |
| 75 | methyl propiolate | (Z)-methyl 3-((2-methoxy-5-(((E)-2,4,6-trimethoxystyrylsulfonyl)methyl)pyridine-3-yl)amino)acrylate |

TABLE 6-continued

| Ex. | Reactant | Product |
| --- | --- | --- |
| 76 | 1-(4-methylpiperazin-1-yl)prop-2-yn-1-one | (Z)-3-((2-methoxy-5-(((E)-2,4,6-trimethoxystyrylsulfonyl)methyl)pyridine-3-yl)amino)-1-(4-methylpiperazin-1yl)prop-2-en-1-one |
| 77 | 1-(piperazin-1-yl)prop-2-yn-1-one | (Z)-3-((2-methoxy-5-(((E)-2,4,6-trimethoxystyrylsulfonyl)methyl)pyridine-3-yl)amino)-1-(piperazin-1yl)prop-2-en-1-one |
| 78 | 1-phenylprop-2-yn-1-one | (Z)-3-((2-methoxy-5-(((E)-2,4,6-trimethoxystyrylsulfonyl)methyl)pyridine-3-yl)amino)-1-phenylprop-2-en-1-one |

TABLE 6-continued

| Ex. | Reactant | Product |
|---|---|---|
| 79 | 1-(4-methoxyphenyl)prop-2-yn-1-one | (Z)-1-(4-methoxyphenyl)-3-((2-methoxy-5-(((E)-2,4,6-trimethoxystyrylsulfonyl)methyl)pyridine-3-yl)amino)prop-2-en-1-one |
| 80 | 1-(4-fluorophenyl)prop-2-yn-1-one | (Z)-1-(4-fluorophenyl)-3-((2-methoxy-5-(((E)-2,4,6-trimethoxystyrylsulfonyl)methyl)pyridine-3-yl)amino)prop-2-en-1-one |
| 81 | 1-(4-chlorophenyl)prop-2-yn-1-one | (Z)-1-(4-chlorophenyl)-3-((2-methoxy-5-(((E)-2,4,6-trimethoxystyrylsulfonyl)methyl)pyridine-3-yl)amino)prop-2-en-1-one |
| 82 | 1-(4-bromophenyl)prop-2-yn-1-one | (Z)-1-(4-bromophenyl)-3-((2-methoxy-5-(((E)-2,4,6-trimethoxystyrylsulfonyl)methyl)pyridine-3-yl)amino)prop-2-en-1-one |

TABLE 6-continued

| Ex. | Reactant | Product |
|---|---|---|
| 83 | 1-(4-methylphenyl)prop-2-yn-1-one | (Z)-1-(4-methylphenyl)-3-((2-methoxy-5-(((E)-2,4,6-trimethoxystyrylsulfonyl)methyl)pyridine-3-yl)amino)prop-2-en-1-one |
| 84 | 1-(benzo[d][1,3]dioxol-5-yl)prop-2-yn-1-one | (Z)-1-(benzo[d][1,3]dioxol-5-yl))-3-((2-methoxy-5-(((E)-2,4,6-trimethoxystyrylsulfonyl)methyl)pyridine-3-yl)amino)prop-2-en-1-one |
| 85 | 1-(3,4-dimethoxyphenyl)prop-2-yn-1-one | (Z)-1-(3,4-dimethoxyphenyl)-3-((2-methoxy-5-(((E)-2,4,6-trimethoxystyrylsulfonyl)methyl)pyridine-3-yl)amino)prop-2-en-1-one |

TABLE 6-continued

| Ex. | Reactant | Product |
| --- | --- | --- |
| 86 | 1-(3,4,5-trimethoxyphenyl)prop-2-yn-1-one | (Z)-1-(3,4,5-trimethoxyphenyl)-3-((2-methoxy-5-(((E)-2,4,6-trimethoxystyrylsulfonyl)methyl)pyridine-3-yl)amino)prop-2-en-1-one |
| 87 | 1-(2,4,6-trimethoxyphenyl)prop-2-yn-1-one | (Z)-1-(2,4,6-trimethoxyphenyl)-3-((2-methoxy-5-(((E)-2,4,6-trimethoxystyrylsulfonyl)methyl)pyridine-3-yl)amino)prop-2-en-1-one |
| 88 | 1-(2-chloro-3,4,5-trimethoxyphenyl)prop-2-yn-1-one | (Z)-1-(2-chloro-3,4,5-trimethoxyphenyl)-3-((2-methoxy-5-(((E)-2,4,6-trimethoxystyrylsulfonyl)methyl)pyridine-3-yl)amino)prop-2-en-1-one |

TABLE 6-continued

| Ex. | Reactant | Product |
|---|---|---|
| 89 | 1-(2-bromo-3,4,5-trimethoxyphenyl)prop-2-yn-1-one | (Z)-1-(2-bromo-3,4,5-trimethoxyphenyl)-3-((2-methoxy-5-(((E)-2,4,6-trimethoxystyrylsulfonyl)methyl)pyridine-3-yl)amino)prop-2-en-1-one |
| 90 | 1-(naphthalen-3-yl)prop-2-yn-1-one | (Z)-1-(naphthalen-3-yl)-3-((2-methoxy-5-(((E)-2,4,6-trimethoxystyrylsulfonyl)methyl)pyridine-3-yl)amino)prop-2-en-1-one |

General Procedure 2 for Examples 91-160 (Formula I, $R^6$=—CH=CH—C(=O)—$R^7$; $R^{13}$=—H; m=Zero)

The compounds of Examples 91-160 (Table 7) are prepared according to Scheme 11 and General Procedure 2, by reacting intermediate 36, 44, 45, 46, or 47 with one of (E)-3-chloro-1-arylprop-2-en-1-ones 138-148 from Scheme 8a, above:

Scheme 11

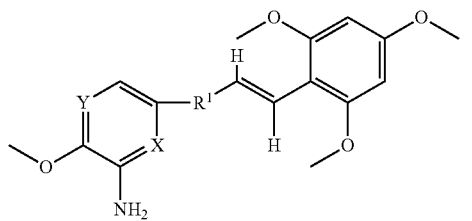

36: X = CH, Y = CH, $R^1$ = $CH_2SO_2$
44: X = CH, Y = CH, $R^1$ = $NHSO_2$
45: X = CH, Y = CH, $R^1$ = NHCO
46: X = N, Y = CH, $R^1$ = $CH_2SO_2$
47: X = CH, Y = N, $R^1$ = $CH_2SO_2$

Cl—CH=CH—C(=O)—$R^7$, $\xrightarrow{\text{Ethanol}}$
(E)-3-chloroacrylic acid or
(E)-alkylchloroacrylate -continued

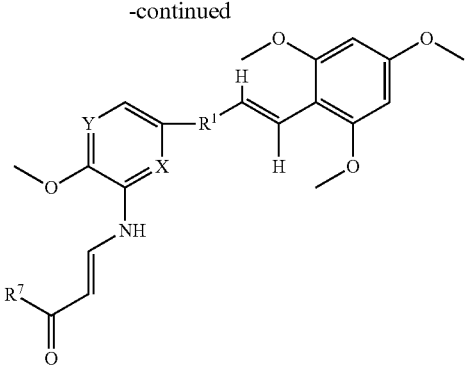

General Procedure 2:

In Scheme 11, a mixture of (i) one of 36, 44, 45, 46 or 47 (1 eq); (ii) one of (E)-3-chloro-1-arylprop-2-en-1-ones 138-148 (i 2 eq), (E)-3-chloroacrylic acid or (E)-alkylchloroacrylate; (iii) anhydrous $K_2CO_3$ (1.5 eq); and (iv) DMF; is stirred at 100° C. for 15 h. When it is cooled to room temperature, the inorganic material is removed by filtration and washed with ethyl acetate. The resulting solution is treated with ethyl acetate and water. The organic layer is separated, washed with brine, dried over $Na_2SO_4$, and concentrated. The crude product is purified by flash chromatography.

TABLE 7
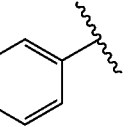
| Ex. No. | X | Y | R¹ | R⁷ | Compound |
|---|---|---|---|---|---|
| 91 | CH | CH | —CH$_2$SO$_2$— | 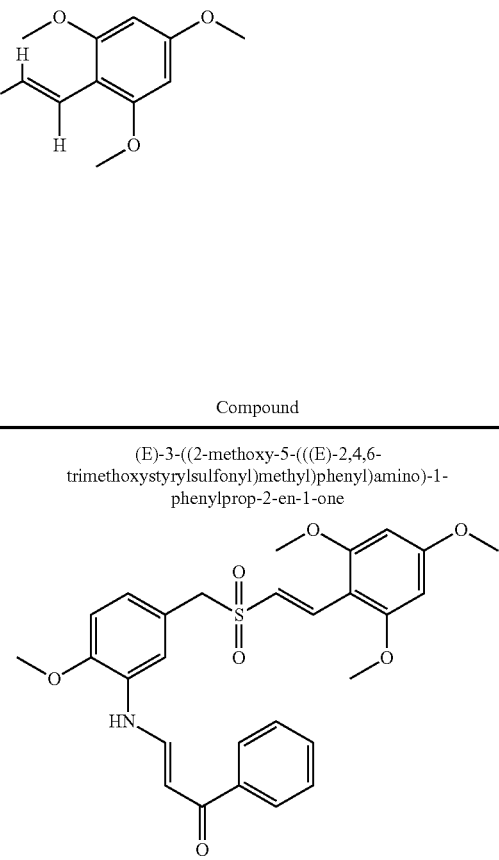 | (E)-3-((2-methoxy-5-(((E)-2,4,6-trimethoxystyrylsulfonyl)methyl)phenyl)amino)-1-phenylprop-2-en-1-one 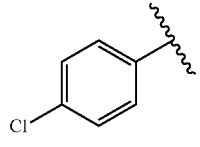 [SMILES: *c1ccc(Cl)cc1] |
| 92 | CH | CH | —CH$_2$SO$_2$— | 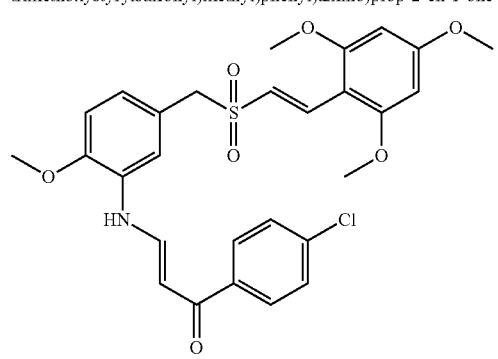 | (E)-1-(4-chlorophenyl)-3-((2-methoxy-5-(((E)-2,4,6-trimethoxystyrylsulfonyl)methyl)phenyl)amino)prop-2-en-1-one 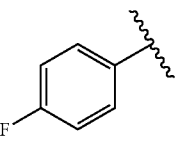 [SMILES: *c1ccc(F)cc1] |
| 93 | CH | CH | —CH$_2$SO$_2$— | 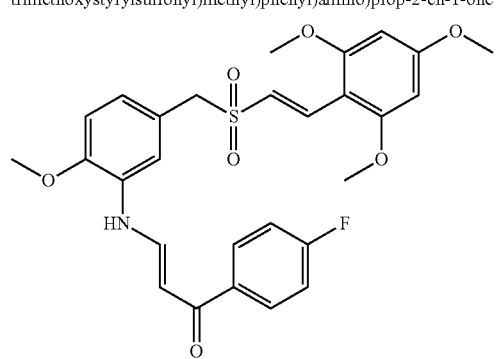 | (E)-1-(4-fluorophenyl)-3-((2-methoxy-5-(((E)-2,4,6-trimethoxystyrylsulfonyl)methyl)phenyl)amino)prop-2-en-1-one |

TABLE 7-continued
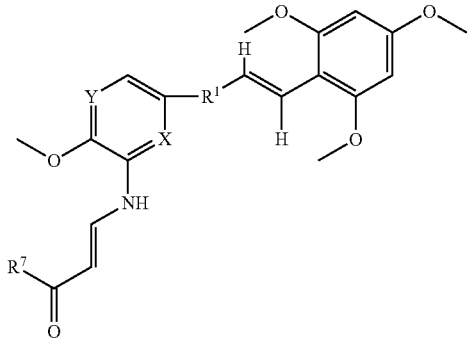
| Ex. No. | X | Y | R¹ | R⁷ | Compound |
|---|---|---|---|---|---|
| 94 | CH | CH | —CH₂SO₂— | 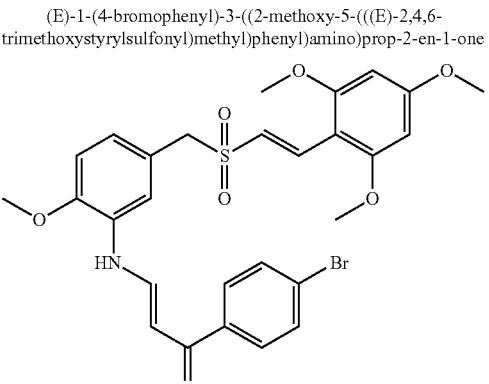 | (E)-1-(4-bromophenyl)-3-((2-methoxy-5-(((E)-2,4,6-trimethoxystyrylsulfonyl)methyl)phenyl)amino)prop-2-en-1-one |
| 95 | CH | CH | —CH₂SO₂— | 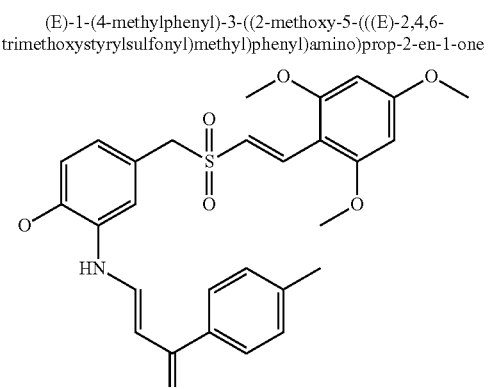 | (E)-1-(4-methylphenyl)-3-((2-methoxy-5-(((E)-2,4,6-trimethoxystyrylsulfonyl)methyl)phenyl)amino)prop-2-en-1-one |
| 96 | CH | CH | —CH₂SO₂— | 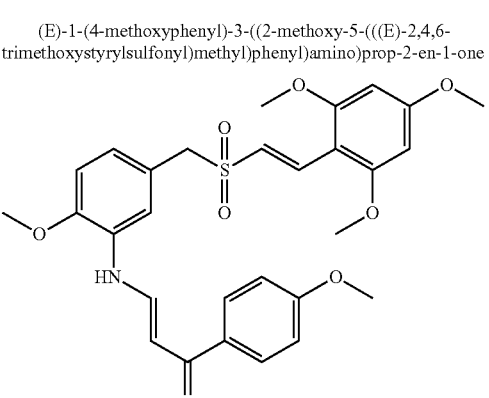 | (E)-1-(4-methoxyphenyl)-3-((2-methoxy-5-(((E)-2,4,6-trimethoxystyrylsulfonyl)methyl)phenyl)amino)prop-2-en-1-one |

TABLE 7-continued

| Ex. No. | X | Y | R¹ | R⁷ | Compound |
|---|---|---|---|---|---|
| 97 | CH | CH | —CH$_2$SO$_2$— | (3,4-dimethoxyphenyl) | (E)-1-(3,4-dimethoxyphenyl)-3-((2-methoxy-5-(((E)-2,4,6-trimethoxystyrylsulfonyl)methyl)phenyl)amino)prop-2-en-1-one |
| 98 | CH | CH | —CH$_2$SO$_2$— | (3,4,5-trimethoxyphenyl) | (E)-1-(3,4,5-trimethoxyphenyl)-3-((2-methoxy-5-(((E)-2,4,6-trimethoxystyrylsulfonyl)methyl)phenyl)-amino)prop-2-en-1-one |
| 99 | CH | CH | —CH$_2$SO$_2$— | (2-chloro-3,4,5-trimethoxyphenyl) | (E)-1-(2-chloro-3,4,5-trimethoxyphenyl)-3-((2-methoxy-5-(((E)-2,4,6-trimethoxystyrylsulfonyl)-methyl)phenyl)amino)prop-2-en-1-one |

TABLE 7-continued
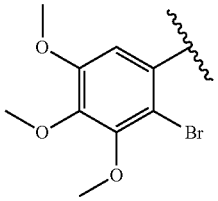 [SMILES: *c1cc(OC)c(OC)c(OC)c1Br]
| Ex. No. | X | Y | R¹ | R⁷ | Compound |
|---|---|---|---|---|---|
| 100 | CH | CH | —CH$_2$SO$_2$— | (structure shown) | (E)-1-(2-bromo-3,4,5-trimethoxyphenyl)-3-((2-methoxy-5-(((E)-2,4,6-trimethoxystyrylsulfonyl)-methyl)phenyl)amino)prop-2-en-1-one |
| 101 | CH | CH | —CH$_2$SO$_2$— | (structure shown) | (E)-1-(2,4,6-trimethoxyphenyl)-3-((2-methoxy-5-(((E)-2,4,6-trimethoxystyrylsulfonyl)methyl)phenyl)amino)prop-2-en-1-one |
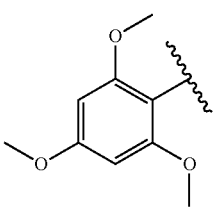

TABLE 7-continued

| Ex. No. | X | Y | R¹ | R⁷ | Compound |
|---|---|---|---|---|---|
| 102 | CH | CH | —CH₂SO₂— | OH | (E)-3-((2-methoxy-5-(((E)-2,4,6-trimethoxystyrylsulfonyl)methyl)phenyl)amino)acrylic acid |
| 103 | CH | CH | —CH₂SO₂— | ⁓O⁻ | (E)-methyl 3-((2-methoxy-5-(((E)-2,4,6-trimethoxystyrylsulfonyl)methyl)phenyl)amino)acrylate |

TABLE 7-continued
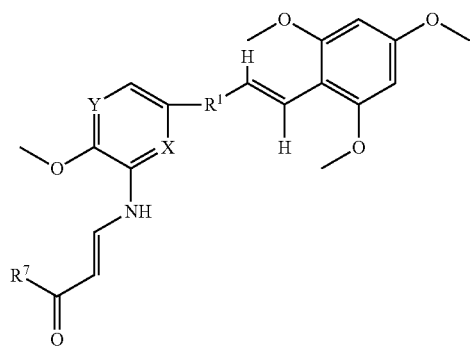
| Ex. No. | X | Y | R¹ | R⁷ | Compound |
|---|---|---|---|---|---|
| 104 | CH | CH | —CH$_2$SO$_2$— | 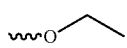 | (E)-ethyl 3-((2-methoxy-5-(((E)-2,4,6-trimethoxystyrylsulfonyl)methyl)phenyl)amino)acrylate 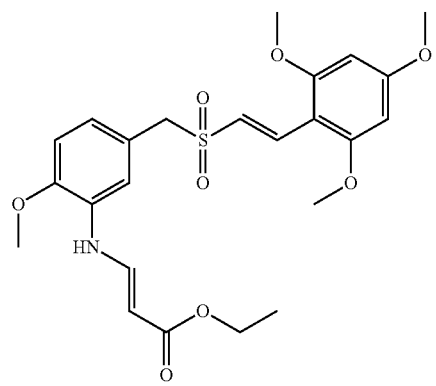 |
| 105 | CH | CH | —NHSO$_2$— | 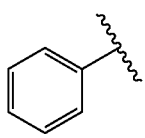 [SMILES: *c1ccccc1] | (E)-N-(4-methoxy-3-(((E)-3-oxo-3-phenylprop-1-en-1-yl)amino)phenyl)-2-(2,4,6-trimethoxyphenyl)ethenesulfonamide 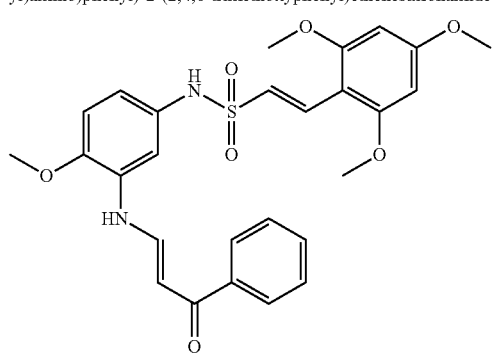 |

TABLE 7-continued
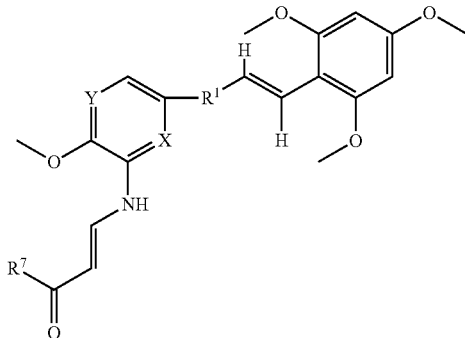
| Ex. No. | X | Y | R¹ | R⁷ | Compound |
|---|---|---|---|---|---|
| 106 | CH | CH | —NHSO₂— | 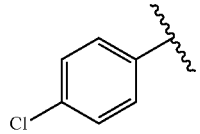 [SMILES: *c1ccc(Cl)cc1] | (E)-N-(3-(((E)-3-(4-chlorophenyl)-3-oxoprop-1-en-1-yl)amino)-4-methoxyphenyl)-2-(2,4,6-trimethoxyphenyl)ethenesulfonamide 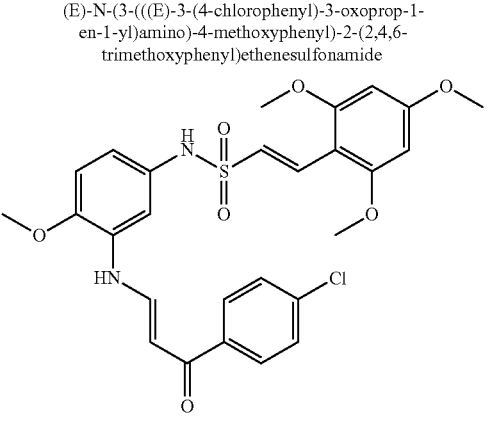 |
| 107 | CH | CH | —NHSO₂— | 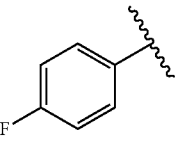 [SMILES: *c1ccc(F)cc1] | (E)-N-(3-(((E)-3-(4-fluorophenyl)-3-oxoprop-1-en-1-yl)amino)-4-methoxyphenyl)-2-(2,4,6-trimethoxyphenyl)ethenesulfonamide 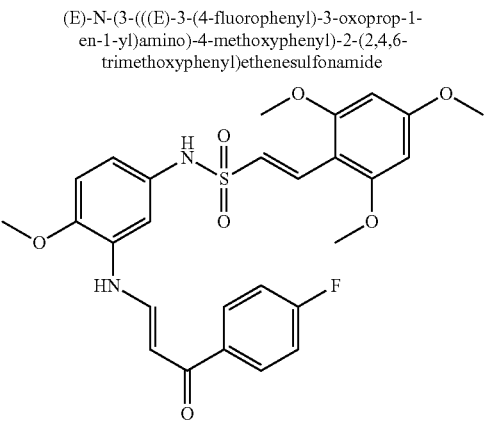 |

TABLE 7-continued
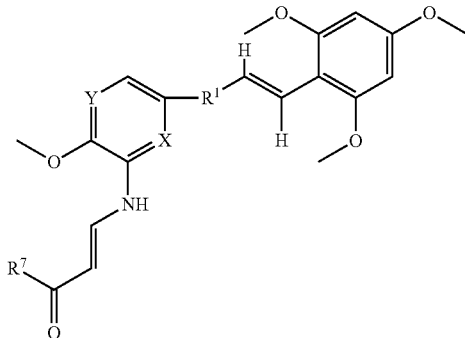
| Ex. No. | X | Y | R¹ | R⁷ | Compound |
|---|---|---|---|---|---|
| 108 | CH | CH | —NHSO₂— | 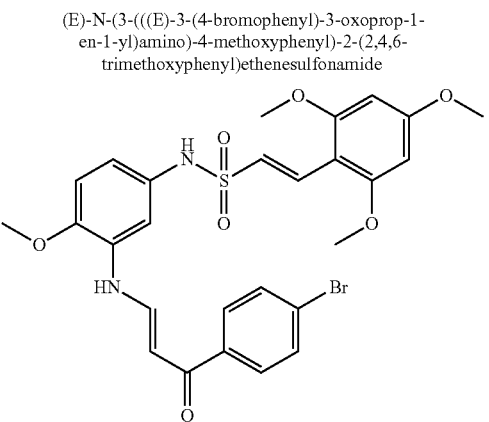 | (E)-N-(3-(((E)-3-(4-bromophenyl)-3-oxoprop-1-en-1-yl)amino)-4-methoxyphenyl)-2-(2,4,6-trimethoxyphenyl)ethenesulfonamide |
| 109 | CH | CH | —NHSO₂— | 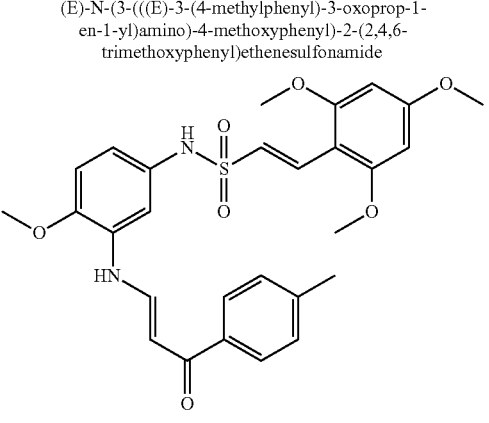 | (E)-N-(3-(((E)-3-(4-methylphenyl)-3-oxoprop-1-en-1-yl)amino)-4-methoxyphenyl)-2-(2,4,6-trimethoxyphenyl)ethenesulfonamide |

TABLE 7-continued
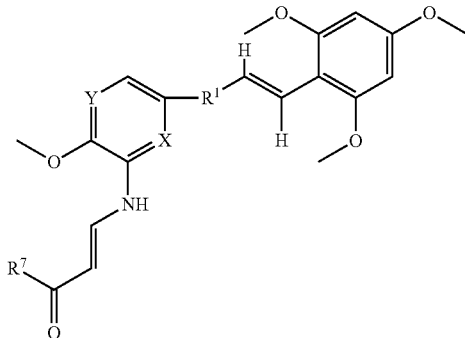
| Ex. No. | X | Y | R¹ | R⁷ | Compound |
|---|---|---|---|---|---|
| 110 | CH | CH | —NHSO₂— |  | (E)-N-(3-(((E)-3-(4-methoxyphenyl)-3-oxoprop-1-en-1-yl)amino)-4-methoxyphenyl)-2-(2,4,6-trimethoxyphenyl)ethenesulfonamide 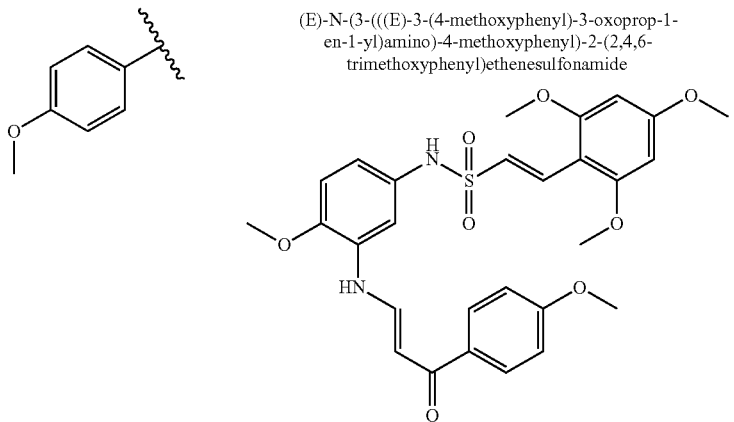 |
| 111 | CH | CH | —NHSO₂— | 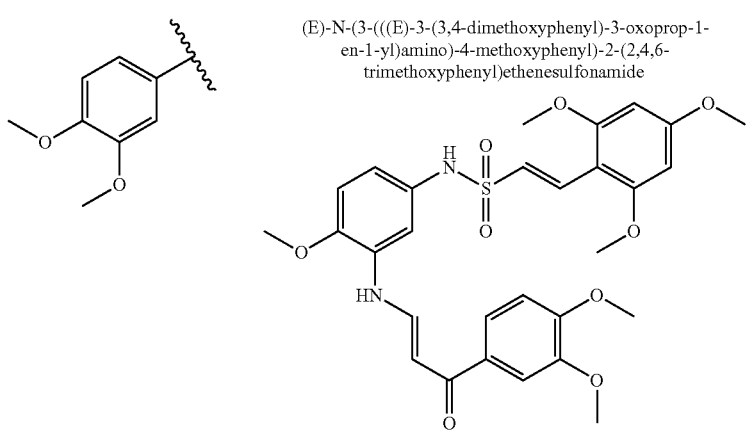 | (E)-N-(3-(((E)-3-(3,4-dimethoxyphenyl)-3-oxoprop-1-en-1-yl)amino)-4-methoxyphenyl)-2-(2,4,6-trimethoxyphenyl)ethenesulfonamide |

TABLE 7-continued
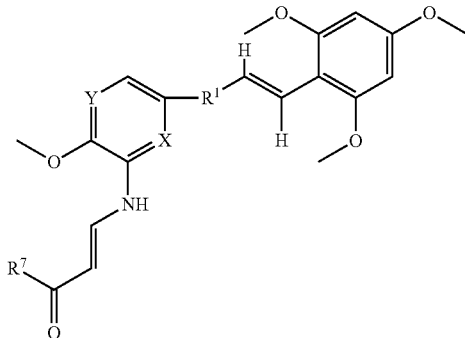
| Ex. No. | X | Y | R¹ | R⁷ | Compound |
|---|---|---|---|---|---|
| 112 | CH | CH | —NHSO$_2$— | 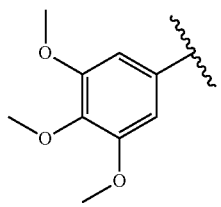 [SMILES: *c1cc(OC)c(OC)c(OC)c1] | (E)-N-(3-(((E)-3-(3,4,5-trimethoxyphenyl)-3-oxoprop-1-en-1-yl)amino)-4-methoxyphenyl)-2-(2,4,6-trimethoxyphenyl)ethenesulfonamide 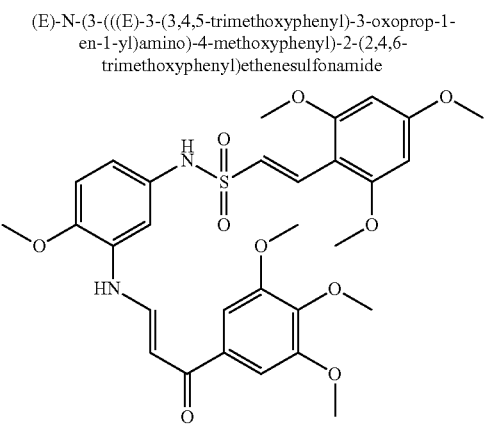 |
| 113 | CH | CH | —NHSO$_2$— | 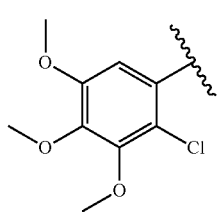 [SMILES: *c1cc(OC)c(OC)c(OC)c1Cl] | (E)-N-(3-(((E)-3-(2-chloro-3,4,5-trimethoxyphenyl)-3-oxoprop-1-en-1-yl)amino)-4-methoxyphenyl)-2-(2,4,6-trimethoxyphenyl)ethenesulfonamide 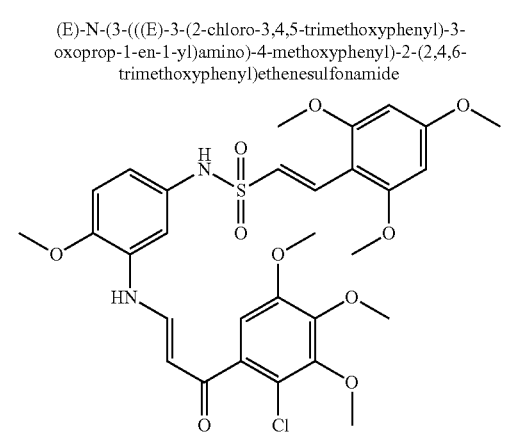 |

TABLE 7-continued
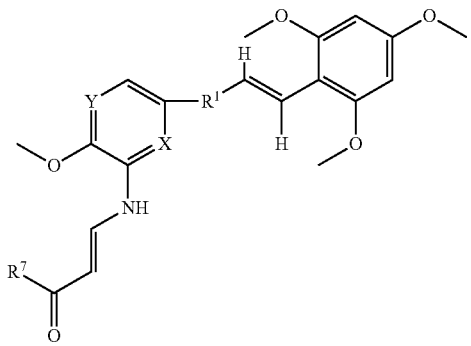
| Ex. No. | X | Y | R¹ | R⁷ | Compound |
|---|---|---|---|---|---|
| 114 | CH | CH | —NHSO₂— | 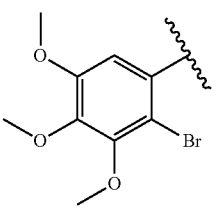 [SMILES: *c1cc(OC)c(OC)c(OC)c1Br] | (E)-N-(3-(((E)-3-(2-bromo-3,4,5-trimethoxyphenyl)-3-oxoprop-1-en-1-yl)amino)-4-methoxyphenyl)-2-(2,4,6-trimethoxyphenyl)ethenesulfonamide 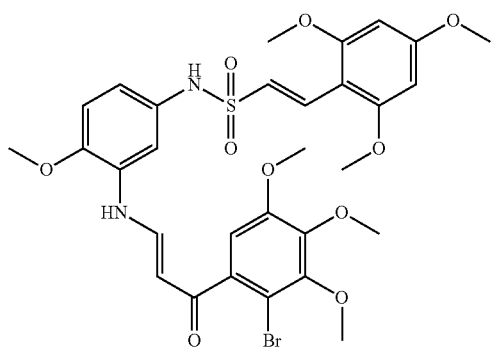 |
| 115 | CH | CH | —NHSO₂— | 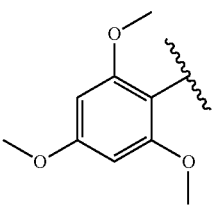 | (E)-N-(3-(((E)-3-(2,4,6-trimethoxyphenyl)-3-oxoprop-1-en-1-yl)amino)-4-methoxyphenyl)-2-(2,4,6-trimethoxyphenyl)ethenesulfonamide 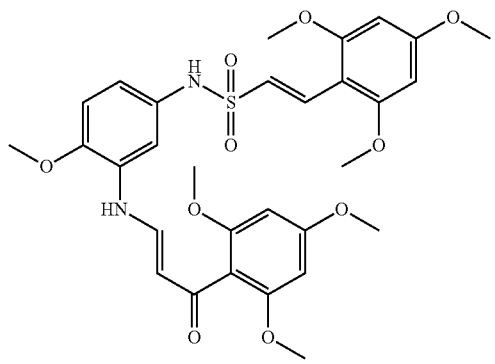 |

TABLE 7-continued
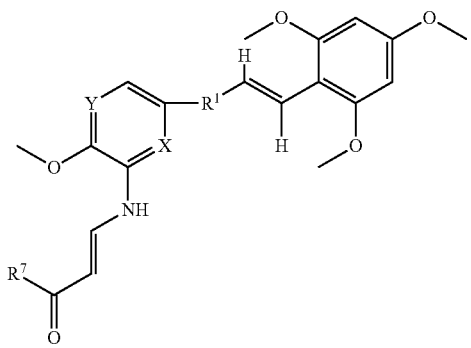
| Ex. No. | X | Y | R¹ | R⁷ | Compound |
|---|---|---|---|---|---|
| 116 | CH | CH | —NHSO₂— | OH | (E)-3-((2-methoxy-5-((E)-2-(2,4,6-trimethoxyphenyl)vinylsulfonamido)phenyl)amino)acrylic acid |
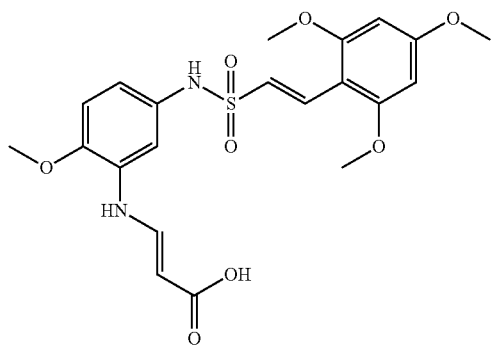
| 117 | CH | CH | —NHSO₂— | ⌇O⌇ | (E)-methyl 3-((2-methoxy-5-((E)-2-(2,4,6-trimethoxyphenyl)vinylsulfonamido)phenyl)amino)acrylate |
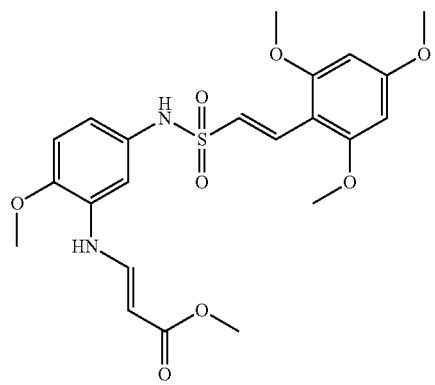

TABLE 7-continued
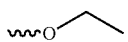
| Ex. No. | X | Y | R¹ | R⁷ | Compound |
|---|---|---|---|---|---|
| 118 | CH | CH | —NHSO₂— | 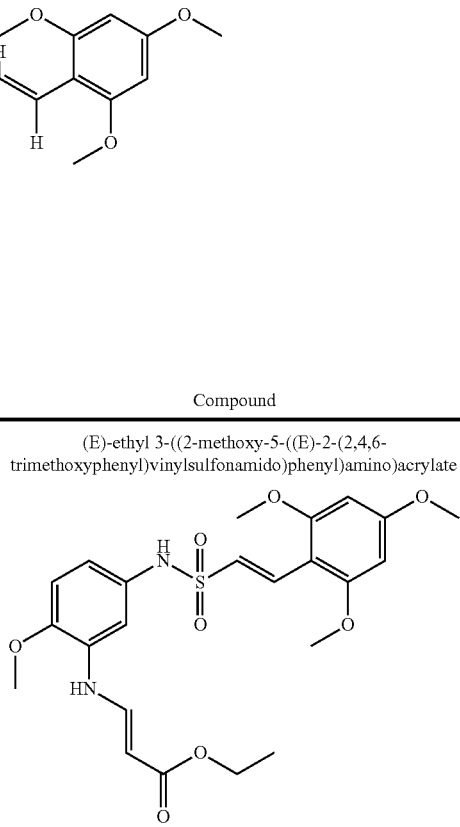 | (E)-ethyl 3-((2-methoxy-5-((E)-2-(2,4,6-trimethoxyphenyl)vinylsulfonamido)phenyl)amino)acrylate |
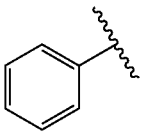 [SMILES: *c1ccccc1]
| 119 | CH | CH | —NHC(=O)— | 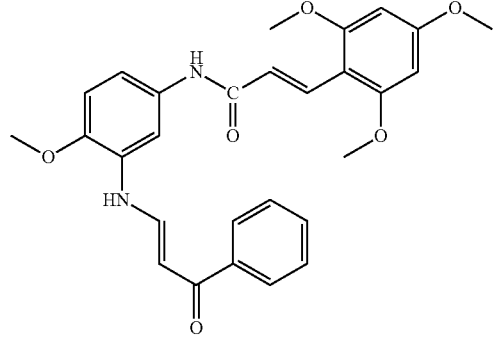 | (E)-N-(4-methoxy-3-(((E)-3-oxo-3-phenylprop-1-en-1-yl)amino)phenyl)-2-(2,4,6-trimethoxyphenyl)ethenecarboxamide |
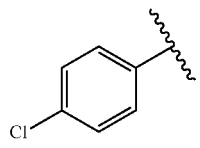 [SMILES: *c1ccc(Cl)cc1]
| 120 | CH | CH | —NHC(=O)— | 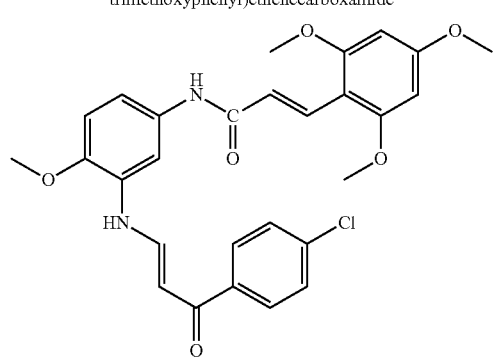 | (E)-N-(3-(((E)-3-(4-chlorophenyl)-3-oxoprop-1-en-1-yl)amino)-4-methoxyphenyl)-2-(2,4,6-trimethoxyphenyl)ethenecarboxamide |

TABLE 7-continued
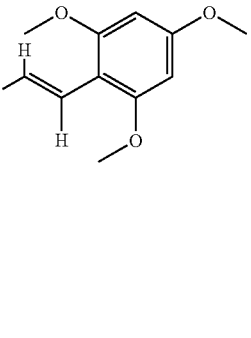
| Ex. No. | X | Y | R¹ | R⁷ | Compound |
|---|---|---|---|---|---|
| 121 | CH | CH | —NHC(=O)— | 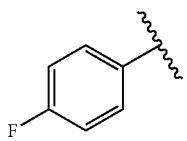 [SMILES: *c1ccc(F)cc1] | (E)-N-(3-(((E)-3-(4-fluorophenyl)-3-oxoprop-1-en-1-yl)amino)-4-methoxyphenyl)-2-(2,4,6-trimethoxyphenyl)ethenecarboxamide 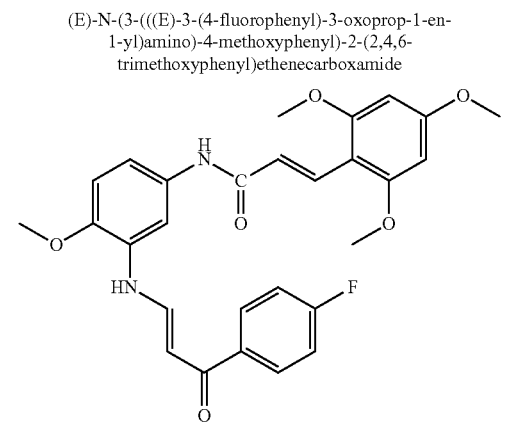 |
| 122 | CH | CH | —NHC(=O)— | 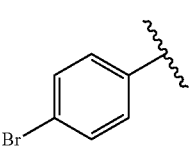 | (E)-N-(3-(((E)-3-(4-bromophenyl)-3-oxoprop-1-en-1-yl)amino)-4-methoxyphenyl)-2-(2,4,6-trimethoxyphenyl)ethenecarboxamide 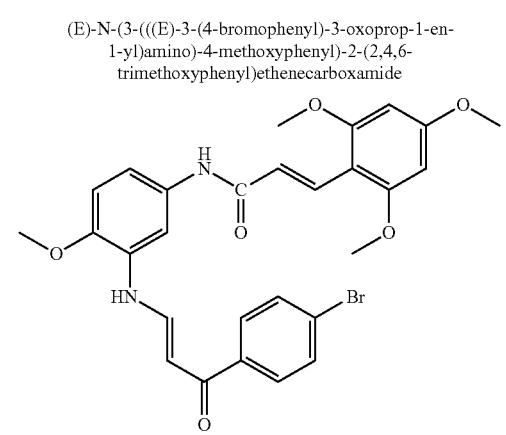 |

TABLE 7-continued
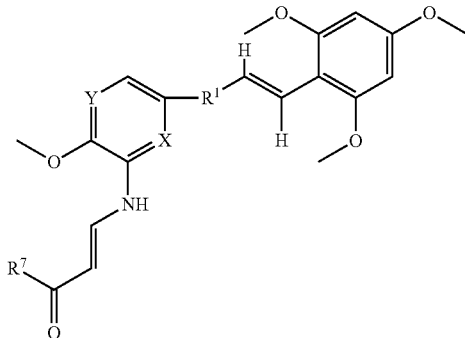
| Ex. No. | X | Y | R¹ | R⁷ | Compound |
|---|---|---|---|---|---|
| 123 | CH | CH | —NHC(=O)— | 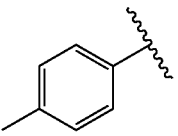 [SMILES: *c1ccc(C)cc1] | (E)-N-(3-(((E)-3-(4-methylphenyl)-3-oxoprop-1-en-1-yl)amino)-4-methoxyphenyl)-2-(2,4,6-trimethoxyphenyl)ethenecarboxamide 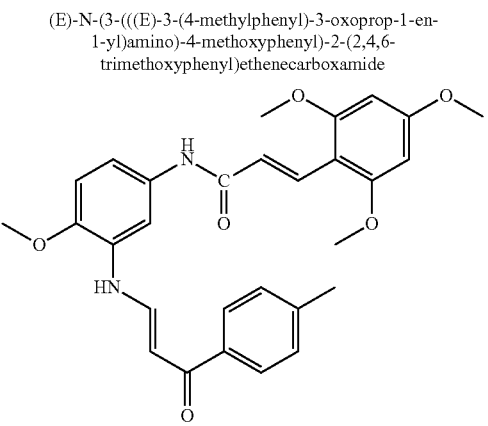 |
| 124 | CH | CH | —NHC(=O)— | 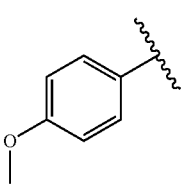 [SMILES: *c1ccc(OC)cc1] | (E)-N-(3-(((E)-3-(4-methoxyphenyl)-3-oxoprop-1-en-1-yl)amino)-4-methoxyphenyl)-2-(2,4,6-trimethoxyphenyl)ethenecarboxamide 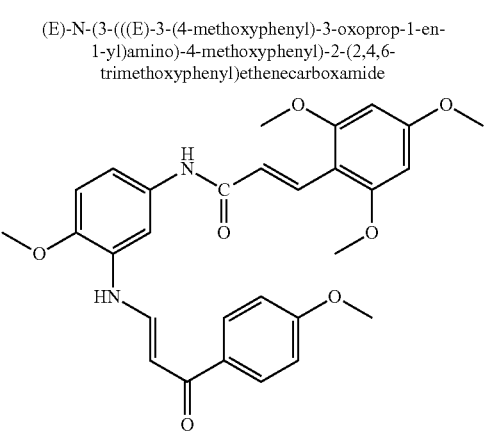 |

TABLE 7-continued
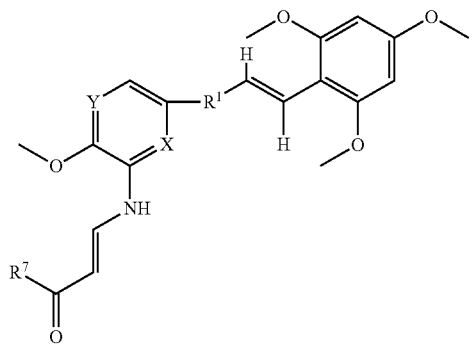
| Ex. No. | X | Y | R¹ | R⁷ | Compound |
|---|---|---|---|---|---|
| 125 | CH | CH | —NHC(=O)— | 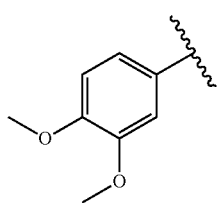 [SMILES: *c1ccc(OC)c(OC)c1] | (E)-N-(3-(((E)-3-(3,4-dimethoxyphenyl)-3-oxoprop-1-en-1-yl)amino)-4-methoxyphenyl)-2-(2,4,6-trimethoxyphenyl)ethenecarboxamide 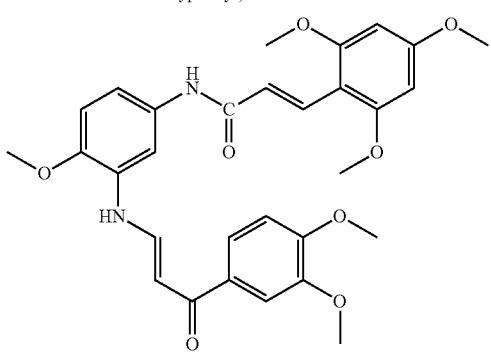 |
| 126 | CH | CH | —NHC(=O)— | 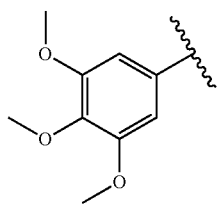 [SMILES: *c1cc(OC)c(OC)c(OC)c1] | (E)-N-(3-(((E)-3-(3,4,5-trimethoxyphenyl)-3-oxoprop-1-en-1-yl)amino)-4-methoxyphenyl)-2-(2,4,6-trimethoxyphenyl)ethenecarboxamide 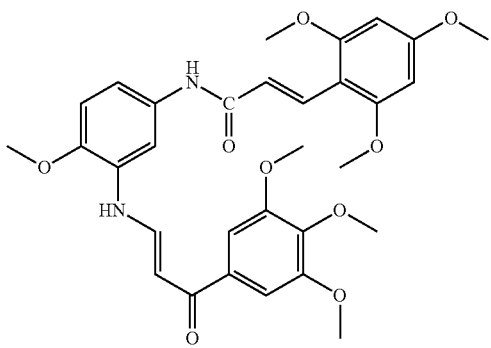 |

TABLE 7-continued
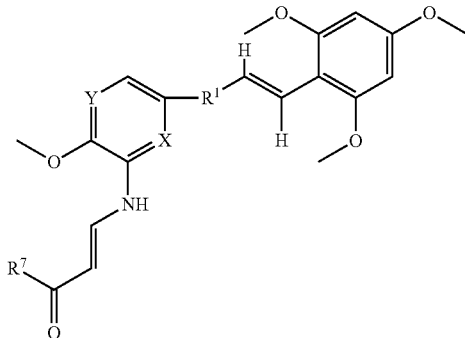
| Ex. No. | X | Y | R¹ | R⁷ | Compound |
|---|---|---|---|---|---|
| 127 | CH | CH | —NHC(=O)— | 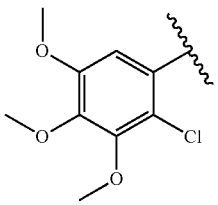 [SMILES: *c1cc(OC)c(OC)c(OC)c1Cl] | (E)-N-(3-(((E)-3-(2-chloro-3,4,5-trimethoxyphenyl)-3-oxoprop-1-en-1-yl)amino)-4-methoxyphenyl)-2-(2,4,6-trimethoxyphenyl)ethenecarboxamide 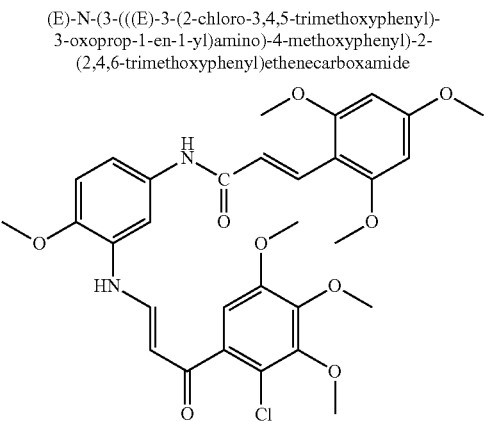 |
| 128 | CH | CH | —NHC(=O)— | 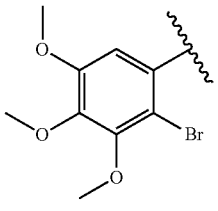 [SMILES: *c1cc(OC)c(OC)c(OC)c1Br] | (E)-N-(3-(((E)-3-(2-bromo-3,4,5-trimethoxyphenyl)-3-oxoprop-1-en-1-yl)amino)-4-methoxyphenyl)-2-(2,4,6-trimethoxyphenyl)ethenecarboxamide 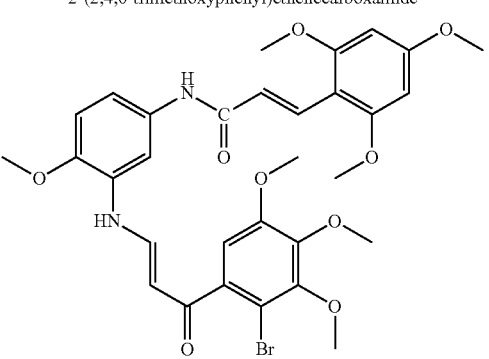 |

TABLE 7-continued
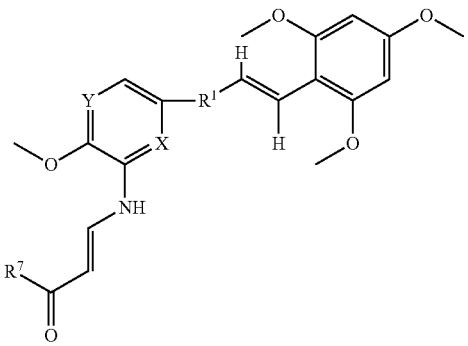
| Ex. No. | X | Y | R¹ | R⁷ | Compound |
|---|---|---|---|---|---|
| 129 | CH | CH | —NHC(=O)— | 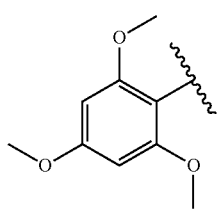 | (E)-N-(3-(((E)-3-(2,4,6-trimethoxyphenyl)-3-oxoprop-1-en-1-yl)amino)-4-methoxyphenyl)-2-(2,4,6-trimethoxyphenyl)ethenecarboxamide 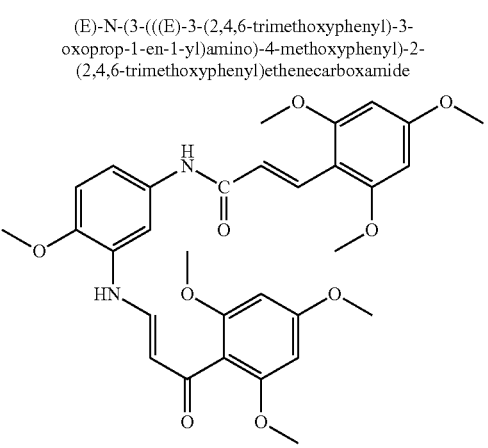 |
| 130 | CH | CH | —NHC(=O)— | OH | (E)-3-((2-methoxy-5-((E)-3-(2,4,6-trimethoxyphenyl)acrylamido)phenyl)amino)acrylic acid 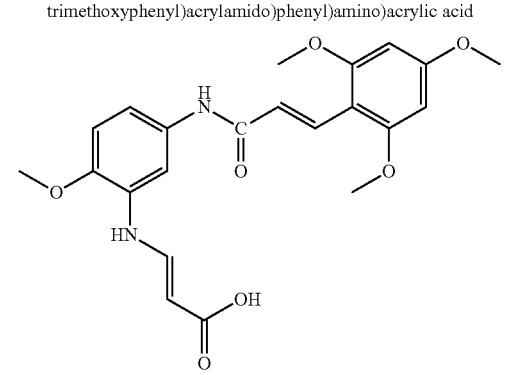 |

TABLE 7-continued
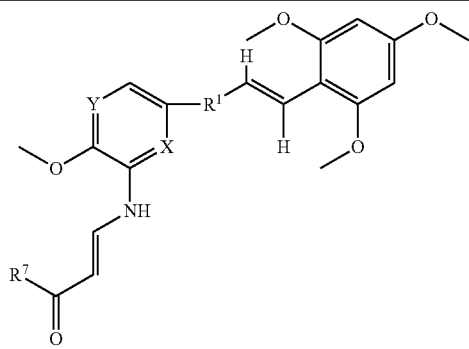
| Ex. No. | X | Y | R¹ | R⁷ | Compound |
|---|---|---|---|---|---|
| 131 | CH | CH | —NHC(=O)— |  | (E)-methyl 3-((2-methoxy-5-((E)-2-(2,4,6-trimethoxyphenyl)acrylamido)phenyl)amino)acrylate 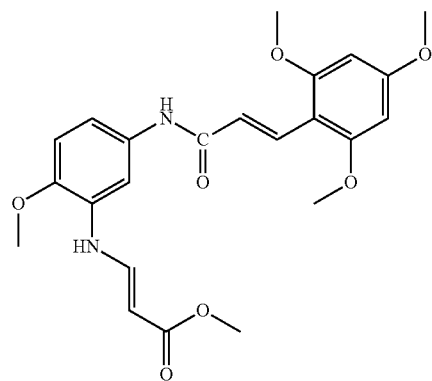 |
| 132 | CH | CH | —NHC(=O)— | 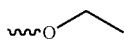 | (E)-ethyl 3-((2-methoxy-5-((E)-2-(2,4,6-trimethoxyphenyl)acrylamido)phenyl)amino)acrylate 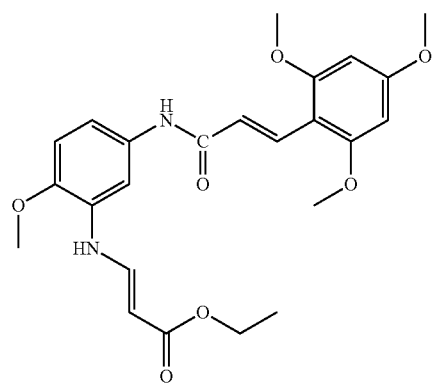 |

TABLE 7-continued
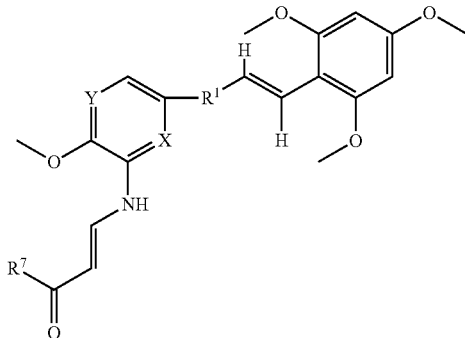
| Ex. No. | X | Y | R¹ | R⁷ | Compound |
|---|---|---|---|---|---|
| 133 | N | CH | —CH₂SO₂— | 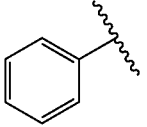 [SMILES: *c1ccccc1] | (E)-3-((3-methoxy-6-(((E)-2,4,6-trimethoxystyrylsulfonyl)methyl)pyridin-2-yl)amino)-1-phenylprop-2-en-1-one 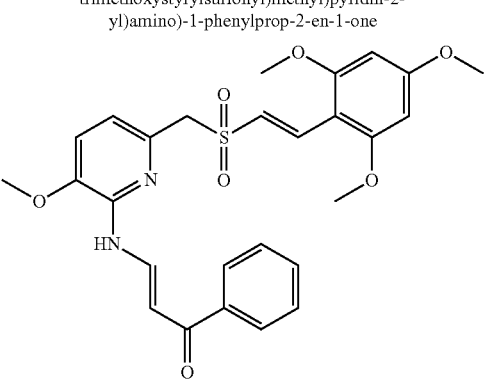 |
| 134 | N | CH | —CH₂SO₂— | 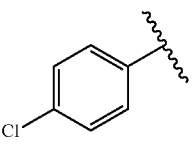 [SMILES: *c1ccc(Cl)cc1] | (E)-1-(4-chlorophenyl)-3-((3-methoxy-6-(((E)-2,4,6-trimethoxystyrylsulfonyl)methyl)pyridin-2-yl)amino)prop-2-en-1-one 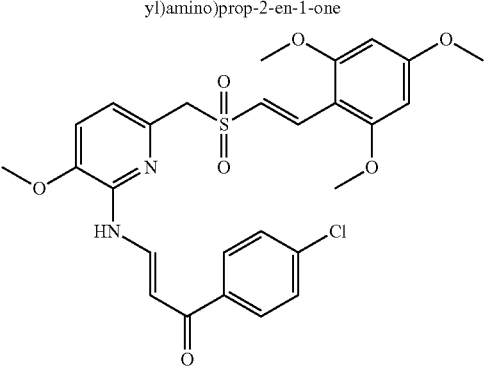 |

TABLE 7-continued

| Ex. No. | X | Y | R¹ | R⁷ | Compound |
|---|---|---|---|---|---|
| 135 | N | CH | —CH$_2$SO$_2$— | 4-fluorophenyl | (E)-1-(4-fluorophenyl)-3-((3-methoxy-6-(((E)-2,4,6-trimethoxystyrylsulfonyl)methyl)pyridin-2-yl)amino)prop-2-en-1-one |
| 136 | N | CH | —CH$_2$SO$_2$— | 4-bromophenyl | (E)-1-(4-bromophenyl)-3-((3-methoxy-6-(((E)-2,4,6-trimethoxystyrylsulfonyl)methyl)pyridin-2-yl)amino)prop-2-en-1-one |

TABLE 7-continued

| Ex. No. | X | Y | R¹ | R⁷ | Compound |
|---|---|---|---|---|---|
| 137 | N | CH | —CH$_2$SO$_2$— | (4-methylphenyl) | (E)-1-(4-methylphenyl)-3-((3-methoxy-6-(((E)-2,4,6-trimethoxystyrylsulfonyl)methyl)pyridin-2-yl)amino)prop-2-en-1-one |
| 138 | N | CH | —CH$_2$SO$_2$— | (4-methoxyphenyl) | (E)-1-(4-methoxyphenyl)-3-((3-methoxy-6-(((E)-2,4,6-trimethoxystyrylsulfonyl)methyl)pyridin-2-yl)amino)prop-2-en-1-one |

TABLE 7-continued
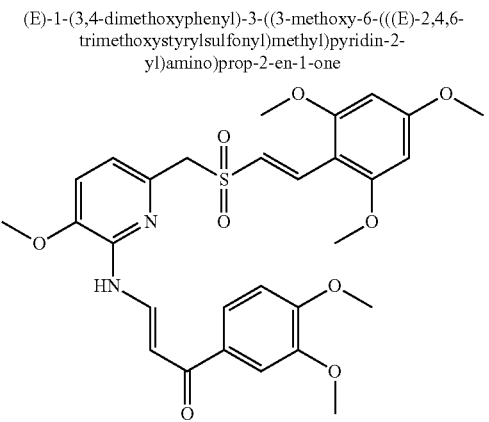
| Ex. No. | X | Y | R¹ | R⁷ | Compound |
|---|---|---|---|---|---|
| 139 | N | CH | —CH$_2$SO$_2$— | (3,4-dimethoxyphenyl) | (E)-1-(3,4-dimethoxyphenyl)-3-((3-methoxy-6-(((E)-2,4,6-trimethoxystyrylsulfonyl)methyl)pyridin-2-yl)amino)prop-2-en-1-one |
| 140 | N | CH | —CH$_2$SO$_2$— | (3,4,5-trimethoxyphenyl) | (E)-1-(3,4,5-trimethoxyphenyl)-3-((3-methoxy-6-(((E)-2,4,6-trimethoxystyrylsulfonyl)methyl)pyridin-2-yl)amino)prop-2-en-1-one |
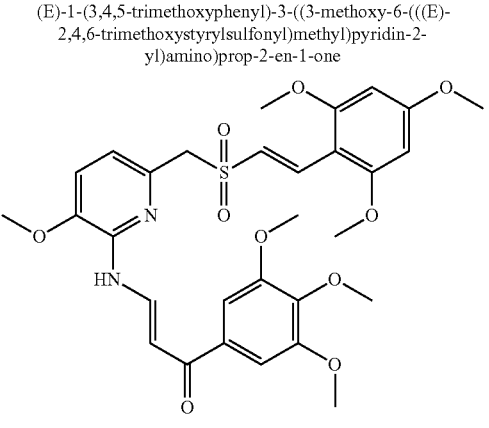

TABLE 7-continued
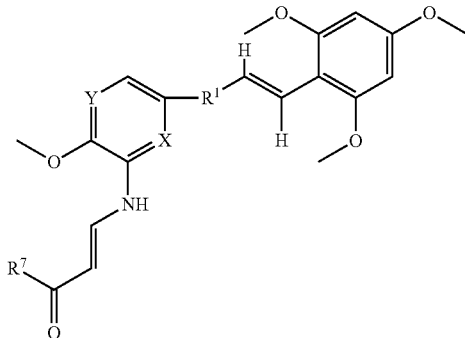
| Ex. No. | X | Y | R¹ | R⁷ | Compound |
|---|---|---|---|---|---|
| 141 | N | CH | —CH$_2$SO$_2$— | (2-chloro-3,4,5-trimethoxyphenyl) | (E)-1-(2-chloro-3,4,5-trimethoxyphenyl)-3-((3-methoxy-6-(((E)-2,4,6-trimethoxystyrylsulfonyl)methyl)pyridin-2-yl)amino)prop-2-en-1-one |
| 142 | N | CH | —CH$_2$SO$_2$— | (2-bromo-3,4,5-trimethoxyphenyl) | (E)-1-(2-bromo-3,4,5-trimethoxyphenyl)-3-((3-methoxy-6-(((E)-2,4,6-trimethoxystyrylsulfonyl)methyl)pyridin-2-yl)amino)prop-2-en-1-one |

TABLE 7-continued

| Ex. No. | X | Y | R¹ | R⁷ | Compound |
|---|---|---|---|---|---|
| 143 | N | CH | —CH$_2$SO$_2$— | (2,4,6-trimethoxyphenyl) | (E)-1-(2,4,6-trimethoxyphenyl)-3-((3-methoxy-6-(((E)-2,4,6-trimethoxystyrylsulfonyl)methyl)pyridin-2-yl)amino)prop-2-en-1-one |
| 144 | N | CH | —CH$_2$SO$_2$— | OH | (E)-3-((3-methoxy-6-(((E)-2,4,6-trimethoxystyrylsulfonyl)methyl)pyridin-2-yl)amino)acrylic acid |

TABLE 7-continued
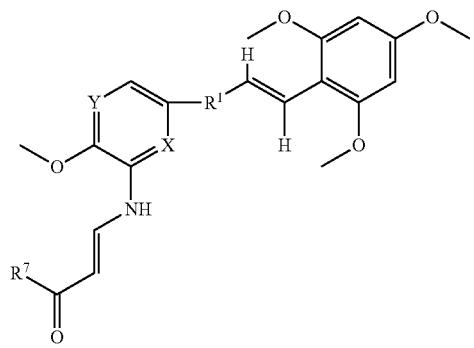
| Ex. No. | X | Y | R¹ | R⁷ | Compound |
|---|---|---|---|---|---|
| 145 | N | CH | —CH$_2$SO$_2$— |  | (E)-methyl 3-((3-methoxy-6-(((E)-2,4,6-trimethoxystyrylsulfonyl)methyl)pyridin-2-yl)amino)acrylate |
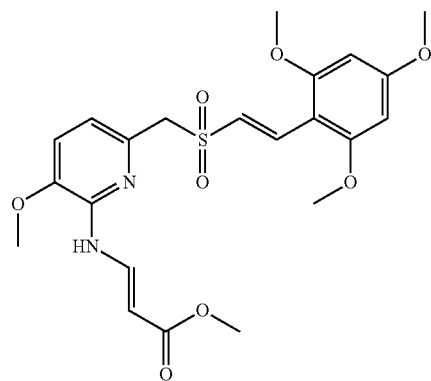
| 146 | N | CH | —CH$_2$SO$_2$— | 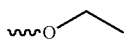 | (E)-methyl 3-((3-methoxy-6-(((E)-2,4,6-trimethoxystyrylsulfonyl)methyl)pyridin-2-yl)amino)acrylate |
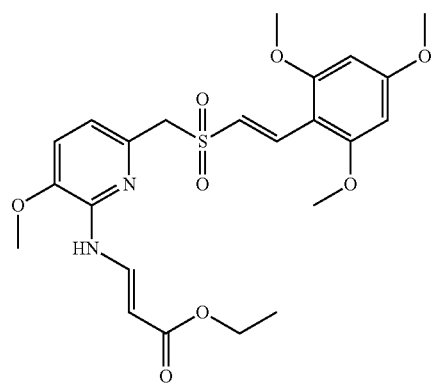

TABLE 7-continued
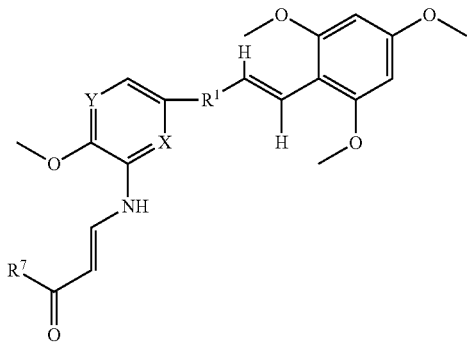
| Ex. No. | X | Y | R¹ | R⁷ | Compound |
|---|---|---|---|---|---|
| 147 | CH | N | —CH₂SO₂— | (phenyl) | (E)-3-((2-methoxy-5-(((E)-2,4,6-trimethoxystyrylsulfonyl)methyl)pyridin-3-yl)amino)-1-phenylprop-2-en-1-one |
| 148 | CH | N | —CH₂SO₂— | (4-chlorophenyl) | (E)-1-(4-chlorophenyl)-3-((2-methoxy-5-(((E)-2,4,6-trimethoxystyrylsulfonyl)methyl)pyridin-3-yl)amino)prop-2-en-1-one |

TABLE 7-continued
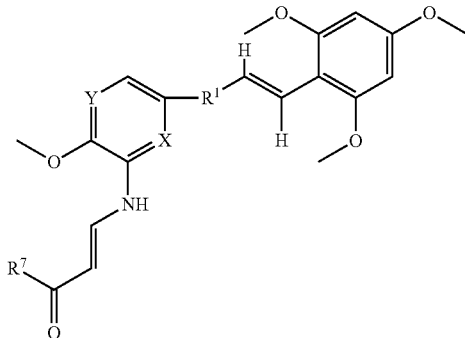
| Ex. No. | X | Y | R¹ | R⁷ | Compound |
|---|---|---|---|---|---|
| 149 | CH | N | —CH$_2$SO$_2$— | 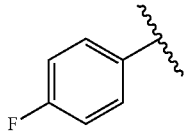 | (E)-1-(4-fluorophenyl)-3-((2-methoxy-5-(((E)-2,4,6-trimethoxystyrylsulfonyl)methyl)pyridin-3-yl)amino)prop-2-en-1-one 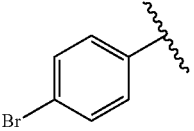 |
| 150 | CH | N | —CH$_2$SO$_2$— | 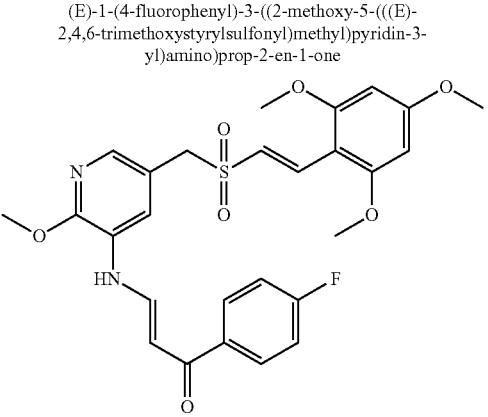 | (E)-1-(4-bromophenyl)-3-((2-methoxy-5-(((E)-2,4,6-trimethoxystyrylsulfonyl)methyl)pyridin-3-yl)amino)prop-2-en-1-one 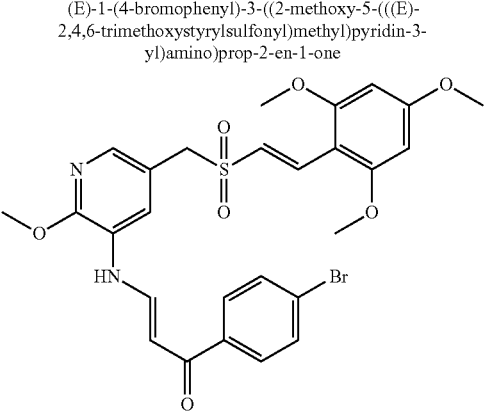 |

TABLE 7-continued

| Ex. No. | X | Y | R¹ | R⁷ | Compound |
|---|---|---|---|---|---|
| 151 | CH | N | —CH$_2$SO$_2$— | 4-methylphenyl | (E)-1-(4-methylphenyl)-3-((2-methoxy-5-(((E)-2,4,6-trimethoxystyrylsulfonyl)methyl)pyridin-3-yl)amino)prop-2-en-1-one |
| 152 | CH | N | —CH$_2$SO$_2$— | 4-methoxyphenyl | (E)-1-(4-methoxyphenyl)-3-((2-methoxy-5-(((E)-2,4,6-trimethoxystyrylsulfonyl)methyl)pyridin-3-yl)amino)prop-2-en-1-one |

TABLE 7-continued
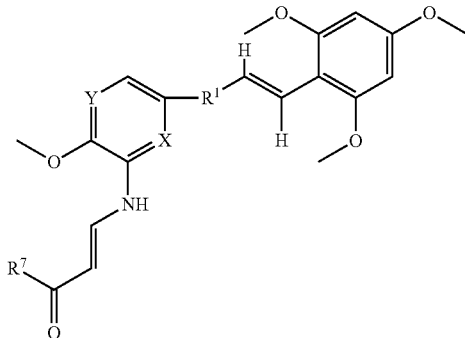
| Ex. No. | X | Y | R¹ | R⁷ | Compound |
|---|---|---|---|---|---|
| 153 | CH | N | —CH$_2$SO$_2$— | 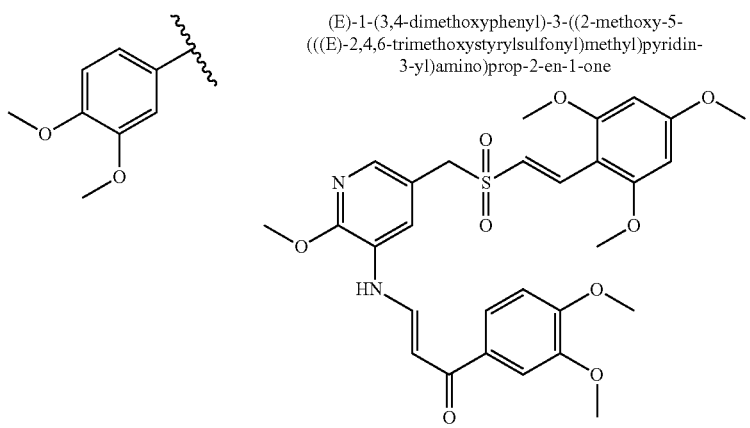 | (E)-1-(3,4-dimethoxyphenyl)-3-((2-methoxy-5-(((E)-2,4,6-trimethoxystyrylsulfonyl)methyl)pyridin-3-yl)amino)prop-2-en-1-one |
| 154 | CH | N | —CH$_2$SO$_2$— | 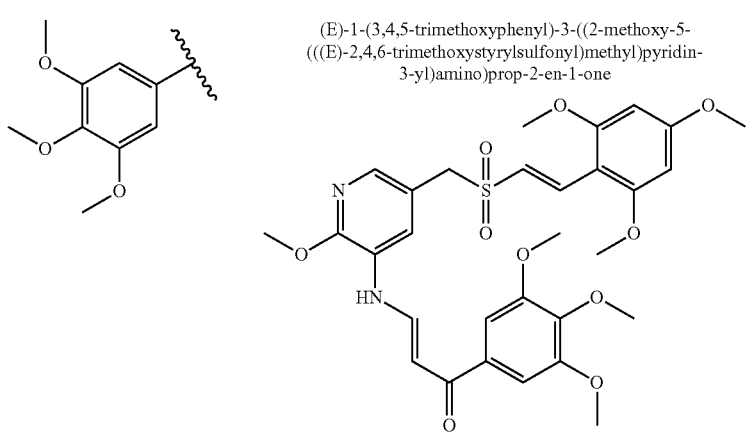 | (E)-1-(3,4,5-trimethoxyphenyl)-3-((2-methoxy-5-(((E)-2,4,6-trimethoxystyrylsulfonyl)methyl)pyridin-3-yl)amino)prop-2-en-1-one |

TABLE 7-continued
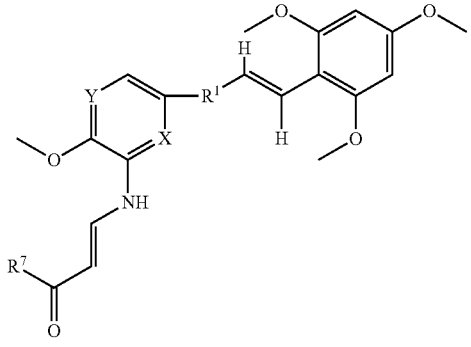
| Ex. No. | X | Y | R¹ | R⁷ | Compound |
|---|---|---|---|---|---|
| 155 | CH | N | —CH$_2$SO$_2$— | 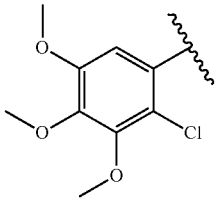 [SMILES: *c1cc(OC)c(OC)c(OC)c1Cl] | (E)-1-(2-chloro-3,4,5-trimethoxyphenyl)-3-((2-methoxy-5-(((E)-2,4,6-trimethoxystyrylsulfonyl)methyl)pyridin-3-yl)amino)prop-2-en-1-one 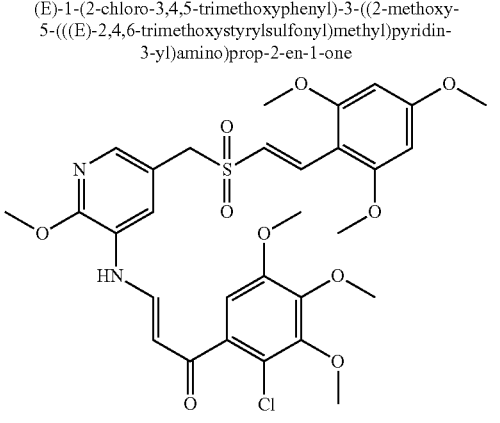 |
| 156 | CH | N | —CH$_2$SO$_2$— | 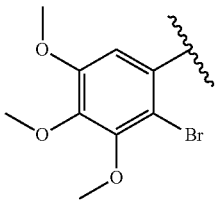 [SMILES: *c1cc(OC)c(OC)c(OC)c1Br] | (E)-1-(2-bromo-3,4,5-trimethoxyphenyl)-3-((2-methoxy-5-(((E)-2,4,6-trimethoxystyrylsulfonyl)methyl)pyridin-3-yl)amino)prop-2-en-1-one 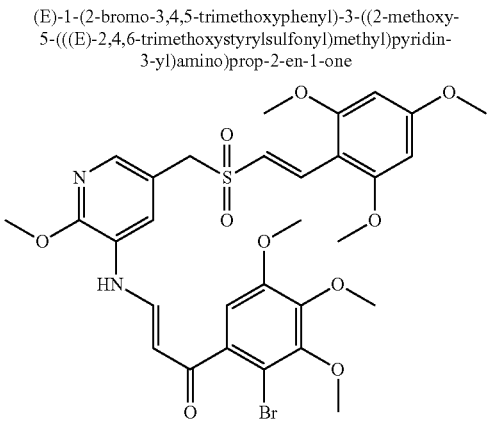 |

TABLE 7-continued

| Ex. No. | X | Y | R¹ | R⁷ | Compound |
|---|---|---|---|---|---|
| 157 | CH | N | —CH₂SO₂— | (2,4,6-trimethoxyphenyl group) | (E)-1-(2,4,6-trimethoxyphenyl)-3-((2-methoxy-5-(((E)-2,4,6-trimethoxystyrylsulfonyl)methyl)pyridin-3-yl)amino)prop-2-en-1-one |
| 158 | CH | N | —CH₂SO₂— | OH | (E)-3-((2-methoxy-5-(((E)-2,4,6-trimethoxystyrylsulfonyl)methyl)pyridin-3-yl)amino)acrylic acid |

TABLE 7-continued

| Ex. No. | X | Y | R¹ | R⁷ | Compound |
|---|---|---|---|---|---|
| 159 | CH | N | —CH₂SO₂— | ~O— (methoxy) | (E)-methyl 3-((2-methoxy-5-(((E)-2,4,6-trimethoxystyrylsulfonyl)methyl)pyridin-3-yl)amino)acrylate |
| 160 | CH | N | —CH₂SO₂— | ~O— (ethoxy) | (E)-ethyl 3-((2-methoxy-5-(((E)-2,4,6-trimethoxystyrylsulfonyl)methyl)pyridin-3-yl)amino)acrylate |

General Procedure 3 for Examples 161-165

The compounds of Examples 161-165 (Table 8) are prepared according to Scheme 12 and General Procedure 3, by reacting intermediate 36, 44, 45, 46, or 47 with BrCH$_2$C≡CH:

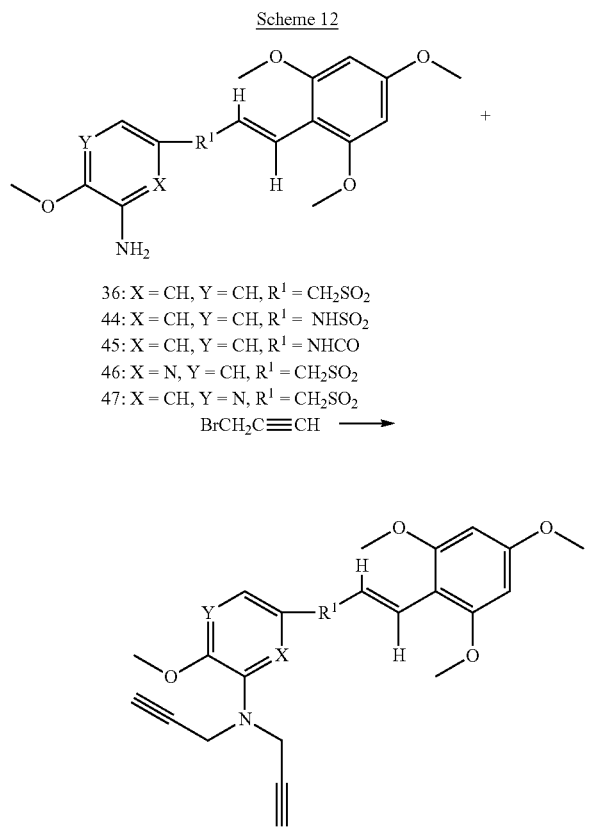

Scheme 12

36: X = CH, Y = CH, R$^1$ = CH$_2$SO$_2$
44: X = CH, Y = CH, R$^1$ = NHSO$_2$
45: X = CH, Y = CH, R$^1$ = NHCO
46: X = N, Y = CH, R$^1$ = CH$_2$SO$_2$
47: X = CH, Y = N, R$^1$ = CH$_2$SO$_2$
BrCH$_2$C≡CH ⟶

General Procedure 3.

In Scheme 12, a mixture of one of 36, 44, 45, 46 or 47 (1 eq), and BrCH$_2$C≡CH (2 eq), anhydrous K$_2$CO$_3$ and DMF is stirred at room temperature for 5 h.

The inorganic material is removed by filtration and washed with ethyl acetate. The resulting solution is treated with ethyl acetate and water. The organic layer is separated, washed with brine, dried over anhydrous Na$_2$SO$_4$, and concentrated. The crude product is purified by flash chromatography.

Example 161

Synthesis of (E)-2-methoxy-N,N-di(prop-2-yn-1-yl)-5-(((2,4,6-trimethoxystyryl)sulfonyl)-methyl)aniline

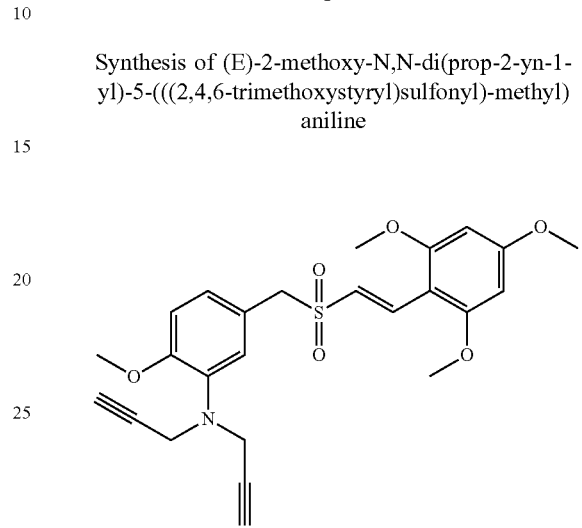

(E)-2-methoxy-5-(((2,4,6-trimethoxystyryl)sulfonyl)methyl)aniline 36 (500 mg, 1.27 mmol) was dissolved in dimethyl formamide (2 mL). Potassium carbonate (1.0 g), followed by propargyl bromide (0.3 g, 2.54 mmol) were added at room temperature and the reaction mixture was stirred for 2 h. The reaction mixture was poured onto crushed ice with stirring and the separated solid was filtered. The solid was washed with water, dried and the crude product was purified with combiflash to obtain pure product. $^1$H NMR: (300 MHz, DMSO-d$_6$) δ 3.08 (s, 2H), 3.79-3.85 (m, 16H), 4.35 (s, 2H), 6.29 (s, 2H), 6.93-7.02 (m, 3H), 7.12 (d, 1H, J=15.6 Hz), 7.51 (d, 1H, J=15.6 Hz). LC-MS found (M+H)$^+$ (m/z), 470.20; calcd for C$_{25}$H$_{27}$NO$_6$S m/z, 469.16.

TABLE 8

| Ex. No. | X | Y | R$^1$ | Compound |
|---|---|---|---|---|
| 161 | CH | CH | —CH$_2$SO$_2$— | (E)-2-methoxy-N,N-di(prop-2-yn-1-yl)-5-(((2,4,6-trimethoxystyryl)sulfonyl)methyl)aniline 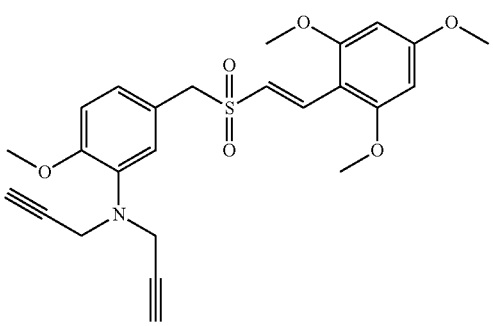 |

TABLE 8-continued

| Ex. No. | X | Y | R¹ | Compound |
|---|---|---|---|---|
| 162 | CH | CH | —NHSO$_2$— | (E)-N-(3-(di(prop-2-yn-1-yl)amino)-4-methoxyphenyl)-2-(2,4,6-trimethoxyphenyl)ethenesulfonamide |
| 163 | CH | CH | —NHC(=O)— | (E)-N-(3-(di(prop-2-yn-1-yl)amino)-4-methoxyphenyl)-3-(2,4,6-trimethoxyphenyl)acrylamide |
| 164 | N | CH | —CH$_2$SO$_2$— | (E)-3-methoxy-N,N-di(prop-2-yn-1-yl)-6-(((2,4,6-trimethoxystyryl)sulfonyl)methyl)pyridin-2-amine |
| 165 | CH | N | —CH$_2$SO$_2$— | (E)-2-methoxy-N,N-di(prop-2-yn-1-yl)-5-(((2,4,6-trimethoxystyryl)sulfonyl)methyl)pyridin-3-amine |

General Procedure 3a for Examples 161a, 162a, 163a, 164a and 165a

General Procedure 3a.

General Procedure 3 is followed, but using a mixture of one equivalent of 36, 44, 45, 46 or 47, and one equivalent of BrCH₂C≡CH. Reacting one equivalent of 36, 44, 45, 46 or 47 with one equivalent of BrCH₂C≡CH yields a mixture of mono (—NHCH₂—C≡CH) and di (—N(CH₂—C≡CH)₂) substitution products. The products are separated by column chomratograpy to obtain the following nonsubstitution products:

Example 161a (E)-2-methoxy-N-(prop-2-yn-1-yl)-5-(((2,4,6-trimethoxystyryl) sulfonyl)methyl) aniline.

Example 162a (E)-N-(4-methoxy-3-(prop-2-yn-1-ylamino)phenyl)-2-(2,4,6-trimethoxyphenyl)ethenesulfonamide.

Example 163a (E)-N-(4-methoxy-3-(prop-2-yn-1-ylamino)phenyl)-3-(2,4,6-trimethoxyphenyl) acrylamide.

Example 164a (E)-3-methoxy-N-(prop-2-yn-1-yl)-6-(((2,4,6-trimethoxystyryl)sulfonyl)methyl)pyridin-2-amine.

Example 165a (E)-2-methoxy-N-(prop-2-yn-1-yl)-5-(((2,4,6-trimethoxystyryl)sulfonyl)methyl)pyridin-3-amine.

General Procedure 4 for Examples 166-170

The compounds of Examples 166-170 (Table 9) are prepared according to Scheme 13 and General Procedure 4, by reacting intermediate 36, 44, 45, 46, or 47 with propiolic acid in the presence of a carbodiimide and a base:

Scheme 13

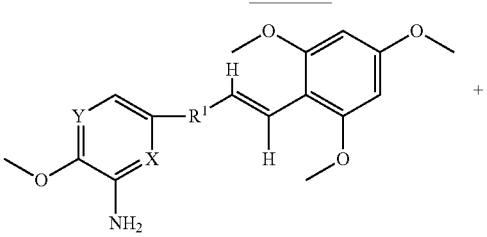

36: X = CH, Y = CH, R¹ = CH₂SO₂
44: X = CH, Y = CH, R¹ = NHSO₂
45: X = CH, Y = CH, R¹ = NHCO
46: X = N, Y = CH, R¹ = CH₂SO₂
47: X = CH, Y = N, R¹ = CH₂SO₂

HC≡CC(=O)OH ⟶

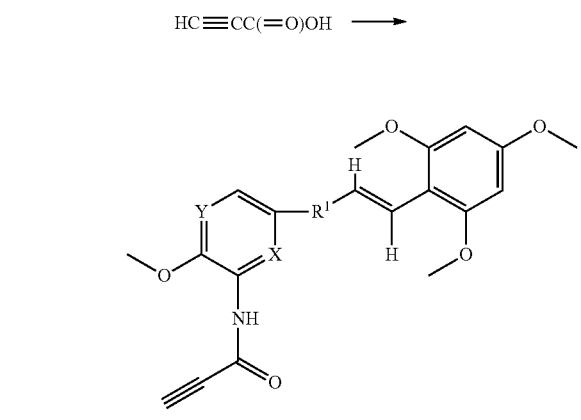

General Procedure 4.

In Scheme 13, propiolic acid (1.5 eq) is combined with EDC (1.5 eq), DMAP (0.2 eq) in methylene chloride and stirred at RT for 1 hr. One of 36, 44, 45, 46 or 47 (1 eq) is added in a single portion and the reaction is stirred at RT for 12 hrs. The mixture is diluted with ethyl acetate, washed with saturated sodium bicarbonate solution, dried over anhydrous sodium sulfate and concentrated under reduced pressure. The crude material is purified by flash chromatography to obtain pure compound.

TABLE 9

| Ex. No. | X | Y | R¹ | Compound |
|---|---|---|---|---|
| 166 | CH | CH | —CH₂SO₂— | (E)-N-(2-methoxy-5-(((2,4,6-trimethoxystyryl)sulfonyl)methyl)phenyl)propiolamide |

TABLE 9-continued

| Ex. No. | X | Y | R¹ | Compound |
|---|---|---|---|---|
| 167 | CH | CH | —NHSO$_2$— | (E)-N-(2-methoxy-5-(2-(2,4,6-trimethoxyphenyl)vinylsulfonamido)phenyl)propiolamide |
| 168 | CH | CH | —NHC(=O)— | (E)-N-(4-methoxy-3-propiolamidophenyl)-3-(2,4,6-trimethoxyphenyl)acrylamide |
| 169 | N | CH | —CH$_2$SO$_2$— | (E)-N-(3-methoxy-6-(((2,4,6-trimethoxystyryl)sulfonyl)methyl)pyridin-2-yl)propiolamide |
| 170 | CH | N | —CH$_2$SO$_2$— | (E)-N-(2-methoxy-5-(((2,4,6-trimethoxystyryl)sulfonyl)methyl)pyridin-3-yl)propiolamide |

General Procedure 5 for Examples 171-175

The compounds of Examples 171-175 are prepared according to Scheme 14 and General Procedure 5, by reacting intermediates 36, 44, 45, 46, or 47 with maleic anhydride:

Scheme 14

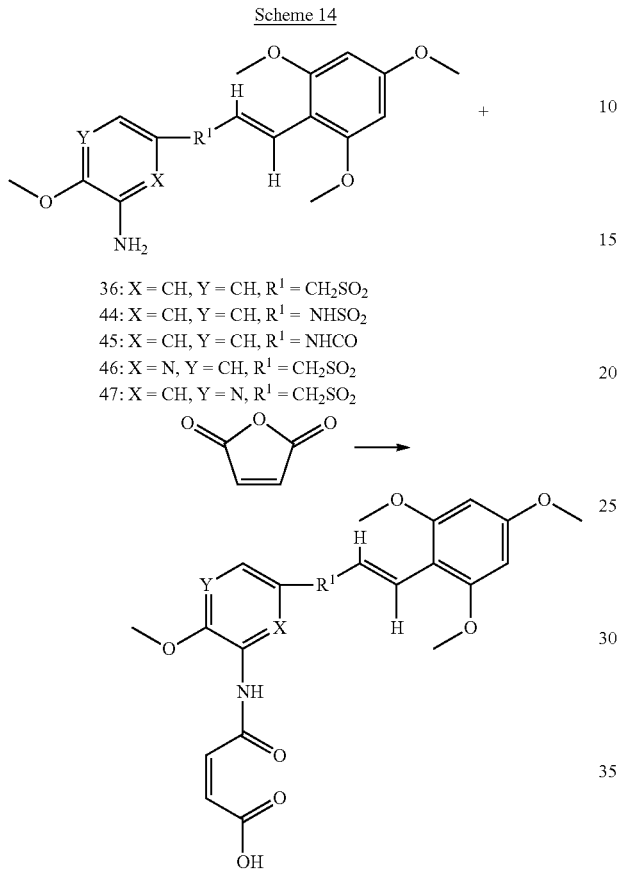

36: X = CH, Y = CH, $R^1$ = $CH_2SO_2$
44: X = CH, Y = CH, $R^1$ = $NHSO_2$
45: X = CH, Y = CH, $R^1$ = NHCO
46: X = N, Y = CH, $R^1$ = $CH_2SO_2$
47: X = CH, Y = N, $R^1$ = $CH_2SO_2$

General Procedure 5.

Maleic anhydride (1.1 eq.) is dissolved in anhydrous dichloromethane and the corresponding amine 36, 44, 45, 46 or 47 is added under nitrogen atmosphere and the reaction mixture is stirred for 2 h at ambient temperature. The solid precipitated after the completion of reaction is filtered and washed with small amount of dichloromethane and is dried to obtain pure compound.

Example 171

(Z)-4-((2-methoxy-5-(((E)-2,4,6-trimethoxy styrylsulfonyl) methyl) phenyl)amino)-4-oxobut-2-enoic acid

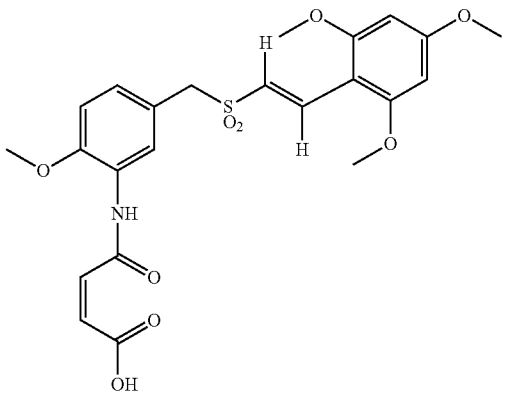

The title compound was obtained from (E)-2-methoxy-5-(((2,4,6-trimethoxystyryl)sulfonyl)methyl)aniline 36 and maleic anhydride, according to General Procedure 5. $^1$H NMR (DMSO-$d_6$, 600 MHz): δ 3.84 (s, 3H, $OCH_3$), 3.85 (s, 9H, 3×$OCH_3$), 4.37 (s, 2H, Ar—$CH_2$), 6.28 (s, 2H, Ar—H), 6.37 (d, J=12.1 Hz, 1H, =CH), 6.61 (d, J=12.1 Hz, 1H, =CH), 7.06 (d, J=8.4 Hz, 1H, Ar—H) 7.10-7.12 (dd, J=1.6, 8.4 Hz, 1H, Ar—H), 7.12 (d, J=15.6 Hz, 1H, =CH), 7.58 (d, J=15.6 Hz, 1H, =CH), 8.05 (d, J=1.6 Hz, 1H, Ar—H), 9.88 (s, 1H, NH).

Examples 172-175

The compounds of Examples 172-175 of Table 10 are prepared according to Scheme 14 and General Procedure 5, starting with intermediate 44, 45, 46, or 47:

TABLE 10

| Ex. No. | X | Y | $R^1$ | Compound |
|---|---|---|---|---|
| 172 | CH | CH | —$NHSO_2$— | (Z)-4-((2-methoxy-5-((E)-3-(2,4,6-trimethoxyphenyl)vinylsulfonamido)phenyl)amino)-4-oxobut-2-enoic acid 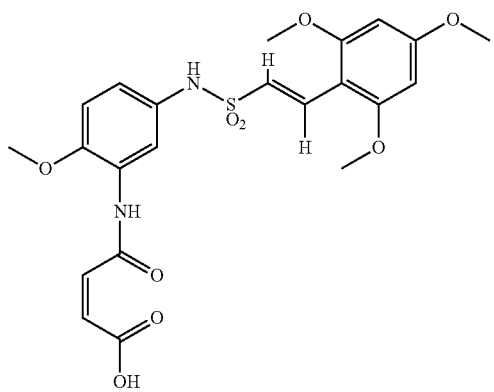 |

TABLE 10-continued
| Ex. No. | X | Y | R¹ | Compound |
|---|---|---|---|---|
| 173 | CH | CH | —NHC(=O)— | (Z)-4-((2-methoxy-5-((E)-3-(2,4,6-trimethoxyphenyl)acrylamido)phenyl)amino)-4-oxobut-2-enoic acid |
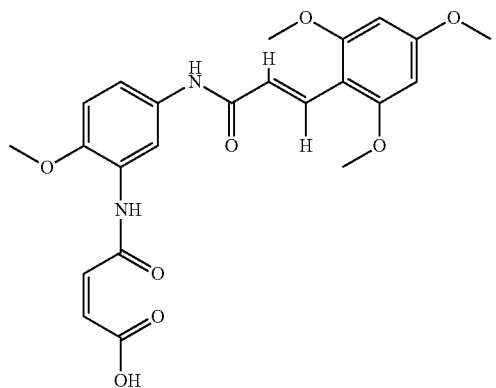
| 174 | N | CH | —CH$_2$SO$_2$— | (Z)-4-((3-methoxy-6-(((E)-2,4,6-trimethoxystyrylsulfonyl)methyl)pyridin-2-yl)amino)-4-oxobut-2-enoic acid |
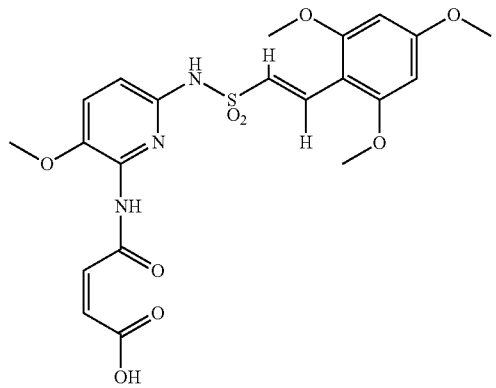
| 175 | CH | N | —CH$_2$SO$_2$— | (Z)-4-((2-methoxy-5-(((E)-2,4,6-trimethoxystyrylsulfonyl)methyl)pyridin-3-yl)amino)-4-oxobut-2-enoic acid |
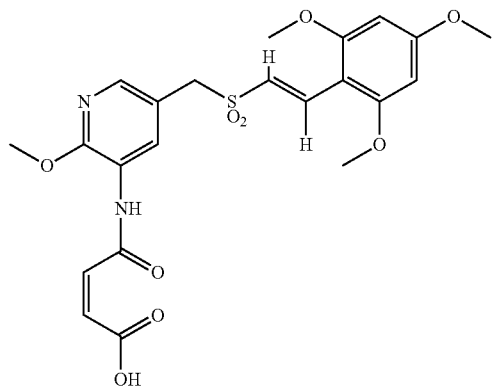

Example 176

(Z)-methyl 4-((2-methoxy-5-(((E)-2,4,6-trimethoxystyrylsulfonyl) methyl)phenyl)amino)-4-oxobut-2-enoate

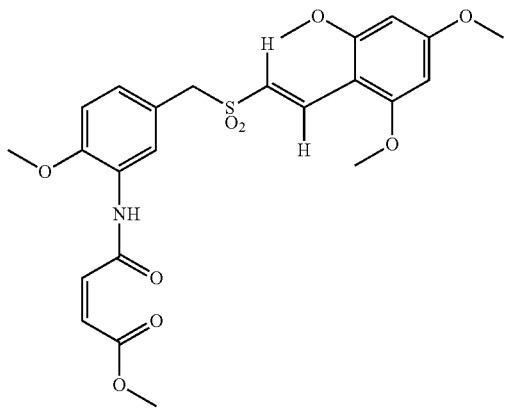

The title compound was obtained by esterification of ((Z)-4-((2-methoxy-5-(((E)-2,4,6-trimethoxy styrylsulfonyl)methyl)phenyl)amino)-4-oxobut-2-enoic acid (compound of Example 171) with methanol and a catalytic amount of concentrated $H_2SO_4$. $^1$H NMR (DMSO-$d_6$, 600 MHz): δ 3.65 (s, 3H), 3.75 (s, 12H, 4×OCH$_3$), 4.37 (s, 2H, Ar—CH$_2$), 6.29 (s, 2H, Ar—H), 6.44 (d, J=11.7 Hz, 1H, =CH), 6.65 (d, J=11.7 Hz, 1H, =CH), 7.04 (d, J=8.4 Hz, 1H, Ar—H) 7.10-7.12 (dd, J=1.6, 8.4 Hz, 1H, Ar—H), 7.13 (d, J=15.6 Hz, 1H, =CH), 7.59 (d, J=15.6 Hz, 1H, =CH), 8.03 (d, J=1.6 Hz, 1H, Ar—H), 9.60 (s, 1H, NH).

Examples 177-180

The compounds of Examples 177-180 in Table 11 are prepared according to the method used for the synthesis of the Example 176 compound, above, by esterification of the compound of Example 172, 173, 174 or 175 with methanol and concentrated sulfuric acid as catalyst.

TABLE 11

| Ex. No. | X | Y | R$^1$ | Compound |
|---|---|---|---|---|
| 177 | CH | CH | —NHSO$_2$— | (Z)-methyl 4-((2-methoxy-5-((E)-2-(2,4,6-trimethoxyphenyl)vinylsulfonamido)phenyl)amino)-4-oxobut-2-enoate |
| 178 | CH | CH | —NHC(=O)— | (Z)-methyl 4-((2-methoxy-5-((E)-3-(2,4,6-trimethoxyphenyl)acrylamido)phenyl)amino)-4-oxobut-2-enoate |

TABLE 11-continued

| Ex. No. | X | Y | R¹ | Compound |
|---|---|---|---|---|
| 179 | N | CH | —CH$_2$SO$_2$— | (Z)-methyl 4-((3-methoxy-6-(((E)-2,4,6-trimethoxystyrylsulfonyl)methyl)pyridin-2-yl)amino)-4-oxobut-2-enoate |

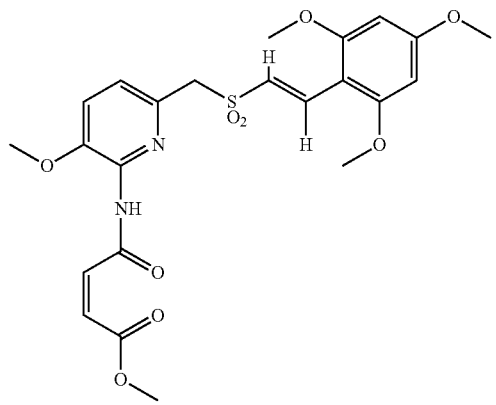

| | | | | |
|---|---|---|---|---|
| 180 | CH | N | —CH$_2$SO$_2$— | (Z)-methyl 4-((2-methoxy-5-(((E)-2,4,6-trimethoxystyrylsulfonyl)methyl)pyridin-3-yl)amino)-4-oxobut-2-enoate |

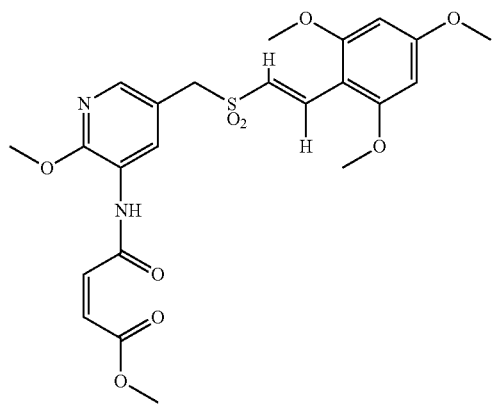

Examples 181-185

The compounds of Examples 181-185 are prepared according to Scheme 15 and General Procedure 6, by reacting intermediate 36, 44, 45, 46, or 47 with ethyl 4-halocrotonate:

Scheme 15

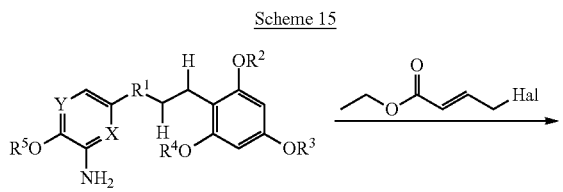

-continued

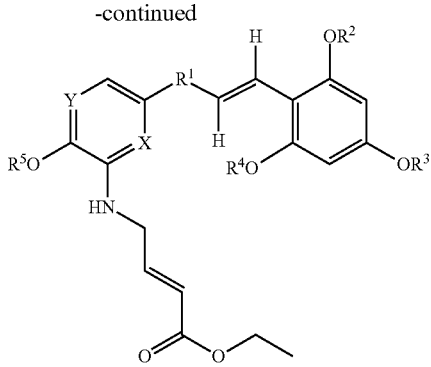

General Procedure 6.

Ethyl 4-halocrotonate (2 eq) is added to the corresponding amine 36, 44, 45, 46 or 47 (1 eq) and sodium acetate (2 eq)

in ethanol at room temperature and the reaction mixture is refluxed for 30 min. The reaction is monitored by TLC and upon completion the reaction mixture is cooled, the separated solid is filtered and washed with a small amount of water, methanol and ether, and then dried to obtain pure compound.

Example 181

(E)-Ethyl 4-((2-methoxy-5-(((E)-2,4,6-trimethoxystyrylsulfonyl)methyl)phenyl)amino)but-2-enoate

Ethyl 4-bromocrotonate (0.35 mL, 2.54 mmol) was added to a solution of (E)-2-methoxy-5-(((2,4,6-trimethoxystyryl) sulfonyl)methyl)aniline 36 (500 mg, 1.27 mmol) and sodium acetate (208 mg, 2.54 mmol) in ethanol (10 mL) at room temperature and the reaction mass was heated at reflux for 30 min. The reaction was monitored by TLC and upon completion the reaction mixture was allowed to attain room temperature. The separated solid was filtered, washed with water (5 mL), methanol (5 mL), diethyl ether (2 mL) and dried to obtain a pure sample.

$^1$H NMR: (600 MHz, DMSO-d$_6$) δ 1.17 (t, 3H, J=7.0 Hz), 3.78 (s, 3H), 3.82 (m, 2H), 3.85 (s, 9H), 4.05-4.09 (q, 2H, J=7.0 Hz), 4.33 (s, 2H), 5.40 (t, 1H, J=5.8 Hz), 5.84 (d, 1H, J=15.6 Hz), 6.29 (s, 2H), 6.43 (s, 1H), 6.56 (d, 1H, J=7.5 Hz), 6.79 (d, 1H, J=8.1 Hz), 6.84-6.89 (dt, 1H, J=15.7 & 5.8 Hz), 7.11 (d, 1H, J=15.7 Hz), 7.55 (d, 1H, J=15.7 Hz). LC-MS found (M+H)$^+$ (m/z), 506.21; calcd for $C_{25}H_{31}NO_8S$ m/z, 505.18.

Examples 182-185

The compounds of Examples 182-185 of Table 12 are prepared according to Scheme 15 and General Procedure 6 in an analogous manner to Example 181, but starting from intermediate 44, 45, 46, or 47:

TABLE 12

| Ex. No. | X | Y | R$^1$ | Compound |
|---|---|---|---|---|
| 182 | CH | CH | —NHSO$_2$— | (E)-ethyl 4-((2-methoxy-5-((E)-2-(2,4,6-trimethoxyphenyl)vinylsulfonamido)phenyl)amino)but-2-enoate |
| 183 | CH | CH | —NHC(=O)— | (E)-ethyl 4-((2-methoxy-5-((E)-3-(2,4,6-trimethoxyphenyl)acrylamido)phenyl)amino)but-2-enoate |
| 184 | N | CH | —CH$_2$SO$_2$— | (E)-ethyl 4-((3-methoxy-6-(((E)-2,4,6-trimethoxystyrylsulfonyl)methyl)pyridin-2-yl)amino)but-2-enoate |
| 185 | CH | N | —CH$_2$SO$_2$— | (E)-ethyl 4-((2-methoxy-5-(((E)-2,4,6-trimethoxystyrylsulfonyl)methyl)pyridin-3-yl)amino)but-2-enoate |

Example 186

(E)-4-((2-methoxy-5-(((E)-2,4,6-trimethoxystyryl-sulfonyl)methyl)phenyl) amino)-4-oxobut-2-enoic acid

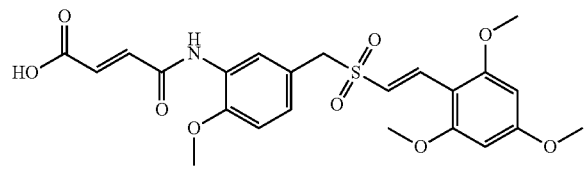 [SMILES: COc1cc(OC)c(/C=C/S(=O)(=O)Cc2ccc(OC)c(NC(=O)/C=C/C(=O)O)c2)c(OC)c1]

(E)-2-methoxy-5-(((2,4,6-trimethoxystyryl)sulfonyl)methyl)aniline 36 (500 mg, 1.27 mmol) in dichloromethane (5 mL) was added drop-wise to a solution of fumaryl chloride (0.275 mL) in dichloromethane (10 mL) at 0° C. under nitrogen atmosphere. The stirring was continued at room temperature for 30 min. After completion of the reaction, 5% aq. sodium hydroxide solution (20 mL) was added and the reaction contents were stirred for 5 min. The separated solid was filtered, washed with chloroform (5 mL each time×2), 3N hydrochloric acid (5 mL) followed by chloroform (5 mL) and dried to obtain pure product. $^1$H NMR: (600 MHz, DMSO-d$_6$) δ 3.84 (s, 3H), 3.85 (s, 9H), 4.38 (s, 2H), 6.29 (s, 2H), 6.62 (d, 1H, J=15.4 Hz), 7.05-7.12 (m, 3H), 7.44 (d, 1H, J=15.4 Hz), 7.57 (d, 1H, J=15.7 Hz), 8.10 (s, 1H), 9.83 (s, 1H), 12.95 (brs, 1H). LC-MS found (M+H)$^+$ (m/z), 492.13; calcd for C$_{23}$H$_{25}$NO$_9$S m/z, 491.13.

Examples 187-190

Following the synthesis method of Example 186, intermediates 43, 44, 45 or 46 is treated with fumaryl chloride as in Example 186 to obtain compounds 187-190 in Table 13 below.

TABLE 13

| Ex. No. | X | Y | R$^1$ | Compound |
|---|---|---|---|---|
| 187 | CH | CH | —NHSO$_2$— | (E)-4-((2-methoxy-5-((E)-2-(2,4,6-trimethoxyphenyl)vinylsulfonamido)phenyl)amino)-4-oxobut-2-enoic acid |
| 188 | CH | CH | —NHC(=O)— | (E)-4-((2-methoxy-5-((E)-3-(2,4,6-trimethoxyphenyl)acrylamido)phenyl)amino)-4-oxobut-2-enoic acid |
| 189 | N | CH | —CH$_2$SO$_2$— | (E)-4-((3-methoxy-6-(((E)-2,4,6-trimethoxystyrylsulfonyl)methyl)pyridin-2-yl)amino-4-oxobut-2-enoic acid |
| 190 | CH | N | —CH$_2$SO$_2$— | (E)-4-((2-methoxy-5-(((E)-2,4,6-trimethoxystyrylsulfonyl)methyl)pyridin-3-yl)amino)-4-oxobut-2-enoic acid |

Example 191

(E)-diethyl-2-(((2-methoxy-5-(((2,4,6-trimethoxystyryl) sulfonyl)methyl)phenyl)-amino)methylene) malonate

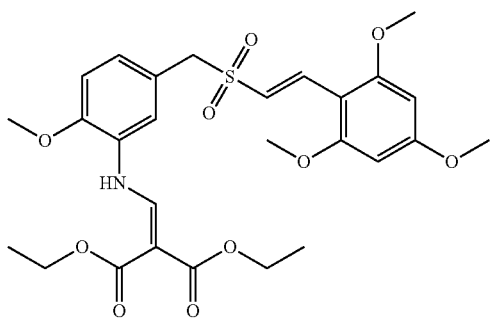

The title compound was obtained by heating (E)-2-methoxy-5-(((2,4,6-trimethoxystyryl)sulfonyl)methyl)aniline 36 with diethyl ethoxymethylenemalonate. $^1$H NMR (DMSO-$d_6$, 600 MHz): δ 1.21 (t, J=7.0 Hz, 3H), 1.26 (t, J=7.0 Hz, 3H), 3.83 (s, 9H, 3×OCH$_3$), 3.90 (s, 3H, OCH$_3$), 4.09-4.12 (q, 2H, OCH$_2$), 4.18-4.22 (q, 2H, OCH$_2$), 4.45 (s, 2H, Ar—CH$_2$), 6.26 (s, 2H, Ar—H), 6.44 (d, J=11.7 Hz, 1H, =CH), 7.07 (d, J=15.6 Hz, 1H, =CH) 7.11 (d, J=8.4 Hz, 1H, Ar—H), 7.13 (d, J=8.4 Hz, 1H, Ar—H), 7.44 (s, 1H, Ar—H), 7.49 (d, J=15.6 Hz, 1H, =CH), 8.40 (d, J=13.9 Hz, 1H, 1H, =CH), 10.99 (d, J=13.9 Hz, 1H, NH).

Examples 192-195

Following the synthesis method of Example 191, intermediate 43, 44, 45 or 46 is heated with diethyl ethoxymethylenemalonate to produce the compounds of Examples 192-195 in Table 14 below.

TABLE 14

| Ex. No. | X | Y | R$^1$ | Compound |
|---|---|---|---|---|
| 192 | CH | CH | —NHSO$_2$— | (E)-diethyl 2-(((2-methoxy-5-(2-(2,4,6-trimethoxyphenyl)vinylsulfonamido)phenyl)amino)methylene) malonate |
| 193 | CH | CH | —NHC(=O)— | (E)-diethyl 2-(((2-methoxy-5-(3-(2,4,6-trimethoxyphenyl)acrylamido)phenyl)amino)methylene) malonate |

TABLE 14-continued

| Ex. No. | X | Y | R¹ | Compound |
|---|---|---|---|---|
| 194 | N | CH | —CH$_2$SO$_2$— | (E)-diethyl 2-(((3-methoxy-6-(((2,4,6-trimethoxystyryl)sulfonyl)methyl)pyridin-2-yl)amino)methylene)malonate |
| 195 | CH | N | —CH$_2$SO$_2$— | (E)-diethyl 2-(((2-methoxy-5-(((2,4,6-trimethoxystyryl)sulfonyl)methyl)pyridin-3-yl)amino)methylene)malonate |

Example 196

(E)-N-(2-methoxy-5-(((2,4,6-trimethoxystyryl) sulfonyl)methyl)phenyl)ethenesulfonamide

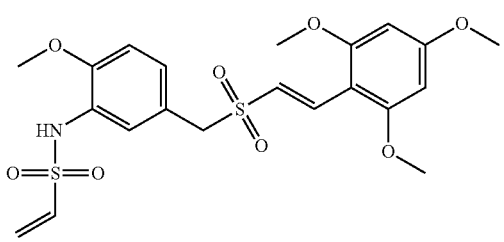 [SMILES: C=CS(=O)(=O)Nc1cc(CS(=O)(=O)/C=C/c2c(OC)cc(OC)cc2OC)ccc1OC]

To a stirring solution of 2-chloroethane-1-sulfonyl chloride (1 g, 6.134 mmol) in DCM (10 mL) at −15° C., is added drop wise a premixed suspension of compound 36 (2.65 g, 6.74 mmol) and NEt$_3$ (1.24 g, 12.27 mmol) in DCM (2.5 mL). The reaction mixture is left to stir for a further 30 minutes after addition, and then left to warm to RT. The reaction is diluted with more DCM (5-10 mL) and washed with 2M HCl (3×10 mL), H$_2$O (1×10 mL), dried (anhydrous MgSO$_4$), and filtered. The filtrate collected is concentrated in vacuo to give the crude product, which is purified by flash chromatography to furnish the title compound product (2.67 g, 90%) as off-white crystals.

Examples 197-200

Following the synthesis method of Example 196, intermediate 43, 44, 45 or 46 is treated with 2-chloroethane-1-sulfonyl chloride to produce the compounds of Examples 197-200 in Table 15 below.

TABLE 15

| Ex. No. | X | Y | R¹ | Compound |
|---|---|---|---|---|
| 197 | CH | CH | —NHSO₂— | (E)-N-(4-methoxy-3-(vinylsulfonamido)phenyl)-2-(2,4,6-trimethoxyphenyl)ethenesulfonamide |
| 198 | CH | CH | —NHC(=O)— | (E)-N-(4-methoxy-3-(vinylsulfonamido)phenyl)-3-(2,4,6-trimethoxyphenyl)acrylamide |
| 199 | N | CH | —CH₂SO₂— | (E)-N-(3-methoxy-6-(((2,4,6-trimethoxystyryl)sulfonyl)methyl)pyridin-2-yl)ethenesulfonamide |
| 200 | CH | N | —CH₂SO₂— | (E)-N-(2-methoxy-5-(((2,4,6-trimethoxystyryl)sulfonyl)methyl)pyridin-3-yl)ethenesulfonamide |

Example 201

(E)-N-(2-methoxy-5-(((2,4,6-trimethoxystyryl)sulfonyl) methyl)phenyl)acrylamide

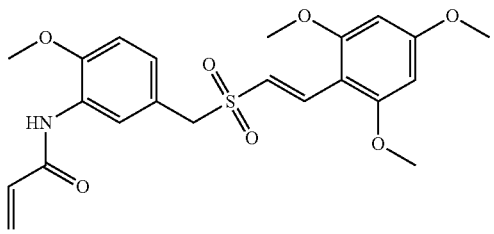

The starting compound 36 (1 eq) was dissolved in anhydrous dichloromethane and maintained at 0° C. To this, triethylamine (1 eq) was added followed by the addition of acryloyl chloride and the reaction mixture was stirred for 2-3 hrs. After the completion of reaction as indicated by TLC, water was added to the reaction solution. The organic phase was then washed with sodium bicarbonate, water and brine solution. The organic phase was then dried over sodium sulfate, filtered, concentrated, and the residue purified by flash chromatography. $^1$H NMR (DMSO-$d_6$, 600 MHz): δ 3.84 (s, 9H, 3×OCH$_3$), 3.85 (s, 3H, OCH$_3$), 4.36 (s, 2H, Ar—CH$_2$), 5.70-5.72 (dd, J=1.7, 10.0 Hz, 1H, =CH), 6.20-6.23 (dd, J=1.9, 16.9 Hz, 1H, =CH), 6.28 (s, 2H, Ar—H), 6.67-6.72 (dd, J=10, 16.8 Hz, 1H, =CH), 7.04 (d, J=8.4 Hz, 1H, Ar—H) 7.10-7.12 (dd, J=1.6, 8.4 Hz, 1H, Ar—H), 7.12 (d, J=15.6 Hz, 1H, =CH), 7.58 (d, J=15.6 Hz, 1H, =CH), 8.09 (d, J=1.6 Hz, 1H, Ar—H), 9.39 (s, 1H, NH).

Examples 202-205

Following the synthesis method of Example 201, intermediate 43, 44, 45 or 46 is substituted for intermediate 36 to produce the compounds of Examples 202-205 in Table 16 below.

TABLE 16

| Ex. No. | X | Y | R$^1$ | Compound |
|---|---|---|---|---|
| 202 | CH | CH | —NHSO$_2$— | (E)-N-(2-methoxy-5-(2-(2,4,6-trimethoxyphenyl)vinylsulfonamido)phenyl)acrylamide |
| 203 | CH | CH | —NHC(=O)— | (E)-N-(3-acrylamido-4-methoxyphenyl)-3-(2,4,6-trimethoxyphenyl)acrylamide |
| 204 | N | CH | —CH$_2$SO$_2$— | (E)-N-(3-methoxy-6-(((2,4,6-trimethoxystyryl)sulfonyl)methyl)pyridin-2-yl)acrylamide |

TABLE 16-continued

| Ex. No. | X | Y | R¹ | Compound |
|---|---|---|---|---|
| 205 | CH | N | —CH$_2$SO$_2$— | (E)-N-(2-methoxy-5-(((2,4,6-trimethoxystyryl)sulfonyl)methyl)pyridin-3-yl)acrylamide |

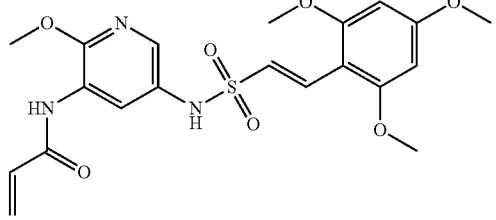

Example 206

Cytotoxicity Assay

The effect of the compounds of the invention on tumor cells was determined by the assay described by Latham et al., *Oncogene* 12:827-837 (1996). Tumor cells K562 (chronic myelogenous leukaemia) or DU145 (prostate cancer) were plated in 12-well dishes at a cell density of 2.5×10$^4$ cells well. The plated cells were treated 24 hours later with a compound of the invention dissolved in DMSO at multiple concentrations ranging from 0.001 to 10 µM. The plates were examined 96 hours later under an inverted microscope, Olympus CK-2 using a 10× objective, and compound activity was noted by physical observation. When necessary, the total number of viable cells was determined by trypsinizing the wells and counting the number of viable cells, as determined by trypan blue exclusion, using a hemacytometer. The results are shown in Table 17.

TABLE 17

| Compound | IC$_{50}$ (µM) K562 | IC$_{50}$ (µM) DU145 |
|---|---|---|
| Ex. 1 | 0.002 | 0.006 |
| Ex. 2 | 0.1 | 0.1 |
| Ex. 3 | 0.004 | 0.004 |
| Ex. 4 | 0.05 | 0.05 |
| Ex. 5 | ND | 0.009 |
| Ex. 7 | 0.05 | 0.05 |
| Ex. 8 | 0.075 | 0.075 |
| Ex. 161 | 2.5 | 2.5 |
| Ex. 171 | 2.0 | 2.0 |
| Ex. 176 | 0.25 | 2.0 |
| Ex. 181 | 0.25 | 0.25 |
| Ex. 186 | 2.0 | 2.0 |
| Ex. 191 | 2.0 | 2.0 |
| Ex. 201 | 0.75 | 0.75 |

Example 207

Cytotoxicity Assay for (Z)-Ethyl 3-((2-methoxy-5-(((E)-2,4,6-trimethoxystyrylsulfonyl)methyl) phenyl)amino)acrylate Cells of the cell lines listed in Table 18 (1×10$^5$) were plated into 6-well dishes. Twenty-four hours later, the compound of Example 1, i.e., (Z)-ethyl 3-((2-methoxy-5-(((E)-2,4,6-trimethoxystyrylsulfonyl)methyl) phenyl)amino)acrylate, or the compound of Comparative Example 1, i.e., sodium (E)-2-(5-((2,4,6-trimethoxystyrylsulfonyl)methyl)-2-methoxyphenylamino) acetate (rigosertib) was added at different concentrations over a 4 log dilution (0.001 to 10 µM). The total number of viable cells was determined after 96 hours of continuous treatment by staining with trypan blue and counting the number of non-staining cells (viable) remaining in each well using a hemacytometer. The percentage of viable cells remaining was calculated as follows: # viable cells (compound treated)/# viable cells (DMSO treated)*100. The GI$_{50}$ (the concentration of drug resulting in 50% net loss of growth inhibition) was determined. The results are shown in Table 18. Despite the similarity in structure to the Comparative Example 1 compound, the Example 1 compound was at least about 4 fold more active, and against some tumor types as much as 10-fold or even 100-fold more active, than the Comparative Example 1 compound. Notably, the compound of Comparative Example 1, while otherwise having a similar structure to the Compound of Example 1, lacks unsaturation in the moiety corresponding to R$^6$ in Formula I. The difference in activity is believed to be attributable to the ability of the Example 1 compound to form a covalent bond with the RBD on RAS effector molecules, thereby blocking binding of RAS to the effector molecules and thus interrupting RAS oncogenic signaling.

TABLE 18

| CELL LINE | Tumor Type | Example 1 Compound GI$_{50}$ (nM) | Comparative Example 1 Compound GI$_{50}$ (nM) |
|---|---|---|---|
| DU145 | Prostate | 10 | 150 |
| PC-3 | Prostate | 7.5 | 75 |
| N417 | Small Cell Lung Carcinoma | 8 | 100 |
| HT-29 | Colo-Rectal | 15 | 250 |
| HCT-116 | Colo-Rectal | 7.5 | 100 |
| HCT-15 | Colo-Rectal | 7.5 | 200 |
| H1299 | Non-Small Cell Lung Carcinoma | 4 | 200 |
| A549 | Non-Small Cell Lung Carcinoma | 7.5 | 75 |
| T-24 | Bladder | 4 | 70 |
| UM-UC-3 | Bladder | 3 | 50 |
| 5367 | Bladder | 3 | 100 |
| 2008 | Ovarian | 6 | 100 |
| Caov-3 | Ovarian | 4 | 150 |
| MDA-MB-231 | Breast | 7.5 | 90 |
| MIA-PaCa-2 | Pancreatic | 5 | 150 |
| WM1617 | Melanoma | 3 | 300 |
| K562 | Chronic Myelogenous Leukemia | 3 | 120 |
| RS4; 11 | ALL-B-Cell Precursor | 7.5 | 75 |
| DAUDI | B-Cell Lymphoma | 7.5 | 75 |
| CEM | T-Cell Lymphoma | 7.5 | 40 |

TABLE 18-continued

| CELL LINE | Tumor Type | Example 1 Compound $GI_{50}$ (nM) | Comparative Example 1 Compound $GI_{50}$ (nM) |
|---|---|---|---|
| MOLT-4 | T-Cell Lymphoma | 7.5 | 40 |
| Z1385 | Mantle Cell Lymphoma | 6 | 40 |
| GRANTA-519 | Mantle Cell Lymphoma | 6 | 40 |

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A compound according to Formula I, wherein:
X and Y are independently selected from CH and N, provided that both X and Y may not be N;
A is —(CH$_2$)$_m$;
m is 0-2;
R$^1$ is —CH(R)SO$_2$, —NHSO$_2$— or —NHC(=O)—;
R is H or —(C$_1$-C$_6$)alkyl;
each of R$^2$, R$^3$, and R$^5$ is independently selected from —(C$_1$-C$_6$)alkyl;
R$^6$ is:
—CH=CH—C(=O)—R$^7$;
—CH=C[C(=O)O—(C$_1$-C$_6$)alkyl]$_2$;
—C(=O)—CH=CH—R$^8$;
—C(=O)—(C$_2$-C$_6$) unsaturated acyclic hydrocarbyl; or
—SO$_2$—CH=CH—R$^9$;
R$^7$ is selected from —OR$^{10}$; —(C$_1$-C$_4$)alkyl; —NR$^{11}$R$^{12}$; aryl; substituted aryl with one or more substituents selected from halo, —(C$_1$-C$_4$)alkoxy, —(C$_1$-C$_4$)alkyl and methylenedioxy; heteroaryl and substituted heteroaryl, said heteroaryl and substituted heteroaryl containing up to ten ring atoms selected from carbon and nitrogen, wherein the ring contains up to three nitrogen atoms, and said substituted heteroaryl has one or more substituents on said ring atoms selected from halo, —(C$_1$-C$_4$)alkoxy, —(C$_1$-C$_4$)alkyl and methylenedioxy;
R$^8$ is selected from —H, —CN, —NO$_2$, —C(=O)OH, —C(=O)O(C$_1$-C$_6$)alkyl, —(C$_1$-C$_4$)alkyl, aryl, substituted aryl, heteroaryl and substituted heteroaryl; wherein said substituted aryl and said substituted heteroaryl are substituted with one or more substituents independently selected from the group consisting of halogen, —CN, —NR$^{14}$$_2$, —(CH$_2$)$_n$NR$^{14}$$_2$, —O(CH$_2$)$_n$NR$^{14}$$_2$, —NR$^{14}$C(=O)(C$_1$-C$_6$)alkyl, —NR$^{14}$C(=O)O(C$_1$-C$_6$)alkyl, —NR$^{14}$C(=O)NR$^{14}$$_2$, —NR$^{14}$C(=NR$^{14}$)NR$^{14}$$_2$, —NH(CH$_2$)$_n$C(=O)OR$^{14}$, —OH, —NO$_2$, —(C$_1$-C$_6$)alkyl, —(CH$_2$)$_n$O(C$_1$-C$_6$)alkyl, —(C$_1$-C$_6$)alkoxy, —(C$_2$-C$_6$)alkenyl, —(C$_2$-C$_6$)alkynyl, —(C$_1$-C$_6$)perfluoroalkyl, —(C$_1$-C$_6$)perfluoroalkoxy, —C(=O)R$^{14}$, —C(=O)OR$^{14}$, —C(=O)NR$^{14}$$_2$, —OC(=O)R$^{14}$, —OC(=O)NR$^{14}$$_2$, —OC(=O)O(C$_1$-C$_6$)alkyl, —SO$_2$NH$_2$ and —SO$_2$(C$_1$-C$_6$)alkyl;
n is 1, 2, 3, 4, or 5;
R$^9$ is —H or —(C$_1$-C$_6$)alkyl;
R$^{10}$ is —H or —(C$_1$-C$_6$)alkyl; and
R$^{11}$ and R$^{12}$
are independently selected from —H, —(C$_1$-C$_4$)alkyl and —(C$_2$-C$_4$)acyl, or
R$^{11}$ and R$^{12}$, with the nitrogen atom to which they are attached, form a 5-, 6- or 7-membered heterocyclic ring containing said nitrogen atom and optionally another heteroatom, wherein when said optional hetroatom is a nitrogen atom, said nitrogen atom is optionally substituted with —(C$_1$-C$_4$)alkyl;
R$^{13}$ is H or (C$_2$-C$_6$) unsaturated hydrocarbyl group; and
each R$^{14}$ is independently selected from the group consisting of —H and —(C$_1$-C$_6$)alkyl; or
two occurrences of R$^{14}$ bound to the same nitrogen form a (C$_2$-C$_6$)heterocycle, together with the nitrogen atom to which they are bound; or
a pharmaceutically acceptable salt thereof.

2. The compound according to claim 1 wherein X and Y are CH, or pharmaceutically acceptable salt thereof.

3. The compound according to claim 2 wherein R$^1$ is —CH(R)SO$_2$—, or pharmaceutically acceptable salt thereof.

4. The compound according to claim 3 wherein R$^6$ is —CH=CH—C(=O)—R$^7$, or pharmaceutically acceptable salt thereof.

5. The compound according to claim 4 wherein R$^7$ is —OR$^{10}$ or —(C$_1$-C$_4$)alkyl, or pharmaceutically acceptable salt thereof.

6. The compound according to claim 5 wherein R$^7$ is hydroxyl, methyl, methoxy, ethyl or ethoxy.

7. The compound according to claim 6 which is:
(E)-3-((2-methoxy-5-(((E)-2,4,6-trimethoxystyrylsulfonyl)methyl)phenyl)amino)acrylic acid;
(Z)-ethyl 3-((2-methoxy-5-(((E)-2,4,6-trimethoxystyrylsulfonyl)methyl)phenyl)amino)acrylate;
(Z)-4-((2-methoxy-5-(((E)-2,4,6-trimethoxystyrylsulfonyl)methyl)phenyl)amino)but-3-en-2-one;
(Z)-methyl 3-((2-methoxy-5-(((E)-2,4,6-trimethoxystyrylsulfonyl) methyl)phenyl)amino)acrylate;
(E)-methyl 3-((2-methoxy-5-(((E)-2,4,6-trimethoxystyrylsulfonyl) methyl)phenyl)amino)acrylate;
(E)-ethyl 3-((2-methoxy-5-(((E)-2,4,6-trimethoxystyrylsulfonyl) methyl)phenyl)amino)acrylate;
(E)-ethyl 4-((2-methoxy-5-(((E)-2,4,6-trimethoxystyrylsulfonyl)methyl)phenyl)-amino)but-2-enoate;
or pharmaceutically acceptable salt thereof.

8. The compound according to claim 7 which is (Z)-ethyl 3-((2-methoxy-5-(((E)-2,4,6-trimethoxystyrylsulfonyl) methyl) phenyl)amino)acrylate, or pharmaceutically acceptable salt thereof.

9. The compound according to claim 4 wherein R$^7$ is NR$^{11}$R$^{12}$.

10. The compound according to claim 9 wherein —NR$^{11}$R$^{12}$ is piperazinyl or 4-methylpiperazinyl.

11. The compound according to claim 10 which is (Z)-3-((2-methoxy-5-(((E)-2,4,6-trimethoxystyrylsulfonyl) methyl) phenyl)amino)-1-(4-methylpiperazin-1-yl)prop-2-en-1-one, (Z)-3-((2-methoxy-5-(((E)-2,4,6-trimethoxystyrylsulfonyl)methyl)phenyl)amino)-1-(piperazin-1-yl)prop-2-en-1-one, or pharmaceutically acceptable salt thereof.

12. The compound according to claim 4 wherein $R^7$ is aryl having up to ten carbon atoms, or substituted aryl having up to ten ring carbons with one or more substituents selected from halo, —($C_1$-$C_4$)alkoxy, —($C_1$-$C_4$) alkyl and methylenedioxy, or pharmaceutically acceptable salt thereof.

13. The compound according to claim 12 which is (Z)-1-(benzo[d][1,3]dioxol-5-yl)-3-((2-methoxy-5-(((E)-2,4,6-trimethoxystyryl sulfonyl) methyl)phenyl) amino)prop-2-en-1-one, or pharmaceutically acceptable salt thereof.

14. The compound according to claim 12 wherein $R^7$ is phenyl, naphthyl, 4-halophenyl, 4-($C_1$-$C_4$)alkoxy, 4-($C_1$-$C_4$) alkyl, dialkoxyphenyl, trialkoxyphenyl, or a pharmaceutically acceptable salt thereof.

15. The compound according to claim 14 which is:
(Z)-1-(4-methoxyphenyl)-3-((2-methoxy-5-(((E)-2,4,6-trimethoxystyryl sulfonyl)methyl)phenyl) amino)prop-2-en-1-one;
(E)-1-(4-methoxyphenyl)-3-((2-methoxy-5-(((E)-2,4,6-trimethoxystyrylsulfonyl)methyl)phenyl) amino)prop-2-en-1-one;
(Z)-1-(3,4,5-trimethoxyphenyl)-3-((2-methoxy-5-(((E)-2,4,6-trimethoxystyrylsulfonyl) methyl)phenyl) amino) prop-2-en-1-one;
(E)-1-(3,4,5-trimethoxyphenyl)-3-((2-methoxy-5-(((E)-2,4,6-trimethoxystyrylsulfonyl) methyl)phenyl) amino) prop-2-en-1-one;
(Z)-1-(2,4,6-trimethoxyphenyl)-3-((2-methoxy-5-(((E)-2,4,6-trimethoxystyrylsulfonyl) methyl)phenyl) amino) prop-2-en-1-one;
(E)-1-(2,4,6-trimethoxyphenyl)-3-((2-methoxy-5-(((E)-2,4,6-trimethoxystyrylsulfonyl) methyl)phenyl) amino) prop-2-en-1-one;
(Z)-1-(2-chloro-3,4,5-trimethoxyphenyl)-3-((2-methoxy-5-(((E)-2,4,6-trimethoxystyrylsulfonyl) methyl)phenyl) amino)prop-2-en-1-one;
(E)-1-(2-chloro-3,4,5-trimethoxyphenyl)-3-((2-methoxy-5-(((E)-2,4,6-trimethoxystyrylsulfonyl) methyl)phenyl) amino)prop-2-en-1-one;
(Z)-1-(2-bromo-3,4,5-trimethoxyphenyl)-3-((2-methoxy-5-(((E)-2,4,6-trimethoxystyrylsulfonyl) methyl)phenyl) amino) prop-2-en-1-one;
(E)-1-(2-bromo-3,4,5-trimethoxyphenyl)-3-((2-methoxy-5-(((E)-2,4,6-trimethoxystyrylsulfonyl) methyl)phenyl) amino)prop-2-en-1-one;
(Z)-3-((2-methoxy-5-(((E)-2,4,6-trimethoxystyrylsulfonyl)methyl)phenyl)amino)-1-phenylprop-2-en-1-one;
(E)-3-((2-methoxy-5-(((E)-2,4,6-trimethoxystyrylsulfonyl)methyl)phenyl)amino)-1-phenylprop-2-en-1-one;
(Z)-1-(4-fluorophenyl)-3-((2-methoxy-5-(((E)-2,4,6-trimethoxystyrylsulfonyl)methyl)phenyl) amino) prop-2-en-1-one;
(E)-1-(4-fluorophenyl)-3-((2-methoxy-5-(((E)-2,4,6-trimethoxystyrylsulfonyl)methyl)phenyl) amino)prop-2-en-1-one;
(Z)-1-(4-chlorophenyl)-3-((2-methoxy-5-(((E)-2,4,6-trimethoxystyrylsulfonyl)methyl)phenyl) amino)prop-2-en-1-one;
(E)-1-(4-chlorophenyl)-3-((2-methoxy-5-(((E)-2,4,6-trimethoxystyrylsulfonyl)methyl)phenyl) amino)prop-2-en-1-one;
(Z)-1-(4-bromophenyl)-3-((2-methoxy-5-(((E)-2,4,6-trimethoxystyrylsulfonyl)methyl)phenyl) amino) prop-2-en-1-one;
(E)-1-(4-bromophenyl)-3-((2-methoxy-5-(((E)-2,4,6-trimethoxystyrylsulfonyl)methyl)phenyl) amino)prop-2-en-1-one;
(Z)-1-(4-methylphenyl)-3-((2-methoxy-5-(((E)-2,4,6-trimethoxystyrylsulfonyl)methyl)phenyl) amino)prop-2-en-1-one;
(E)-1-(4-methylphenyl)-3-((2-methoxy-5-(((E)-2,4,6-trimethoxystyrylsulfonyl)methyl)phenyl) amino)prop-2-en-1-one;
(Z)-1-(3,4-dimethoxyphenyl)-3-((2-methoxy-5-(((E)-2,4,6-trimethoxystyrylsulfonyl)methyl)phenyl)amino) prop-2-en-1-one;
(E)-1-(3,4-dimethoxyphenyl)-3-((2-methoxy-5-(((E)-2,4,6-trimethoxystyrylsulfonyl)methyl)phenyl) amino) prop-2-en-1-one;
(Z)-1-(naphthalen-3-yl)-3-((2-methoxy-5-(((E)-2,4,6-trimethoxystyrylsulfonyl)methyl)phenyl) amino)prop-2-en-1-one;
or pharmaceutically acceptable salt thereof.

16. The compound according to claim 3 wherein $R^6$ is —CH=C[C(=O)O—($C_1$-$C_6$)alkyl]$_2$, or pharmaceutically acceptable salt thereof.

17. The compound according to claim 16 which is (E)-diethyl-2-(((2-methoxy-5-(((2,4,6-trimethoxystyryl) sulfonyl)methyl)phenyl)-amino)methylene)malonate, or pharmaceutically acceptable salt thereof.

18. The compound according to claim 3 wherein $R^6$ is —C(=O)—CH=CH—$R^8$, or pharmaceutically acceptable salt thereof.

19. The compound according to claim 18 wherein $R^8$ is —H or —C(=O)OH, —C(=O)O($C_1$-$C_6$)alkyl or pharmaceutically acceptable salt thereof.

20. The compound according to claim 19 which is (E)-N-(2-methoxy-5-(((2,4,6-trimethoxystyryl) sulfonyl)methyl)phenyl)acrylamide; (Z)-4-((2-methoxy-5-(((E)-2,4,6-trimethoxystyrylsulfonyl)methyl) phenyl)amino)-4-oxobut-2-enoic acid; (E)-4-((2-methoxy-5-(((E)-2,4,6-trimethoxystyrylsulfonyl)methyl)phenyl) amino)-4-oxobut-2-enoic acid; (Z)-methyl 4-((2-methoxy-5-(((E)-2,4,6-trimethoxystyrylsulfonyl) methyl)phenyl)amino)-4-oxobut-2-enoate; or pharmaceutically acceptable salt thereof.

21. The compound according to claim 3 wherein $R^6$ is —C(=O)—($C_2$-$C_6$) unsaturated acyclic hydrocarbyl, or pharmaceutically acceptable salt thereof.

22. The compound according to claim 21 which is (E)-2-methoxy-N,N-di(prop-2-yn-1-yl)-5-(((2,4,6-trimethoxystyryl)sulfonyl)methyl)aniline, (E)-N-(2-methoxy-5-(((2,4,6-trimethoxystyryl)sulfonyl)methyl)phenyl)propiolamide, (E)-2-methoxy-N-(prop-2-yn-1-yl)-5-(((2,4,6-trimethoxystyryl)sulfonyl)methyl)aniline, or pharmaceutically acceptable salt thereof.

23. The compound according to claim 2 wherein $R^1$ is —NHSO$_2$—, or pharmaceutically acceptable salt thereof.

24. The compound according to claim 23 wherein $R^6$ is —CH=CH—C(=O)—$R^7$, or pharmaceutically acceptable salt thereof.

25. The compound according to claim 24 wherein $R^7$ is —OR$^{10}$ or —($C_1$-$C_4$)alkyl, or pharmaceutically acceptable salt thereof.

26. The compound according to claim 25 wherein $R^7$ is hydroxyl, methyl, methoxy, ethyl or ethoxy.

27. The compound according to claim 26 which is:
(E)-3-((2-methoxy-5-((E)-2-(2,4,6-trimethoxyphenyl)vinylsulfonamido)phenyl)amino) acrylic acid;

(Z)-ethyl 3-((2-methoxy-5-((E)-2-(2,4,6-trimethoxyphenyl)vinylsulfonamido)phenyl)amino)acrylate;
(E)-N-(4-Methoxy-3-(((Z)-3-oxobut-1-en-1-yl)amino)phenyl)-2-(2,4,6-trimethoxyphenyl)ethenesulfonamide;
(Z)-methyl 3-((2-methoxy-5-((E)-2-(2,4,6-trimethoxyphenyl)vinylsulfonamido)phenyl)amino)acrylate;
(E)-methyl 3-((2-methoxy-5-((E)-2-(2,4,6-trimethoxyphenyl)vinylsulfonamido)phenyl)amino)acrylate;
(E)-ethyl 3-((2-methoxy-5-((E)-2-(2,4,6-trimethoxyphenyl)vinylsulfonamido)phenyl)amino)acrylate;
(E)-ethyl 4-((2-methoxy-5-((E)-2-(2,4,6-trimethoxyphenyl)vinylsulfonamido)phenyl) amino)but-2-enoate;
or pharmaceutically acceptable salt thereof.

28. The compound according to claim 24 wherein $R^7$ is $NR^{11}R^{12}$.

29. The compound according to claim 28 wherein $-NR^{11}R^{12}$ is piperazinyl or 4-methylpiperazinyl.

30. The compound according to claim 29 which is (E)-N-(4-methoxy-3-(((Z)-3-(4-methylpiperazin-1-yl)-3-oxoprop-1-en-1yl)amino)phenyl)-2-(2,4,6-trimethoxyphenyl)ethenesulfonamide, (E)-N-(4-methoxy-3-(((Z)-3-(piperazin-1-yl)-3-oxoprop-1-en-1yl)amino)phenyl)-2-(2,4,6-trimethoxyphenyl)ethenesulfonamide, or pharmaceutically acceptable salt thereof.

31. The compound according to claim 24 wherein $R^7$ is aryl having up to ten carbon atoms, or substituted aryl having up to ten ring carbons with one or more substituents selected from halo, $-(C_1-C_4)$alkoxy, $-(C_1-C_4)$alkyl and methylenedioxy, or pharmaceutically acceptable salt thereof.

32. The compound according to claim 31 which is (E)-N-(3-(((Z)-3-(benzo[d][1,3]dioxol-5-yl)-3-oxoprop-1-en-1-yl)amino)-4-methoxy phenyl)-2-(2,4,6-trimethoxyphenyl)ethenesulfonamide.

33. The compound according to claim 31 wherein $R^7$ is phenyl, naphthyl, 4-halophenyl, 4-$(C_1-C_4)$alkoxy, 4-$(C_1-C_4)$alkyl, dialkoxyphenyl, trialkoxyphenyl, or a pharmaceutically acceptable salt thereof.

34. The compound according to claim 33 which is:
(E)-N-(4-methoxy-3-(((Z)-3-oxo-3-phenylprop-1-en-1yl)amino)phenyl)-2-(2,4,6-trimethoxyphenyl)ethenesulfonamide;
(E)-N-(4-methoxy-3-(((E)-3-oxo-3-phenylprop-1-en-1-yl)amino)phenyl)-2-(2,4,6-trimethoxyphenyl)ethenesulfonamide;
(E)-N-(3-(((Z)-3-(4-methoxyphenyl)-3-oxoprop-1-en-1-yl)amino)-4-methoxyphenyl)-2-(2,4,6-trimethoxyphenyl)ethenesulfonamide;
(E)-N-(3-(((E)-3-(4-methoxyphenyl)-3-oxoprop-1-en-1-yl)amino)-4-methoxyphenyl)-2-(2,4,6-trimethoxyphenyl)ethane sulfonamide;
(E)-N-(3-(((Z)-3-(4-fluorophenyl)-3-oxoprop-1-en-1-yl)amino)-4-methoxy phenyl)-2-(2,4,6-trimethoxyphenyl)ethenesulfonamide;
(E)-N-(3-(((E)-3-(4-fluorophenyl)-3-oxoprop-1-en-1-yl)amino)-4-methoxyphenyl)-2-(2,4,6-trimethoxyphenyl)ethenesulfonamide;
(E)-N-(3-(((Z)-3-(4-chlorophenyl)-3-oxoprop-1-en-1-yl)amino)-4-methoxy phenyl)-2-(2,4,6-trimethoxyphenyl)ethenesulfonamide;
(E)-N-(3-(((E)-3-(4-chlorophenyl)-3-oxoprop-1-en-1-yl)amino)-4-methoxyphenyl)-2-(2,4,6-trimethoxyphenyl)ethenesulfonamide;
(E)-N-(3-(((Z)-3-(4-bromophenyl)-3-oxoprop-1-en-1-yl)amino)-4-methoxy phenyl)-2-(2,4,6-trimethoxyphenyl)ethenesulfonamide;
(E)-N-(3-(((E)-3-(4-bromophenyl)-3-oxoprop-1-en-1-yl)amino)-4-methoxyphenyl)-2-(2,4,6-trimethoxyphenyl)ethenesulfonamide;
(E)-N-(3-(((Z)-3-(4-methylphenyl)-3-oxoprop-1-en-1-yl)amino)-4-methoxy phenyl)-2-(2,4,6-trimethoxyphenyl)ethenesulfonamide;
(E)-N-(3-(((E)-3-(4-methylphenyl)-3-oxoprop-1-en-1-yl)amino)-4-methoxyphenyl)-2-(2,4,6-trimethoxyphenyl)ethenesulfonamide;
(E)-N-(3-(((Z)-3-(3,4-dimethoxyphenyl)-3-oxoprop-1-en-1-yl)amino)-4-methoxyphenyl)-2-(2,4,6-trimethoxyphenyl)ethenesulfonamide;
(E)-N-(3-(((E)-3-(3,4-dimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(3,4,5-trimethoxyphenyl)-3-oxoprop-1-en-1-yl)amino)-4-methoxyphenyl)-2-(2,4,6-trimethoxyphenyl)ethenesulfonamide;
(E)-N-(3-(((E)-3-(3,4,5-trimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(2,4,6-trimethoxyphenyl)-3-oxoprop-1-en-1-yl)amino)-4-methoxyphenyl)-2-(2,4,6-trimethoxyphenyl)ethenesulfonamide;
(E)-N-(3-(((E)-3-(2,4,6-trimethoxyphenyl)-3-oxoprop-1-en-1-yl)amino)-4-methoxyphenyl)-2-(2,4,6-trimethoxyphenyl)ethenesulfonamide;
(E)-N-(3-(((Z)-3-(2-chloro-3,4,5-trimethoxyphenyl)-3-oxoprop-1-en-1-yl) amino)-4-methoxy phenyl)-2-(2,4,6-trimethoxyphenyl)ethenesulfonamide;
(E)-N-(3-(((E)-3-(2-chloro-3,4,5-trimethoxyphenyl)-3-oxoprop-1-en-1-yl)amino)-4-methoxyphenyl)-2-(2,4,6-trimethoxyphenyl) ethenesulfonamide;
(E)-N-(3-(((Z)-3-(2-bromo-3,4,5-trimethoxyphenyl)-3-oxoprop-1-en-1-yl) amino)-4-methoxy phenyl)-2-(2,4,6-trimethoxyphenyl)ethenesulfonamide;
(E)-N-(3-(((E)-3-(2-bromo-3,4,5-trimethoxyphenyl)-3-oxoprop-1-en-1-yl) amino)-4-methoxyphenyl)-2-(2,4,6-trimethoxyphenyl)ethenesulfonamide;
(E)-N-(3-(((Z)-3-(naphthalen-3-yl)-3-oxoprop-1-en-1-yl)amino)-4-methoxy phenyl)-2-(2,4,6-trimethoxyphenyl)ethenesulfonamide;
or pharmaceutically acceptable salt thereof.

35. The compound according to claim 23 wherein $R^6$ is CH=C[C(=O)O—$(C_1-C_6)$alkyl]2', or pharmaceutically acceptable salt thereof.

36. The compound according to claim 35 which is (E)-diethyl 2-(((2-methoxy-5-(2-(2,4,6-trimethoxyphenyl)vinylsulfonamido)phenyl)amino)methylene)malonate, or pharmaceutically acceptable salt thereof.

37. The compound according to claim 23 wherein $R^6$ is $-C(=O)-CH=CH-R^8$, or pharmaceutically acceptable salt thereof.

38. The compound according to claim 37 wherein $R^8$ is $-H$, $-C(=O)OH$ or $-C(=O)O(C_1-C_6)$alkyl, or pharmaceutically acceptable salt thereof.

39. The compound according to claim 38 which is (E)-N-(2-methoxy-5-(2-(2,4,6-trimethoxyphenyl)vinylsulfonamido)phenyl)acrylamide; (Z)-4-((2-methoxy-5-((E)-2-(2,4,6-trimethoxyphenyl)vinylsulfonamido)phenyl)amino)-4-oxobut-2-enoic acid; (E)-4-((2-methoxy-5-((E)-2-(2,4,6-trimethoxyphenyl)vinylsulfonamido)phenyl)amino)-4-oxobut-2-enoic acid; (Z)-methyl 4-((2-methoxy-5-((E)-2-(2,4,6-trimethoxyphenyl)vinylsulfonamido)phenyl)amino)-4-oxobut-2-enoate; or pharmaceutically acceptable salt thereof.

40. The compound according to claim 23 wherein $R^6$ is —C(=O)—($C_2$-$C_6$) unsaturated acyclic hydrocarbyl, or pharmaceutically acceptable salt thereof.

41. The compound according to claim 40 which is (E)-N-(3-(di(prop-2-yn-1-yl)amino)-4-methoxyphenyl)-2-(2,4,6-trimethoxyphenyl)ethenesulfonamide, (E)-N-(2-methoxy-5-(2-(2,4,6-trimethoxyphenyl)vinylsulfonamido)phenyl) propiolamide, (E)-N-(4-methoxy-3-(prop-2-yn-1-ylamino) phenyl)-2-(2,4,6-trimethoxyphenyl)ethenesulfonamide, or pharmaceutically acceptable salt thereof.

42. The compound according to claim 2 wherein $R^1$ is —NH(C=O)—, or pharmaceutically acceptable salt thereof.

43. The compound according to claim 42 wherein $R^6$ is —CH=CH—C(=O)—$R^7$, or pharmaceutically acceptable salt thereof.

44. The compound according to claim 43 wherein $R^7$ is —$OR^{10}$ or —($C_1$-$C_4$)alkyl, or pharmaceutically acceptable salt thereof.

45. The compound according to claim 44 wherein $R^7$ is hydroxyl, methyl, methoxy, ethyl or ethoxy.

46. The compound according to claim 45 which is:
(E)-3-((2-methoxy-5-((E)-3-(2,4,6-trimethoxyphenyl) acrylamido)phenyl)amino)acrylic acid;
(E)-N-(4-Methoxy-3-(((Z)-3-oxobut-1-en-1-yl)amino) phenyl)-3-(2,4,6-trimethoxyphenyl)acrylamide;
(Z)-methyl 3-((2-methoxy-5-((E)-3-(2,4,6-trimethoxyphenyl)acrylamido)phenyl)amino)acrylate;
((Z)-ethyl 3-((2-methoxy-5-((E)-3-(2,4,6-trimethoxyphenyl)acrylamido)phenyl)amino)acrylate;
(E)-methyl 3-((2-methoxy-5-((E)-2-(2,4,6-trimethoxyphenyl)acrylamido)phenyl)amino)acrylate;
(E)-ethyl 3-((2-methoxy-5-((E)-2-(2,4,6-trimethoxyphenyl)acrylamido)phenyl)amino)acrylate;
(E)-ethyl 4-((2-methoxy-5-((E)-3-(2,4,6-trimethoxyphenyl)acrylamido)phenyl)amino)but-2-enoate;
or pharmaceutically acceptable salt thereof.

47. The compound according to claim 43 wherein $R^7$ is $NR^{11}R^{12}$.

48. The compound according to claim 47 wherein —$NR^{11}R^{12}$ is piperazinyl or 4-methylpiperazinyl.

49. The compound according to claim 48 which is (E)-N-(4-methoxy-3-(((Z)-3-(4-methylpiperazin-1-yl)-3-oxoprop-1-en-1yl)amino)phenyl)-2-(2,4,6-trimethoxyphenyl) ethenecarboxamide, (E)-N-(4-methoxy-3-(((Z)-3-(piperazin-1-yl)-3-oxoprop-1-en-1yl)amino)phenyl)-2-(2,4,6-trimethoxyphenyl)ethenecarboxamide, or pharmaceutically acceptable salt thereof.

50. The compound according to claim 43 wherein $R^7$ is aryl having up to ten carbon atoms, or substituted aryl having up to ten ring carbons with one or more substituents selected from halo, —($C_1$-$C_4$)alkoxy, —($C_1$-$C_4$) alkyl and methylenedioxy, or pharmaceutically acceptable salt thereof.

51. The compound according to claim 50 which is (E)-N-(3-(((Z)-3-(benzo[d][1,3]dioxol-5-yl)-3-oxoprop-1-en-1-yl)amino)-4-methoxy phenyl)-2-(2,4,6-trimethoxyphenyl) ethenecarboxamide, or pharmaceutically acceptable salt thereof.

52. The compound according to claim 50 wherein $R^7$ is phenyl, naphthyl, 4-halophenyl, 4-($C_1$-$C_4$)alkoxy, 4-($C_1$-$C_4$) alkyl, dialkoxyphenyl, trialkoxyphenyl, or pharmaceutically acceptable salt thereof.

53. The compound according to claim 52 which is:
(E)-N-(4-methoxy-3-(((Z)-3-oxo-3-phenylprop-1-en-1yl) amino)phenyl)-2-(2,4,6-trimethoxyphenyl)ethenecarboxamide;
(E)-N-(4-methoxy-3-(((E)-3-oxo-3-phenylprop-1-en-1-yl)amino)phenyl)-2-(2,4,6-trimethoxyphenyl)ethenecarboxamide;
(E)-N-(3-(((Z)-3-(4-methoxyphenyl)-3-oxoprop-1-en-1-yl)amino)-4-methoxy phenyl)-2-(2,4,6-trimethoxyphenyl)ethenecarboxmide;
(E)-N-(3-(((E)-3-(4-methoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(4-fluorophenyl)-3-oxoprop-1-en-1-yl) amino)-4-methoxy phenyl)-2-(2,4,6-trimethoxyphenyl)ethenecarboxamide;
(E)-N-(3-(((E)-3-(4-fluorophenyl)-3-oxoprop-1-en-1-yl) amino)-4-methoxyphenyl)-2-(2,4,6-trimethoxyphenyl) ethenecarboxamide;
(E)-N-(3-(((Z)-3-(4-chlorophenyl)-3-oxoprop-1-en-1-yl) amino)-4-methoxy phenyl)-2-(2,4,6-trimethoxyphenyl)ethenecarboxamide;
(E)-N-(3-(((E)-3-(4-chlorophenyl)-3-oxoprop-1-en-1-yl) amino)-4-methoxyphenyl)-2-(2,4,6-trimethoxyphenyl) ethenecarboxamide;
(E)-N-(3-(((Z)-3-(4-bromophenyl)-3-oxoprop-1-en-1-yl) amino)-4-methoxy phenyl)-2-(2,4,6-trimethoxyphenyl)ethenecarboxamide;
(E)-N-(3-(((E)-3-(4-bromophenyl)-3-oxoprop-1-en-1-yl) amino)-4-methoxyphenyl)-2-(2,4,6-trimethoxyphenyl) ethenecarboxamide;
(E)-N-(3-(((Z)-3-(4-methylphenyl)-3-oxoprop-1-en-1-yl) amino)-4-methoxy phenyl)-2-(2,4,6-trimethoxyphenyl)ethenecarboxamide;
(E)-N-(3-(((E)-3-(4-methylphenyl)-3-oxoprop-1-en-1-yl) amino)-4-methoxyphenyl)-2-(2,4,6-trimethoxyphenyl) ethenecarboxamide;
(E)-N-(3-(((Z)-3-(3,4-dimethoxyphenyl)-3-oxoprop-1-en-1-yl)amino)-4-methoxyphenyl)-2-(2,4,6-trimethoxyphenyl)ethenecarboxamide;
(E)-N-(3-(((E)-3-(3,4-dimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((E)-3-(3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(2,4,6-trimethoxyphenyl)-3-oxoprop-1-en-1-yl)amino)-4-methoxyphenyl)-2-(2,4,6-trimethoxyphenyl)ethenecarboxamide;
(E)-N-(3-(((E)-3-(2,4,6-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(2-chloro-3,4,5-trimethoxyphenyl)-3-oxoprop-1-en-1-yl)amino)-4-methoxy phenyl)-2-(2,4,6-trimethoxyphenyl)ethenecarboxamide;
(E)-N-(3-(((E)-3-(2-chloro-3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(2-bromo-3,4,5-trimethoxyphenyl)-3-oxoprop-1-en-1-yl)amino)-4-methoxy phenyl)-2-(2,4,6-trimethoxyphenyl)ethenecarboxamide;
(E)-N-(3-(((E)-3-(2-bromo-3,4,5-trimethoxyphenyl)-3-oxoprop-1-en-1-yl)amino)-4-methoxyphenyl)-2-(2,4,6-trimethoxyphenyl)ethenecarboxamide;
(E)-N-(3-(((Z)-3-(naphthalen-3-yl)-3-oxoprop-1-en-1-yl) amino)-4-methoxy phenyl)-2-(2,4,6-trimethoxyphenyl)ethenecarboxamide;
or a pharmaceutically acceptable salt thereof.

54. The compound according to claim 42 wherein $R^6$ is —C(=O)—CH=CH—$R^8$, or pharmaceutically acceptable salt thereof.

55. The compound according to claim 54 wherein $R^8$ is —H, —C(=O)OH or —C(=O)O($C_1$-$C_6$)alkyl, or pharmaceutically acceptable salt thereof.

56. The compound according to claim 55 which is (E)-N-(3-acrylamido-4-methoxyphenyl)-3-(2,4,6-trimethoxyphenyl)acrylamide; (Z)-4-((2-methoxy-5-((E)-3-(2,4,6-trimethoxyphenyl)acrylamido)phenyl)amino)-4-oxobut-2-enoic acid; (E)-4-((2-methoxy-5-((E)-3-(2,4,6-trimethoxyphenyl)acrylamido)phenyl)amino)-4-oxobut-2-enoic acid; (Z)-methyl 4-((2-methoxy-5-((E)-3-(2,4,6-trimethoxyphenyl)acrylamido)phenyl)amino)-4-oxobut-2-enoate; or pharmaceutically acceptable salt thereof.

57. The compound according to claim 42 wherein $R^6$ is —CH=C[C(=O)O—($C_1$-$C_6$)alkyl]$_2$', or pharmaceutically acceptable salt thereof.

58. The compound according to claim 57 which is 4 (E)-diethyl 2-(((2-methoxy-5-(3-(2,4,6-trimethoxyphenyl)acrylamido)phenyl)amino)methylene)malonate, or pharmaceutically acceptable salt thereof.

59. The compound according to claim 42 wherein $R^6$ is —C(=O)—($C_2$-$C_6$) unsaturated acyclic hydrocarbyl.

60. The compound according to claim 59 which is (E)-N-(3-('-2-yn-1-yl)amino)-4-methoxyphenyl)-3-(2,4,6-trimethoxyphenyl)acrylamide, (E)-N-(4-methoxy-3-propionamidophenyl)-3-(2,4,6-trimethoxyphenyl)acrylamide, (E)-N-(4-methoxy-3-(prop-2-yn-1-ylamino)phenyl)-3-(2,4,6-trimethoxyphenyl)acrylamide, or pharmaceutically acceptable salt thereof.

61. The compound according to claim 1 wherein one of X or Y is N, or pharmaceutically acceptable salt thereof.

62. The compound according to claim 61 wherein $R^1$ is —CH(R)$SO_2$—, or pharmaceutically acceptable salt thereof.

63. The compound according to claim 62 wherein $R^6$ is —CH=CH—C(=O)—$R^7$, or pharmaceutically acceptable salt thereof.

64. The compound according to claim 63 wherein $R^7$ is —$OR^{10}$ or —($C_1$-$C_4$)alkyl, or pharmaceutically acceptable salt thereof.

65. The compound according to claim 64 wherein $R^7$ is hydroxyl, methyl, methoxy, ethyl or ethoxy.

66. The compound according to claim 65 which is:
(Z)-4-((3-Methoxy-6-(((E)-2,4,6-trimethoxystyrylsulfonyl)methyl)pyridin-2-yl)amino)but-3-en-2-one;
(Z)-methyl 3-((3-methoxy-6(((E)-2,4,6-trimethoxystyrylsulfonyl)methyl)pyridine-2-yl)amino)acrylate;
(Z)-ethyl 3-((3-methoxy-6(((E)-2,4,6-trimethoxystyrylsulfonyl)methyl)pyridine-2-yl)amino)acrylate;
(Z)-4-((2-methoxy-5-(((E)-2,4,6-trimethoxystyrylsulfonyl)methyl)pyridin-3-yl)amino)but-3-en-2-one;
(Z)-methyl 3-((2-methoxy-5-(((E)-2,4,6-trimethoxystyrylsulfonyl)methyl)pyridine-3-yl)amino)acrylate;
(Z)-ethyl 3-((2-methoxy-5-(((E)-2,4,6-trimethoxystyrylsulfonyl)methyl)pyridine-3-yl)amino)acrylate;
(E)-3-((3-methoxy-6-(((E)-2,4,6-trimethoxystyrylsulfonyl)methyl)pyridin-2-yl)amino)acrylic acid;
(E)-methyl 3-((3-methoxy-6-(((E)-2,4,6-trimethoxystyrylsulfonyl)methyl)pyridin-2-yl)amino)acrylate;
(E)-3-((2-methoxy-5-(((E)-2,4,6-trimethoxystyrylsulfonyl)methyl)pyridin-3-yl)amino)acrylic acid;
(E)-methyl 3-((2-methoxy-5-(((E)-2,4,6-trimethoxystyrylsulfonyl)methyl)pyridin-3-yl)amino)acrylate;
(E)-ethyl 3-((2-methoxy-5-(((E)-2,4,6-trimethoxystyrylsulfonyl)methyl)pyridin-3-yl)amino)acrylate;
(E)-ethyl 4-((3-methoxy-6-(((E)-2,4,6-trimethoxystyrylsulfonyl)methyl)pyridin-2-yl)amino)but-2-enoate;
(E)-ethyl 4-((2-methoxy-5-(((E)-2,4,6-trimethoxystyrylsulfonyl)methyl)pyridin-3-yl)amino)but-2-enoate;
or pharmaceutically acceptable salt thereof.

67. The compound according to claim 63 wherein $R^7$ is $NR^{11}R^{12}$.

68. The compound according to claim 67 wherein —$NR^{11}R^{12}$ is piperazinyl or 4-methylpiperazinyl.

69. The compound according to claim 68 which is:
(Z)-3-((3-methoxy-6(((E)-2,4,6-trimethoxystyrylsulfonyl)methyl)pyridine-2-yl)amino)-1-(4-methylpiperazin-1yl)prop-2-en-1-one;
(Z)-3-((3-methoxy-6(((E)-2,4,6-trimethoxystyrylsulfonyl)methyl)pyridine-2-yl)amino)-1-(piperazin-1 yl)prop-2-en-1-one;
(Z)-3-((2-methoxy-5-(((E)-2,4,6-trimethoxystyrylsulfonyl)methyl)pyridine-3-yl) amino)-1-(4-methylpiperazin-1yl)prop-2-en-1-one;
(Z)-3-((2-methoxy-5-(((E)-2,4,6-trimethoxystyrylsulfonyl)methyl)pyridine-3-yl)amino)-1-(piperazin-1yl)prop-2-en-1-one;
or pharmaceutically acceptable salt thereof.

70. The compound according to claim 63 wherein $R^7$ is aryl having up to ten carbon atoms, or substituted aryl having up to ten ring carbons with one or more substituents selected from halo, —($C_1$-$C_4$)alkoxy, —($C_1$-$C_4$)alkyl and methylenedioxy, or pharmaceutically acceptable salt thereof.

71. The compound according to claim 70 wherein $R^7$ is phenyl, naphthyl, 4-halophenyl, 4-($C_1$-$C_4$)alkoxy, 4-($C_1$-$C_4$)alkyl, dialkoxyphenyl, trialkoxyphenyl, or a pharmaceutically acceptable salt thereof.

72. The compound according to claim 71 which is:
(Z)-3-((3-methoxy-6(((E)-2,4,6-trimethoxystyrylsulfonyl)methyl)pyridine-2-yl)amino)-1-phenylprop-2-en-1-one
(Z)-1-(4-methoxyphenyl)-3-((3-methoxy-6(((E)-2,4,6-trimethoxystyrylsulfonyl)methyl)pyridine-2-yl)amino)prop-2-en-1-one;
(Z)-1-(4-fluorophenyl)-3-((3-methoxy-6(((E)-2,4,6-trimethoxystyrylsulfonyl)methyl)pyridine-2-yl)amino)prop-2-en-1-one;
(Z)-1-(4-chlorophenyl)-3-((3-methoxy-6(((E)-2,4,6-trimethoxystyrylsulfonyl)methyl)pyridine-2-yl)amino)prop-2-en-1-one;
(Z)-1-(4-bromophenyl)-3-((3-methoxy-6(((E)-2,4,6-trimethoxystyrylsulfonyl)methyl)pyridine-2-yl)amino)prop-2-en-1-one;
Z)-1-(4-methylphenyl)-3-((3-methoxy-6(((E)-2,4,6-trimethoxystyrylsulfonyl)methyl)pyridine-2-yl)amino)prop-2-en-1-one;
(Z)-1-(3,4-dimethoxyphenyl)-3-((3-methoxy-6(((E)-2,4,6-trimethoxystyrylsulfonyl)methyl)pyridine-2-yl)amino)prop-2-en-1-one;
(Z)-1-(3,4,5-trimethoxyphenyl)-3-((3-methoxy-6(((E)-2,4,6-trimethoxystyrylsulfonyl)methyl)pyridine-2-yl)amino)prop-2-en-1-one;
(Z)-1-(2,4,6-trimethoxyphenyl)-3-((3-methoxy-6(((E)-2,4,6-trimethoxystyrylsulfonyl)methyl)pyridine-2-yl)amino)prop-2-en-1-one;
(Z)-1-(2-chloro-3,4,5-trimethoxyphenyl)-3-((3-methoxy-6(((E)-2,4,6-trimethoxystyrylsulfonyl)methyl)pyridine-2-yl)amino)prop-2-en-1-one;
(Z)-1-(2-bromo-3,4,5-trimethoxyphenyl)-3-((3-methoxy-6(((E)-2,4,6-trimethoxystyrylsulfonyl)methyl)pyridine-2-yl)amino)prop-2-en-1-one;

Z)-1-(naphthalen-3-yl)-3-((3-methoxy-6-(((E)-2,4,6-trimethoxystyrylsulfonyl)methyl)pyridine-2-yl)amino)prop-2-en-1-one;
(Z)-1-(benzo[d][1,3]dioxol-5-yl))-3-((3-methoxy-6-(((E)-2,4,6-trimethoxystyrylsulfonyl) methyl)pyridine-2-yl)amino)prop-2-en-1-one;
(Z)-3-((2-methoxy-5-(((E)-2,4,6-trimethoxystyrylsulfonyl)methyl)pyridine-3-yl)amino)-1-phenylprop-2-en-1-one;
(Z)-1-(4-methoxyphenyl)-3-((2-methoxy-5-(((E)-2,4,6-trimethoxystyrylsulfonyl)methyl)pyridine-3-yl)amino)prop-2-en-1-one;
(Z)-1-(4-fluorophenyl)-3-((2-methoxy-5-(((E)-2,4,6-trimethoxystyrylsulfonyl)methyl)pyridine-3-yl)amino)prop-2-en-1-one;
(Z)-1-(4-chlorophenyl)-3-((2-methoxy-5-(((E)-2,4,6-trimethoxystyrylsulfonyl)methyl)pyridine-3-yl)amino)prop-2-en-1-one;
(Z)-1-(4-bromophenyl)-3-((2-methoxy-5-(((E)-2,4,6-trimethoxystyrylsulfonyl)methyl)pyridine-3-yl)amino)prop-2-en-1-one;
(Z)-1-(4-methylphenyl)-3-((2-methoxy-5-(((E)-2,4,6-trimethoxystyrylsulfonyl)methyl)pyridine-3-yl)amino)prop-2-en-1-one;
(Z)-1-(3,4-dimethoxyphenyl)-3-((2-methoxy-5-(((E)-2,4,6-trimethoxystyrylsulfonyl)methyl)pyridine-3-yl)amino)prop-2-en-1-one;
(Z)-1-(3,4,5-trimethoxyphenyl)-3-((2-methoxy-5-(((E)-2,4,6-trimethoxystyrylsulfonyl)methyl)pyridine-3-yl)amino)prop-2-en-1-one;
(Z)-1-(2,4,6-trimethoxyphenyl)-3-((2-methoxy-5-(((E)-2,4,6-trimethoxystyrylsulfonyl)methyl)pyridine-3-yl)amino)prop-2-en-1-one;
(Z)-1-(2-chloro-3,4,5-trimethoxyphenyl)-3-((2-methoxy-5-(((E)-2,4,6-trimethoxystyrylsulfonyl)methyl)pyridine-3-yl)amino)prop-2-en-1-one;
(Z)-1-(2-bromo-3,4,5-trimethoxyphenyl)-3-((2-methoxy-5-(((E)-2,4,6-trimethoxystyrylsulfonyl)methyl)pyridine-3-yl)amino)prop-2-en-1-one;
(Z)-1-(naphthalen-3-yl)-3-((2-methoxy-5-(((E)-2,4,6-trimethoxystyrylsulfonyl)methyl)pyridine-3-yl)amino)prop-2-en-1-one;
(Z)-1-(benzo[d][1,3]dioxol-5-yl))-3-((2-methoxy-5-(((E)-2,4,6-trimethoxystyrylsulfonyl)methyl)pyridine-3-yl)amino)prop-2-en-1-one;
(E)-3-((3-methoxy-6-(((E)-2,4,6-trimethoxystyrylsulfonyl)methyl)pyridin-2-yl)amino)-1-phenylprop-2-en-1-one;
(E)-1-(4-methoxyphenyl)-3-((3-methoxy-6-(((E)-2,4,6-trimethoxystyrylsulfonyl)methyl)pyridin-2-yl)amino)prop-2-en-1-one;
(E)-1-(4-fluorophenyl)-3-((3-methoxy-6-(((E)-2,4,6-trimethoxystyrylsulfonyl)methyl)pyridin-2-yl)amino)prop-2-en-1-one;
(E)-1-(4-chlorophenyl)-3-((3-methoxy-6-(((E)-2,4,6-trimethoxystyrylsulfonyl)methyl)pyridin-2-yl)amino)prop-2-en-1-one;
(E)-1-(4-bromophenyl)-3-((3-methoxy-6-(((E)-2,4,6-trimethoxystyrylsulfonyl)methyl)pyridin-2-yl)amino)prop-2-en-1-one;
(E)-1-(4-methylphenyl)-3-((3-methoxy-6-(((E)-2,4,6-trimethoxystyrylsulfonyl)methyl)pyridin-2-yl)amino)prop-2-en-1-one;
(E)-1-(3,4-dimethoxyphenyl)-3-((3-methoxy-6-(((E)-2,4,6-trimethoxystyrylsulfonyl)methyl)pyridin-2-yl)amino)prop-2-en-1-one;
(E)-1-(3,4,5-trimethoxyphenyl)-3-((3-methoxy-6-(((E)-2,4,6-trimethoxystyrylsulfonyl)methyl)pyridin-2-yl)amino)prop-2-en-1-one;
(E)-1-(2,4,6-trimethoxyphenyl)-3-((3-methoxy-6-(((E)-2,4,6-trimethoxystyrylsulfonyl)methyl)pyridin-2-yl)amino)prop-2-en-1-one;
(E)-1-(2-chloro-3,4,5-trimethoxyphenyl)-3-((3-methoxy-6-(((E)-2,4,6-trimethoxystyrylsulfonyl)methyl)pyridin-2-yl)amino)prop-2-en-1-one;
(E)-1-(2-bromo-3,4,5-trimethoxyphenyl)-3-((3-methoxy-6-(((E)-2,4,6-trimethoxystyrylsulfonyl)methyl)pyridin-2-yl)amino)prop-2-en-1-one;
(E)-3-((2-methoxy-5-(((E)-2,4,6-trimethoxystyrylsulfonyl)methyl)pyridin-3-yl)amino)-1-phenylprop-2-en-1-one;
(E)-1-(4-methoxyphenyl)-3-((2-methoxy-5-(((E)-2,4,6-trimethoxystyrylsulfonyl)methyl)pyridin-3-yl)amino)prop-2-en-1-one;
(E)-1-(4-fluorophenyl)-3-((2-methoxy-5-(((E)-2,4,6-trimethoxystyrylsulfonyl)methyl)pyridin-3-yl)amino)prop-2-en-1-one;
(E)-1-(4-chlorophenyl)-3-((2-methoxy-5-(((E)-2,4,6-trimethoxystyrylsulfonyl)methyl)pyridin-3-yl)amino)prop-2-en-1-one;
(E)-1-(4-bromophenyl)-3-((2-methoxy-5-(((E)-2,4,6-trimethoxystyrylsulfonyl)methyl)pyridin-3-yl)amino)prop-2-en-1-one;
(E)-1-(4-methylphenyl)-3-((2-methoxy-5-(((E)-2,4,6-trimethoxystyrylsulfonyl)methyl)pyridin-3-yl) amino)prop-2-en-1-one;
(E)-1-(3,4-dimethoxyphenyl)-3-((2-methoxy-5-(((E)-2,4,6-trimethoxystyrylsulfonyl)methyl)pyridin-3-yl)amino)prop-2-en-1-one;
(E)-1-(3,4,5-trimethoxyphenyl)-3-((2-methoxy-5-(((E)-2,4,6-trimethoxystyrylsulfonyl)methyl)pyridin-3-yl)amino)prop-2-en-1-one;
(E)-1-(2,4,6-trimethoxyphenyl)-3-((2-methoxy-5-(((E)-2,4,6-trimethoxystyrylsulfonyl)methyl)pyridin-3-yl)amino)prop-2-en-1-one;
(E)-1-(2-chloro-3,4,5-trimethoxyphenyl)-3-((2-methoxy-5-(((E)-2,4,6-trimethoxystyrylsulfonyl)methyl)pyridin-3-yl) amino)prop-2-en-1-one;
(E)-1-(2-bromo-3,4,5-trimethoxyphenyl)-3-((2-methoxy-5-(((E)-2,4,6-trimethoxystyrylsulfonyl)methyl)pyridin-3-yl) amino)prop-2-en-1-one;
or pharmaceutically acceptable salt thereof.

73. The compound according to claim 62 wherein $R^6$ is CH=C[C(=O)O—($C_1$-$C_6$)alkyl]$_2$, or pharmaceutically acceptable salt thereof.

74. The compound according to claim 73 which is (E)-diethyl 2-(((3-methoxy-6-(((2,4,6-trimethoxy styryl) sulfonyl)methyl)pyridin-2-yl) amino)methylene)malonate, (E)-diethyl 2-(((2-methoxy-5-(((2,4,6-trimethoxy styryl) sulfonyl)methyl)pyridin-3-yl)amino)methylene)malonate, or pharmaceutically acceptable salt thereof.

75. The compound according to claim 62 wherein $R^6$ is —C(=O)—CH=CH—$R^8$, or pharmaceutically acceptable salt thereof.

76. The compound according to claim 75 wherein $R^8$ is —H, —C(=O)OH or —C(=O)O($C_1$-$C_6$)alkyl, or pharmaceutically acceptable salt thereof.

77. The compound according to claim 76 which is (E)-N-(3-methoxy-6-(((2,4,6-trimethoxystyryl)sulfonyl)methyl)pyridin-2-yl)acrylamide; (E)-N-(2-methoxy-5-(((2,4,6-trimethoxystyryl)sulfonyl)methyl)pyridin-3-yl)acrylamide; (Z)-4-((3-methoxy-6-(((E)-2,4,6-trimethoxystyrylsulfonyl)methyl)pyridin-2-yl)amino)-4-oxobut-2-enoic acid; (Z)-4-

((2-methoxy-5-(((E)-2,4,6-trimethoxystyrylsulfonyl) methyl)pyridin-3-yl)amino)-4-oxobut-2-enoic acid; (E)-4-((3-methoxy-6-(((E)-2,4,6-trimethoxystyrylsulfonyl) methyl)pyridin-2-yl)amino)-4-oxobut-2-enoic acid; (E)-4-((2-methoxy-5-(((E)-2,4,6-trimethoxystyrylsulfonyl) methyl)pyridin-3-yl)amino)-4-oxobut-2-enoic acid; (Z)-methyl 4-((3-methoxy-6-(((E)-2,4,6-trimethoxystyrylsulfonyl)methyl)pyridin-2-yl)amino)-4-oxobut-2-enoate; (Z)-methyl 4-((2-methoxy-5-(((E)-2,4,6-trimethoxystyrylsulfonyl)methyl)pyridin-3-yl)amino)-4-oxobut-2-enoate; or pharmaceutically acceptable salt thereof.

78. The compound according to claim 62 wherein $R^6$ is —C(=O)—($C_2$-$C_6$) unsaturated acyclic hydrocarbyl, or pharmaceutically acceptable salt thereof.

79. The compound according to claim 78 which is:
(E)-3-methoxy-N,N-di(prop-2-yn-1-yl)-6-(((2,4,6-trimethoxystyryl)sulfonyl)methyl)pyridin-2-amine;
(E)-2-methoxy-N,N-di(prop-2-yn-1-yl)-5-(((2,4,6-trimethoxystyryl)sulfonyl)methyl)pyridin-3-amine;
(E)-3-methoxy-N-(prop-2-yn-1-yl)-6-(((2,4,6-trimethoxy styryl) sulfonyl)methyl)pyridin-2-amine;
(E)-2-methoxy-N-(prop-2-yn-1-yl)-5-(((2,4,6-trimethoxy styryl) sulfonyl)methyl)pyridin-3-amine;
(E)-N-(3-methoxy-6-(((2,4,6-trimethoxy styryl) sulfonyl) methyl)pyridin-2-yl)propiolamide;
(E)-N-(2-methoxy-5-(((2,4,6-trimethoxystyryl)sulfonyl) methyl)pyridin-3-yl)propiolamide;
or pharmaceutically acceptable salt thereof.

80. A process for preparing a compound or pharmaceutically acceptable salt thereof according to claim 1 wherein the compound has the Formula IV,

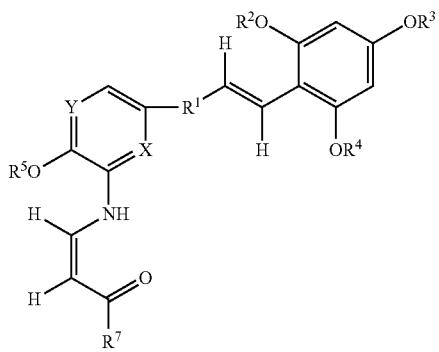

IV comprising reacting a compound of Formula II:

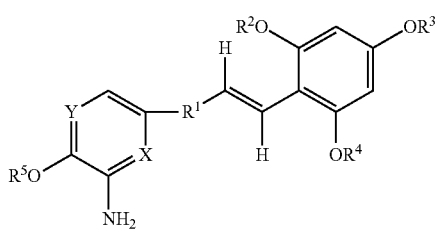

II with a compound of Formula III:

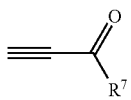

III wherein X, Y, $R^1$, $R^2$, $R^3$, $R^4$, $R^5$ and $R^7$ are as defined in claim 1, and isolating from the reaction mixture the compound according to claim 1 having the Formula IV, and optionally converting the compound to a pharmaceutically acceptable salt thereof.

81. A process for preparing a compound or pharmaceutically acceptable salt thereof according to claim 1 wherein the compound has the Formula VI,

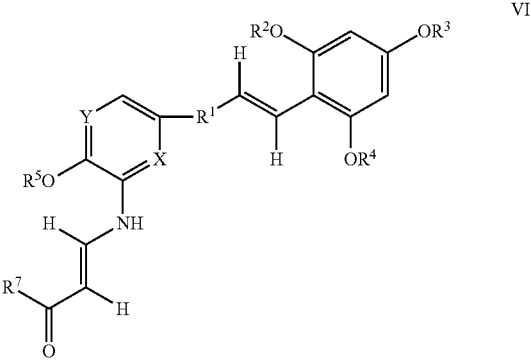

VI comprising reacting a compound of Formula II:

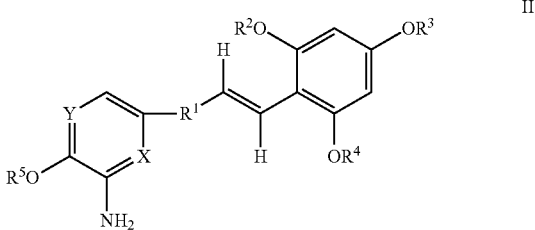

II with a compound of Formula V:

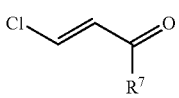

V wherein X, Y, $R^1$, $R^2$, $R^3$, $R^4$, $R^5$ and $R^7$ are as defined in claim 1, and isolating from the reaction mixture the compound according to claim 1 having the Formula VI, and optionally converting the compound to a pharmaceutically acceptable salt thereof.

82. A process for preparing a compound or pharmaceutically acceptable salt thereof according to claim 1 wherein the compound has the Formula X,

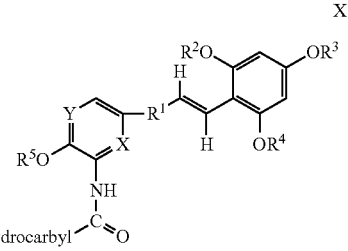

X comprising reacting a compound of Formula II:

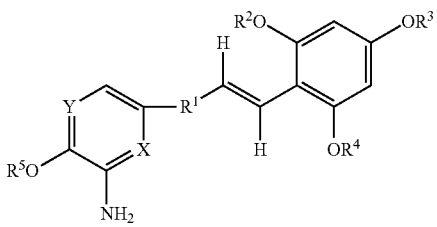

with a compound of Formula IX:

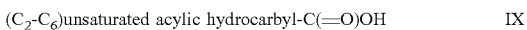

(C$_2$-C$_6$)unsaturated acylic hydrocarbyl-C(=O)OH    IX wherein X, Y, R$^1$, R$^2$, R$^3$, R$^4$ and R$^5$ are as defined in claim 1, and isolating from the reaction mixture the compound according to claim 1 having the Formula X, and optionally converting the compound to a pharmaceutically acceptable salt thereof.

83. A process for preparing a compound or pharmaceutically acceptable salt thereof according to claim 1 wherein the compound has the Formula XII,

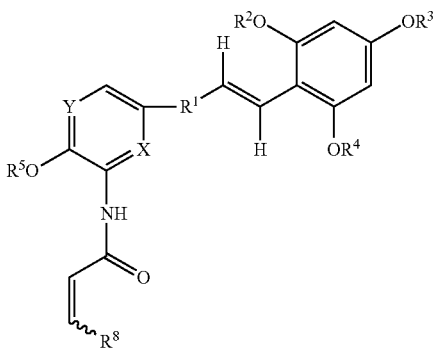

comprising reacting a compound of Formula II:

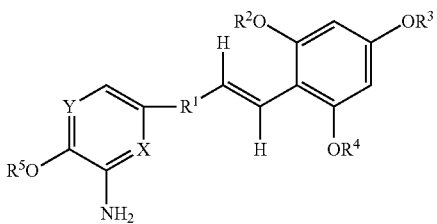

with a compound of Formula XI:

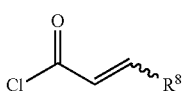

wherein X, Y, R$^1$, R$^2$, R$^3$, R$^4$, R$^5$ and R$^8$ are as defined in claim 1, and isolating from the reaction mixture the compound according to claim 1 having the Formula XI, and optionally converting the compound to a pharmaceutically acceptable salt thereof.

84. A pharmaceutical composition comprising a pharmaceutically acceptable carrier and a compound, or a pharmaceutically acceptable salt thereof, according to claim 1.

85. The pharmaceutical composition according to claim 84 wherein the compound is (Z)-ethyl 3-((2-methoxy-5-(((E)-2,4,6-trimethoxystyrylsulfonyl)methyl)phenyl)amino) acrylate, or a pharmaceutically acceptable salt thereof.

86. A method of treating an individual suffering from a cellular proliferative disorder by the inhibition of RAS activity in the individual, comprising administering to the individual an effective amount of at least one compound, or a pharmaceutically acceptable salt thereof, according to claim 1.

87. The method according to claim 86, wherein the compound is (Z)-ethyl 3-((2-methoxy-5-(((E)-2,4,6-trimethoxystyrylsulfonyl)methyl)phenyl)amino)acrylate, or a pharmaceutically acceptable salt thereof.

88. The method according to claim 86, wherein the cellular proliferative disorder is cancer.

89. The method according to claim 88, wherein the cancer is a cardiac cancer, a lung cancer, a gastroinestingal cancer, a genitourinary tract cancer, a liver cancer, a head or neck cancer, a bone cancer, a nervous system cancer, a gynecological cancer, a breast cancer, a hematologic cancer, or a skin cancer.

90. The method according to claim 89 wherein the cancer is lung cancer, pancreatic, cancer, colorectal cancer, stomach cancer, kidney cancer, bladder cancer, prostate cancer, testicular cancer, head or neck cancer, liver cancer, brain cancer, uterine cancer, cervical cancer, ovarian cancer, vaginal cancer, breast cancer, skin cancer, leukemia or lymphoma.

91. The process according to claim 80, wherein:
X is CH;
Y is CH;
R$^1$ is —CH(R)SO$_2$—;
each of R$^2$, R$^3$, R$^4$, and R$^5$ is (CO alkyl; and
R$^7$ is selected from —OR$^{10}$ and substituted aryl with one or more substituents selected from halo, —(C$_1$-C$_4$)alkoxy, —(C$_1$-C$_4$)alkyl and methylenedioxy.

92. The pharmaceutical composition according to claim 84 wherein the compound is:
(Z)-methyl 3-((2-methoxy-5-(((E)-2,4,6-trimethoxystyrylsulfonyl)methyl)phenyl)amino)acrylate;
(Z)-1-(4-methoxyphenyl)-3-((2-methoxy-5-(((E)-2,4,6-trimethoxystyrylsulfonyl)methyl)phenyl) amino)prop-2-en-1-one;
(Z)-1-(2-chloro-3,4,5-trimethoxyphenyl)-3-((2-methoxy-5-(((E)-2,4,6-trimethoxystyrylsulfonyl) methyl)phenyl) amino)prop-2-en-1-one;
(Z)-1-(2-bromo-3,4,5-trimethoxyphenyl)-3-((2-methoxy-5-(((E)-2,4,6-trimethoxystyrylsulfonyl) methyl)phenyl) amino) prop-2-en-1-one or pharmaceutically acceptable salt thereof.

93. The method according to claim 86, wherein the compound is:
(Z)-methyl 3-((2-methoxy-5-(((E)-2,4,6-trimethoxystyrylsulfonyl)methyl)phenyl)amino)acrylate;
(Z)-1-(4-methoxyphenyl)-3-((2-methoxy-5-(((E)-2,4,6-trimethoxystyrylsulfonyl)methyl)phenyl) amino)prop-2-en-1-one;

(Z)-1-(2-chloro-3,4,5-trimethoxyphenyl)-3-((2-methoxy-5-(((E)-2,4,6-trimethoxystyrylsulfonyl) methyl)phenyl) amino)prop-2-en-1-one;

(Z)-1-(2-bromo-3,4,5-trimethoxyphenyl)-3-((2-methoxy-5-(((E)-2,4,6-trimethoxystyrylsulfonyl) methyl)phenyl) amino) prop-2-en-1-one or pharmaceutically acceptable salt thereof.

* * * * *